US010876164B2

(12) United States Patent
Stone et al.

(10) Patent No.: US 10,876,164 B2
(45) Date of Patent: Dec. 29, 2020

(54) GENE SIGNATURES FOR CANCER PROGNOSIS

(71) Applicant: Myriad Genetics, Inc., Salt Lake City, UT (US)

(72) Inventors: Steven Stone, Salt Lake City, UT (US); Alexander Gutin, Salt Lake City, UT (US); Susanne Wagner, Salt Lake City, UT (US); Julia Reid, Salt Lake City, UT (US)

(73) Assignee: MYRIAD GENETICS, INC., Salt Lake City, UT (US)

( * ) Notice: Subject to any disclaimer, the term of this patent is extended or adjusted under 35 U.S.C. 154(b) by 0 days.

(21) Appl. No.: 14/713,636

(22) Filed: May 15, 2015

(65) Prior Publication Data

US 2015/0247208 A1 Sep. 3, 2015

Related U.S. Application Data

(63) Continuation of application No. PCT/US2013/070373, filed on Nov. 15, 2013.

(60) Provisional application No. 61/727,533, filed on Nov. 16, 2012.

(51) Int. Cl.
*C12Q 1/6886* (2018.01)

(52) U.S. Cl.
CPC ...... *C12Q 1/6886* (2013.01); *C12Q 2600/118* (2013.01); *C12Q 2600/158* (2013.01)

(58) Field of Classification Search
CPC ............ C12Q 1/6886; C12Q 2600/118; C12Q 2600/158
See application file for complete search history.

(56) References Cited

U.S. PATENT DOCUMENTS

| | | | |
|---|---|---|---|
| 5,993,388 A | 11/1999 | Kattan et al. | |
| 6,409,664 B1 | 6/2002 | Kattan et al. | |
| 7,056,674 B2 | 6/2006 | Baker et al. | |
| 7,081,340 B2 | 6/2006 | Baker et al. | |
| 7,569,345 B2 | 8/2009 | Cobleigh et al. | |
| 7,598,031 B2 | 10/2009 | Liew et al. | |
| 7,622,251 B2 | 11/2009 | Baker et al. | |
| 7,666,595 B2 | 2/2010 | Rubin et al. | |
| 7,695,913 B2 | 4/2010 | Cowens et al. | |
| 7,723,033 B2 | 5/2010 | Baker et al. | |
| 7,767,391 B2 | 8/2010 | Scott et al. | |
| 7,871,769 B2 | 1/2011 | Baker et al. | |
| 7,914,988 B1 | 3/2011 | Chudin et al. | |
| 7,930,104 B2 | 4/2011 | Baker et al. | |
| 8,110,363 B2 | 2/2012 | Chudin et al. | |
| 8,338,109 B2 | 12/2012 | Vasmatzis et al. | |
| 2003/0235816 A1 | 12/2003 | Slawin et al. | |
| 2005/0064455 A1 | 3/2005 | Baker et al. | |
| 2005/0244872 A1 | 11/2005 | Harris | |
| 2005/0272644 A1 | 12/2005 | Chung et al. | |
| 2007/0026424 A1 | 2/2007 | Powell et al. | |
| 2007/0059720 A9* | 3/2007 | Fuqua ............... | C12Q 1/6886 435/6.16 |
| 2007/0099209 A1 | 5/2007 | Clarke et al. | |
| 2007/0128599 A1 | 6/2007 | Ridder et al. | |
| 2007/0128636 A1 | 6/2007 | Baker et al. | |
| 2007/0253953 A1 | 11/2007 | Chen et al. | |
| 2008/0275652 A1 | 11/2008 | Sotirou et al. | |
| 2009/0123925 A1 | 5/2009 | Collie-Duguid et al. | |
| 2009/0215054 A1 | 8/2009 | Carter et al. | |
| 2009/0258795 A1 | 10/2009 | Cowens et al. | |
| 2009/0297500 A1 | 12/2009 | Nakamura et al. | |
| 2009/0305277 A1 | 12/2009 | Baker et al. | |
| 2009/0311702 A1 | 12/2009 | Shak et al. | |
| 2010/0130377 A1* | 5/2010 | Vasmatzis ........ | G01N 33/57434 506/9 |
| 2010/0184041 A1 | 7/2010 | Baker et al. | |
| 2010/0184063 A1 | 7/2010 | Ming-Sound et al. | |
| 2010/0196902 A1 | 8/2010 | Pestano et al. | |
| 2010/0222229 A1 | 9/2010 | Cobleigh et al. | |
| 2010/0267032 A1 | 10/2010 | Baker et al. | |
| 2010/0284908 A1 | 11/2010 | Christian et al. | |
| 2011/0123990 A1 | 5/2011 | Baker et al. | |
| 2011/0129833 A1 | 6/2011 | Baker et al. | |
| 2011/0166838 A1 | 7/2011 | Gehrmann et al. | |
| 2011/0178374 A1 | 7/2011 | Baker et al. | |
| 2012/0028264 A1 | 2/2012 | Shak et al. | |
| 2012/0039805 A1 | 2/2012 | Lisanti et al. | |
| 2012/0041274 A1 | 2/2012 | Stone et al. | |
| 2012/0053842 A9 | 3/2012 | Gehrmann et al. | |
| 2012/0108453 A1 | 5/2012 | Smit et al. | |
| 2012/0109535 A1 | 5/2012 | Chudin et al. | |
| 2012/0190565 A1 | 7/2012 | Lisanti et al. | |

FOREIGN PATENT DOCUMENTS

| | | |
|---|---|---|
| EP | 2404998 | 1/2012 |
| WO | WO 2004/065583 | 8/2004 |
| WO | WO 2004-074518 | 9/2004 |

(Continued)

OTHER PUBLICATIONS

GEO Accession GSE4412.*
GEO Accession GSE4271.*
GEO Accession GSE5287.*
Michiels et al. Lancet. 2005. 365:488-492.*
Slonim et al. Nature Genetics Supplement. 2002. 32:502-508.*
Simon et al. Journal of Clinical Oncology. 2005. 23(29): 7332-7341.*
McDoniels-Silvers et al. Neoplasia. 2002. 4(2):141-150.*
McDoniels-Silvers et al. Clinical Cancer Research. 2002. 8:1127-1138.*
Kuner et al. Lung Cancer. 2009. 63:32-38.*

(Continued)

*Primary Examiner* — Joseph G. Dauner
(74) *Attorney, Agent, or Firm* — Fisherbroyles, LLP; Richard R. Eckman; Victoria Boyd

(57) ABSTRACT

Biomarkers and methods using the biomarkers for classifying cancer in a patient (e.g., predicting the risk of cancer-specific death or cancer recurrence) are provided.

4 Claims, 25 Drawing Sheets

(56) References Cited

FOREIGN PATENT DOCUMENTS

| WO | WO 2004-111603 | 12/2004 |
|---|---|---|
| WO | WO 2005-007830 | 1/2005 |
| WO | WO 2005-039382 | 5/2005 |
| WO | WO 2005-100606 | 10/2005 |
| WO | WO 2006-052731 | 5/2006 |
| WO | WO 2006-052862 | 5/2006 |
| WO | WO 2006-119593 | 11/2006 |
| WO | WO 2006-135886 | 12/2006 |
| WO | WO 2007-067672 | 6/2007 |
| WO | WO 2007-070621 | 6/2007 |
| WO | WO 2008-058018 | 5/2008 |
| WO | WO 2008-077165 | 7/2008 |
| WO | WO 2008/103971 | 8/2008 |
| WO | WO 2008-115419 | 9/2008 |
| WO | 2008151072 | 12/2008 |
| WO | WO 2009-032915 | 3/2009 |
| WO | WO 2009-045115 | 4/2009 |
| WO | WO 2009-114836 | 9/2009 |
| WO | WO 2009-140304 | 11/2009 |
| WO | WO 2009-158620 | 12/2009 |
| WO | WO 2010-003771 | 1/2010 |
| WO | WO 2010-080933 | 7/2010 |
| WO | WO 2010-119126 | 10/2010 |
| WO | WO 2010-127322 | 11/2010 |
| WO | WO 2011-063274 | 5/2011 |
| WO | W02011097509 | 8/2011 |
| WO | WO 2012-152811 | 11/2011 |
| WO | WO 2012-006447 | 1/2012 |
| WO | WO 2012-012225 | 1/2012 |
| WO | W02012106718 | 8/2012 |
| WO | WO 2012-122626 | 9/2012 |
| WO | WO 2012-135008 | 10/2012 |
| WO | WO 2012-152800 | 11/2012 |
| WO | 2013028554 | 2/2013 |
| WO | WO 2012-030840 | 3/2013 |
| WO | 2014078700 | 5/2014 |

OTHER PUBLICATIONS

Malhotra et al. Cancer Biology & Therapy. 2010. 10(10):955-960.*
Simon et al., "Diagnostic and prognostic prediction using gene expression profiles in high-dimensional microarray data," British Journal of Cancer, Jan. 1, 2003, vol. 89, No. 9, p. 1599-1604.
Sotiriou et al, "Gene Expression Profiling in Breast Cancer: Understanding the Molecular Basis of Histologic Grade to Improve Prognosis", Journal of the National Cancer Institute, Feb. 15, 2006, 98(4):262-272.
Stephenson et al., "Integration of Gene Expression Profiling and Clinical Variables to Predict Prostate Carcinoma Recurrence after Radical Prostatectomy", American Cancer Society, 2005, 104:290-298.
Stephenson et al., "Postoperative Nomogram Predicting the 10-Year Probability of Prostate Cancer Recurrence After Radical Prostatectomy", Journal of Clinical Oncology, Oct. 1, 2005, 23(28):7005-7012.
Stone et al., "PTEN expression predicts biochemical recurrrence in prostate cancer", American Association for Cancer Research, vol. 51, Apr. 1, 2010, p. 287, XP009174127.
Tabach et al., "The promoters of human cell cycle genes integrate signals from two tumor suppressive pathways during cellular transformation", Molecular Systems Biology, 2005, pp. 1-15.
Teschendorff et al., "A consensus prognostic gene expression classifier for ER positive breast cancer", Genome Biology, Oct. 31, 2006, 7:R101.
Toillon et al., "Estrogens decrease •-ray-induced senescence and maintain cell cycle progression in breast cancer cells independently of p53" International Journal of Radiation Oncology, Biology, Physics, vol. 67, No. 4, pp. 1187-1200 (Mar. 15, 2007) See abstract and table 1.
Vandevijver et al., "A Gene-Expression Signature as a Predictor of Survival in Breast Cancer", The New England Journal of Medicine, Dec. 19, 2002, 347(25):1999-2009.

Wang et al., "Gene networks and microRNAs implicated in aggressive prostate cancer," Cancer Research, Dec. 15, 2009, vol. 69, No. 24, pp. 9490-9497.
Wang et al., "Gene-expression profiles to predict distant metastasis of lymph-node-negative primary breast cancer", The Lancet, Feb. 19, 2005, 365:671-679.
Whitfield et al, "Identification of Genes Periodically Expressed in the Human Cell Cycle and Their Expression in Tumors", Molecular Biology of the Cell, Jun. 2002, 13:1977-2000.
Willman et al. (The Prostate, vol. 42, pp. 280-286, 2000).
Wistuba et al., "Validation of a Proliferation-Based Expression Signature as Prognostic Marker in Early Stage Lung Adenocarcinoma", Clinical Cancer Research, vol. 19, No. 22, Nov. 15, 2013, pp. 6261-6271.
Wu et al., "Cdc6 and Cyclin E2 Are PTEN-Regulated Genes Associated with Human Prostate Cancer Metastasis1", Neoplasia, Jan. 2009, 11(1):66-76.
Wu, C-L. et al., PNAS USA, vol. 110, pp. 6121-6125 + Supplement pp. 1-9 (2013).
Yoshimoto et al., "FISH analysis of 107 prostate cancers shows that PTEN genomic deletion is associated with poor clinical outcome", British Journal of Cancer, 2007, 97:678-685.
Zaman et al., "Up-regulation of microRNA-21 correlates with lower kidney cancer survival" PLoS One, vol. 7, No. 2, e31060 (internal pp. 1-9).
Zhu et al., "Rad9 Has Functional Role in Human Prostate Carcinogenesis", Cancer Research, Mar. 1, 2008, 68(5):1267-1274.
Affymetrix website search results. Retrieved on May 8, 2015 from: https://www.affymetrix.com/analysis/netaffx/xmlquery.affx?netaffx=netaffx4_annot&_requestid=118226#.
Bedolla et al., "Determining Risk of Biochemical Recurrence in Prostate Cancer by Immunohistochemical Detection of PTEN Expression and Akt Activation", Clinical Cancer Research, 2007, 13(13):3860-3867.
Beresford et al., "Measuring proliferation in breast cancer: practicalities and applications," Breast Cancer Research, Nov. 30, 2006, Retrieved from internet: URL: http://www.ncbi.nlm.nih.gov/pmc/articles/pmc1797032/pdf/bcr1618.pdf, p. 4.
Bibikova et al., "Expression signatures that correlated with Gleason score and relapse in prostate cancer", Genomics, 2007, 89:666-672.
Carter et al., "A signature of chromosomal instability inferred from gene expression profiles predicts clinical outcome in multiple human cancers", Nature Genetics, Sep. 2006, 38(9):1043-1048.
Cooperberg et al., "Validation of a Cell-Cycle Progression Gene Panel to Improve Risk-Stratification in a Contemporary Prostatectom Cohort", Journal of Urology, vol. 187, No. 4, Suppl. S, Apr. 2012, p. E850, XP002720976.
Cuzick, J. et al, "Prognostic value of an RNA expressive signature derived from cell cycle proliferation genes in patients with prostate cancer: a retrospective study," The Lancet, Mar. 1, 2011, vol. 12, pp. 245-255.
Cuzick, J. et al., "Prognostic value of a cell cycle progression signature for prostate cancer death in a conservatively managed needle biopsy cohort," British Journal of Cancer, Mar. 13, 2012, vol. 106, No. 6, pp. 1095-1099.
Dai et al., "A Cell Proliferation Signature Is a Marker of Extremely Poor Outcome in a Subpopulation of Breast Cancer Patients", Cancer Research, May 15, 2005, 65(10):4059-4066.
European Search Report and Annex from Application No. 10729525.5, dated Nov. 30, 2012.
European Search Report and Annex from Application No. 11804357.9, dated Nov. 14, 2013.
European Search Report and Annex from Application No. 11822498.9, dated Dec. 17, 2013.
European Search Report and Annex from Application No. 12825690.6, dated Mar. 3, 2015.
Foley, R. et al., "Molecular pathology of prostate cancer: the key to identifying new biomarkers of disease," European Journal of Cancer, Apr. 1, 2005, vol. 41, No. 6, pp. 858-887.
Freedland et al., "Prognostic Utility of Cell Cycle Progression Score in Men with Prostate Cancer After Primary External Beam Radiation Therapy", Internation al Journal of Radiation, vol. 86, No. 5, Aug. 1, 2013, pp. 848-853.

(56) References Cited

OTHER PUBLICATIONS

Freije et al. Cancer Research (2004) 64: 6503-6510.
Glinsky, G. V. et al., "Gene expression profiling predicts clinical outcome of prostate cancer," Journal of Clinical Investigation, Mar. 1, 2004, vol. 113, No. 6, pp. 913-923.
Habel et al., "A population-based study of tumor gene expression and risk of breast cancer death among lymph node-negative patients", Breast Cancer Research, 2006, 8(3):1-15.
Halvorsen et al., "Combined Loss of PTEN and p27 Expression Is Associated with Tumor Cell Proliferation by Ki-67 and Increased Risk of Recurrent Disease in Localized Prostate Cancer", Clinical Cancer Research, Apr. 2003, 9:1474-1479.
Henshall, S. et al., "Survival Analysis of Genome-Wide Gene Expression Profiles of Prostate Cancers Identifies New Prognostic Targets of Disease Relapse," Cancer Research, Jul. 15, 2003, vol. 63, pp. 4196-4203.
Hess et al., "Pharmacogenomic Predictor of Sensitivity to Preoperative Chemotherapy With Paclitaxel and Fluorouracil, Doxorubicin, and Cyclophosphamide in Breast Cancer", Journal of Clinical Oncology, Sep. 10, 2006, 24(26):4236-4244.
Hughes et al. (J. Clin. Pathol. vol. 59, pp. 721-724, 2006).
International Search Report and Written Opinion from Application No. PCT/US2010/020397, dated Feb. 10, 2010.
International Search Report and Written Opinion from Application No. PCT/US2011/043228, dated Feb. 24, 2012.
International Search Report and Written Opinion from Application No. PCT/US2013/021839, dated May 27, 2013.
International Search Report and Written Opinion from Application No. PCT/US2012/051447, dated Feb. 21, 2013.
International Search Report and Written Opinion from Application No. PCT/US2013/070373, dated Apr. 1, 2014.
International Search Report and Written Opinionfrom Application No. PCT/US2014/017706, dated Jun. 24, 2014.
International Search Report and Written Opinionfrom Application No. PCT/US2014/068628, dated Apr. 16, 2015.
Ishibashi et al., "Detection of significant prognostic factors using gene-expression profiling in patients with esophageal squamous cell carcinoma," Gastroenterology, Apr. 1, 2007, vol. 132, No. 4, Suppl. 2, p. A852.
Kerner et al., "Expression of cell cycle regulatory proteins in ovaries prophylactically removed from Jewish Ashkenazi BRCA1 and BRCA2 mutation carriers: Correlation with histopathology", Gynecol. Oncol., Nov. 2005, 99(2):367-75. Abstract.
Kosari et al., "Identification of Prognostic Biomarkers for Prostate Cancer", Clinical Cancer Research, Mar. 15, 2008, 14(6):1734-1743.
LaTulippe et al. (Cancer Research, vol. 62, pp. 4499-4506, Aug. 2002).
Lauss, M. et al., "Consensus genes of the literature to predict breast cancer recurrence," Breast Cancer Research and Treatment, Sep. 26, 2007, vol. 110, No. 2, pp. 235-244.
Lee et al., "Targeting prostate cancer based on signal transduction and cell cycle pathways", Cell Cycle, Jun. 15, 2008, 7(12):1745-1762.
Liu et al., "Identification of a gene signature in cell cycle pathway for breast cancer prognosis using gene expression profiling data," BMC Medial Genomics, Sep. 11, 2008, vol. 1, No. 1, pp. 1-12.
Liu et al., "Quantitative analysis of a panel of gene expression in prostate cancer—with emphasis on NPY expression analysis", Journal of Zhejiang University Science B, 2007, 8(12):853-859.
McCall, P. et al., "Is PTEN loss associated with clinical outcome measures in human prostate cancer?" British Journal of Cancer, Oct. 21, 2008, vol. 99, No. 8, pp. 1296-1301.
Miller et al., "Utilizing Nottingham Prognostic Index in microarray gene expression profiling of breast carcinomas", Modern Pathology, Jul. 2004, 17(7):756-764.
Mosley & Keri, "Cell cycle correlated genes dictate the prognostic power of breast cancer gene lists", MBC Medical Genomics, Apr. 25, 2008, 3 pages. Abstract.
Nakopoulou et al. (J. Clin. Pathol. vol. 54, pp. 309-313, 2001).

Oligo Ge Array. Human Breast Cancer Biomarkers Microarray. Jul. 16, 2006 [online]. [retrieved on Feb. 9, 2010]. Retrieved from the internet: URL:http://web.archive.org/web/20060716064356/www.superarray.com/gene_array_product/HTML/OHS-402.html. Especially p. 1 cell cycle genes.
Paik et al. NEJM (2004) 351-28174-2826.
Porter et al., "Prognostic value of cell cycle regulators p27 and cyclin E: Tissue microarray analysis of 1753 women enrolled in SWOG breast cancer trial 9313", Journal of Clinical Oncology, 2005 ASCO Annual Meeting Proceedings, Jun. 1, 2005, vol. 23, No. 16S, Abstract: 507. Abstract only.
Quinn, D. I. et al., "Molecular markers of prostate cancer outcome," European Journal of Cancer, Apr. 1, 2005, vol. 41, No. 6, pp. 858-887.
Romanuik et al., "Novel Biomarkers for Prostate Cancer Including Noncoding Transcripts", American Journal of Pathology, vol. 175, Dec. 1, 2009, pp. 2264-2276.
Schmidt et al., "Asynchronous Growth of Prostate Cancer Is Reflected by Circulating Tumor Cells Delivered from Distinct, Even Small Foci, Harboring Loss of Heterozygosity of the PTEN Gene", Cancer Research, Sep. 15, 2006, 66(18):8959-8965.
Scholmm et al., "Value of Cell Cycle Progression (CCP) Score to Predict Biochemical Recurrence and Definitive Post-Surgical Pathology," Journal of Urology, Apr. 1, 2013, vol. 189, No. 4, p. E404.
Shariat et al., "542 Improved Prediction of Clinical Outcomes in Patients With Advanced Bladder Cancer Using a Panel of Four Cell Cycle Regulators ," European Urology Supplements, Mar. 1, 2009, vol. 8, No. 4, p. 256.
Sheikh et al., "Predictive Value of PTEN and AR Coexpression of Sustained Responsiveness to Hormonal Therapy in Prostate Cancer—A Pilot Study", Neoplasia, Sep. 2008, 10(9):949-953.
European Communication from Application No. 11804357.9, dated Dec. 8, 2016.
Affymetrix GeneChip Human Genome Arrays Data Sheet, 2003.
Austrailian Examination Report from Application No. 2010203542, dated Jan. 24, 2017.
European Communication from Application No. 12825690.3, dated Feb. 9, 2017.
Affymetrix U95 Set. Retrieved on Oct. 22, 2015 from the internet: https://www.affymetrix.com/user/login.jsp?toURL=/analysis/netaffx/showresults.affx-#.
Beer et al. Nature Medicine. 2002.8(8): 816-824.
Chan et al. G&P magazine. 2006. 6(3): 20-26.
Cortes et al., Translational Lung Cancer, 2015, 4(2), pp. 191-197.
European Communication from Application No. 10729525.5, dated Jan. 2, 2014.
European Communication from Application No. 10729525.5, dated Jun. 11, 2015.
European Communication from Application No. 10729525.5, dated Nov. 13, 2015.
European Communication from Application No. 11822498.9, dated Jun. 3, 2016.
European Communication from Application No. 12825690.6, dated Jun. 16, 2016.
European Search Report and Annex from Application No. 14754889.5, dated Sep. 16, 2016.
European Search Report and Annex from Application No. 16170659.3, dated Dec. 13, 2016.
Foley et al., Endocrine-Related Cancer, 2004, vol. 11, pp. 477-488.
Galea et al., Breast Cancer Research and Treatment, 1992, vol. 22, pp. 207-219.
Ho et al. Lung Cancer. 2008. 59:105-110.
Holzbeirlein et al. Am J Pathol. 2004. 164: 217-227.
International Preliminary Report on Patentability from Application No. PCT/US11/043228, dated Jan. 17, 2013.
International Preliminary Report on Patentability from Application No. PCT/US2011/049760, dated Mar. 14, 2013.
International Preliminary Report on Patentability from Application No. PCT/US2012/051447, dated Mar. 6, 2014.
International Preliminary Report on Patentability from Application No. PCT/US2013/021839, dated Jul. 31, 2014.
International Preliminary Report on Patentability from Application No. PCT/US2013/070373, dated May 28, 2015.

(56) References Cited

OTHER PUBLICATIONS

International Preliminary Report on Patentability from Application No. PCT/US2014/017706, dated Sep. 3, 2015.
International Preliminary Report on Patentability from Application No. PCT/US2015/030617, dated Nov. 24, 2016.
International Search Report and Written Opinion from Application No. PCT/US2011/049760, dated Apr. 26, 2012.
International Search Report and Written Opinion from Application No. PCT/US2015/030617, dated Aug. 20, 2015.
Lee et al., Clinical Cancer Research, vol. 14, No. 2, pp. 7397-7404, 2008.
Ma et al., "Diagnostic and Prognostic Score System for Prostate Cancer Using Urine and Plasma Biomarkers" Genetic Testing and Molecular Biomarkers, vol. 18, No. 3, Mar. 1, 2014.
"Oligo Ge Array. Human Cell Cycle Microarray., Jun. 11, 2006 [online]. [retrieved on Feb. 9, 2010]. Retrieved from the internet: <URL:http://web.archive.org!web/200611 05215154/www. superarray .comlgene_array_producVHTMUOHS-020.html >."
Response to European Communication from Application No. 10729525. 5, dated May 9, 2014.
Response to European Communication from Application No. 10729525. 5, dated Oct. 16, 2015.
Response to European Communication from Application No. 10729525. 5, dated Jun. 19, 2013.
Response to European Communication from Application No. 11804357. 9, dated Jun. 20, 2014.
Response to European Communication from Application No. 11822498. 9, dated Oct. 18, 2016.
Response to European Communication from Application No. 11822498. 9, dated Jul. 24, 2014.
Response to European Communication from Application No. 12825690. 6, dated Sep. 22, 2015.
Response to European Communication from Application No. 12825690. 6, dated Oct. 24, 2016.
Shedden et al. Nature Medicine. 2008. 14(8):822-827.
Shore et al. The Journal of Urology. 2016. 195:612-618.
Subramanian et al., Journal of the National Cancer Institute, vol. 102, No. 7, pp. 464-474, 2010.
Yanaihara et al. Cancer Cell. 2006. 9: 189-198.
Yu et al. Journal of Clinical Oncology. 2004. 22 (14): 2790-2799.
Japanese Office Action from Application No. 2015-558997, dated Oct. 16, 2017.
Han et al., Urologic Oncology, 2013, vol. 1, No. 1, pp. 72-82.
Loeb et al., European Association of Urology, 2014, vol. 65, pp. 1046-1055.
Mottet et al., European Association of Urology, 2016, vol. 71, pp. 618-629.
Rakha et al., European Journal of Cancer, vol. 51, pp. 1897-1903, 2015.
Response to European Communication from Application No. 12825690. 6, dated Aug. 17, 2017.
Stone et al., ASCO-GU, 2017, Abstract 249, pp. 1.
Venet et al., PLoS Computational Biology, vol. 7, No. 10, 2011, pp. e100240.
Anonymous: "Expression of the PTTG1 Oncogene Is Associated with Aggressive Clear Cell Renal Cell Carcinoma" Cancer Research, 2012.
Canadian Office Action from Application No. 2,749,103, dated Feb. 28, 2017.
Canadian Office Action from Application No. 2,804,391, dated Jul. 27, 2017.
Canadian Office Action from Application No. 2,809,829, dated Jun. 15, 2017.
Chen et al., Molecular & Cellular Proteomics, 2002, vol. 1, pp. 304-313.
Cheville et al. Journal of Clinical Oncology. 2008. 26(24):3930-3936. (Year: 2008).
Ding et al., Cancer Research, vol. 71, No. 15, 2011.
European Communication from Application No. 11804357.9, dated Jul. 17, 2017.
Extended European Search Report from Application No. 14868575. 3, dated Jun. 20, 2017.
Gao et al. Mol Pharmacol. 2000. 58:1001-1010. (Year: 2000).
Gulzar, Z.G. et al., Oncogene, vol. 32, pp. 70-77 (2013).
Pascal et al. BMC Genomics. 2008. 9:246. (Year: 2008).
Pena-Diaz et al. Nucleic Acids Research. 2013.41 (5):2846-2856 and Supplementary Dataset 1. (Year: 2013).
Response to European Communication from Application No. 11804357. 9, dated Nov. 24, 2017.
Response to European Communication from Application No. 14754889. 5, dated Apr. 13, 2017.
Response to European Communication from Application No. 14868575. 3, dated Jan. 8, 2018.
Response to European Communication from Application No. 16170659. 3, dated Jul. 18, 2017.
Zhang et al., The Journal of the International Society for Oncodevelopmental Biology and Medicine, vol. 34, No. 3, 2013.
European Communication from Application No. 11804357.9, dated May 18, 2018, 31 pages.
European Communication from Application No. 14868575.3, dated Jun. 12, 2018, 9 pages.
European Communication from Application No. 15727137.0, dated Mar. 22, 2018, 5 pages.
European Communication from Application No. 16170659.3, dated May 23, 2018, 6 pages.

* cited by examiner

GENE SIGNATURES FOR CANCER PROGNOSIS

CROSS-REFERENCE TO RELATED APPLICATIONS

This application is a continuation of International Application No. PCT/US2013/070373 filed Nov. 15, 2013, which claims the benefit of U.S. provisional application Ser. No. 61/727,533, filed Nov. 16, 2012, the contents of all of which are hereby incorporated by reference in their entirety.

FIELD OF THE INVENTION

The disclosure generally relates to a molecular classification of disease and particularly to molecular markers for cancer prognosis and methods of use thereof.

BACKGROUND OF THE INVENTION

Cancer is a major public health problem, accounting for roughly 25% of all deaths in the United States. Though many treatments have been devised for various cancers, these treatments often vary in severity of side effects. It is useful for clinicians to know how aggressive a patient's cancer is in order to determine how aggressively to treat the cancer.

For example, most patients with early-stage asymptomatic prostate cancer are treated with radical prostatectomy or radiotherapy and optionally adjuvant therapy (e.g., hormone or chemotherapy), all of which have severe side effects. For many of these patients, however, these treatments and their associated side effects and costs are unnecessary because the cancer in these patients is not aggressive (i.e., grows slowly and is unlikely to cause mortality or significant morbidity during the patient's lifetime). In other patients the cancer is virulent (i.e., more likely to recur) and aggressive treatment is necessary to save the patient's life.

Some tools have been devised to help physicians in deciding which patients need aggressive treatment and which do not. In fact, several clinical parameters are currently in use for this purpose in various different cancers. In prostate cancer, for example, such clinical parameters include serum prostate-specific antigen (PSA), Gleason grade, pathologic stage, and surgical margins. In recent years clinical parameters have been made more helpful through their incorporation into continuous multivariable postoperative nomograms that calculate a patient's probability of having cancer progression/recurrence. See, e.g., Kattan et al., J. CLIN. ONCOL. (1999) 17:1499-1507; Stephenson et al., J. CLINT. ONCOL. (2005) 23:7005-7012. Despite these advances, however, many patients are given improper cancer treatments and there is still a serious need for novel and improved tools for predicting cancer recurrence.

SUMMARY OF THE INVENTION

The present disclosure is based in part on the surprising discovery that the expression of those genes whose expression closely tracks the cell cycle ("cell-cycle genes" or "CCGs" as further defined below) is particularly useful in classifying selected types of cancer and determining the prognosis of these cancers.

Accordingly, in a first aspect of the present disclosure, a method is provided for determining gene expression in a tumor sample from a patient (e.g., one identified as having prostate cancer, lung cancer, bladder cancer or brain cancer). Generally, the method includes at least the following steps:

(1) obtaining a tumor sample from a patient (e.g., one identified as having prostate cancer, lung cancer, bladder cancer or brain cancer); (2) determining the expression of a panel of genes in said tumor sample including at least 4 cell-cycle genes; and (3) providing a test value by (a) weighting the determined expression of each of a plurality of test genes selected from said panel of genes with a predefined coefficient, and (b) combining the weighted expression to provide said test value, wherein at least 50%, at least 75% or at least 90% of said plurality of test genes are cell-cycle genes.

In some embodiments, the plurality of test genes includes at least 8 cell-cycle genes, or at least 10, 15, 20, 25 or 30 cell-cycle genes. In some embodiments, at least some proportion of the test genes (e.g., at least 10%, 15%, 20%, 25%, 30%, 40%, 50%, 60%, 70%, 80%, 85%, 90%, 95%, or 99%) are cell-cycle genes. In some embodiments, all of the test genes are cell-cycle genes.

Also in some embodiments, the step of determining the expression of the panel of genes in the tumor sample comprises measuring the amount of mRNA in the tumor sample transcribed from each of from 4 to about 200 cell-cycle genes; and measuring the amount of mRNA of one or more housekeeping genes in the tumor sample.

In another aspect of the present disclosure, a method is provided for determining the prognosis of prostate cancer, lung cancer, bladder cancer or brain cancer, which comprises determining in a tumor sample from a patient diagnosed of prostate cancer, lung cancer, bladder cancer or brain cancer, the expression of at least 6, 8 or 10 cell-cycle genes, wherein overexpression of said at least 6, 8 or 10 cell-cycle genes indicates a poor prognosis or an increased likelihood of recurrence of cancer in the patient.

In one embodiment, the prognosis method comprises (1) determining in a tumor sample from a patient diagnosed of prostate cancer, lung cancer, bladder cancer or brain cancer, the expression of a panel of genes in said tumor sample including at least 4 or at least 8 cell-cycle genes; and (2) providing a test value by (a) weighting the determined expression of each of a plurality of test genes selected from the panel of genes with a predefined coefficient, and (b) combining the weighted expression to provide the test value, wherein at least 50%, at least 75% or at least 85% of the plurality of test genes are cell-cycle genes, and wherein an increased level of overall expression of the plurality of test genes indicates a poor prognosis, whereas if there is no increase in the overall expression of the test genes, it would indicate a good prognosis or a low likelihood of recurrence of cancer in the patient.

In preferred embodiments, the prognosis method further includes a step of comparing the test value provided in step (2) above to one or more reference values, and correlating the test value to a risk of cancer progression or risk of cancer recurrence. In preferred embodiments, the prognosis method further includes a step of comparing the test value provided in step (2) above to one or more reference values, and correlating the test value to a likelihood (e.g., increased, decreased, specific percentage probability, etc.) of cancer progression, likelihood of cancer recurrence, likelihood of cancer-specific death, or likelihood of response to the particular treatment regimen. Optionally a test value greater than the reference value is correlated to an increased likelihood of response to treatment comprising chemotherapy. In some embodiments the test value is correlated to an increased likelihood of response to treatment (e.g., treatment comprising chemotherapy) if the test value exceeds the reference value by at least some amount (e.g., at least 0.5, 0.75, 0.85, 0.90, 0.95, 1, 2, 3, 4, 5, 6, 7, 8, 9, or 10 or more fold or standard deviations). Optionally an increased likelihood of poor prognosis is indicated if the test value is greater than the reference value.

In yet another aspect, the present disclosure also provide a method of treating cancer in a patient identified as having prostate cancer, lung cancer, bladder cancer or brain cancer, comprising: (1) determining in a tumor sample from a patient diagnosed of prostate cancer, lung cancer, bladder cancer or brain cancer, the expression of a panel of genes in the tumor sample including at least 4 or at least 8 cell-cycle genes; (2) providing a test value by (a) weighting the determined expression of each of a plurality of test genes selected from said panel of genes with a predefined coefficient, and (b) combining the weighted expression to provide said test value, wherein at least 50% or 75% or 85% of the plurality of test genes are cell-cycle genes, wherein an increased level of expression of the plurality of test genes indicates a poor prognosis, and an un-increased level of expression of the plurality of test genes indicates a good prognosis; and recommending, prescribing or administering a treatment regimen or watchful waiting based on the prognosis provided in step (2).

The present disclosure further provides a diagnostic kit for prognosing cancer in a patient diagnosed of prostate cancer, lung cancer, bladder cancer or brain cancer, comprising, in a compartmentalized container, a plurality of oligonucleotides hybridizing to at least 8 test genes, wherein less than 10%, 30% or less than 40% of all of the at least 8 test genes are non-cell-cycle genes; and one or more oligonucleotides hybridizing to at least one housekeeping gene. The oligonucleotides can be hybridizing probes for hybridization with the test genes under stringent conditions or primers suitable for PCR amplification of the test genes. In one embodiment, the kit consists essentially of, in a compartmentalized container, a first plurality of PCR reaction mixtures for PCR amplification of from 5 or 10 to about 300 test genes, wherein at least 50%, at least 60% or at least 80% of such test genes are cell-cycle genes, and wherein each reaction mixture comprises a PCR primer pair for PCR amplifying one of the test genes; and a second plurality of PCR reaction mixtures for PCR amplification of at least one housekeeping gene. In some embodiments the kit comprises one or more computer software programs for calculating a test value derived from the expression of the test genes (either the overall expression of all test genes or of some subset) and for comparing this test value to some reference value (and optionally for assigning a risk level based on this comparison). In some embodiments such computer software is programmed to weight the test genes such that cell-cycle genes are weighted to contribute at least 50%, at least 75% or at least 85% of the test value. In some embodiments such computer software is programmed to communicate (e.g., display) that the patient has an increased likelihood of progression, recurrence, cancer-specific death, or response to a particular treatment regimen (e.g., comprising adjuvant radiation or chemotherapy) if the test value is greater than the reference value (e.g., by more than some predetermined amount). In some embodiments the computer software is programmed to communicate (e.g., display) the risk level of progression, recurrence, cancer-specific death, or response to a particular treatment regimen assignable to the patient based on the test value (e.g., based on comparison of the test value to a reference value).

The present disclosure also provides the use of (1) a plurality of oligonucleotides hybridizing to at least 4 or at least 8 cell-cycle genes; and (2) one or more oligonucleotides hybridizing to at least one housekeeping gene, for the manufacture of a diagnostic product for determining the expression of the test genes in a tumor sample from a patient (e.g., one diagnosed with prostate cancer, lung cancer, bladder cancer or brain cancer) to predict the prognosis of cancer, wherein an increased level of the overall expression of the test genes indicates a poor prognosis or an increased likelihood of recurrence of cancer in the patient, whereas if there is no increase in the overall expression of the test genes, it would indicate a good prognosis or a low likelihood of recurrence of cancer in the patient. In some embodiments, the oligonucleotides are PCR primers suitable for PCR amplification of the test genes. In other embodiments, the oligonucleotides are probes hybridizing to the test genes under stringent conditions. In some embodiments, the plurality of oligonucleotides are probes for hybridization under stringent conditions to, or are suitable for PCR amplification of, from 4 to about 300 test genes, at least 50%, 70% or 80% or 90% of the test genes being cell-cycle genes. In some other embodiments, the plurality of oligonucleotides are hybridization probes for, or are suitable for PCR amplification of, from 20 to about 300 test genes, at least 30%, 40%, 50%, 70% or 80% or 90% of the test genes being cell-cycle genes.

The present disclosure further provides a system for determining gene expression in a tumor sample, comprising: (1) a sample analyzer for determining the expression levels of a panel of genes in a tumor sample including at least 4 cell-cycle genes, wherein the sample analyzer contains the tumor sample (e.g., from a patient identified as having prostate cancer, lung cancer, bladder cancer or brain cancer), mRNA expressed from the panel of genes in the tumor sample, or cDNA molecules from mRNA expressed from the panel of genes in the tumor sample; (2) a first computer program for (a) receiving gene expression data on at least 4 test genes selected from the panel of genes, (b) weighting the determined expression of each of the test genes with a predefined coefficient, and (c) combining the weighted expression to provide a test value, wherein at least 50%, at least at least 75% of at least 4 test genes are cell-cycle genes; and optionally (3) a second computer program for comparing the test value to one or more reference values each associated with a predetermined degree of risk of cancer recurrence or progression of the prostate cancer, lung cancer, bladder cancer or brain cancer. In some embodiments, the system further comprises a display module displaying the comparison between the test value to the one or more reference values, or displaying a result of the comparing step.

In some embodiments the disclosure provides a system for determining the the prognosis of a patient having cancer, comprising: (1) a sample analyzer for determining the expression levels of a panel of genes in a tumor sample including at least 4 cell-cycle genes, wherein the sample analyzer contains the tumor sample, mRNA molecules expressed from the panel of genes and extracted from the sample, or cDNA molecules from said mRNA molecules; (2) a first computer program for (a) receiving gene expression data on at least 4 test genes selected from the panel of genes, (b) weighting the determined expression of each of the test genes with a predefined coefficient, and (c) combining the weighted expression to provide a test value, wherein the cell-cycle genes are weighted to contribute at least 50%, at least 75% or at least 85% of the test value; and (3) a second computer program for comparing the test value to one or more reference values each associated with a predetermined prognosis (e.g., a predetermined likelihood of recurrence, progression, cancer-specific death, or likelihood of response to a particular treatment regimen). In some embodiments, the system further comprises a display module displaying the comparison between the test value and the one or more reference values, or displaying a result of the comparing step.

Unless otherwise defined, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. In case of conflict, the present specification, including definitions, will control. In addition, the materials, methods, and examples are illustrative only and not intended to be limiting.

Other features and advantages of the disclosure will be apparent from the following Detailed Description, and from the Claims.

Combined Score=0.39*(Clinical Variable(s)(e.g., CAPRA))+0.57*(CCP Score).

Figure 25:
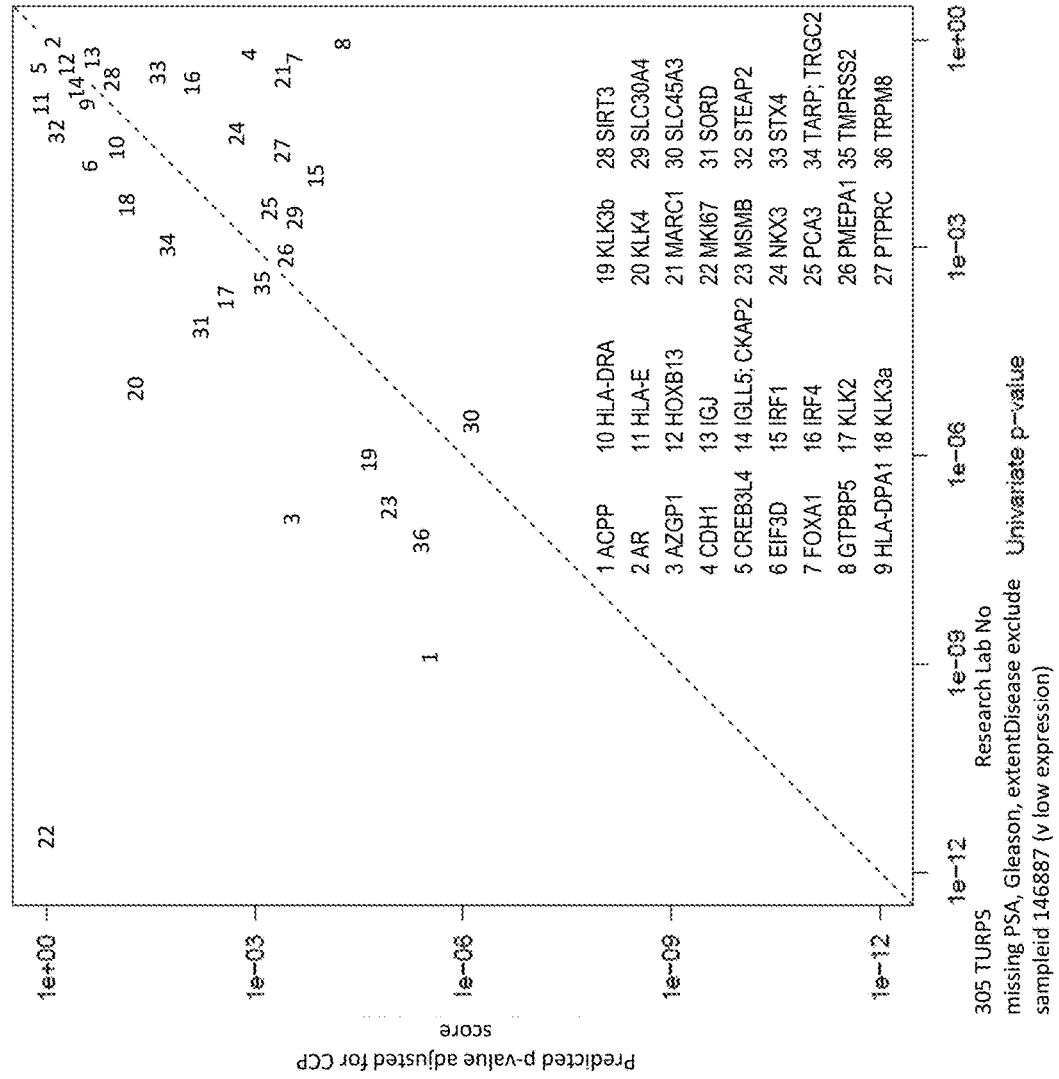

FIG. 25 shows how the genes tested in Example 9 predicted outcome both independently and after adjusting for CCP score.

DETAILED DESCRIPTION OF THE INVENTION

I. Determining Cell-Cycle Gene Expression

The present disclosure is based in part on the discovery that genes whose expression closely tracks the cell cycle ("cell-cycle genes" or "CCGs") are particularly powerful genes for classifying selected cancers including prostate cancer, lung cancer, bladder cancer, brain cancer and breast cancer, but not other types of cancer.

"Cell-cycle gene" and "CCG" herein refer to a gene whose expression level closely tracks the progression of the cell through the cell-cycle. See, e.g., Whitfield et al., MOL. BIOL. CELL (2002) 13:1977-2000. The term "cell-cycle progression" or "CCP" will also be used in this application and will generally be interchangeable with CCG (i.e., a CCP gene is a CCG; a CCP score is a CCG score). More specifically, CCGs show periodic increases and decreases in expression that coincide with certain phases of the cell cycle—e.g., STK15 and PLK show peak expression at G2/M. Id. Often CCGs have clear, recognized cell-cycle related function—e.g., in DNA synthesis or repair, in chromosome condensation, in cell-division, etc. However, some CCGs have expression levels that track the cell-cycle without having an obvious, direct role in the cell-cycle—e.g., UBE2S encodes a ubiquitin-conjugating enzyme, yet its expression closely tracks the cell-cycle. Thus a CCG according to the present disclosure need not have a recognized role in the cell-cycle. Exemplary CCGs are listed in Tables 1, 2, 7-11, 13, 14 & A. A fuller discussion of CCGs can be found in International Application No. PCT/US2010/020397 (pub. no. WO/2010/080933) (see, e.g., Table 1 in WO/2010/080933), U.S. utility application Ser. No. 13/177,887 (pub. no. US20120041274), International Application No. PCT/US2011/043228 (pub. no. WO/2012/006447), and U.S. utility application Ser. No. 13/178,380 (pub. no. US20120053253), the contents of which are hereby incorporated by reference in their entirety.

Whether a particular gene is a CCG may be determined by any technique known in the art, including those taught in Whitfield et al., MOL. BIOL. CELL (2002) 13:1977-2000; Whitfield et al., MOL. CELL. BIOL. (2000) 20:4188-4198; WO/2010/080933 (¶[0039]). All of the CCGs in Table 2 below form a panel of CCGs ("Panel A") useful in the disclosure. As will be shown detail throughout this document, individual CCGs (e.g., CCGs in Table 2) and subsets of these genes can also be used in the disclosure.

TABLE 2

| Gene Symbol | Entrez GeneID | ABI Assay ID | RefSeq Accession Nos. |
|---|---|---|---|
| APOBEC3B* | 9582 | Hs00358981_m1 | NM_004900.3 |
| ASF1B* | 55723 | Hs00216780_m1 | NM_018154.2 |
| ASPM* | 259266 | Hs00411505_m1 | NM_018136.4 |
| ATAD2* | 29028 | Hs00204205_m1 | NM_014109.3 |
| BIRC5* | 332 | Hs00153353_m1; Hs03043576_m1 | NM_001012271.1; NM_001012270.1; NM_001168.2 |
| BLM* | 641 | Hs00172060_m1 | NM_000057.2 |
| BUB1 | 699 | Hs00177821_m1 | NM_004336.3 |
| BUB1B* | 701 | Hs01084828_m1 | NM_001211.5 |
| C12orf48* | 55010 | Hs00215575_m1 | NM_017915.2 |
| C18orf24* | 220134 | Hs00536843_m1 | NM_145060.3; NM_001039535.2 |
| C1orf135* | 79000 | Hs00225211_m1 | NM_024037.1 |
| C21orf45* | 54069 | Hs00219050_m1 | NM_018944.2 |
| CCDC99* | 54908 | Hs00215019_m1 | NM_017785.4 |
| CCNA2* | 890 | Hs00153138_m1 | NM_001237.3 |
| CCNB1* | 891 | Hs00259126_m1 | NM_031966.2 |
| CCNB2* | 9133 | Hs00270424_m1 | NM_004701.2 |
| CCNE1* | 898 | Hs01026536_m1 | NM_001238.1; NM_057182.1 |
| CDC2* | 983 | Hs00364293_m1 | NM_033379.3; NM_001130829.1; NM_001786.3 |
| CDC20* | 991 | Hs03004916_g1 | NM_001255.2 |
| CDC45L* | 8318 | Hs00185895_m1 | NM_003504.3 |
| CDC6* | 990 | Hs00154374_m1 | NM_001254.3 |
| CDCA3* | 83461 | Hs00229905_m1 | NM_031299.4 |
| CDCA8* | 55143 | Hs00983655_m1 | NM_018101.2 |
| CDKN3* | 1033 | Hs00193192_m1 | NM_001130851.1; NM_005192.3 |
| CDT1* | 81620 | Hs00368864_m1 | NM_030928.3 |
| CENPA | 1058 | Hs00156455_m1 | NM_001042426.1; NM_001809.3 |
| CENPE* | 1062 | Hs00156507_m1 | NM_001813.2 |
| CENPF* | 1063 | Hs00193201_m1 | NM_016343.3 |
| CENPI* | 2491 | Hs00198791_m1 | NM_006733.2 |
| CENPM* | 79019 | Hs00608780_m1 | NM_024053.3 |
| CENPN* | 55839 | Hs00218401_m1 | NM_018455.4; NM_001100624.1; NM_001100625.1 |
| CEP55* | 55165 | Hs00216688_m1 | NM_018131.4; NM_001127182.1 |
| CHEK1* | 1111 | Hs00967506_m1 | NM_001114121.1; NM_001114122.1; NM_001274.4 |
| CKAP2* | 26586 | Hs00217068_m1 | NM_018204.3; NM_001098525.1 |
| CKS1B* | 1163 | Hs01029137_g1 | NM_001826.2 |
| CKS2* | 1164 | Hs01048812_g1 | NM_001827.1 |
| CTPS* | 1503 | Hs01041851_m1 | NM_001905.2 |
| CTSL2* | 1515 | Hs00952036_m1 | NM_001333.2 |
| DBF4* | 10926 | Hs00272696_m1 | NM_006716.3 |
| DDX39* | 10212 | Hs00271794_m1 | NM_005804.2 |
| DLGAP5/DLG7* | 9787 | Hs00207323_m1 | NM_014750.3 |
| DONSON* | 29980 | Hs00375083_m1 | NM_017613.2 |
| DSN1* | 79980 | Hs00227760_m1 | NM_024918.2 |
| DTL* | 51514 | Hs00978565_m1 | NM_016448.2 |
| E2F8* | 79733 | Hs00226635_m1 | NM_024680.2 |
| ECT2* | 1894 | Hs00216455_m1 | NM_018098.4 |
| ESPL1* | 9700 | Hs00202246_m1 | NM_012291.4 |
| EXO1* | 9156 | Hs00243513_m1 | NM_130398.2; NM_003686.3; NM_006027.3 |
| EZH2* | 2146 | Hs00544830_m1 | NM_152998.1; NM_004456.3 |
| FANCI* | 55215 | Hs00289551_m1 | NM_018193.2; NM_001113378.1 |
| FBXO5* | 26271 | Hs03070834_m1 | NM_001142522.1; NM_012177.3 |

TABLE 2-continued

| Gene Symbol | Entrez GeneID | ABI Assay ID | RefSeq Accession Nos. |
|---|---|---|---|
| FOXM1* | 2305 | Hs01073586_m1 | NM_202003.1; NM_202002.1; NM_021953.2 |
| GINS1* | 9837 | Hs00221421_m1 | NM_021067.3 |
| GMPS* | 8833 | Hs00269500_m1 | NM_003875.2 |
| GPSM2* | 29899 | Hs00203271_m1 | NM_013296.4 |
| GTSE1* | 51512 | Hs00212681_m1 | NM_016426.5 |
| H2AFX* | 3014 | Hs00266783_s1 | NM_002105.2 |
| HMMR* | 3161 | Hs00234864_m1 | NM_001142556.1; NM_001142557.1; NM_012484.2; NM_012485.2 |
| HN1* | 51155 | Hs00602957_m1 | NM_001002033.1; NM_001002032.1; NM_016185.2 |
| KIAA0101* | 9768 | Hs00207134_m1 | NM_014736.4 |
| KIF11* | 3832 | Hs00189698_m1 | NM_004523.3 |
| KIF15* | 56992 | Hs00173349_m1 | NM_020242.2 |
| KIF18A* | 81930 | Hs01015428_m1 | NM_031217.3 |
| KIF20A* | 10112 | Hs00993573_m1 | NM_005733.2 |
| KIF20B/MPHOSPH1* | 9585 | Hs01027505_m1 | NM_016195.2 |
| KIF23* | 9493 | Hs00370852_m1 | NM_138555.1; NM_004856.4 |
| KIF2C* | 11004 | Hs00199232_m1 | NM_006845.3 |
| KIF4A* | 24137 | Hs01020169_m1 | NM_012310.3 |
| KIFC1* | 3833 | Hs00954801_m1 | NM_002263.3 |
| KPNA2 | 3838 | Hs00818252_g1 | NM_002266.2 |
| LMNB2* | 84823 | Hs00383326_m1 | NM_032737.2 |
| MAD2L1 | 4085 | Hs01554513_g1 | NM_002358.3 |
| MCAM* | 4162 | Hs00174838_m1 | NM_006500.2 |
| MCM10* | 55388 | Hs00960349_m1 | NM_018518.3; NM_182751.1 |
| MCM2* | 4171 | Hs00170472_m1 | NM_004526.2 |
| MCM4* | 4173 | Hs00381539_m1 | NM_005914.2; NM_182746.1 |
| MCM6* | 4175 | Hs00195504_m1 | NM_005915.4 |
| MCM7* | 4176 | Hs01097212_m1 | NM_005916.3; NM_182776.1 |
| MELK | 9833 | Hs00207681_m1 | NM_014791.2 |
| MKI67* | 4288 | Hs00606991_m1 | NM_002417.3 |
| MYBL2* | 4605 | Hs00231158_m1 | NM_002466.2 |
| NCAPD2* | 9918 | Hs00274505_m1 | NM_014865.3 |
| NCAPG* | 64151 | Hs00254617_m1 | NM_022346.3 |
| NCAPG2* | 54892 | Hs00375141_m1 | NM_017760.5 |
| NCAPH* | 23397 | Hs01010752_m1 | NM_015341.3 |
| NDC80* | 10403 | Hs00196101_m1 | NM_006101.2 |
| NEK2* | 4751 | Hs00601227_mH | NM_002497.2 |
| NUSAP1* | 51203 | Hs01006195_m1 | NM_018454.6; NM_001129897.1; NM_016359.3 |
| OIP5* | 11339 | Hs00299079_m1 | NM_007280.1 |
| ORC6L* | 23594 | Hs00204876_m1 | NM_014321.2 |
| PAICS* | 10606 | Hs00272390_m1 | NM_001079524.1; NM_001079525.1; NM_006452.3 |
| PBK* | 55872 | Hs00218544_m1 | NM_018492.2 |
| PCNA* | 5111 | Hs00427214_g1 | NM_182649.1; NM_002592.2 |
| PDSS1* | 23590 | Hs00372008_m1 | NM_014317.3 |
| PLK1* | 5347 | Hs00153444_m1 | NM_005030.3 |
| PLK4* | 10733 | Hs00179514_m1 | NM_014264.3 |
| POLE2* | 5427 | Hs00160277_m1 | NM_002692.2 |
| PRC1* | 9055 | Hs00187740_m1 | NM_199413.1; NM_199414.1; NM_003981.2 |
| PSMA7* | 5688 | Hs00895424_m1 | NM_002792.2 |
| PSRC1* | 84722 | Hs00364137_m1 | NM_032636.6; NM_001005290.2; NM_001032290.1; NM_001032291.1 |
| PTTG1* | 9232 | Hs00851754_u1 | NM_004219.2 |
| RACGAP1* | 29127 | Hs00374747_m1 | NM_013277.3 |
| RAD51* | 5888 | Hs00153418_m1 | NM_133487.2; NM_002875.3 |
| RAD51AP1* | 10635 | Hs01548891_m1 | NM_001130862.1; NM_006479.4 |
| RAD54B* | 25788 | Hs00610716_m1 | NM_012415.2 |

TABLE 2-continued

| Gene Symbol | Entrez GeneID | ABI Assay ID | RefSeq Accession Nos. |
|---|---|---|---|
| RAD54L* | 8438 | Hs00269177_m1 | NM_001142548.1; NM_003579.3 |
| RFC2* | 5982 | Hs00945948_m1 | NM_181471.1; NM_002914.3 |
| RFC4* | 5984 | Hs00427469_m1 | NM_181573.2; NM_002916.3 |
| RFC5* | 5985 | Hs00738859_m1 | NM_181578.2; NM_001130112.1; NM_001130113.1; NM_007370.4 |
| RNASEH2A* | 10535 | Hs00197370_m1 | NM_006397.2 |
| RRM2* | 6241 | Hs00357247_g1 | NM_001034.2 |
| SHCBP1* | 79801 | Hs00226915_m1 | NM_024745.4 |
| SMC2* | 10592 | Hs00197593_m1 | NM_001042550.1; NM_001042551.1; NM_006444.2 |
| SPAG5* | 10615 | Hs00197708_m1 | NM_006461.3 |
| SPC25* | 57405 | Hs00221100_m1 | NM_020675.3 |
| STIL* | 6491 | Hs00161700_m1 | NM_001048166.1; NM_003035.2 |
| STMN1* | 3925 | Hs00606370_m1; Hs01033129_m1 | NM_005563.3; NM_203399.1 |
| TACC3* | 10460 | Hs00170751_m1 | NM_006342.1 |
| TIMELESS* | 8914 | Hs01086966_m1 | NM_003920.2 |
| TK1* | 7083 | Hs01062125_m1 | NM_003258.4 |
| TOP2A* | 7153 | Hs00172214_m1 | NM_001067.2 |
| TPX2* | 22974 | Hs00201616_m1 | NM_012112.4 |
| TRIP13* | 9319 | Hs01020073_m1 | NM_004237.2 |
| TTK* | 7272 | Hs00177412_m1 | NM_003318.3 |
| TUBA1C* | 84790 | Hs00733770_m1 | NM_032704.3 |
| TYMS* | 7298 | Hs00426591_m1 | NM_001071.2 |
| UBE2C | 11065 | Hs00964100_g1 | NM_181799.1; NM_181800.1; NM_181801.1; NM_181802.1; NM_181803.1; NM_007019.2 |
| UBE2S | 27338 | Hs00819350_m1 | NM_014501.2 |
| VRK1* | 7443 | Hs00177470_m1 | NM_003384.2 |
| ZWILCH* | 55055 | Hs01555249_m1 | NM_017975.3; NR_003105.1 |
| ZWINT* | 11130 | Hs00199952_m1 | NM_032997.2; NM_001005413.1; NM_007057.3 |

*124-gene subset of CCGs useful in the disclosure ("Panel B"). ABI Assay ID means the catalogue ID number for the gene expression assay commercially available from Applied Biosystems Inc. (Foster City, CA) for the particular gene.

Accordingly, in a first aspect of the present disclosure, a method is provided for determining gene expression in a tumor sample from a patient (e.g., one identified as having prostate cancer, lung cancer, bladder cancer or brain cancer). Generally, the method includes at least the following steps: (1) obtaining a tumor sample from a patient (e.g., one identified as having prostate cancer, lung cancer, bladder cancer or brain cancer); (2) determining the expression of a panel of genes in the tumor sample including at least 2, 4, 6, 8 or 10 cell-cycle genes; and (3) providing a test value by (a) weighting the determined expression of each of a plurality of test genes selected from said panel of genes with a predefined coefficient, and (b) combining the weighted expression to provide said test value, wherein at least 20%, 50%, at least 75% or at least 90% of said plurality of test genes are cell-cycle genes. In some embodiments the test genes are weighted such that the cell-cycle genes are weighted to contribute at least 50%, at least 55%, at least 60%, at least 65%, at least 75%, at least 80%, at least 85%, at least 90%, at least 95%, at least 99% or 100% of the test value. In some embodiments 20%, 25%, 30%, 35%, 40%, 45%, 50%, 55%, 60%, 65%, 75%, 80%, 85%, 90%, 95%, or at least 99% or 100% of the plurality of test genes are cell-cycle genes.

Gene expression can be determined either at the RNA level (i.e., mRNA or noncoding RNA (ncRNA)) (e.g., miRNA, tRNA, rRNA, snoRNA, siRNA and piRNA) or at the protein level. Measuring gene expression at the mRNA level includes measuring levels of cDNA corresponding to mRNA. Levels of proteins in a tumor sample can be determined by any known techniques in the art, e.g., HPLC, mass spectrometry, or using antibodies specific to selected proteins (e.g., IHC, ELISA, etc.).

In preferred embodiment, the amount of RNA transcribed from the panel of genes including test genes is measured in the tumor sample. In addition, the amount of RNA of one or more housekeeping genes in the tumor sample is also measured, and used to normalize or calibrate the expression of the test genes. The terms "normalizing genes" and "housekeeping genes" are defined herein below.

In any embodiment of the disclosure involving a "plurality of test genes," the plurality of test genes may include at least 2, 3 or 4 cell-cycle genes, which constitute at least 50%, 75% or 80% of the plurality of test genes, and preferably 100% of the plurality of test genes. In some embodiments, the plurality of test genes includes at least 5, 6, 7, or at least 8 cell-cycle genes, which constitute at least 20%, 25%, 30%, 40%, 50%, 60%, 70%, 75%, 80% or 90% of the plurality of test genes, and preferably 100% of the plurality of test genes. As will be clear from the context of this document, a panel of genes is a plurality of genes. Typically these genes are assayed together in one or more samples from a patient.

In some other embodiments, the plurality of test genes includes at least 8, 10, 12, 15, 20, 25 or 30 cell-cycle genes, which constitute at least 20%, 25%, 30%, 40%, 50%, 60%, 70%, 75%, 80% or 90% of the plurality of test genes, and preferably 100% of the plurality of test genes.

As will be apparent to a skilled artisan apprised of the present disclosure and the disclosure herein, "tumor sample" means any biological sample containing one or more tumor cells, or one or more tumor derived RNA or protein, and obtained from a cancer patient. For example, a tissue sample obtained from a tumor tissue of a cancer patient is a useful tumor sample in the present disclosure. The tissue sample can be an FFPE sample, or fresh frozen sample, and preferably contain largely tumor cells. A single malignant cell from a cancer patient's tumor is also a useful tumor sample. Such a malignant cell can be obtained directly from the patient's tumor, or purified from the patient's bodily fluid (e.g., blood, urine). Thus, a bodily fluid such as blood, urine, sputum and saliva containing one or tumor cells, or tumor-derived RNA or proteins, can also be useful as a tumor sample for purposes of practicing the present disclosure.

Those skilled in the art are familiar with various techniques for determining the status of a gene or protein in a tissue or cell sample including, but not limited to, microarray analysis (e.g., for assaying mRNA or microRNA expression, copy number, etc.), quantitative real-time PCR™ ("qRT-PCR™", e.g., TaqMan™), immunoanalysis (e.g., ELISA, immunohistochemistry), etc. The activity level of a polypeptide encoded by a gene may be used in much the same way as the expression level of the gene or polypeptide. Often higher activity levels indicate higher expression levels and while lower activity levels indicate lower expression levels. Thus, in some embodiments, the disclosure provides any of the methods discussed above, wherein the activity level of a polypeptide encoded by the CCG is determined rather than or in addition to the expression level of the CCG. Those skilled in the art are familiar with techniques for measuring the activity of various such proteins, including those encoded by the genes listed in Tables 1 & 2. The methods of the disclosure may be practiced independent of the particular technique used.

In preferred embodiments, the expression of one or more normalizing (often called "housekeeping") genes is also obtained for use in normalizing the expression of test genes. As used herein, "normalizing genes" referred to the genes whose expression is used to calibrate or normalize the measured expression of the gene of interest (e.g., test genes). Importantly, the expression of normalizing genes should be independent of cancer outcome/prognosis, and the expression of the normalizing genes is very similar among all the tumor samples. The normalization ensures accurate comparison of expression of a test gene between different samples. For this purpose, housekeeping genes known in the art can be used. Housekeeping genes are well known in the art, with examples including, but are not limited to, GUSB (glucuronidase, beta), HMBS (hydroxymethylbilane synthase), SDHA (succinate dehydrogenase complex, subunit A, flavoprotein), UBC (ubiquitin C) and YWHAZ (tyrosine 3-monooxygenase/tryptophan 5-monooxygenase activation protein, zeta polypeptide). One or more housekeeping genes can be used. Preferably, at least 2, 5, 10 or 15 housekeeping genes are used to provide a combined normalizing gene set. The amount of gene expression of such normalizing genes can be averaged, combined together by straight additions or by a defined algorithm. Some examples of particularly useful housekeeper genes for use in the methods and compositions of the disclosure include those listed in Table 3 below.

TABLE 3

| Gene Symbol | Entrez GeneID | Applied Biosystems Assay ID | RefSeq Accession Nos. |
|---|---|---|---|
| CLTC* | 1213 | Hs00191535_m1 | NM_004859.3 |
| GUSB | 2990 | Hs99999908_m1 | NM_000181.2 |
| HMBS | 3145 | Hs00609297_m1 | NM_000190.3 |
| MMADHC* | 27249 | Hs00739517_g1 | NM_015702.2 |
| MRFAP1* | 93621 | Hs00738144_g1 | NM_033296.1 |
| PPP2CA* | 5515 | Hs00427259_m1 | NM_002715.2 |
| PSMA1* | 5682 | Hs00267631_m1 | |
| PSMC1* | 5700 | Hs02386942_g1 | NM_002802.2 |
| RPL13A* | 23521 | Hs03043885_g1 | NM_012423.2 |
| RPL37* | 6167 | Hs02340038_g1 | NM_000997.4 |
| RPL38* | 6169 | Hs00605263_g1 | NM_000999.3 |
| RPL4* | 6124 | Hs03044647_g1 | NM_000968.2 |
| RPL8* | 6132 | Hs00361285_g1 | NM_033301.1; NM_000973.3 |
| RPS29* | 6235 | Hs03004310_g1 | NM_001030001.1; NM_001032.3 |
| SDHA | 6389 | Hs00188166_m1 | NM_004168.2 |
| SLC25A3* | 6515 | Hs00358082_m1 | NM_213611.1; NM_002635.2; NM_005888.2 |
| TXNL1* | 9352 | Hs00355488_m1 | NR_024546.1; NM_004786.2 |
| UBA52* | 7311 | Hs03004332_g1 | NM_001033930.1; NM_003333.3 |
| UBC | 7316 | Hs00824723_m1 | NM_021009.4 |
| YWHAZ | 7534 | Hs00237047_m1 | NM_003406.3 |

*Subset of housekeeping genes used in, e.g., Example 5.

In the case of measuring RNA levels for the genes, one convenient and sensitive approach is real-time quantitative PCR™ (qPCR) assay, following a reverse transcription reaction. Typically, a cycle threshold ($C_t$) is determined for each test gene and each normalizing gene, i.e., the number of cycles at which the fluorescence from a qPCR reaction above background is detectable.

The overall expression of the one or more normalizing genes can be represented by a "normalizing value" which can be generated by combining the expression of all normalizing genes, either weighted equally (straight addition or averaging) or by different predefined coefficients. For example, in a simplest manner, the normalizing value $C_{tH}$ can be the cycle threshold ($C_t$) of one single normalizing gene, or an average of the $C_t$ values of 2 or more, preferably 10 or more, or 15 or more normalizing genes, in which case, the predefined coefficient is 1/N, where N is the total number of normalizing genes used. Thus, $C_{tH}=(C_{tH1}+C_{tH2}+ \ldots C_{tHn})/N$. As will be apparent to skilled artisans, depending on the normalizing genes used, and the weight desired to be given to each normalizing gene, any coefficients (from 0/N to N/N) can be given to the normalizing genes in weighting the expression of such normalizing genes. That is, $C_{tH}=xC_{tH1}+yC_{tH2}+ \ldots zC_{tHn}$, wherein $x+y+ \ldots +z=1$.

As discussed above, the methods of the disclosure generally involve determining the level of expression of a panel of CCGs. With modern high-throughput techniques, it is often possible to determine the expression level of tens, hundreds or thousands of genes. Indeed, it is possible to determine the level of expression of the entire transcriptome (i.e., each transcribed sequence in the genome). Once such a global assay has been performed, one may then informatically analyze one or more subsets of transcripts (i.e., panels or, as often used herein, pluralities of test genes). After measuring the expression of hundreds or thousands of transcripts in a sample, for example, one may analyze (e.g., informatically) the expression of a panel or plurality of test genes comprising primarily CCGs according to the present disclosure by combining the expression level values of the individual test genes to obtain a test value.

As will be apparent to a skilled artisan, the test value provided in the present disclosure represents the overall expression level of the plurality of test genes composed substantially of cell-cycle genes. In one embodiment, to provide a test value in the methods of the disclosure, the normalized expression for a test gene can be obtained by normalizing the measured $C_t$ for the test gene against the $C_{tH}$, i.e., $\Delta C_{t1} = (C_{t1} - C_{tH})$. Thus, the test value representing the overall expression of the plurality of test genes can be provided by combining the normalized expression of all test genes, either by straight addition or averaging (i.e., weighted equally) or by a different predefined coefficient. For example, the simplest approach is averaging the normalized expression of all test genes: test value=$(\Delta C_{t1} + \Delta C_{t2} + \ldots + \Delta C_{tn})/n$. As will be apparent to skilled artisans, depending on the test genes used, different weight can also be given to different test genes in the present disclosure. In each case where this document discloses using the expression of a plurality of genes (e.g., "determining [in a tumor sample from the patient] the expression of a plurality of test genes" or "correlating increased expression of said plurality of test genes to an increased likelihood of recurrence"), this includes in some embodiments using a test value representing, corresponding to or derived or calculated from the overall expression of this plurality of genes (e.g., "determining [in a tumor sample from the patient] a test value representing the expression of a plurality of test genes" or "correlating an increased test value [or a test value above some reference value] (optionally representing the expression of said plurality of test genes) to an increased likelihood of response").

It has been determined that, once the CCP phenomenon reported herein is appreciated, the choice of individual CCGs for a test panel can often be somewhat arbitrary. In other words, many CCGs have been found to be very good surrogates for each other. Thus any CCG (or panel of CCGs) can be used in the various embodiments of the disclosure. In other embodiments of the disclosure, optimized CCGs are used. One way of assessing whether particular CCGs will serve well in the methods and compositions of the disclosure is by assessing their correlation with the mean expression of CCGs (e.g., all known CCGs, a specific set of CCGs, etc.). Those CCGs that correlate particularly well with the mean are expected to perform well in assays of the disclosure, e.g., because these will reduce noise in the assay.

126 CCGs and 47 housekeeping genes had their expression compared to the CCG and housekeeping mean in order to determine preferred genes for use in some embodiments of the disclosure. Rankings of select CCGs according to their correlation with the mean CCG expression as well as their ranking according to predictive value are given in Tables 9-11, & 13-14.

Thus, in some embodiments of each of the various aspects of the disclosure the plurality of test genes comprises the top 2, 3, 4, 5, 6, 7, 8, 9, 10, 11, 12, 13, 14, 15, 20, 25, 30, 35, 40 or more CCGs listed in Tables 9-11, & 13-14. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises at least 1, 2, 3, 4, 5, 6, 7, 8, 9, 10, 15, or 20 of the following genes: ASPM, BIRC5, BUB1B, CCNB2, CDC2, CDC20, CDCA8, CDKN3, CENPF, DLGAP5, FOXM1, KIAA0101, KIF11, KIF2C, KIF4A, MCM10, NUSAP1, PRC1, RACGAP1, and TPX2. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any two, three, four, five, six, seven, eight, nine, or ten or all of gene numbers 1 & 2, 1 to 3, 1 to 4, 1 to 5, 1 to 6, 1 to 7, 1 to 8, 1 to 9, or 1 to 10 of any of Tables 9-11, & 13-14. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, or nine or all of gene numbers 2 & 3, 2 to 4, 2 to 5, 2 to 6, 2 to 7, 2 to 8, 2 to 9, or 2 to 10 of any of Tables 9-11, & 13-14. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, or eight or all of gene numbers 3 & 4, 3 to 5, 3 to 6, 3 to 7, 3 to 8, 3 to 9, or 3 to 10 of any of Tables 9-11, & 13-14. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, or seven or all of gene numbers 4 & 5, 4 to 6, 4 to 7, 4 to 8, 4 to 9, or 4 to 10 of any of Tables 9-11, & 13-14. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, nine, 10, 11, 12, 13, 14, or 15 or all of gene numbers 1 & 2, 1 to 3, 1 to 4, 1 to 5, 1 to 6, 1 to 7, 1 to 8, 1 to 9, 1 to 10, 1 to 11, 1 to 12, 1 to 13, 1 to 14, or 1 to 15 of any of Tables 9-11, & 13-14.

II. Cancer Prognosis

It has been surprisingly discovered that in selected cancers such as prostate cancer, lung cancer, bladder cancer and brain cancer, but not other cancers including certain colon cancer, the expression of cell-cycle genes in tumor cells can accurately predict the degree of aggression of the cancer and risk of recurrence after treatment (e.g., surgical removal of cancer tissue, chemotherapy and radiation therapy, etc.). Thus, the above-described method of determining cell-cycle gene expression can be applied in the prognosis and treatment of such cancers.

Generally, a method is provided for prognosing cancer selected from prostate cancer, lung cancer, bladder cancer or brain cancer, which comprises determining in a tumor sample from a patient diagnosed of prostate cancer, lung cancer, bladder cancer or brain cancer, the expression of at least 2, 4, 5, 6, 7 or at least 8, 9, 10 or 12 cell-cycle genes, wherein high expression (or increased expression or overexpression) of the at least 4 cell-cycle genes indicates a poor prognosis or an increased likelihood of recurrence of cancer in the patient. The expression can be determined in accordance with the method described above. In some embodiments, the method comprises at least one of the following steps: (a) correlating high expression (or increased expression or overexpression) of the cell-cycle genes to a poor prognosis or an increased likelihood of recurrence of cancer in the patient; (b) concluding that the patient has a poor prognosis or an increased likelihood of recurrence of cancer based at least in part on high expression (or increased expression or overexpression) of the cell-cycle genes; or (c) communicating that the patient has a poor prognosis or an increased likelihood of recurrence of cancer based at least in part on high expression (or increased expression or overexpression) of the cell-cycle genes.

In each embodiment described in this document involving correlating a particular assay or analysis output (e.g., high CCP expression, test value incorporating CCP expression greater than some reference value, etc.) to some likelihood (e.g., increased, not increased, decreased, etc.) of some clinical event or outcome (e.g., recurrence, progression, cancer-specific death, etc.), such correlating may comprise assigning a risk or likelihood of the clinical event or outcome occurring based at least in part on the particular assay or analysis output. In some embodiments, such risk is a percentage probability of the event or outcome occurring. In some embodiments, the patient is assigned to a risk group (e.g., low risk, intermediate risk, high risk, etc.). In some embodiments "low risk" is any percentage probability below 5%, 10%, 15%, 20%, 25%, 30%, 35%, 40%, 45%, or 50%. In some embodiments "intermediate risk" is any percentage probability above 5%, 10%, 15%, 20%, 25%, 30%, 35%, 40%, 45%, or 50% and below 15%, 20%, 25%, 30%, 35%, 40%, 45%, 50%, 55%, 60%, 65%, 70%, or 75%. In some embodiments "high risk" is any percentage probability above 25%, 30%, 35%, 40%, 45%, 50%, 55%, 60%, 65%, 70%, 75%, 80%, 85%, 90%, 95%, or 99%.

As used herein, "communicating" a particular piece of information means to make such information known to another person or transfer such information to a thing (e.g., a computer). In some methods of the disclosure, a patient's prognosis or risk of recurrence is communicated. In some embodiments, the information used to arrive at such a prognosis or risk prediction (e.g., expression levels of a panel of biomarkers comprising a plurality of CCGs, clinical or pathologic factors, etc.) is communicated. This communication may be auditory (e.g., verbal), visual (e.g., written), electronic (e.g., data transferred from one computer system to another), etc. In some embodiments, communicating a cancer classification comprises generating a report that communicates the cancer classification. In some embodiments the report is a paper report, an auditory report, or an electronic record. In some embodiments the report is displayed and/or stored on a computing device (e.g., handheld device, desktop computer, smart device, website, etc.). In some embodiments the cancer classification is communicated to a physician (e.g., a report communicating the classification is provided to the physician). In some embodiments the cancer classification is communicated to a patient (e.g., a report communicating the classification is provided to the patient). Communicating a cancer classification can also be accomplished by transferring information (e.g., data) embodying the classification to a server computer and allowing an intermediary or end-user to access such information (e.g., by viewing the information as displayed from the server, by downloading the information in the form of one or more files transferred from the server to the intermediary or end-user's device, etc.).

Figure 7:
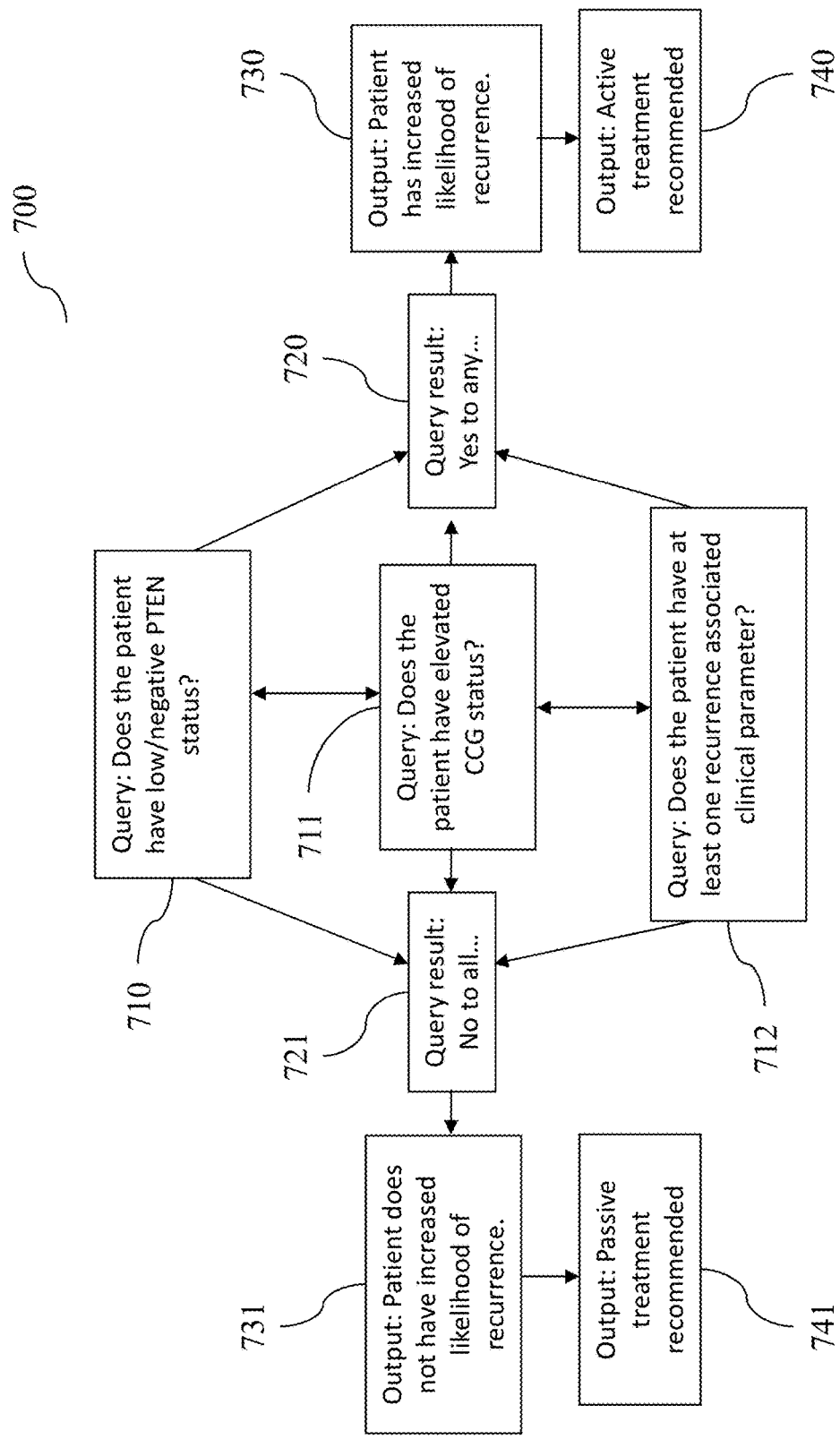
FIG. 7 is a flowchart illustrating an example of a computer-implemented method of the disclosure.

Wherever an embodiment of the disclosure comprises concluding some fact (e.g., a patient's prognosis or a patient's likelihood of recurrence), this may include a computer program concluding such fact, typically after performing an algorithm that applies information on CCG status, PTEN status, KLK3 status, and/or clinical variables in a patient sample, as shown in FIG. 7).

In some embodiments, the prognosis method includes (1) obtaining a tumor sample from a patient identified as having prostate cancer, lung cancer, bladder cancer or brain cancer; (2) determining the expression of a panel of genes in the tumor sample including at least 2, 4, 6, 8 or 10 cell-cycle genes; and (3) providing a test value by (a) weighting the determined expression of each of a plurality of test genes selected from the panel of genes with a predefined coefficient, and (b) combining the weighted expression to provide said test value, wherein at least 20%, 50%, at least 75% or at least 90% of said plurality of test genes are cell-cycle genes, and wherein high expression (or increased expression or overexpression) of the plurality of test genes indicates a poor prognosis or an increased likelihood of cancer recurrence. In some embodiments, the method comprises at least one of the following steps: (a) correlating high expression (or increased expression or overexpression) of the plurality of test genes to a poor prognosis or an increased likelihood of recurrence of cancer in the patient; (b) concluding that the patient has a poor prognosis or an increased likelihood of recurrence of cancer based at least in part on high expression (or increased expression or overexpression) of the plurality of test genes; or (c) communicating that the patient has a poor prognosis or an increased likelihood of recurrence of cancer based at least in part on high expression (or increased expression or overexpression) of the plurality of test genes.

In some embodiments, the expression levels measured in a sample are used to derive or calculate a value or score. This value may be derived solely from these expression levels (e.g., a CCG score) or optionally derived from a combination of the expression value/score with other components (e.g., year of RP, surgical margins, extracapsular extension, seminal vesicle invasion, lymph node involvement, primary Gleason score, secondary Gleason score, or preoperative PSA level, etc.) to give a more comprehensive value/score. Thus, in every case where an embodiment of the disclosure described herein involves determining the status of a biomarker (e.g., RNA expression levels of a CCG, PTEN, or KLK3), related embodiments involve deriving or calculating a value or score from the measured status (e.g., expression score).

In some such embodiments, multiple scores (e.g., CCG, Gleason, PSA, PTEN, KLK3) can be combined into a more comprehensive score. Single component (e.g., CCG) or combined test scores for a particular patient can be compared to single component or combined scores for reference populations as described below, with differences between test and reference scores being correlated to or indicative of some clinical feature. Thus, in some embodiments the disclosure provides a method of determining a cancer patient's prognosis comprising (1) obtaining the measured expression levels of a plurality of genes comprising a plurality of CCGs in a sample from the patient, (2) calculating a test value from these measured expression levels, (3) comparing said test value to a reference value calculated from measured expression levels of the plurality of genes in a reference population of patients, and (4)(a) correlating a test value greater than the reference value to a poor prognosis or (4)(b) correlating a test value equal to or less than the reference value to a good prognosis.

In some such embodiments the test value is calculated by averaging the measured expression of the plurality of genes (as discussed below). In some embodiments the test value is calculated by weighting each of the plurality of genes in a particular way.

In some embodiments the plurality of CCGs are weighted such that they contribute at least some proportion of the test value (e.g., 10%, 20%, 30%, 40%, 50%, 60%, 70%, 80%, 90%, 95%, 99%, 100%). In some embodiments each of the plurality of genes is weighted such that not all are given equal weight (e.g., KLK3 weighted to contribute more to the test value than one, some or all CCGs).

In some embodiments CCP expression is weighted and combined with other factors into a combined score (similar to the test value discussed above). In some embodiments such a combined score is calculated by adding the CCP score and the other factor(s) linearly according to the following formula:

Combined score=$A$*(CCP score)+$B$*(One or more other factors)     (1)

It will be appreciated that this disclosure encompasses other means of combination (e.g., multiplication, logarithms, exponents, etc.). In some embodiments the other factors are expression of other genes, physical characteristics of the patient (e.g., height, weight, etc.), clinical characteristics of the patient (e.g., clinical variables as discussed below), etc. In some embodiments one or more clinical variables can be combined into a clinical score, which can then be combined with the CCP score to yield a Combined Score of the disclosure.

Thus, in some embodiments the disclosure provides an method of determining a cancer patient's prognosis comprising: (1) obtaining the measured expression levels of a plurality of genes comprising a plurality of CCGs in a sample from the patient; (2) obtaining a score for the patient comprising one or more of year of RP, surgical margins, extracapsular extension, seminal vesicle invasion, lymph node involvement, primary Gleason score, secondary Gleason score, or preoperative PSA level; (3) deriving a combined test value from the measured levels obtained in (1) and the score obtained in (2); (4) comparing the combined test value to a combined reference value derived from measured expression levels of the plurality of genes and a score comprising one or more of year of RP, surgical margins, extracapsular extension, seminal vesicle invasion, lymph node involvement, primary Gleason score, secondary Gleason score, or preoperative PSA level in a reference population of patients; and (5)(a) correlating a combined test value greater than the combined reference value to a poor prognosis or (5)(b) correlating a combined test value equal to or less than the combined reference value to a good prognosis.

In some embodiments the combined score includes CCP score, PSA, and Gleason score. CCP can be a continuous numeric variable. PSA concentrations (e.g., ng/dL), adding 1 to avoid zero values, can be transformed by the natural logarithm. Gleason scores can be a continuous numeric variable or can be categorized, e.g., as <7 (reference level), 7, and >7. In some embodiments Gleason scores can be input as their numerical value (rather than being grouped). In some embodiments a Gleason score of 7 can be further delineated by (3+4) versus (4+3).

In some embodiments the combined score is calculated according to the following formula:

Combined score=$A$*(CCP score)+$B$*(ln(1+[PSA]))+ {$C$(if Gleason=7) or $D$(if Gleason>7)}     (2)

In some embodiments clinical variables (e.g., PSA, Gleason, etc.) can be combined into a clinical score (e.g., nomogram score), which can then be combined with the CCP score to yield a Combined Score according to the following formula:

Combined Score=$A$*(CCP score)+$B$*(clinical score)     (3)

In some embodiments the clinical score is the CAPRA score or the Kattan-Stephenson nomogram score. CAPRA score may be calculated as discussed herein (see especially Example 8 below). In some embodiments the clinical score is not a combination of clinical variables but instead a score representing one variable (e.g., Gleason score).

The Combined Score with CCP and other components weighted as discussed herein encompasses, mutatis mutandis, any modified or scaled version thereof. For instance, the elements can be multiplied or divided by a factor (e.g., constant or new variable) and/or have a factor (e.g., constant or new variable) added or subtracted. As an example, a Combined Score according to formula (3)

Combined Score=$A$*(CCP score)+$B$*(clinical score)     (3)

encompasses a version thereof scales by the factors C and D according to the following formula (3A)

Combined Score=$C$*($A$*(CCP score)+$B$*(clinical score))+$D$     (3A)

In some embodiments, any of the formulae discussed herein is used in the methods, systems, etc. of the disclosure to determine prognosis based on a patient's radical prostatectomy sample. In some embodiments, any of the formulae discussed herein is used in the methods, systems, etc. of the disclosure to determine prognosis based on a patient's prostate biopsy sample. In some embodiments CCP score is the unweighted mean of $C_T$ values for expression of the CCP genes being analyzed, optionally normalized by the unweighted mean of the HK genes so that higher values indicate higher expression (in some embodiments one unit is equivalent to a two-fold change in expression). In some embodiments the CCP score ranges from −8 to 8 or from −1.6 to 3.7.

In some embodiments A=0.95, B=0.61, C=0.90 (where applicable), & D=1.00 (where applicable); A=0.57 & B=0.39; or A=0.58 & B=0.41. In some embodiments, A, B, C, and/or D is within rounding of these values (e.g., A is between 0.945 and 0.954, etc.). In some cases a formula may not have all of the specified coefficients (and thus not incorporate the corresponding variable(s)). For example, the embodiment mentioned immediately previously may be applied to formula (3) where A in formula (3) is 0.95 and B in formula (3) is 0.61. C and D would not be applicable as these coefficients and their corresponding variables are not found in formula (3) (though the clinical variables may be incorporated into the clinical score found in formula (3)). In some embodiments A is between 0.9 and 1, 0.9 and 0.99, 0.9 and 0.95, 0.85 and 0.95, 0.86 and 0.94, 0.87 and 0.93, 0.88 and 0.92, 0.89 and 0.91, 0.85 and 0.9, 0.8 and 0.95, 0.8 and 0.9, 0.8 and 0.85, 0.75 and 0.99, 0.75 and 0.95, 0.75 and 0.9, 0.75 and 0.85, or between 0.75 and 0.8. In some embodiments B is between 0.40 and 1, 0.45 and 0.99, 0.45 and 0.95, 0.55 and 0.8, 0.55 and 0.7, 0.55 and 0.65, 0.59 and 0.63, or between 0.6 and 0.62. In some embodiments C is, where applicable, between 0.9 and 1, 0.9 and 0.99, 0.9 and 0.95, 0.85 and 0.95, 0.86 and 0.94, 0.87 and 0.93, 0.88 and 0.92, 0.89 and 0.91, 0.85 and 0.9, 0.8 and 0.95, 0.8 and 0.9, 0.8 and 0.85, 0.75 and 0.99, 0.75 and 0.95, 0.75 and 0.9, 0.75 and 0.85, or between 0.75 and 0.8. In some embodiments D is, where applicable, between 0.9 and 1, 0.9 and 0.99, 0.9 and 0.95, 0.85 and 0.95, 0.86 and 0.94, 0.87 and 0.93, 0.88 and 0.92, 0.89 and 0.91, 0.85 and 0.9, 0.8 and 0.95, 0.8 and 0.9, 0.8 and 0.85, 0.75 and 0.99, 0.75 and 0.95, 0.75 and 0.9, 0.75 and 0.85, or between 0.75 and 0.8.

In some embodiments A is between 0.1 and 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.2 and 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.3 and 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.4 and 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.5 and 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.6 and 0.7, 0.8, 0.9, 1, 1.5, 2, 2.5, 3, 3.5, 4, 4.5, 5, 6, 7, 8, 9, 10, 11, 12, 13, 14, 15, or 20; or between 0.7 and 0.8, 0.9, 1, 1.5, 2, 2.5, 3, 3.5, 4, 4.5, 5, 6, 7, 8, 9, 10, 11, 12, 13, 14, 15, or 20; or between 0.8 and 0.9, 1, 1.5, 2, 2.5, 3, 3.5, 4, 4.5, 5, 6, 7, 8, 9, 10, 11, 12, 13, 14, 15, or 20; or between 0.9 and 1, 1.5, 2, 2.5, 3, 3.5, 4, 4.5, 5, 6, 7, 8, 9, 10, 11, 12, 13, 14, 15, or 20; or between 1 and 1.5, 2, 2.5, 3, 3.5, 4, 4.5, 5, 6, 7, 8, 9, 10, 11, 12, 13, 14, 15, or 20; or between 1.5 and 2, 2.5, 3, 3.5, 4, 4.5, 5, 6, 7, 8, 9, 10, 11, 12, 13, 14, 15, or 20; or between 2 and 2.5, 3, 3.5, 4, 4.5, 5, 6, 7, 8, 9, 10, 11, 12, 13, 14, 15, or 20; or between 2.5 and 3, 3.5, 4, 4.5, 5, 6, 7, 8, 9, 10, 11, 12, 13, 14, 15, or 20; or between 3 and 3.5, 4, 4.5, 5, 6, 7, 8, 9, 10, 11, 12, 13, 14, 15, or 20; or between 3.5 and 4, 4.5, 5, 6, 7, 8, 9, 10, 11, 12, 13, 14, 15, or 20; or between 4 and 4.5, 5, 6, 7, 8, 9, 10, 11, 12, 13, 14, 15, or 20; or between 4.5 and 5, 6, 7, 8, 9, 10, 11, 12, 13, 14, 15, or 20; or between 5 and 6, 7, 8, 9, 10, 11, 12, 13, 14, 15, or 20; or between 6 and 7, 8, 9, 10, 11, 12, 13, 14, 15, or 20; or between 7 and 8, 9, 10, 11, 12, 13, 14, 15, or 20; or between 8 and 9, 10, 11, 12, 13, 14, 15, or 20; or between 9 and 10, 11, 12, 13, 14, 15, or 20; or between 10 and 11, 12, 13, 14, 15, or 20; or between 11 and 12, 13, 14, 15, or 20; or between 12 and 13, 14, 15, or 20; or between 13 and 14, 15, or 20; or between 14 and 15, or 20; or between 15 and 20; B is between 0.1 and 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.2 and 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.3 and 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.4 and 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.5 and 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.6 and 0.7, 0.8, 0.9, 1, 1.5, 2, 2.5, 3, 3.5, 4, 4.5, 5, 6, 7, 8, 9, 10, 11, 12, 13, 14, 15, or 20; or between 0.7 and 0.8, 0.9, 1, 1.5, 2, 2.5, 3, 3.5, 4, 4.5, 5, 6, 7, 8, 9, 10, 11, 12, 13, 14, 15, or 20; or between 0.8 and 0.9, 1, 1.5, 2, 2.5, 3, 3.5, 4, 4.5, 5, 6, 7, 8, 9, 10, 11, 12, 13, 14, 15, or 20; or between 0.9 and 1, 1.5, 2, 2.5, 3, 3.5, 4, 4.5, 5, 6, 7, 8, 9, 10, 11, 12, 13, 14, 15, or 20; or between 1 and 1.5, 2, 2.5, 3, 3.5, 4, 4.5, 5, 6, 7, 8, 9, 10, 11, 12, 13, 14, 15, or 20; or between 1.5 and 2, 2.5, 3, 3.5, 4, 4.5, 5, 6, 7, 8, 9, 10, 11, 12, 13, 14, 15, or 20; or between 2 and 2.5, 3, 3.5, 4, 4.5, 5, 6, 7, 8, 9, 10, 11, 12, 13, 14, 15, or 20; or between 2.5 and 3, 3.5, 4, 4.5, 5, 6, 7, 8, 9, 10, 11, 12, 13, 14, 15, or 20; or between 3 and 3.5, 4, 4.5, 5, 6, 7, 8, 9, 10, 11, 12, 13, 14, 15, or 20; or between 3.5 and 4, 4.5, 5, 6, 7, 8, 9, 10, 11, 12, 13, 14, 15, or 20; or between 4 and 4.5, 5, 6, 7, 8, 9, 10, 11, 12, 13, 14, 15, or 20; or between 4.5 and 5, 6, 7, 8, 9, 10, 11, 12, 13, 14, 15, or 20; or between 5 and 6, 7, 8, 9, 10, 11, 12, 13, 14, 15, or 20; or between 6 and 7, 8, 9, 10, 11, 12, 13, 14, 15, or 20; or between 7 and 8, 9, 10, 11, 12, 13, 14, 15, or 20; or between 8 and 9, 10, 11, 12, 13, 14, 15, or 20; or between 9 and 10, 11, 12, 13, 14, 15, or 20; or between 10 and 11, 12, 13, 14, 15, or 20; or between 11 and 12, 13, 14, 15, or 20; or between 12 and 13, 14, 15, or 20; or between 13 and 14, 15, or 20; or between 14 and 15, or 20; or between 15 and 20; C is, where applicable, between 0.1 and 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.2 and 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.3 and 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.4 and 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.5 and 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.6 and 0.7, 0.8, 0.9, 1, 1.5, 2, 2.5, 3, 3.5, 4, 4.5, 5, 6, 7, 8, 9, 10, 11, 12, 13, 14, 15, or 20; or between 0.7 and 0.8, 0.9, 1, 1.5, 2, 2.5, 3, 3.5, 4, 4.5, 5, 6, 7, 8, 9, 10, 11, 12, 13, 14, 15, or 20; or between 0.8 and 0.9, 1, 1.5, 2, 2.5, 3, 3.5, 4, 4.5, 5, 6, 7, 8, 9, 10, 11, 12, 13, 14, 15, or 20; or between 0.9 and 1, 1.5, 2, 2.5, 3, 3.5, 4, 4.5, 5, 6, 7, 8, 9, 10, 11, 12, 13, 14, 15, or 20; or between 1 and 1.5, 2, 2.5, 3, 3.5, 4, 4.5, 5, 6, 7, 8, 9, 10, 11, 12, 13, 14, 15, or 20; or between 1.5 and 2, 2.5, 3, 3.5, 4, 4.5, 5, 6, 7, 8, 9, 10, 11, 12, 13, 14, 15, or 20; or between 2 and 2.5, 3, 3.5, 4, 4.5, 5, 6, 7, 8, 9, 10, 11, 12, 13, 14, 15, or 20; or between 2.5 and 3, 3.5, 4, 4.5, 5, 6, 7, 8, 9, 10, 11, 12, 13, 14, 15, or 20; or between 3 and 3.5, 4, 4.5, 5, 6, 7, 8, 9, 10, 11, 12, 13, 14, 15, or 20; or between 3.5 and 4, 4.5, 5, 6, 7, 8, 9, 10, 11, 12, 13, 14, 15, or 20; or between 4 and 4.5, 5, 6, 7, 8, 9, 10, 11, 12, 13, 14, 15, or 20; or between 4.5 and 5, 6, 7, 8, 9, 10, 11, 12, 13, 14, 15, or 20; or between 5 and 6, 7, 8, 9, 10, 11, 12, 13, 14, 15, or 20; or between 6 and 7, 8, 9, 10, 11, 12, 13, 14, 15, or 20; or between 7 and 8, 9, 10, 11, 12, 13, 14, 15, or 20; or between 8 and 9, 10, 11, 12, 13, 14, 15, or 20; or between 9 and 10, 11, 12, 13, 14, 15, or 20; or between 10 and 11, 12, 13, 14, 15, or 20; or between 11 and 12, 13, 14, 15, or 20; or between 12 and 13, 14, 15, or 20; or between 13 and 14, 15, or 20; or between 14 and 15, or 20; or between 15 and 20; and D is, where applicable, between 0.1 and 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.2 and 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.3 and 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.4 and 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.5 and 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.6 and 0.7, 0.8, 0.9, 1, 1.5, 2, 2.5, 3, 3.5, 4, 4.5, 5, 6, 7, 8, 9, 10, 11, 12, 13, 14, 15, or 20; or between 0.7 and 0.8, 0.9, 1, 1.5, 2, 2.5, 3, 3.5, 4, 4.5, 5, 6, 7, 8, 9, 10, 11, 12, 13, 14, 15, or 20; or between 0.8 and 0.9, 1, 1.5, 2, 2.5, 3, 3.5, 4, 4.5, 5, 6, 7, 8, 9, 10, 11, 12, 13, 14, 15, or 20; or between 0.9 and 1, 1.5, 2, 2.5, 3, 3.5, 4, 4.5, 5, 6, 7, 8, 9, 10, 11, 12, 13, 14, 15, or 20; or between 1 and 1.5, 2, 2.5, 3, 3.5, 4, 4.5, 5, 6, 7, 8, 9, 10, 11, 12, 13, 14, 15, or 20; or between 1.5 and 2, 2.5, 3, 3.5, 4, 4.5, 5, 6, 7, 8, 9, 10, 11, 12, 13, 14, 15, or 20; or between 2 and 2.5, 3, 3.5, 4, 4.5, 5, 6, 7, 8, 9, 10, 11, 12, 13, 14, 15, or 20; or between 2.5 and 3, 3.5, 4, 4.5, 5, 6, 7, 8, 9, 10, 11, 12, 13, 14, 15, or 20; or between 3 and 3.5, 4, 4.5, 5, 6, 7, 8, 9, 10, 11, 12, 13, 14, 15, or 20; or between 3.5 and 4, 4.5, 5, 6, 7, 8, 9, 10, 11, 12, 13, 14, 15, or 20; or between 4 and 4.5, 5, 6, 7, 8, 9, 10, 11, 12, 13, 14, 15, or 20; or between 4.5 and 5, 6, 7, 8, 9, 10, 11, 12, 13, 14, 15, or 20; or between 5 and 6, 7, 8, 9, 10, 11, 12, 13, 14, 15, or 20; or between 6 and 7, 8, 9, 10, 11, 12, 13, 14, 15, or 20; or between 7 and 8, 9, 10, 11, 12, 13, 14, 15, or 20; or between 8 and 9, 10, 11, 12, 13, 14, 15, or 20; or between 9 and 10, 11, 12, 13, 14, 15, or 20; or between 10 and 11, 12, 13, 14, 15, or 20; or between 11 and 12, 13, 14, 15, or 20; or between 12 and 13, 14, 15, or 20; or between 13 and 14, 15, or 20; or between 14 and 15, or 20; or between 15 and 20. In some embodiments, A, B, and/or C is within rounding of any of these values (e.g., A is between 0.45 and 0.54, etc.).

In some embodiments the patient's percentage risk (absolute or relative) of a particular clinical event or outcome (e.g., cancer-specific death, recurrence after surgery, etc.) is estimated (e.g., calculated) according to the disclosure (e.g., according to one or more of the formulae above). Such risk may be estimated by applying the hazard ratio for a particular parameter (e.g., CCP score, Combined Score) to that parameter to yield a patient's relative risk of a particular clinical outcome (e.g., cancer recurrence or cancer-specific death). In some cases, the hazard ratio represents the relative risk increase per unit of the parameter. In some of the examples below, for instance, a single unit increase in CCP score (which represents a doubling of expression) represents a relative risk increased by the multiple of the hazard ration. Where the hazard ratio is equal to 2, for example, a single unit increase in CCP score corresponds to a doubling of relative risk (i.e., a first patient with a CCP score that is one unit higher than a second patient has twice the risk of cancer recurrence or cancer-specific death). This relative risk can be used with the average risk in a particular population to determine how a specific patient's risk compares to such population. One way to do this is to set the average value of the parameter in the population as zero and then compare specific patient's values for the parameter, meaning a patient with, e.g., a CCP score of 1 would have double the average risk of cancer recurrence or cancer-specific death.

Some embodiments of the disclosure, therefore, provide a method of calculating a patient's risk of cancer recurrence or cancer-specific death comprising (1) obtaining the measured expression levels of a plurality of genes comprising at least 3 genes chosen from any of Tables 1, 2, 7-11, 13-14 and/or Y or Panels A through I in a sample from the patient, (2) calculating a test value from these measured expression levels as discussed herein (e.g., CCP genes contributing at least some weight, at least some number of CCP genes, etc.), and (3) calculating said patient's risk of cancer recurrence or cancer-specific death by multiplying the number of increased units of the test value over some reference value (e.g., average values in a particular population) by the hazard ratio for the value. In some embodiments, the test value comprises the CCP score or a Combined Score as described herein and the hazard ration is any of the hazard ratios reported herein.

Figure 23:
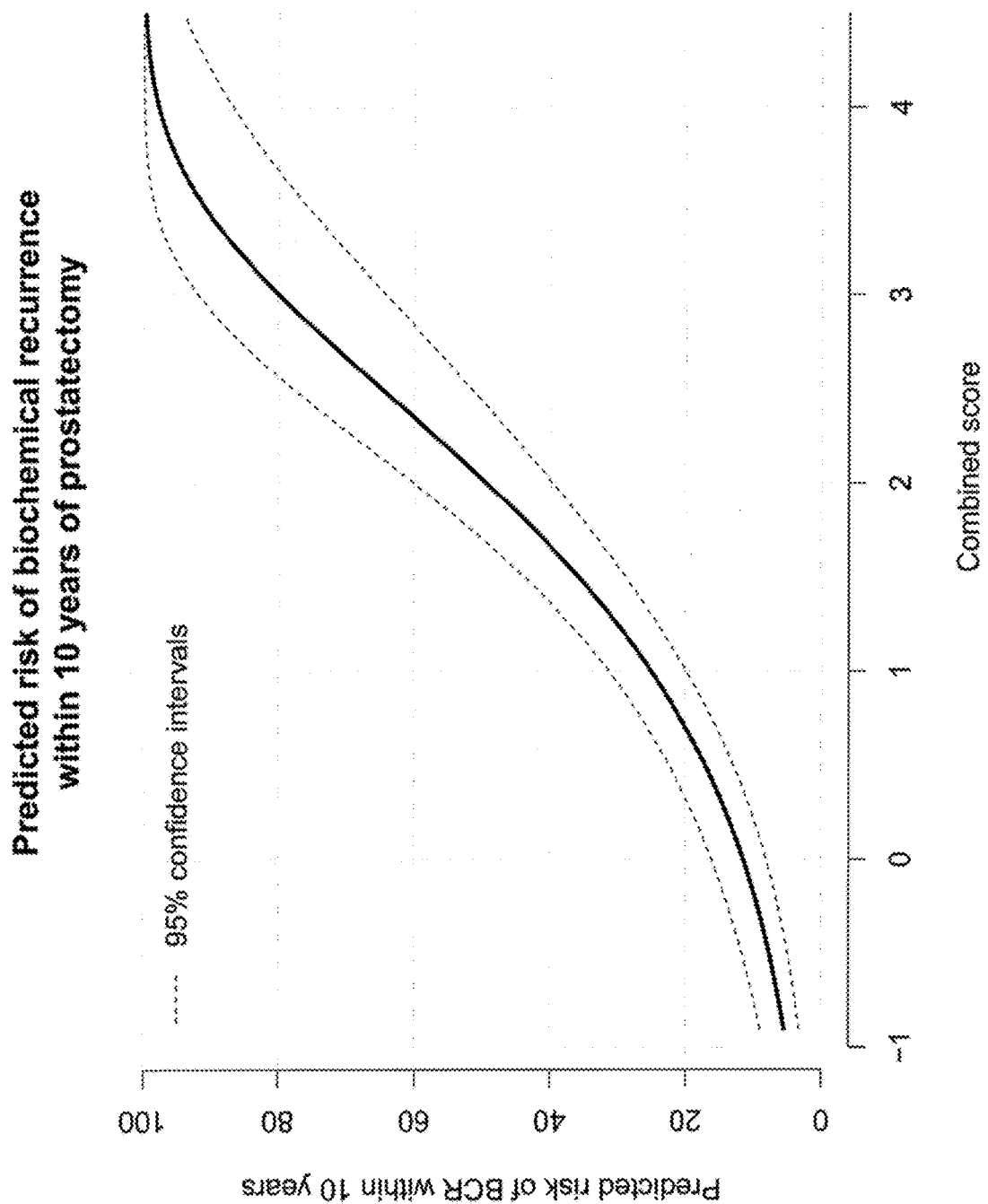
FIG. 23 shows, graphically, exemplary prognoses (e.g., proportional risk of negative clinical outcome [biochemical recurrence or BCR]) corresponding to various combined scores combining CCP score and clinical variables according to the equation: Combined Score=0.38*(Clinical Variable(s))+0.57*(CCP Score).

A more absolute (rather than relative) risk of recurrence may also be estimated by gathering data from a study patient cohort and correlating test values and scores for such patients with their eventual clinical events or outcomes. Such data may be used in a graphical form (FIGS. 23 & 24), tabular form, or as embodied in a formula (e.g., formula (4) below) to, based on a test patient's score, determine such test patient's risk of the particular clinical event or outcome. For example, one may measure a patient's CCP Score as 1.7, calculate a patient's CAPRA score as 5, and then calculate the patient's (e.g., biopsy) Combined Score using formula (2), with A=0.57 & B=0.39, as 2.92. One may then use this Combined Score to calculate such patient's risk of cancer-specific death within 10 years by, e.g., using a pre-specified formula (e.g., formula (4)), using a curve (e.g., FIG. 23 or 24), or a risk table. In some embodiments, the risk is anything within the 95% confidence interval, e.g., the intervals shown in FIG. 23 or 24.

Using these empirical data (e.g., those embodied in FIGS. 23 & 24), one may derive formulae of the following general form to estimate risk:

$$\text{Estimated Risk of } A = B * e^{C*D} \quad (4)$$

Figure 24:
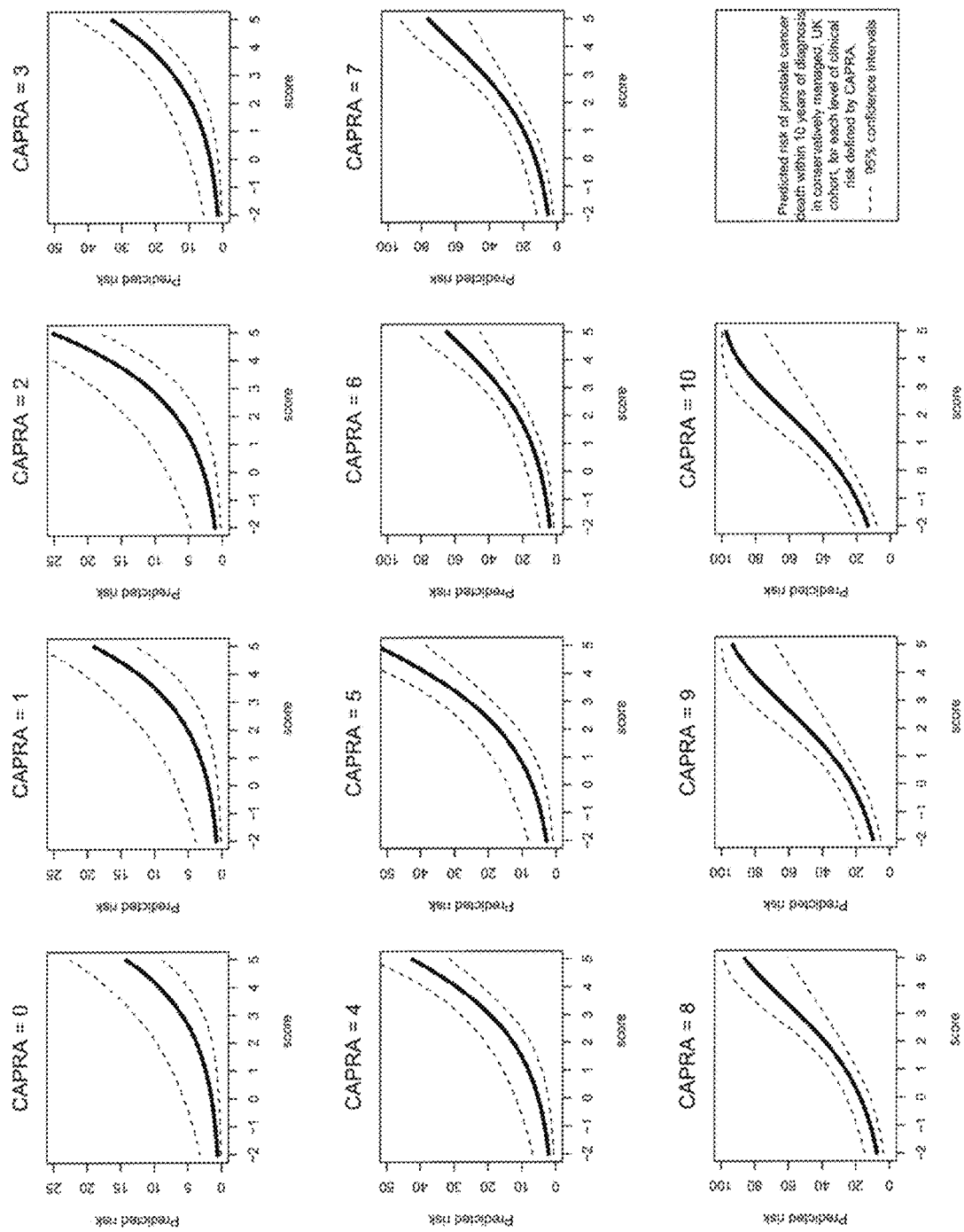
FIG. 24 shows, graphically, exemplary prognoses (e.g., proportional risk of negative clinical outcome [prostate cancer-specific death or simply "death"]) corresponding to various combined scores combining CCP score and clinical variables according to the equation.

Often, these formulae will be derived by plotting risk versus CCP Score or Combined Score for a set of study patient samples and fitting a curve to the resultant line (e.g., one of the lines shown in FIG. 24). In some embodiments, A is cancer-specific death or biochemical recurrence. In some embodiments, D is CCP score or a Combined Score (each as described in the various aspects and embodiments herein). In some embodiments B=0.0155 & C=0.0054 (as derived from, e.g., a line as shown in FIG. 24). In such a case, formula (4) would be modified as follows:

$$\text{Estimated Risk of Cancer-Specific Death} = 0.0155 * e^{0.0054*(Combined\ Score)} \quad (5)$$

where the Combined Score is calculated according to any of the formulae discussed herein. In some such specific embodiments, the Combined Score is calculated according to formula (2) with A=0.57 & B=0.39 and the clinical score being the CAPRA score.

Thus, in some embodiments the disclosure provides a method of calculating a patient's risk of prostate cancer-specific death comprising: (1) obtaining the measured expression levels of a plurality of genes comprising at least 4 genes from any of Tables 1, 2, 7-11, 13-14 and/or Y or Panels A through I; (2) optionally obtaining a score for the patient calculated from at least one clinical variable (e.g., one or more of year of RP, surgical margins, extracapsular extension, seminal vesicle invasion, lymph node involvement, primary Gleason score, secondary Gleason score, or preoperative PSA level); (3) optionally deriving a combined test value from the measured levels obtained in (1) and the score obtained in (2); (4) and calculating the patient's risk of prostate cancer-specific death according to the following formula:

$$\text{Risk of Cancer-Specific Death} = 0.0155 e^{*0.0054*([Measured\ expression\ levels\ in\ (1)]\ or\ [Combined\ Score\ obtained\ in\ (2)])}$$

In some embodiments the disclosure provides a method of calculating a patient's risk of prostate cancer-specific death comprising: (1) obtaining the measured expression levels of a plurality of genes comprising at least 4 genes from any of Tables 1, 2, 7-11, 13-14 and/or Y or Panels A through I; (2) optionally obtaining a CAPRA score for the patient sample as discussed herein; (3) optionally deriving a combined test value from the measured levels obtained in (1) and the score obtained in (2) according to the formula: Combined Score= (0.57*(Score in (2))+(0.39*Score in (1)); (4) and calculating the patient's risk of prostate cancer-specific death according to the table in FIG. 26.

In some embodiments, the test value derived or calculated from a particular gene (e.g., KLK3) or from the overall expression of the plurality of test genes (e.g., CCGs) is compared to one or more reference values (or index values), and the test value is optionally correlated to prognosis, risk of cancer progression, risk of cancer recurrence, or risk of cancer-specific death if it differs from the index value.

For example, the index value may be derived or calculated from the gene expression levels found in a normal sample obtained from the patient of interest, in which case a test value (derived or calculated from an expression level in the tumor sample) significantly higher than this index value would indicate, e.g., a poor prognosis or increased likelihood of cancer recurrence or cancer-specific death or a need for aggressive treatment. In some embodiments the test value is deemed "greater than" the reference value (e.g., the threshold index value), and thus correlated to an increased likelihood of response to treatment comprising chemotherapy, if the test value exceeds the reference value by at least some amount (e.g., at least 0.5, 0.75, 0.85, 0.90, 0.95, 1, 2, 3, 4, 5, 6, 7, 8, 9, or 10 or more fold or standard deviations).

Alternatively, the index value may be derived or calculated from the average expression level of for a set of individuals from a diverse cancer population or a subset of the population. For example, one may determine the average expression level of a gene or gene panel in a random sampling of patients with cancer (e.g., prostate, bladder, brain, breast, or lung cancer). This average expression level may be termed the "threshold index value," with patients having CCG expression higher than this value expected to have a poorer prognosis than those having expression lower than this value.

Alternatively the index value may represent the average expression level of a particular gene marker or plurality of markers in a plurality of training patients (e.g., prostate cancer patients) with similar outcomes whose clinical and follow-up data are available and sufficient to define and categorize the patients by disease outcome, e.g., recurrence or prognosis. See, e.g., Examples, infra. For example, a "good prognosis index value" can be generated from a plurality of training cancer patients characterized as having "good outcome", e.g., those who have not had cancer recurrence five years (or ten years or more) after initial treatment, or who have not had progression in their cancer five years (or ten years or more) after initial diagnosis. A "poor prognosis index value" can be generated from a plurality of training cancer patients defined as having "poor outcome", e.g., those who have had cancer recurrence within five years (or ten years, etc.) after initial treatment, or who have had progression in their cancer within five years (or ten years, etc.) after initial diagnosis. Thus, a good prognosis index value of a particular gene may represent the average level of expression of the particular gene in patients having a "good outcome," whereas a poor prognosis index value of a particular gene represents the average level of expression of the particular gene in patients having a "poor outcome."

Thus one aspect of the disclosure provides a method of classifying cancer comprising determining the status of a panel of genes comprising at least two CCGs, in tissue or cell sample, particularly a tumor sample, from a patient, wherein an abnormal status indicates a negative cancer classification. As used herein, "determining the status" of a gene refers to determining the presence, absence, or extent/level of some physical, chemical, or genetic characteristic of the gene or its expression product(s). Such characteristics include, but are not limited to, expression levels, activity levels, mutations, copy number, methylation status, etc.

In the context of CCGs as used to determine risk of cancer recurrence or progression or need for aggressive treatment, particularly useful characteristics include expression levels (e.g., mRNA or protein levels) and activity levels. Characteristics may be assayed directly (e.g., by assaying a CCG's expression level) or determined indirectly (e.g., assaying the level of a gene or genes whose expression level is correlated to the expression level of the CCG). Thus some embodiments of the disclosure provide a method of classifying cancer comprising determining the expression level, particularly mRNA level of a panel of genes comprising at least two CCGs, in a tumor sample, wherein high expression (or increased expression or overexpression) indicates a negative cancer classification, or an increased risk of cancer recurrence or progression, or a need for aggressive treatment. In some embodiments, the method comprises at least one of the following steps: (a) correlating high expression (or increased expression or overexpression) of the panel of genes to a negative cancer classification, an increased risk of cancer recurrence or progression, or a need for aggressive treatment; (b) concluding that the patient has a negative cancer classification, an increased risk of cancer recurrence or progression, or a need for aggressive treatment based at least in part on high expression (or increased expression or overexpression) of the panel of genes; or (c) communicating that the patient has a negative cancer classification, an increased risk of cancer recurrence or progression, or a need for aggressive treatment based at least in part on high expression (or increased expression or overexpression) of the panel of genes.

"Abnormal status" means a marker's status in a particular sample differs from the status generally found in average samples (e.g., healthy samples or average diseased samples). Examples include mutated, elevated, decreased, present, absent, etc. An "elevated status" means that one or more of the above characteristics (e.g., expression or mRNA level) is higher than normal levels. Generally this means an increase in the characteristic (e.g., expression or mRNA level) as compared to an index value. Conversely a "low status" means that one or more of the above characteristics (e.g., gene expression or mRNA level) is lower than normal levels. Generally this means a decrease in the characteristic (e.g., expression) as compared to an index value. In this context, a "negative status" generally means the characteristic is absent or undetectable. For example, PTEN status is negative if PTEN nucleic acid and/or PTEN protein is absent or undetectable in a sample. However, negative PTEN status also includes a mutation or copy number reduction in PTEN.

In some embodiments of the disclosure the methods comprise determining the expression of one or more CCGs and, if this expression is "increased," the patient has a poor prognosis. In the context of the disclosure, "increased" expression of a CCG means the patient's expression level is either elevated over a normal index value or a threshold index (e.g., by at least some threshold amount) or closer to the "poor prognosis index value" than to the "good prognosis index value."

Thus, when the determined level of expression of a relevant gene marker is closer to the good prognosis index value of the gene than to the poor prognosis index value of the gene, then it can be concluded that the patient is more likely to have a good prognosis, i.e., a low (or no increased) likelihood of cancer recurrence. On the other hand, if the determined level of expression of a relevant gene marker is closer to the poor prognosis index value of the gene than to the good prognosis index value of the gene, then it can be concluded that the patient is more likely to have a poor prognosis, i.e., an increased likelihood of cancer recurrence.

Alternatively index values may be determined thusly: In order to assign patients to risk groups, a threshold value will be set for the cell cycle mean. The optimal threshold value is selected based on the receiver operating characteristic (ROC) curve, which plots sensitivity vs (1—specificity). For each increment of the cell cycle mean, the sensitivity and specificity of the test is calculated using that value as a threshold. The actual threshold will be the value that optimizes these metrics according to the artisans requirements (e.g., what degree of sensitivity or specificity is desired, etc.). Example 5 demonstrates determination of a threshold value determined and validated experimentally.

Panels of CCGs (e.g., 2, 3, 4, 5, 6, 7, 8, 9, or 10 or more CCGs) can accurately predict prognosis, as shown in Example 3. Those skilled in the art are familiar with various ways of determining the expression of a panel of genes (i.e., a plurality of genes). One may determine the expression of a panel of genes by determining the average expression level (normalized or absolute) of all panel genes in a sample obtained from a particular patient (either throughout the sample or in a subset of cells from the sample or in a single cell). Increased expression in this context will mean the average expression is higher than the average expression level of these genes in normal patients (or higher than some index value that has been determined to represent the average expression level in a reference population such as patients with the same cancer). Alternatively, one may determine the expression of a panel of genes by determining the average expression level (normalized or absolute) of at least a certain number (e.g., 1, 2, 3, 4, 5, 6, 7, 8, 9, 10, 15, 20, 25, 30 or more) or at least a certain proportion (e.g., 10%, 20%, 30%, 40%, 50%, 60%, 70%, 80%, 90%, 95%, 99%, 100%) of the genes in the panel. Alternatively, one may determine the expression of a panel of genes by determining the absolute copy number of the mRNA (or protein) of all the genes in the panel and either total or average these across the genes.

As used herein, "classifying a cancer" and "cancer classification" refer to determining one or more clinically-relevant features of a cancer and/or determining a particular prognosis of a patient having said cancer. Thus "classifying a cancer" includes, but is not limited to: (i) evaluating metastatic potential, potential to metastasize to specific organs, risk of recurrence, and/or course of the tumor; (ii) evaluating tumor stage; (iii) determining patient prognosis in the absence of treatment of the cancer; (iv) determining prognosis of patient response (e.g., tumor shrinkage or progression-free survival) to treatment (e.g., chemotherapy, radiation therapy, surgery to excise tumor, etc.); (v) diagnosis of actual patient response to current and/or past treatment; (vi) determining a preferred course of treatment for the patient; (vii) prognosis for patient relapse after treatment (either treatment in general or some particular treatment); (viii) prognosis of patient life expectancy (e.g., prognosis for overall survival), etc.

Thus, a "negative classification" means an unfavorable clinical feature of the cancer (e.g., a poor prognosis). Examples include (i) an increased metastatic potential, potential to metastasize to specific organs, and/or risk of recurrence; (ii) an advanced tumor stage; (iii) a poor patient prognosis in the absence of treatment of the cancer; (iv) a poor prognosis of patient response (e.g., tumor shrinkage or progression-free survival) to a particular treatment (e.g., chemotherapy, radiation therapy, surgery to excise tumor, etc.); (v) a poor prognosis for patient relapse after treatment (either treatment in general or some particular treatment); (vi) a poor prognosis of patient life expectancy (e.g., prognosis for overall survival), etc. In some embodiments a recurrence-associated clinical parameter (or a high nomogram score) and increased expression of a CCG indicate a negative classification in cancer (e.g., increased likelihood of recurrence or progression).

A patient with a sample showing a high CCP score or value (or increased CCP expression) has an increased likelihood of recurrence after treatment (e.g., the cancer cells not killed or removed by the treatment will quickly grow back). Such a patient also has an increased likelihood of cancer progression for more rapid progression (e.g., the rapidly proliferating cells will cause any tumor to grow quickly, gain in virulence, and/or metastasize). Such a patient may also require a relatively more aggressive treatment. Thus, in some embodiments the disclosure provides a method of classifying cancer comprising determining the status of a panel of genes comprising at least two CCGs, wherein an abnormal status indicates an increased likelihood of recurrence or progression. In some embodiments, the method comprises at least one of the following steps: (a) correlating abnormal status of the panel of genes to an increased likelihood of recurrence or progression; (b) concluding that the patient has an increased likelihood of recurrence or progression based at least in part on abnormal status of the panel of genes; or (c) communicating that the patient has an increased likelihood of recurrence or progression based at least in part on abnormal status of the panel of genes. As discussed above, in some embodiments the status to be determined is gene expression levels. Thus in some embodiments the disclosure provides a method of determining the prognosis of a patient's cancer comprising determining the expression level of a panel of genes comprising at least two CCGs, wherein high expression (or increased expression or overexpression) indicates an increased likelihood of recurrence or progression of the cancer. In some embodiments, the method comprises at least one of the following steps: (a) correlating high expression (or increased expression or overexpression) of the panel of genes to an increased likelihood of recurrence or progression; (b) concluding that the patient has an increased likelihood of recurrence or progression based at least in part on high expression (or increased expression or overexpression) of the panel of genes; or (c) communicating that the patient has an increased likelihood of recurrence or progression based at least in part on high expression (or increased expression or overexpression) of the panel of genes.

"Recurrence" and "progression" are terms well-known in the art and are used herein according to their known meanings. Because the methods of the disclosure can predict or determine a patient's likelihood of each, "recurrence," "progression," "cancer-specific death," and "response to a particular treatment" are used interchangeably, unless specified otherwise, in the sense that a reference to one applies equally to the others. As an example, the meaning of "progression" may be cancer-type dependent, with progression in lung cancer meaning something different from progression in prostate cancer. However, within each cancer-type and subtype "progression" is clearly understood to those skilled in the art. Because predicting recurrence and predicting progression are prognostic endeavors, "predicting prognosis" will often be used herein to refer to either or both. In these cases, a "poor prognosis" will generally refer to an increased likelihood of recurrence, progression, or both.

"Response" (e.g., response to a particular treatment regimen) is a well-known term in the art and is used herein according to its known meaning. As an example, the meaning of "response" may be cancer-type dependent, with response in lung cancer meaning something different from response in prostate cancer. However, within each cancer-type and subtype "response" is clearly understood to those skilled in the art. For example, some objective criteria of response include Response Evaluation Criteria In Solid Tumors (RECIST), a set of published rules (e.g., changes in tumor size, etc.) that define when cancer patients improve ("respond"), stay the same ("stabilize"), or worsen ("progression") during treatments. See, e.g., Eisenhauer et al., EUR. J. CANCER (2009) 45:228-247. "Response" can also include survival metrics (e.g., "disease-free survival" (DFS), "overall survival" (OS), etc). In some cases RECIST criteria can include: (a) Complete response (CR): disappearance of all metastases; (b) Partial response (PR): at least a 30% decrease in the sum of the largest diameter (LD) of the metastatic lesions, taking as reference the baseline sum LD; (c) Stable disease (SD): neither sufficient shrinkage to qualify for PR nor sufficient increase to qualify for PD taking as references the smallest sum LD since the treatment started; (d) Progression (PD): at least a 20% increase in the sum of the LD of the target metastatic lesions taking as reference the smallest sum LD since the treatment started or the appearance of one or more new lesions.

As used herein, a patient has an "increased likelihood" of some clinical feature or outcome (e.g., recurrence or progression) if the probability of the patient having the feature or outcome exceeds some reference probability or value. The reference probability may be the probability of the feature or outcome across the general relevant patient population. For example, if the probability of recurrence in the general prostate cancer population is X % and a particular patient has been determined by the methods of the present disclosure to have a probability of recurrence of Y %, and if Y>X, then the patient has an "increased likelihood" of recurrence. Alternatively, as discussed above, a threshold or reference value may be determined and a particular patient's probability of recurrence may be compared to that threshold or reference.

In some embodiments the method correlates the patient's specific score (e.g., CCP score, combined score of CCP with clinical variables) to a specific probability (e.g., 10%, 15%, 20%, 25%, 30%, 35%, 40%, 45%, 50%, 55%, 60%, 65%, 70%, 75%, 80%, 85%, 90%, 95%, 99%, 100%) of recurrence, progression, or cancer-specific death (each optionally within a specific timeframe, e.g., 5 years, 10 years), or response to a particular treatment. In some embodiments the disclosure provides a method for determining a prostate cancer patient's prognosis comprising: (1) determining from a patient sample the expression levels of a plurality of test genes, wherein the plurality of test genes comprises at least 5 of the genes in any one of Panels A to G; (2) deriving a test value from the expression levels determined in (1), wherein the at least 5 genes in any one of Panels A to G contribute at least 25% to the test value; (3) comparing the test value to a reference value; and (4) assigning a likelihood of recurrence, progression, cancer-specific death, or response to a particular treatment based at least in part on the comparison in (3).

In some embodiments, the patient sample is from a prostate biopsy, the test value is the mean $C_T$ for the genes in Panel F normalized against the genes in Table 3, and the likelihood of prostate cancer-specific death within 10 years of diagnosis is calculated as follows:

TABLE 4

| Test Value | Likelihood of Cancer-Specific Death |
|---|---|
| −1 | 5.9% |
| 0 | 11.6% |
| 1 | 22% |
| 2 | 39.5% |
| 3 | 63.8% |
| 4 | 87.2% |

In some embodiments, the patient sample is from a prostatectomy, the test value is the mean $C_T$ for the genes in Panel F normalized against the genes in Table A, and the likelihood of prostate cancer recurrence within 10 years of surgery is calculated as follows:

TABLE 5

| Test Value | Likelihood of Recurrence |
|---|---|
| −1 | 12.6% |
| 0 | 24.9% |
| 1 | 45.5% |

TABLE 5-continued

| Test Value | Likelihood of Recurrence |
|---|---|
| 2 | 72.5% |
| 3 | 93.6% |

In some embodiments, the patient sample is from a prostatectomy, the test value is a combined score calculated and the likelihood of prostate cancer recurrence within 10 years of surgery is calculated as follows:

TABLE 6

| Test Value | Likelihood of Recurrence |
|---|---|
| 0 | 11.5% |
| 1 | 25% |
| 2 | 49.3% |
| 3 | 79.8% |
| 4 | 97.7% |

As shown in Example 3, individual CCGs can predict prognosis quite well. Thus the disclosure provides a method of predicting prognosis comprising determining the expression of at least one CCG listed in Table 1 or Panels A through G.

Example 3 also shows that panels of CCGs (e.g., 2, 3, 4, 5, or 6 CCGs) can accurately predict prognosis. Thus in some aspects the disclosure provides a method of classifying a cancer comprising determining the status of a panel of genes (e.g., a plurality of test genes) comprising a plurality of CCGs. For example, increased expression in a panel of genes (or plurality of test genes) may refer to the average expression level of all panel or test genes in a particular patient being higher than the average expression level of these genes in normal patients (or higher than some index value that has been determined to represent the normal average expression level). Alternatively, increased expression in a panel of genes may refer to increased expression in at least a certain number (e.g., 1, 2, 3, 4, 5, 6, 7, 8, 9, 10, 15, 20, 25, 30 or more) or at least a certain proportion (e.g., 10%, 20%, 30%, 40%, 50%, 60%, 70%, 80%, 90%, 95%, 99%, 100%) of the genes in the panel as compared to the average normal expression level.

In some embodiments the panel comprises at least 3, 4, 5, 6, 7, 8, 9, 10, 15, 20, 25, 30, 35, 40, 45, 50, 70, 80, 90, 100, 200, or more CCGs. In some embodiments the panel comprises at least 10, 15, 20, or more CCGs. In some embodiments the panel comprises between 5 and 100 CCGs, between 7 and 40 CCGs, between 5 and 25 CCGs, between 10 and 20 CCGs, or between 10 and 15 CCGs. In some embodiments CCGs comprise at least a certain proportion of the panel. Thus in some embodiments the panel comprises at least 25%, 30%, 40%, 50%, 60%, 70%, 75%, 80%, 85%, 90%, 95%, 96%, 97%, 98%, or 99% CCGs. In some preferred embodiments the panel comprises at least 10, 15, 20, 25, 30, 35, 40, 45, 50, 70, 80, 90, 100, 200, or more CCGs, and such CCGs constitute of at least 50%, 60%, 70%, preferably at least 75%, 80%, 85%, more preferably at least 90%, 95%, 96%, 97%, 98%, or 99% or more of the total number of genes in the panel. In some embodiments the CCGs are chosen from the group consisting of the genes in Table 1 and Panels A through G. In some embodiments the panel comprises at least 2, 3, 4, 5, 6, 7, 8, 9, 10, 11, 12, 13, 14, 15, 20, 25, 30, or more of the genes in any of Table 1 and Panels A through G. In some embodiments the disclosure provides a method of predicting prognosis comprising determining the status of the CCGs in Panels A through G, wherein abnormal status indicates a poor prognosis. In some embodiments, the method comprises at least one of the following steps: (a) correlating abnormal status (e.g., high or increased expression) of the CCGs in Panels A through G to a poor prognosis; (b) concluding that the patient has a poor prognosis based at least in part on abnormal status (e.g., high or increased expression) of the CCGs in Panels A through G; or (c) communicating that the patient has a poor prognosis based at least in part on abnormal status (e.g., high or increased expression) of the CCGs in Panels A through G.

In some of these embodiments elevated expression indicates an increased likelihood of recurrence or progression. Thus in a preferred embodiment the disclosure provides a method of predicting risk of cancer recurrence or progression in a patient comprising determining the status of a panel of genes, wherein the panel comprises between about 10 and about 15 CCGs, the CCGs constitute at least 90% of the panel, and an elevated status for the CCGs indicates an increased likelihood or recurrence or progression. In some embodiments, the method comprises at least one of the following steps: (a) correlating elevated status (e.g., high or increased expression) of the panel of genes to a poor prognosis; (b) concluding that the patient has a poor prognosis based at least in part on elevated status (e.g., high or increased expression) of the panel of genes; or (c) communicating that the patient has a poor prognosis based at least in part on elevated status (e.g., high or increased expression) of the panel of genes.

Several panels of CCGs (Table 2, supra, and Tables 7 & 8, infra) have been evaluated for their ability to predict prognosis in several different cancers. The results of these studies are described in Examples 1 through 6 below.

TABLE 7

"Panel C" Evaluated in Examples 1 through 4

| Gene Symbol | Entrez GeneID |
|---|---|
| AURKA | 6790 |
| BUB1* | 699 |
| CCNB1* | 891 |
| CCNB2* | 9133 |
| CDC2* | 983 |
| CDC20* | 991 |
| CDC45L* | 8318 |
| CDCA8* | 55143 |
| CENPA | 1058 |
| CKS2* | 1164 |
| DLG7* | 9787 |
| DTL* | 51514 |
| FOXM1* | 2305 |
| HMMR* | 3161 |
| KIF23* | 9493 |
| KPNA2 | 3838 |
| MAD2L1* | 4085 |
| MELK | 9833 |
| MYBL2* | 4605 |
| NUSAP1* | 51203 |
| PBK* | 55872 |
| PRC1* | 9055 |
| PTTG1* | 9232 |
| RRM2* | 6241 |
| TIMELESS* | 8914 |
| TPX2* | 22974 |
| TRIP13* | 9319 |
| TTK* | 7272 |
| UBE2C | 11065 |

TABLE 7-continued

"Panel C" Evaluated in Examples 1 through 4

| Gene Symbol | Entrez GeneID |
|---|---|
| UBE2S* | 27338 |
| ZWINT* | 11130 |

*These genes were used as a 26-gene subset panel ("Panel D") in the validation arm of the experiment described in Example 2.

TABLE 8

"Panel E"

| Name | GeneID |
|---|---|
| ASF1B* | 55723 |
| ASPM* | 259266 |
| BIRC5* | 332 |
| BUB1B* | 701 |
| C18orf24* | 220134 |
| CDC2* | 983 |
| CDC20* | 991 |
| CDCA3* | 83461 |
| CDCA8* | 55143 |
| CDKN3* | 1033 |
| CENPF* | 1063 |
| CENPM* | 79019 |
| CEP55* | 55165 |
| DLGAP5* | 9787 |
| DTL* | 51514 |
| FOXM1* | 2305 |
| KIAA0101* | 9768 |
| KIF11* | 3832 |
| KIF20A* | 10112 |
| KIF4A | 24137 |
| MCM10* | 55388 |
| NUSAP1* | 51203 |
| ORC6L* | 23594 |
| PBK* | 55872 |
| PLK1* | 5347 |
| PRC1* | 9055 |
| PTTG1* | 9232 |
| RAD51* | 5888 |
| RAD54L* | 8438 |
| RRM2* | 6241 |
| TK1* | 7083 |
| TOP2A* | 7153 |

*These genes were used as a 31-gene subset panel ("Panel F") in the experiment described in Example 5.

It has been determined that the choice of individual CCGs for a panel can often be relatively arbitrary. In other words, most CCGs have been found to be very good surrogates for each other. One way of assessing whether particular CCGs will serve well in the methods and compositions of the disclosure is by assessing their correlation with the mean expression of CCGs (e.g., all known CCGs, a specific set of CCGs, etc.). Those CCGs that correlate particularly well with the mean are expected to perform well in assays of the disclosure, e.g., because these will reduce noise in the assay. A ranking of select CCGs according to their correlation with the mean CCG expression is given in Tables 9-11.

In CCG signatures the particular CCGs assayed is often not as important as the total number of CCGs. The number of CCGs assayed can vary depending on many factors, e.g., technical constraints, cost considerations, the classification being made, the cancer being tested, the desired level of predictive power, etc. Increasing the number of CCGs assayed in a panel according to the disclosure is, as a general matter, advantageous because, e.g., a larger pool of mRNAs to be assayed means less "noise" caused by outliers and less chance of an assay error throwing off the overall predictive power of the test. However, cost and other considerations will generally limit this number and finding the optimal number of CCGs for a signature is desirable.

Figure 1:
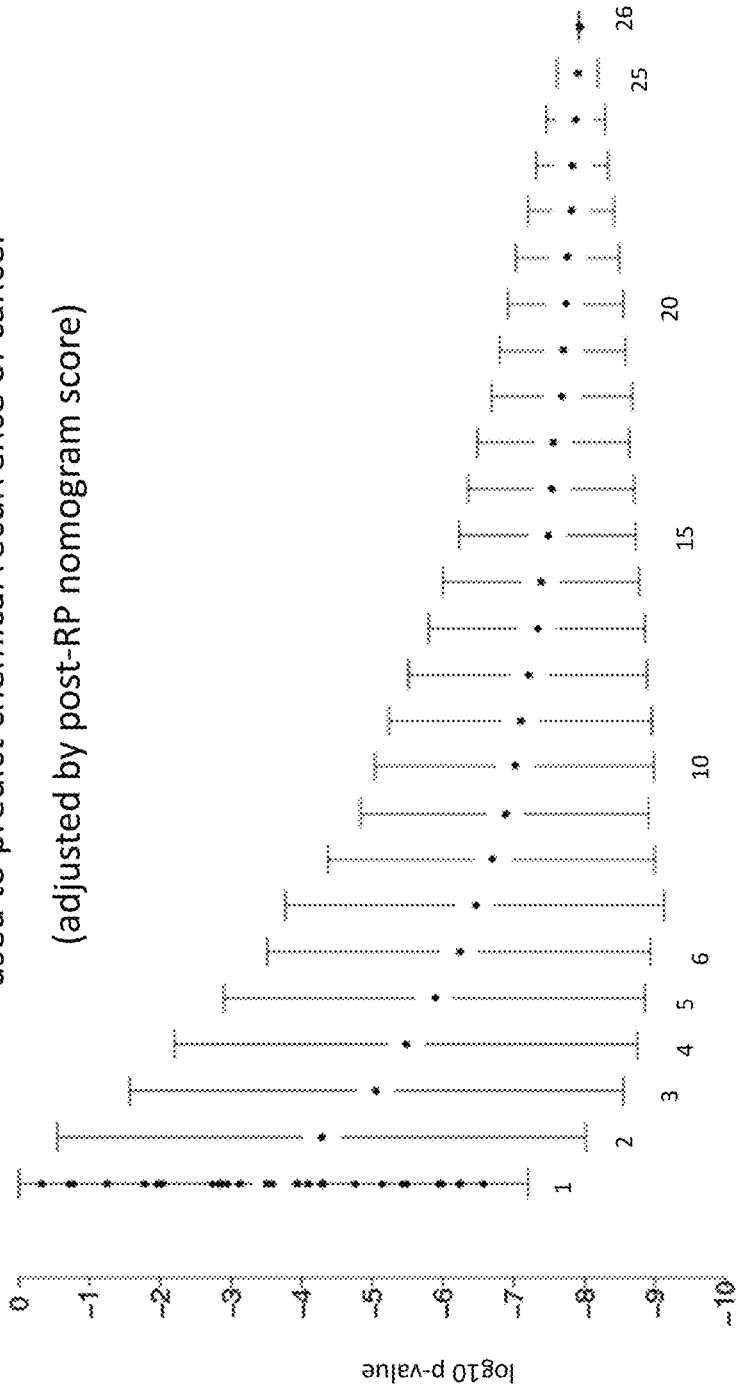
FIG. 1 is an illustration of the predictive power over nomogram for CCG panels of different sizes.

It has been discovered that the predictive power of a CCG signature often ceases to increase significantly beyond a certain number of CCGs (see FIG. 1; Example 1). More specifically, the optimal number of CCGs in a signature ($n_O$) can be found wherever the following is true $$(P_{n+1}-P_n)<C_O,$$

wherein P is the predictive power (i.e., $P_n$ is the predictive power of a signature with n genes and $P_{n+1}$ is the predictive power of a signature with n genes plus one) and $C_O$ is some optimization constant. Predictive power can be defined in many ways known to those skilled in the art including, but not limited to, the signature's p-value. $C_O$ can be chosen by the artisan based on his or her specific constraints. For example, if cost is not a critical factor and extremely high levels of sensitivity and specificity are desired, $C_O$ can be set very low such that only trivial increases in predictive power are disregarded. On the other hand, if cost is decisive and moderate levels of sensitivity and specificity are acceptable, $C_O$ can be set higher such that only significant increases in predictive power warrant increasing the number of genes in the signature.

Alternatively, a graph of predictive power as a function of gene number may be plotted (as in FIG. 1) and the second derivative of this plot taken. The point at which the second derivative decreases to some predetermined value ($C_O'$) may be the optimal number of genes in the signature.

Figure 17:
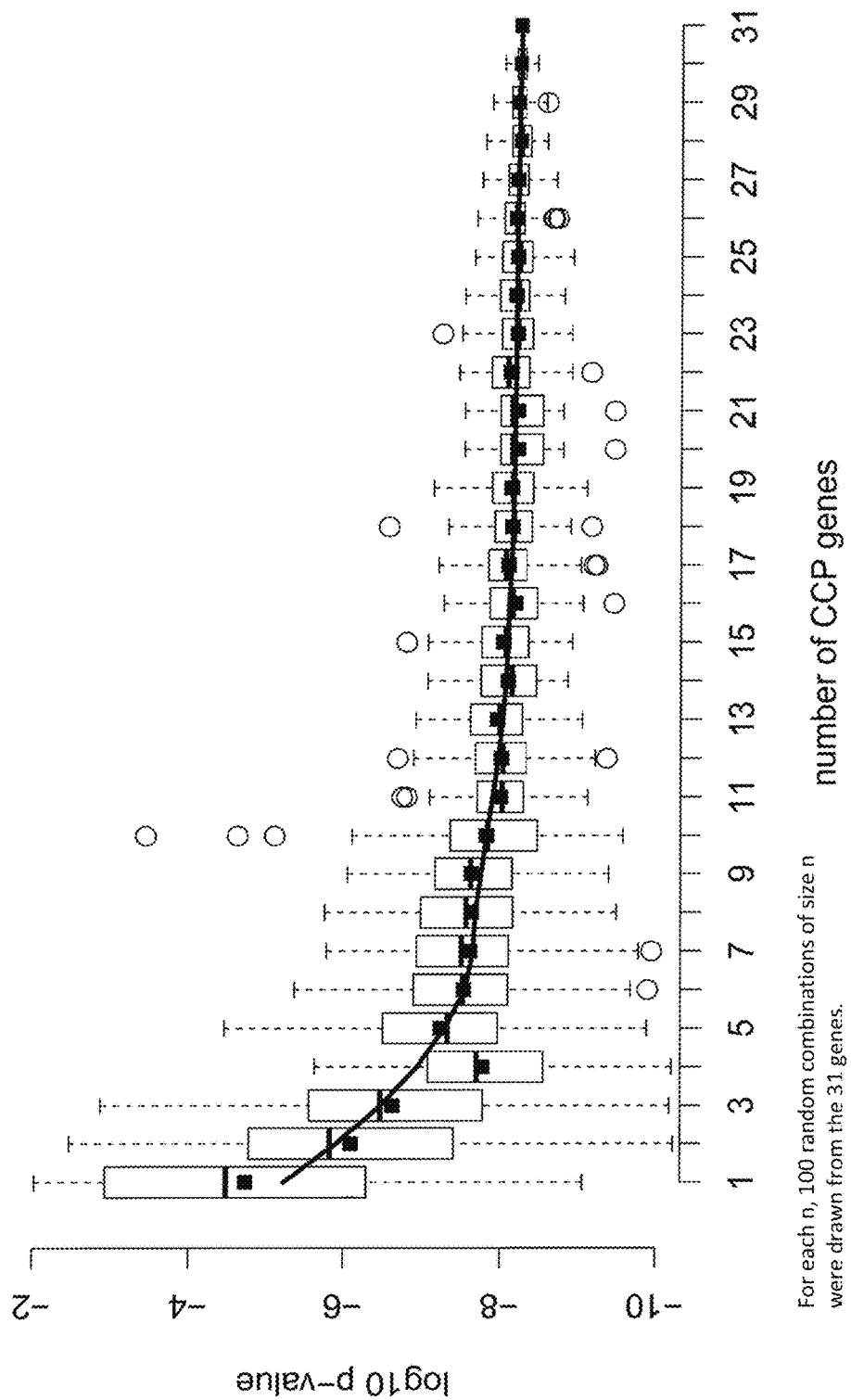
FIG. 17 is an illustration of the predictive power over nomogram for CCG panels of different sizes.

Examples 1 & 3 and FIGS. 1 & 17 illustrate the empirical determination of optimal numbers of CCGs in CCG panels of the disclosure. Randomly selected subsets of the 31 CCGs listed in Table 7 were tested as distinct CCG signatures and predictive power (i.e., p-value) was determined for each. As FIG. 1 shows, p-values ceased to improve significantly between about 10 and about 15 CCGs, thus indicating that an optimal number of CCGs in a prognostic panel is from about 10 to about 15. Thus some embodiments of the disclosure provide a method of predicting prognosis in a patient having prostate cancer comprising determining the status of a panel of genes, wherein the panel comprises between about 10 and about 15 CCGs and an elevated status for the CCGs indicates a poor prognosis. In some embodiments, the method comprises at least one of the following steps: (a) correlating elevated status (e.g., high or increased expression) of the panel of genes to a poor prognosis; (b) concluding that the patient has a poor prognosis based at least in part on elevated status (e.g., high or increased expression) of the panel of genes; or (c) communicating that the patient has a poor prognosis based at least in part on elevated status (e.g., high or increased expression) of the panel of genes. In some embodiments the panel comprises between about 10 and about 15 CCGs and the CCGs constitute at least 90% of the panel. In other embodiments the panel comprises CCGs plus one or more additional markers that significantly increase the predictive power of the panel (i.e., make the predictive power significantly better than if the panel consisted of only the CCGs). Any other combination of CCGs (including any of those listed in Table 1 or Panels A through G) can be used to practice the disclosure.

It has been discovered that CCGs are particularly predictive in certain cancers. For example, panels of CCGs have been determined to be accurate in predicting recurrence in prostate cancer (Examples 1 through 5). Further, CCGs can determine prognosis in bladder, brain, breast and lung cancers, as summarized in Example 6 below.

Thus the disclosure provides a method comprising determining the status of a panel of genes comprising at least two CCGs, wherein an abnormal status indicates a poor prognosis. In some embodiments the panel comprises at least 2 genes chosen from the group of genes in at least one of Panels A through G. In some embodiments the panel comprises at least 10 genes chosen from the group of genes in at least one of Panels A through G. In some embodiments the panel comprises at least 15 genes chosen from the group of genes in at least one of Panels A through G. In some embodiments the panel comprises all of the genes in at least one of Panels A through G. The disclosure also provides a method of determining the prognosis of bladder cancer, comprising determining the status of a panel of genes comprising at least two CCGs (e.g., at least two of the genes in any of Panels B, C, & F), wherein an abnormal status indicates a poor prognosis. The disclosure also provides a method of determining the prognosis of brain cancer, comprising determining the status of a panel of genes comprising at least two CCGs (e.g., at least two of the genes in any of Panels B, C, & F), wherein an abnormal status indicates a poor prognosis. The disclosure further provides a method of determining the prognosis of breast cancer, comprising determining the status of a panel of genes comprising at least two CCGs (e.g., at least two of the genes in any of Panels B, C, & F), wherein an abnormal status indicates a poor prognosis. The disclosure also provides a method of determining the prognosis of lung cancer, comprising determining the status of a panel of genes comprising at least two CCGs (e.g., at least two of the genes in any of Panels B, C, & F), wherein an abnormal status indicates a poor prognosis. In some embodiments, the method comprises at least one of the following steps: (a) correlating abnormal status (e.g., high or increased expression) of the panel of genes to a poor prognosis; (b) concluding that the patient has a poor prognosis based at least in part on abnormal status (e.g., high or increased expression) of the panel of genes; or (c) communicating that the patient has a poor prognosis based at least in part on high expression (or increased expression or overexpression) of the panel of genes.

In some embodiments the panel comprises at least 3, 4, 5, 6, 7, 8, 9, 10, 15, 20, 25, 30, 35, 40, 45, 50 or more CCGs. In some embodiments the panel comprises between 5 and 100 CCGs, between 7 and 40 CCGs, between 5 and 25 CCGs, between 10 and 20 CCGs, or between 10 and 15 CCGs. In some embodiments CCGs comprise at least a certain proportion of the panel. Thus in some embodiments the panel comprises at least 25%, 30%, 40%, 50%, 60%, 70%, 75%, 80%, 85%, 90%, 95%, 96%, 97%, 98%, or 99% CCGs. In some embodiments the CCGs are chosen from the group consisting of the genes listed in Tables 1, 2, 7-11, 13-14 and/or Y and Panels A through I. In some embodiments the panel comprises at least 2, 3, 4, 5, 6, 7, 8, 9, 10, 15, 20, 25, 30, 35, 40, 45, 50 or more genes chosen from the group of genes in any of Tables 1, 2, 7-11, 13-14 and/or Y or Panels A through I. In some embodiments the panel comprises all of the genes in any of Tables 1, 2, 7-11, 13-14 and/or Y or Panels A through I.

As mentioned above, many of the CCGs of the disclosure have been analyzed to determine their correlation to the CCG mean and also to determine their relative predictive value within a panel (see Tables 9-11, & 13-14). The following tables rank CCGs according to these criteria.

Tables 9-11 below provide rankings of select CCGs according to their correlation with the mean CCG expression. Table 9 provides a ranking of select control genes according to their correlation to the control mean expression.

TABLE 9

| Gene # | Gene Symbol | Correl. w/ Mean |
|---|---|---|
| 1 | TPX2 | 0.931 |
| 2 | CCNB2 | 0.9287 |
| 3 | KIF4A | 0.9163 |
| 4 | KIF2C | 0.9147 |
| 5 | BIRC5 | 0.9077 |
| 6 | BIRC5 | 0.9077 |
| 7 | RACGAP1 | 0.9073 |
| 8 | CDC2 | 0.906 |
| 9 | PRC1 | 0.9053 |
| 10 | DLGAP5 (DLG7) | 0.9033 |
| 11 | CEP55 | 0.903 |
| 12 | CCNB1 | 0.9 |
| 13 | TOP2A | 0.8967 |
| 14 | CDC20 | 0.8953 |
| 15 | KIF20A | 0.8927 |
| 16 | BUB1B | 0.8927 |
| 17 | CDKN3 | 0.8887 |
| 18 | NUSAP1 | 0.8873 |
| 19 | CCNA2 | 0.8853 |
| 20 | KIF11 | 0.8723 |
| 21 | CDCA8 | 0.8713 |
| 22 | NCAPG | 0.8707 |
| 23 | ASPM | 0.8703 |
| 24 | FOXM1 | 0.87 |
| 25 | NEK2 | 0.869 |
| 26 | ZWINT | 0.8683 |
| 27 | PTTG1 | 0.8647 |
| 28 | RRM2 | 0.8557 |
| 29 | TTK | 0.8483 |
| 30 | TRIP13 | 0.841 |
| 31 | GINS1 | 0.841 |
| 32 | CENPF | 0.8397 |
| 33 | HMMR | 0.8367 |
| 34 | NCAPH | 0.8353 |
| 35 | NDC80 | 0.8313 |
| 36 | KIF15 | 0.8307 |
| 37 | CENPE | 0.8287 |
| 38 | TYMS | 0.8283 |
| 39 | KIAA0101 | 0.8203 |
| 40 | FANCI | 0.813 |
| 41 | RAD51AP1 | 0.8107 |
| 42 | CKS2 | 0.81 |
| 43 | MCM2 | 0.8063 |
| 44 | PBK | 0.805 |
| 45 | ESPL1 | 0.805 |
| 46 | MKI67 | 0.7993 |
| 47 | SPAG5 | 0.7993 |
| 48 | MCM10 | 0.7963 |
| 49 | MCM6 | 0.7957 |
| 50 | OIP5 | 0.7943 |
| 51 | CDC45L | 0.7937 |
| 52 | KIF23 | 0.7927 |
| 53 | EZH2 | 0.789 |
| 54 | SPC25 | 0.7887 |
| 55 | STIL | 0.7843 |
| 56 | CENPN | 0.783 |
| 57 | GTSE1 | 0.7793 |
| 58 | RAD51 | 0.779 |
| 59 | CDCA3 | 0.7783 |
| 60 | TACC3 | 0.778 |
| 61 | PLK4 | 0.7753 |
| 62 | ASF1B | 0.7733 |
| 63 | DTL | 0.769 |
| 64 | CHEK1 | 0.7673 |
| 65 | NCAPG2 | 0.7667 |
| 66 | PLK1 | 0.7657 |
| 67 | TIMELESS | 0.762 |
| 68 | E2F8 | 0.7587 |
| 69 | EXO1 | 0.758 |
| 70 | ECT2 | 0.744 |
| 71 | STMN1 | 0.737 |
| 72 | STMN1 | 0.737 |
| 73 | RFC4 | 0.737 |

TABLE 9-continued

| Gene # | Gene Symbol | Correl. w/ Mean |
|---|---|---|
| 74 | CDC6 | 0.7363 |
| 75 | CENPM | 0.7267 |
| 76 | MYBL2 | 0.725 |
| 77 | SHCBP1 | 0.723 |
| 78 | ATAD2 | 0.723 |
| 79 | KIFC1 | 0.7183 |
| 80 | DBF4 | 0.718 |
| 81 | CKS1B | 0.712 |
| 82 | PCNA | 0.7103 |
| 83 | FBXO5 | 0.7053 |
| 84 | C12orf48 | 0.7027 |
| 85 | TK1 | 0.7017 |
| 86 | BLM | 0.701 |
| 87 | KIF18A | 0.6987 |
| 88 | DONSON | 0.688 |
| 89 | MCM4 | 0.686 |
| 90 | RAD54B | 0.679 |
| 91 | RNASEH2A | 0.6733 |
| 92 | TUBA1C | 0.6697 |
| 93 | C18orf24 | 0.6697 |
| 94 | SMC2 | 0.6697 |
| 95 | CENPI | 0.6697 |
| 96 | GMPS | 0.6683 |
| 97 | DDX39 | 0.6673 |
| 98 | POLE2 | 0.6583 |
| 99 | APOBEC3B | 0.6513 |
| 100 | RFC2 | 0.648 |
| 101 | PSMA7 | 0.6473 |
| 102 | KIF20B (MPHOSPH1) | 0.6457 |
| 103 | CDT1 | 0.645 |
| 104 | H2AFX | 0.6387 |
| 105 | ORC6L | 0.634 |
| 106 | C1orf135 | 0.6333 |
| 107 | PSRC1 | 0.633 |
| 108 | VRK1 | 0.6323 |
| 109 | CKAP2 | 0.6307 |
| 110 | CCDC99 | 0.6303 |
| 111 | CCNE1 | 0.6283 |
| 112 | LMNB2 | 0.625 |
| 113 | GPSM2 | 0.625 |
| 114 | PAICS | 0.6243 |
| 115 | MCAM | 0.6227 |
| 116 | DSN1 | 0.622 |
| 117 | NCAPD2 | 0.6213 |
| 118 | RAD54L | 0.6213 |
| 119 | PDSS1 | 0.6203 |
| 120 | HN1 | 0.62 |
| 121 | C21orf45 | 0.6193 |
| 122 | CTSL2 | 0.619 |
| 123 | CTPS | 0.6183 |
| 124 | MCM7 | 0.618 |
| 125 | ZWILCH | 0.618 |
| 126 | RFC5 | 0.6177 |

TABLE 10

| Gene # | Gene Symbol | Correl. w/ CCG mean |
|---|---|---|
| 1 | DLGAP5 | 0.931 |
| 2 | ASPM | 0.931 |
| 3 | KIF11 | 0.926 |
| 4 | BIRC5 | 0.916 |
| 5 | CDCA8 | 0.902 |
| 6 | CDC20 | 0.9 |
| 7 | MCM10 | 0.899 |
| 8 | PRC1 | 0.895 |
| 9 | BUB1B | 0.892 |
| 10 | FOXM1 | 0.889 |
| 11 | NUSAP1 | 0.888 |
| 12 | C18orf24 | 0.885 |
| 13 | PLK1 | 0.879 |
| 14 | CDKN3 | 0.874 |
| 15 | RRM2 | 0.871 |
| 16 | RAD51 | 0.864 |
| 17 | CEP55 | 0.862 |

TABLE 10-continued

| Gene # | Gene Symbol | Correl. w/ CCG mean |
|---|---|---|
| 18 | ORC6L | 0.86 |
| 19 | RAD54L | 0.86 |
| 20 | CDC2 | 0.858 |
| 21 | CENPF | 0.855 |
| 22 | TOP2A | 0.852 |
| 23 | KIF20A | 0.851 |
| 24 | KIAA0101 | 0.839 |
| 25 | CDCA3 | 0.835 |
| 26 | ASF1B | 0.797 |
| 27 | CENPM | 0.786 |
| 28 | TK1 | 0.783 |
| 29 | PBK | 0.775 |
| 30 | PTTG1 | 0.751 |
| 31 | DTL | 0.737 |

TABLE 11

56 CCGs Ranked by Correlation to Mean in Example 5 ("Panel G")

| Gene # | Gene Symbol | Correl. w/ CCG mean |
|---|---|---|
| 1 | FOXM1 | 0.908 |
| 2 | CDC20 | 0.907 |
| 3 | CDKN3 | 0.9 |
| 4 | CDC2 | 0.899 |
| 5 | KIF11 | 0.898 |
| 6 | KIAA0101 | 0.89 |
| 7 | NUSAP1 | 0.887 |
| 8 | CENPF | 0.882 |
| 9 | ASPM | 0.879 |
| 10 | BUB1B | 0.879 |
| 11 | RRM2 | 0.876 |
| 12 | DLGAP5 | 0.875 |
| 13 | BIRC5 | 0.864 |
| 14 | KIF20A | 0.86 |
| 15 | PLK1 | 0.86 |
| 16 | TOP2A | 0.851 |
| 17 | TK1 | 0.837 |
| 18 | PBK | 0.831 |
| 19 | ASF1B | 0.827 |
| 20 | C18orf24 | 0.817 |
| 21 | RAD54L | 0.816 |
| 22 | PTTG1 | 0.814 |
| 23 | KIF4A | 0.814 |
| 24 | CDCA3 | 0.811 |
| 25 | MCM10 | 0.802 |
| 26 | PRC1 | 0.79 |
| 27 | DTL | 0.788 |
| 28 | CEP55 | 0.787 |
| 29 | RAD51 | 0.783 |
| 30 | CENPM | 0.781 |
| 31 | CDCA8 | 0.774 |
| 32 | OIP5 | 0.773 |
| 33 | SHCBP1 | 0.762 |
| 34 | ORC6L | 0.736 |
| 35 | CCNB1 | 0.727 |
| 36 | CHEK1 | 0.723 |
| 37 | TACC3 | 0.722 |
| 38 | MCM4 | 0.703 |
| 39 | FANCI | 0.702 |
| 40 | KIF15 | 0.701 |
| 41 | PLK4 | 0.688 |
| 42 | APOBEC3B | 0.67 |
| 43 | NCAPG | 0.667 |
| 44 | TRIP13 | 0.653 |
| 45 | KIF23 | 0.652 |
| 46 | NCAPH | 0.649 |
| 47 | TYMS | 0.648 |
| 48 | GINS1 | 0.639 |
| 49 | STMN1 | 0.63 |
| 50 | ZWINT | 0.621 |
| 51 | BLM | 0.62 |
| 52 | TTK | 0.62 |
| 53 | CDC6 | 0.619 |

TABLE 11-continued

56 CCGs Ranked by Correlation to Mean in Example 5 ("Panel G")

| Gene # | Gene Symbol | Correl. w/ CCG mean |
|---|---|---|
| 54 | KIF2C | 0.596 |
| 55 | RAD51AP1 | 0.567 |
| 56 | NCAPG2 | 0.535 |

TABLE 12

15 Housekeeping (HK) Genes Ranked by Correlation to Mean in Example 5

| Gene Symbol | Correaltion with HK Mean |
|---|---|
| RPL38 | 0.989 |
| UBA52 | 0.986 |
| PSMC1 | 0.985 |
| RPL4 | 0.984 |
| RPL37 | 0.983 |
| RPS29 | 0.983 |
| SLC25A3 | 0.982 |
| CLTC | 0.981 |
| TXNL1 | 0.98 |
| PSMA1 | 0.98 |
| RPL8 | 0.98 |
| MMADHC | 0.979 |
| RPL13A; LOC728658 | 0.979 |
| PPP2CA | 0.978 |
| MRFAP1 | 0.978 |

Table 13 below provides a ranking of the CCGs in Panel F according to their relative predictive value in Example 5.

TABLE 13

| Gene # | Gene Symbol | p-value |
|---|---|---|
| 1 | MCM10 | 8.60E−10 |
| 2 | ASPM | 2.30E−09 |
| 3 | DLGAP5 | 1.20E−08 |
| 4 | CENPF | 1.40E−08 |
| 5 | CDC20 | 2.10E−08 |
| 6 | FOXM1 | 3.40E−07 |
| 7 | TOP2A | 4.30E−07 |
| 8 | NUSAP1 | 4.70E−07 |
| 9 | CDKN3 | 5.50E−07 |
| 10 | KIF11 | 6.30E−06 |
| 11 | KIF20A | 6.50E−06 |
| 12 | BUB1B | 1.10E−05 |
| 13 | RAD54L | 1.40E−05 |
| 14 | CEP55 | 2.60E−05 |
| 15 | CDCA8 | 3.10E−05 |
| 16 | TK1 | 3.30E−05 |
| 17 | DTL | 3.60E−05 |
| 18 | PRC1 | 3.90E−05 |
| 19 | PTTG1 | 4.10E−05 |
| 20 | CDC2 | 0.00013 |
| 21 | ORC6L | 0.00017 |
| 22 | PLK1 | 0.0005 |
| 23 | C18orf24 | 0.0011 |
| 24 | BIRC5 | 0.00118 |
| 25 | RRM2 | 0.00255 |
| 26 | CENPM | 0.0027 |
| 27 | RAD51 | 0.0028 |
| 28 | KIAA0101 | 0.00348 |
| 29 | CDCA3 | 0.00863 |
| 30 | PBK | 0.00923 |
| 31 | ASF1B | 0.00936 |

Table 14 below provides a ranking of the CCGs in Panel C according to their relative predictive value in Example 3.

TABLE 14

| Gene # | Gene Symbol | p-value* |
|---|---|---|
| 1 | NUSAP1 | 2.8E-07 |
| 2 | DLG7 | 5.9E-07 |
| 3 | CDC2 | 6.0E-07 |
| 4 | FOXM1 | 1.1E-06 |
| 5 | MYBL2 | 1.1E-06 |
| 6 | CDCA8 | 3.3E-06 |
| 7 | CDC20 | 3.8E-06 |
| 8 | RRM2 | 7.2E-06 |
| 9 | PTTG1 | 1.8E-05 |
| 10 | CCNB2 | 5.2E-05 |
| 11 | HMMR | 5.2E-05 |
| 12 | BUB1 | 8.3E-05 |
| 13 | PBK | 1.2E-04 |
| 14 | TTK | 3.2E-04 |
| 15 | CDC45L | 7.7E-04 |
| 16 | PRC1 | 1.2E-03 |
| 17 | DTL | 1.4E-03 |
| 18 | CCNB1 | 1.5E-03 |
| 19 | TPX2 | 1.9E-03 |
| 20 | ZWINT | 9.3E-03 |
| 21 | KIF23 | 1.1E-02 |
| 22 | TRIP13 | 1.7E-02 |
| 23 | KPNA2 | 2.0E-02 |
| 24 | UBE2C | 2.2E-02 |
| 25 | MELK | 2.5E-02 |
| 26 | CENPA | 2.9E-02 |
| 27 | CKS2 | 5.7E-02 |
| 28 | MAD2L1 | 1.7E-01 |
| 29 | UBE2S | 2.0E-01 |
| 30 | AURKA | 4.8E-01 |
| 31 | TIMELESS | 4.8E-01 |

*p-value for likelihood ratio test of full (post-RP nomogram score + cell cycle expression + nomogram:cell cycle) vs reduced (post-RP nomogram score only) CoxPH model of time-to-recurrence.

Thus in some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises the top 2, 3, 4, 5, 6, 7, 8, 9, 10, 11, 12, 13, 14, 15, 20, 25, 30, 35, 40 or more CCGs listed in Tables 9-11, & 13-14. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises at least 1, 2, 3, 4, 5, 6, 7, 8, 9, 10, 15, or 20 of the following genes: ASPM, BIRC5, BUB1B, CCNB2, CDC2, CDC20, CDCA8, CDKN3, CENPF, DL GAP5, FOXM1, KIAA0101, KIF11, KIF2C, KIF4A, MCM10, NUSAP1, PRC1, RACGAP1, and TPX2. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, nine, or ten or all of gene numbers 1 & 2, 1 to 3, 1 to 4, 1 to 5, 1 to 6, 1 to 7, 1 to 8, 1 to 9, or 1 to 10 of any of Tables 9-11, & 13-14. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, or nine or all of gene numbers 2 & 3, 2 to 4, 2 to 5, 2 to 6, 2 to 7, 2 to 8, 2 to 9, or 2 to 10 of any of Tables 9-11, & 13-14. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, or eight or all of gene numbers 3 & 4, 3 to 5, 3 to 6, 3 to 7, 3 to 8, 3 to 9, or 3 to 10 of any of Tables 9-11, & 13-14. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, or seven or all of gene numbers 4 & 5, 4 to 6, 4 to 7, 4 to 8, 4 to 9, or 4 to 10 of any of Tables 9-11, & 13-14. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, nine, 10, 11, 12, 13, 14, or 15 or all of gene numbers 1 & 2, 1 to 3, 1 to 4, 1 to 5, 1 to 6, 1 to 7, 1 to 8, 1 to 9, 1 to 10, 1 to 11, 1 to 12, 1 to 13, 1 to 14, or 1 to 15 of any of Tables 9-11, & 13-14.

It has further been discovered that CCG status synergistically adds to clinical parameters in prognosing cancer. In the case of prostate cancer, for example, it has been discovered that a high level of gene expression of any one of the genes in Panels C through F is associated with an increased risk of prostate cancer recurrence or progression in patients whose clinical nomogram score indicates a relatively low risk of recurrence or progression. Because evaluating CCG expression levels can thus detect increased risk not detected using clinical parameters alone, the disclosure generally provides methods combining evaluating at least one clinical parameter with evaluating the status of at least one CCG.

As Example 3 shows, even individual CCGs add to clinical parameters in predicting cancer recurrence. Thus one aspect of the disclosure provides an in vitro diagnostic method comprising determining at least one clinical parameter for a cancer patient and determining the status of at least one CCG in a sample obtained from the patient. However, assessing the status of multiple CCGs improves predictive power even more (also shown in Example 1). Thus in some embodiments the status of a plurality of CCGs (e.g., 2, 3, 4, 5, 6, 7, 8, 9, 10, 15, 20, 25, 30, 40, 50 or more) is determined. In some embodiments abnormal status indicates an increased likelihood of recurrence or progression. In some embodiments the patient has prostate cancer. In some embodiments the patient has lung cancer. Often the clinical parameter is at least somewhat independently predictive of recurrence or progression and the addition of CCG status improves the predictive power. As used herein, "clinical parameter" and "clinical measure" refer to disease or patient characteristics that are typically applied to assess disease course and/or predict outcome. Examples in cancer generally include tumor stage, tumor grade, lymph node status, histology, performance status, type of surgery, surgical margins, type of treatment, and age of onset. In prostate cancer clinicians often use pre-sugary blood PSA levels, stage (defined by size of tumor and evidence of metastasis), and Gleason score (similar to concept of grade). After surgical intervention, important clinical parameters in prostate cancer include margin and lymph node status. In breast cancer clinicians often use size of index lesion in cm, invasion, number of nodes involved, and grade.

Often certain clinical parameters are correlated with a particular disease character. For example, in cancer generally as well as in specific cancers, certain clinical parameters are correlated with, e.g., likelihood of recurrence or metastasis, prognosis for survival for a certain amount of time, likelihood of response to treatment generally or to a specific treatment, etc. In prostate cancer some clinical parameters are such that their status (presence, absence, level, etc.) is associated with increased likelihood of recurrence. Examples of such recurrence-associated parameters (some but not all of which are specific to prostate cancer) include high PSA levels (e.g., greater than 4 ng/ml), high Gleason score, large tumor size, evidence of metastasis, advanced tumor stage, nuclear grade, lymph node involvement, early age of onset. Other types of cancer may have different parameters correlated to likelihood of recurrence or progression, and CCG status, as a measure of proliferative activity, adds to these parameters in predicting prognosis in these cancers. As used herein, "recurrence-associated clinical parameter" has its conventional meaning for each specific cancer, with which those skilled in the art are quite familiar. In fact, those skilled in the art are familiar with various recurrence-associated clinical parameters beyond those listed here.

Often a physician will assess more than one clinical parameter in a patient and make a more comprehensive evaluation for the disease characters of interest. Example 5 shows how CCG status can add to one particular grouping of clinical parameters used to determine risk of recurrence in prostate cancer. Clinical parameters in Example 5 include binary variables for organ-confined disease and Gleason score less than or equal to 6, and a continuous variable for logarithmic PSA (Table I). This model includes all of the clinical parameters incorporated in the post-RP nomogram (i.e., Kattan-Stephenson nomogram) except for Year of RP and the two components of the Gleason score. Thus in some embodiments at least two clinical parameters (e.g., two of the above listed parameters) are assessed along with the expression level of at least one CCG.

One way in which single, but more often multiple, clinical parameters are utilized by physicians is with the help of nomograms. In the clinical setting, nomograms are representations (often visual) of a correlation between one or more parameters and one or more patient or disease characters. An example of a prevalent clinical nomogram used in determining a prostate cancer patient's likelihood of recurrence is described in Kattan et al., J. CLIN. ONCOL. (1999) 17:1499-1507, and updated in Stephenson et al., J. CLIN. ONCOL. (2005) 23:7005-7012 ("Kattan-Stephenson nomogram"). This nomogram evaluates a patient by assigning a point value to each of several clinical parameters (year of RP, surgical margins, extracapsular extension, seminal vesicle invasion, lymph node involvement, primary Gleason score, secondary Gleason score, and preoperative PSA level), totalling the points for a patient into a nomogram score, and then predicting the patient's likelihood of being recurrence-free at varying time intervals (up to 10 years) based on this nomogram score. An example of a prevalent clinical nomogram used in determining a breast cancer patient's prognosis for survival is the Nottingham Prognostic Index (NPI). See, e.g., Galea et al., BREAST CANCER RES. & TREAT. (1992) 22:207-19.

It has been discovered that determining the status of a CCG in a sample obtained from a prostate cancer patient, along with the patient's Kattan-Stephenson nomogram score, is a better predictor of 10-year recurrence-free survival than the nomogram score alone. See, e.g., Examples 2 & 5, infra. Specifically, adding CCG status to the Kattan-Stephenson nomogram detects patients at significantly increased risk of recurrence that the nomogram alone does not. Table 7 above provides an exemplary panel of 31 CCGs (Panel C) and a subset panel of 26 CCGs (Panel D, shown with *) determined in Example 2 to show predictive synergy with the Kattan-Stephenson nomogram in prostate cancer prognosis. It has also been discovered that determining the status of a CCG in a sample obtained from a breast cancer patient, along with the patient's NPI score, is a better prognostic predictor than NPI score alone. See, e.g., Example 6, infra. Specifically, adding CCG status to the NPI nomogram detects patients at significantly increased risk of recurrence that the nomogram alone does not. Panels B, C and D were determined in Example 2 to show predictive synergy with the NPI nomogram in breast cancer prognosis.

Thus another aspect of the disclosure provides an in vitro method comprising determining a clinical nomogram score (e.g., Kattan-Stephenson or NPI nomogram score) for a cancer patient and determining the status of at least one CCG in a sample obtained from the patient. Example 3 illustrates the empirical determination of the predictive power of individual CCGs and of several CCG panels of varying size over the Kattan-Stephenson nomogram. Randomly selected subsets of the 31 CCGs listed in Table 7 were tested as distinct CCG signatures and predictive power (i.e., p-value) was determined for each. As FIG. 1 shows, CCG signatures of 2, 3, 4, 5, 6, 10, 15, 20, 25, and 26 genes each add predictive power to the nomogram. Thus the disclosure provides a method of determining whether a prostate cancer patient has an increased likelihood of recurrence comprising determining the status of a panel of genes comprising at least 2, 3, 4, 5, 6, 10, 15, 20, 25, 26, 27, 28, 29, 30, 31, 32, 33, 34, 35, 40, 45, 50, 60, 70, 80, 90, or 100 or more CCGs, wherein an elevated status (e.g., increased expression) for the CCGs indicates an increased likelihood of recurrence. In some embodiments the method further comprises determining a clinical nomogram score of the patient. The disclosure further provides a method of determining whether a breast cancer patient has an increased likelihood of recurrence comprising determining the status of a panel of genes comprising at least 2, 3, 4, 5, 6, 10, 15, 20, 25, 26, 27, 28, 29, 30, 31, 32, 33, 34, 35, 40, 45, 50, 60, 70, 80, 90, or 100 or more CCGs, wherein an elevated status (e.g., increased expression) for the CCGs indicates an increased likelihood of recurrence. In some embodiments the method further comprises determining a clinical nomogram score of the patient. In some embodiments, the method comprises at least one of the following steps: (a) correlating elevated status (e.g., high or increased expression) of the panel of genes to an increased likelihood of recurrence; (b) concluding that the patient has an increased likelihood of recurrence based at least in part on elevated status (e.g., high or increased expression) of the panel of genes; or (c) communicating that the patient has an increased likelihood of recurrence based at least in part on elevated status (e.g., high or increased expression) of the panel of genes.

Often clinical nomograms for cancer are designed such that a particular value (e.g., high score) correlates with an increased risk of recurrence. Elevated CCG status (e.g., increased expression or activity) is also correlated with increased risk. Thus, in some embodiments the disclosure provides a method of determining whether a cancer patient has an increased likelihood of recurrence or progression comprising determining a clinical nomogram score for the patient and determining the status of at least one CCG in a sample obtained from the patient, wherein a high nomogram score and/or an elevated CCG status indicate the patient has an increased likelihood of recurrence or progression. In some embodiments the cancer is prostate cancer. In some embodiments the cancer is lung cancer. In some embodiments, the method comprises at least one of the following steps: (a) correlating a high nomogram score and/or an elevated CCG status (e.g., high or increased expression) to an increased likelihood of recurrence or progression; (b) concluding that the patient has an increased likelihood of recurrence or progression based at least in part on a high nomogram score and/or an elevated CCG status (e.g., high or increased expression); or (c) communicating that the patient has an increased likelihood of recurrence or progression based at least in part on a high nomogram score and/or an elevated CCG status (e.g., high or increased expression).

In some embodiments this assessment is made before radical prostatectomy (e.g., using a prostate biopsy sample) while in some embodiments it is made after (e.g., using the resected prostate sample). In some embodiments, a sample of one or more cells are obtained from a prostate cancer patient before or after treatment for analysis according to the present disclosure. Prostate cancer treatment currently applied in the art includes, e.g., prostatectomy, radiotherapy, hormonal therapy (e.g., using GnRH antagonists, GnRH agonists, antiandrogens), chemotherapy, and high intensity focused ultrasound. In some embodiments, one or more prostate tumor cells from prostate cancer tissue are obtained from a prostate cancer patient during biopsy or prostatectomy and are used for analysis in the method of the present disclosure.

The present disclosure is also based on the discovery that PTEN status predicts aggressive prostate cancer. PTEN status adds to both clinical parameters (e.g., Kattan-Stephenson nomogram) and CCGs (e.g., the genes in Table 1 or Panels A through G). As described in more detail in Example 4 below, PTEN status was determined in 191 prostate cancer patient samples with accompanying clinical history data and CCG signature data. Negative PTEN status was found to be a significant predictor for risk of recurrence (p-value 0.031). PTEN remained a significant predictor of recurrence after adjusting for post-surgery clinical parameters and the CCG signature shown in Table 7 (p-value 0.026). In addition, and importantly, the combination of PTEN and the CCG signature seems to be a better predictor of recurrence than post-surgery clinical parameters (p-value 0.0002).

Because PTEN is an independent predictor of prostate cancer recurrence, one aspect of the disclosure provides a method of predicting a patient's likelihood of prostate cancer recurrence comprising determining PTEN status in a sample from the patient, wherein a low or negative PTEN status indicates the patient has an increased likelihood of recurrence. In some embodiments, the method comprises at least one of the following steps: (a) correlating low or negative PTEN status (e.g., low or negative expression) to an increased likelihood of recurrence; (b) concluding that the patient has an increased likelihood of recurrence based at least in part on low or negative PTEN status (e.g., low or negative expression); or (c) communicating that the patient has an increased likelihood of recurrence based at least in part on low or negative PTEN status (e.g., low or negative expression). PTEN status can be determined by any technique known in the art, including but not limited to those discussed herein.

Because PTEN adds to CCG status in predicting prostate cancer recurrence, another aspect of the disclosure provides an in vitro method comprising determining PTEN status and determining the status of a plurality of CCGs in a sample obtained from a patient. Different combinations of techniques can be used to determine the status the various markers. For example, in one embodiment PTEN status is determined by immunohistochemistry (IHC) while the status of the plurality of CCGs is determined by quantitative polymerase chain reaction (qPCR™), e.g., TaqMan™. Some embodiments of the disclosure provide a method of determining a prostate cancer patient's likelihood of recurrence comprising determining PTEN status in a sample obtained from the patient, determining the status of a plurality of CCGs in a sample obtained from the patient, wherein low or negative PTEN status and/or elevated CCG status indicate the patient has an increased likelihood of recurrence. In some embodiments, the method comprises at least one of the following steps: (a) correlating low or negative PTEN status (e.g., low or negative expression) and/or elevated CCG status (e.g., high or increased expression) to an increased likelihood of recurrence; (b) concluding that the patient has an increased likelihood of recurrence based at least in part on low or negative PTEN status (e.g., low or negative expression) and/or elevated CCG status (e.g., high or increased expression); or (c) communicating that the patient has an increased likelihood of recurrence based at least in part on low or negative PTEN status (e.g., low or negative expression) and/or elevated CCG status (e.g., high or increased expression).

Because PTEN status adds predictive value to clinical parameters in predicting prostate recurrence, yet another aspect of the disclosure provides an in vitro method comprising determining PTEN status and determining at least one clinical parameter for a cancer patient. Often the clinical parameter is at least somewhat independently predictive of recurrence and the addition of PTEN status improves the predictive power. In some embodiments the disclosure provides a method of determining whether a cancer patient has an increased likelihood of recurrence comprising determining the status of PTEN in a sample obtained from the patient and determining a clinical nomogram score for the patient, wherein low or negative PTEN status and/or a unfavorable (e.g., high) nomogram score indicate the patient has an increased likelihood of recurrence. In some embodiments, the method comprises at least one of the following steps: (a) correlating low or negative PTEN status (e.g., low or negative expression) and/or unfavorable (e.g., high) nomogram score to an increased likelihood of recurrence; (b) concluding that the patient has an increased likelihood of recurrence based at least in part on low or negative PTEN status (e.g., low or negative expression) and/or unfavorable (e.g., high) nomogram score; or (c) communicating that the patient has an increased likelihood of recurrence based at least in part on low or negative PTEN status (e.g., low or negative expression) and/or unfavorable (e.g., high) nomogram score.

Because all three of the above markers are additive, some embodiments of the disclosure provide a method of determining whether a cancer patient has an increased likelihood of recurrence comprising determining the status of PTEN in a sample obtained from the patient, determining a clinical nomogram score for the patient and determining the status of at least one CCG in a sample obtained from the patient, wherein low or negative PTEN status, an unfavorable (e.g., high) nomogram score and/or an elevated CCG status indicate the patient has an increased likelihood of recurrence. In some embodiments, the method comprises at least one of the following steps: (a) correlating low or negative PTEN status (e.g., low or negative expression), an unfavorable (e.g., high) nomogram score and/or elevated CCG status (e.g., high or increased expression) to an increased likelihood of recurrence; (b) concluding that the patient has an increased likelihood of recurrence based at least in part on low or negative PTEN status (e.g., low or negative expression), an unfavorable (e.g., high) nomogram score and/or elevated CCG status (e.g., high or increased expression); or (c) communicating that the patient has an increased likelihood of recurrence based at least in part on low or negative PTEN status (e.g., low or negative expression), an unfavorable (e.g., high) nomogram score and/or elevated CCG status (e.g., high or increased expression).

The present disclosure is also based on the discovery that kallikrein-related peptidase 3 (KLK3) RNA status predicts aggressive prostate cancer. KLK3 (Entrez Gene Id No. 354)

is the gene encoding PSA protein. KLK3 status adds to both clinical parameters (e.g., Kattan-Stephenson nomogram) and CCGs (e.g., the genes in Table 1 or Panels A through G). As described in more detail in Examples 7 & 9 below, KLK3 RNA expression was measured in prostate cancer patient samples with accompanying clinical history data and CCG signature data. Of note, KLK3 RNA expression in FFPE was not well-correlated to serum PSA protein levels. Decreased KLK3 expression was found to be a significant predictor for risk of recurrence (p-value<0.0005). KLK3 was a significant predictor of recurrence independent of post-surgery clinical parameters (e.g., Gleason score, PSA) and the CCG signature shown in Panel F (p-value $2 \times 10^{-6}$).

Other genes were analyzed specifically for their ability to add prognostic power beyond CCP score and clinical variables. These genes are found in Tables R, S & Y below and form Panels H & I of the disclosure. Each of these genes can independently be used to diagnose a patient's prognosis for cancer recurrence or cancer-specific death according to the methods, systems, kits, etc. of the disclosure discussed herein. Or one or more of these genes can be added to a panel of the disclosure comprising CCP genes to form a larger panel with improved predictive power.

Because KLK3 and the genes of Panel H or I are independent predictors of cancer recurrence and cancer-specific death, one aspect of the disclosure provides a method of predicting a patient's prognosis (e.g., likelihood of prostate cancer recurrence or cancer-specific death) comprising determining KLK3 status and/or the status of one or more genes in Panel H or I in a sample from the patient, wherein an abnormal status (e.g., decreased expression, increased expression) indicates the patient has a poor prognosis (e.g., high likelihood of recurrence or cancer-specific death). In some embodiments, the method comprises at least one of the following steps: (a) correlating abnormal status (e.g., decreased mRNA expression) to a poor prognosis (e.g., high likelihood of recurrence or cancer-specific death); (b) concluding that the patient has a poor prognosis (e.g., high likelihood of recurrence or cancer-specific death) based at least in part abnormal status (e.g., decreased mRNA expression); or (c) communicating that the patient has a poor prognosis (e.g., high likelihood of recurrence or cancer-specific death) based at least in part on abnormal status (e.g., decreased mRNA expression). KLK3 status or the status of one or more genes in Panel H or I an be determined by applying and adapting techniques known in the art, including but not limited to those discussed herein. In some embodiments, RNA expression is measured, e.g., by directly measuring RNA levels or by measuring levels of cDNA derived from RNA.

Because KLK3 and each of the genes in Panel H or I adds to CCG status in predicting cancer recurrence and cancer-specific death, another aspect of the disclosure provides an in vitro method comprising determining KLK3 status and/or the status of one or more genes in Panel H or I and determining the status of a plurality of CCGs in a sample obtained from a patient. Some embodiments of the disclosure provide a method of determining a prostate cancer patient's prognosis comprising determining KLK3 expression and/or the expression of one or more genes in Panel H or I in a sample obtained from the patient, determining the expression of a plurality of CCGs in a sample obtained from the patient, wherein abnormal KLK3 status (e.g., decreased mRNA expression) and/or abnormal status of one or more genes in Panel H or I (e.g., increased mRNA expression) and/or elevated CCG status indicate the patient has a poor prognosis. In some embodiments, the method comprises at least one of the following steps: (a) correlating abnormal KLK3 status (e.g., decreased mRNA expression) and/or abnormal status of one or more genes in Panel H or I and/or elevated CCG status (e.g., high or increased expression) to a poor prognosis (e.g., high likelihood of recurrence or cancer-specific death); (b) concluding that the patient has a poor prognosis (e.g., high likelihood of recurrence or cancer-specific death) based at least in part on a abnormal KLK3 status (e.g., decreased mRNA expression) and/or abnormal status of one or more genes in Panel H or I and/or elevated CCG status (e.g., high or increased expression); or (c) communicating that the patient has a poor prognosis (e.g., high likelihood of recurrence or cancer-specific death) based at least in part on abnormal KLK3 status (e.g., decreased mRNA expression) and/or abnormal status of one or more genes in Panel H or I and/or elevated CCG status (e.g., high or increased expression).

Because KLK3 status and each of the genes in Panel H or I adds predictive value to clinical parameters in predicting prostate recurrence, yet another aspect of the disclosure provides an in vitro method comprising determining KLK3 status and/or the status of one or more genes in Panel H or I and determining at least one clinical parameter for a cancer patient. Often the clinical parameter is at least somewhat independently predictive of recurrence and the addition of KLK3 status and/or the status of one or more genes in Panel H or I improves the predictive power. In some embodiments the disclosure provides a method of predicting a patient's prognosis (e.g., likelihood of prostate cancer recurrence or cancer-specific death) comprising determining KLK3 expression in a sample obtained from the patient and/or the status of one or more genes in Panel H or I and determining a clinical score for the patient, wherein abnormal KLK3 status (e.g., decreased mRNA expression) and/or abnormal status of one or more genes in Panel H or I and/or an unfavorable (e.g., high) score indicate the patient has a poor prognosis (e.g., increased likelihood of prostate cancer recurrence or cancer-specific death). In some embodiments, the method comprises at least one of the following steps: (a) correlating abnormal KLK3 status (e.g., decreased mRNA expression) and/or abnormal status of one or more genes in Panel H or I and/or unfavorable (e.g., high) clinical score to a poor prognosis (e.g., high likelihood of recurrence or cancer-specific death); (b) concluding that the patient has a poor prognosis (e.g., high likelihood of recurrence or cancer-specific death) based at least in part on abnormal KLK3 status (e.g., decreased mRNA expression) and/or abnormal status of one or more genes in Panel H or I and/or unfavorable (e.g., high) clinical score; or (c) communicating that the patient has a poor prognosis (e.g., high likelihood of recurrence or cancer-specific death) based at least in part on abnormal KLK3 status (e.g., decreased mRNA expression) and/or abnormal status of one or more genes in Panel H or I and/or unfavorable (e.g., high) clinical score.

Because all four of the above markers are additive, some embodiments of the disclosure provide a method of predicting a patient's prognosis (e.g., likelihood of prostate cancer recurrence or cancer-specific death) comprising determining the status of PTEN in a sample obtained from the patient, determining KLK3 expression in a sample obtained from the patient, determining a clinical nomogram score for the patient, and determining the status of a plurality of CCGs (e.g., Panel F) in a sample obtained from the patient, wherein any of (1) low or negative PTEN status, (2) abnormal KLK3 status (e.g., decreased mRNA expression), (3) an unfavorable (e.g., high) nomogram score and/or (4) an elevated CCG status indicate the patient has a poor prognosis (e.g., increased likelihood of prostate cancer recurrence or cancer-specific death). In some embodiments, the method comprises at least one of the following steps: (a) correlating low or negative PTEN status, abnormal KLK3 status (e.g., decreased mRNA expression), an unfavorable (e.g., high) nomogram score and/or an elevated CCG status to a poor prognosis (e.g., high likelihood of recurrence or cancer-specific death); (b) concluding that the patient has a poor prognosis (e.g., high likelihood of recurrence or cancer-specific death) based at least in part on low or negative PTEN status, abnormal KLK3 status (e.g., decreased mRNA expression), an unfavorable (e.g., high) nomogram score and/or an elevated CCG status; or (c) communicating that the patient has a poor prognosis (e.g., high likelihood of recurrence or cancer-specific death) based at least in part on low or negative PTEN status, abnormal KLK3 status (e.g., decreased mRNA expression), an unfavorable (e.g., high) nomogram score and/or an elevated CCG status. Determining the status of one or more genes in Panel H or I can also be added to any of these analyses, with abnormal status (e.g., high expression) indicating poor prognosis.

The genes in Tables R, S & Y are ranked according to their p-value (e.g., after adjusting for CCP score). Thus, the various aspects of the disclosure involving these genes (e.g., the preceding several paragraphs) may incorporate these genes according this ranking. In some embodiments the plurality of test genes comprises at least some number of genes from any of Tables R, S or Y (e.g., at least 3, 4, 5, 6, 7, 8, 9, 10, 15, 20, 25, 30, 35 or more) and this plurality of genes comprises the top 2, 3, 4, 5, 6, 7, 8, 9, 10, 11, 12, 13, 14, 15, 20, 25, 30, 35 or more genes listed in Table Y. In some embodiments the plurality of test genes comprises at least some number of genes from any of Tables R, S or Y (e.g., at least 3, 4, 5, 6, 7, 8, 9, 10, 15, 20, 25, 30, 35 or more) and this plurality of genes comprises any one, two, three, four, five, six, seven, eight, nine, or ten or all of gene numbers 1 & 2, 1 to 3, 1 to 4, 1 to 5, 1 to 6, 1 to 7, 1 to 8, 1 to 9, or 1 to 10 from any of Tables R, S or Y. In some embodiments the plurality of test genes comprises at least some number of genes from any of Tables R, S or Y (e.g., at least 3, 4, 5, 6, 7, 8, 9, 10, 15, 20, 25, 30, 35 or more) and this plurality of genes comprises any one, two, three, four, five, six, seven, eight, or nine or all of gene numbers 2 & 3, 2 to 4, 2 to 5, 2 to 6, 2 to 7, 2 to 8, 2 to 9, or 2 to 10 from any of Tables R, S or Y. In some embodiments the plurality of test genes comprises at least some number of genes from any of Tables R, S or Y (e.g., at least 3, 4, 5, 6, 7, 8, 9, 10, 15, 20, 25, 30, 35 or more) and this plurality of genes comprises any one, two, three, four, five, six, seven, or eight or all of gene numbers 3 & 4, 3 to 5, 3 to 6, 3 to 7, 3 to 8, 3 to 9, or 3 to 10 from any of Tables R, S or Y. In some embodiments the plurality of test genes comprises at least some number of genes from any of Tables R, S or Y (e.g., at least 3, 4, 5, 6, 7, 8, 9, 10, 15, 20, 25, 30, 35 or more) and this plurality of genes comprises any one, two, three, four, five, six, or seven or all of gene numbers 4 & 5, 4 to 6, 4 to 7, 4 to 8, 4 to 9, or 4 to 10 from any of Tables R, S or Y. In some embodiments the plurality of test genes comprises at least some number of genes from any of Tables R, S or Y (e.g., at least 3, 4, 5, 6, 7, 8, 9, 10, 15, 20, 25, 30, 35 or more) and this plurality of genes comprises any one, two, three, four, five, six, seven, eight, nine, 10, 11, 12, 13, 14, or 15 or all of gene numbers 1 & 2, 1 to 3, 1 to 4, 1 to 5, 1 to 6, 1 to 7, 1 to 8, 1 to 9, 1 to 10, 1 to 11, 1 to 12, 1 to 13, 1 to 14, or 1 to 15 from any of Tables R, S or Y.

The results of any analyses according to the disclosure will often be communicated to physicians, genetic counselors and/or patients (or other interested parties such as researchers) in a transmittable form that can be communicated or transmitted to any of the above parties. Such a form can vary and can be tangible or intangible. The results can be embodied in descriptive statements, diagrams, photographs, charts, images or any other visual forms. For example, graphs showing expression or activity level or sequence variation information for various genes can be used in explaining the results. Diagrams showing such information for additional target gene(s) are also useful in indicating some testing results. The statements and visual forms can be recorded on a tangible medium such as papers, computer readable media such as floppy disks, compact disks, etc., or on an intangible medium, e.g., an electronic medium in the form of email or website on internet or intranet. In addition, results can also be recorded in a sound form and transmitted through any suitable medium, e.g., analog or digital cable lines, fiber optic cables, etc., via telephone, facsimile, wireless mobile phone, internet phone and the like.

Thus, the information and data on a test result can be produced anywhere in the world and transmitted to a different location. As an illustrative example, when an expression level, activity level, or sequencing (or genotyping) assay is conducted outside the United States, the information and data on a test result may be generated, cast in a transmittable form as described above, and then imported into the United States. Accordingly, the present disclosure also encompasses a method for producing a transmittable form of information on at least one of (a) expression level or (b) activity level for at least one patient sample. The method comprises the steps of (1) determining at least one of (a) or (b) above according to methods of the present disclosure; and (2) embodying the result of the determining step in a transmittable form. The transmittable form is the product of such a method.

Techniques for analyzing such expression, activity, and/or sequence data (indeed any data obtained according to the disclosure) will often be implemented using hardware, software or a combination thereof in one or more computer systems or other processing systems capable of effectuating such analysis.

Thus, the present disclosure further provides a system for determining gene expression in a tumor sample, comprising: (1) a sample analyzer for determining the expression levels of a panel of genes in a tumor sample including at least 2, 4, 6, 8 or 10 cell-cycle genes, wherein the sample analyzer contains the tumor sample which is from a patient identified as having prostate cancer, lung cancer, bladder cancer or brain cancer, or cDNA molecules from mRNA expressed from the panel of genes; (2) a first computer program for (a) receiving gene expression data on at least 4 test genes selected from the panel of genes, (b) weighting the determined expression of each of the test genes, and (c) combining the weighted expression to provide a test value, wherein at least 20%, 50%, at least 75% or at least 90% of the test genes are cell-cycle genes; and optionally (3) a second computer program for comparing the test value to one or more reference values each associated with a predetermined degree of risk of cancer recurrence or progression of the prostate cancer, lung cancer, bladder cancer or brain cancer. In some embodiments, the system further comprises a display module displaying the comparison between the test value to the one or more reference values, or displaying a result of the comparing step.

In preferred embodiment, the amount of RNA transcribed from the panel of genes including test genes is measured in the tumor sample. In addition, the amount of RNA of one or more housekeeping genes in the tumor sample is also measured, and used to normalize or calibrate the expression of the test genes, as described above.

In some embodiments, the plurality of test genes includes at least 2, 3 or 4 cell-cycle genes, which constitute at least 50%, 75% or 80% of the plurality of test genes, and preferably 100% of the plurality of test genes. In some embodiments, the plurality of test genes includes at least 5, 6 or 7, or at least 8 cell-cycle genes, which constitute at least 20%, 25%, 30%, 40%, 50%, 60%, 70%, 75%, 80% or 90% of the plurality of test genes, and preferably 100% of the plurality of test genes.

In some other embodiments, the plurality of test genes includes at least 8, 10, 12, 15, 20, 25 or 30 cell-cycle genes, which constitute at least 20%, 25%, 30%, 40%, 50%, 60%, 70%, 75%, 80% or 90% of the plurality of test genes, and preferably 100% of the plurality of test genes.

The sample analyzer can be any instruments useful in determining gene expression, including, e.g., a sequencing machine, a real-time PCR machine, and a microarray instrument.

The computer-based analysis function can be implemented in any suitable language and/or browsers. For example, it may be implemented with C language and preferably using object-oriented high-level programming languages such as Visual Basic, SmallTalk, C++, and the like. The application can be written to suit environments such as the Microsoft Windows™ environment including Windows™ 98, Windows™ 2000, Windows™ NT, and the like. In addition, the application can also be written for the MacIntosh™, SUN™, UNIX or LINUX environment. In addition, the functional steps can also be implemented using a universal or platform-independent programming language. Examples of such multi-platform programming languages include, but are not limited to, hypertext markup language (HTML), JAVA™, JavaScript™, Flash programming language, common gateway interface/structured query language (CGI/SQL), practical extraction report language (PERL), AppleScript™ and other system script languages, programming language/structured query language (PL/SQL), and the like. Java™- or JavaScript™-enabled browsers such as HotJava™, Microsoft™ Explorer™, or Netscape™ can be used. When active content web pages are used, they may include Java™ applets or ActiveX™ controls or other active content technologies.

The analysis function can also be embodied in computer program products and used in the systems described above or other computer- or internet-based systems. Accordingly, another aspect of the present disclosure relates to a computer program product comprising a computer-usable medium having computer-readable program codes or instructions embodied thereon for enabling a processor to carry out gene status analysis. These computer program instructions may be loaded onto a computer or other programmable apparatus to produce a machine, such that the instructions which execute on the computer or other programmable apparatus create means for implementing the functions or steps described above. These computer program instructions may also be stored in a computer-readable memory or medium that can direct a computer or other programmable apparatus to function in a particular manner, such that the instructions stored in the computer-readable memory or medium produce an article of manufacture including instructions which implement the analysis. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions or steps described above.

Thus one aspect of the present disclosure provides a system for determining whether a patient has increased likelihood of recurrence. Generally speaking, the system comprises (1) computer program for receiving, storing, and/or retrieving a patient's gene status data (e.g., expression level, activity level, variants) and optionally clinical parameter data (e.g., Gleason score, nomogram score); (2) computer program for querying this patient data; (3) computer program for concluding whether there is an increased likelihood of recurrence based on this patient data; and optionally (4) computer program for outputting/displaying this conclusion. In some embodiments this computer program for outputting the conclusion may comprise a computer program for informing a health care professional of the conclusion.

Figure 6:
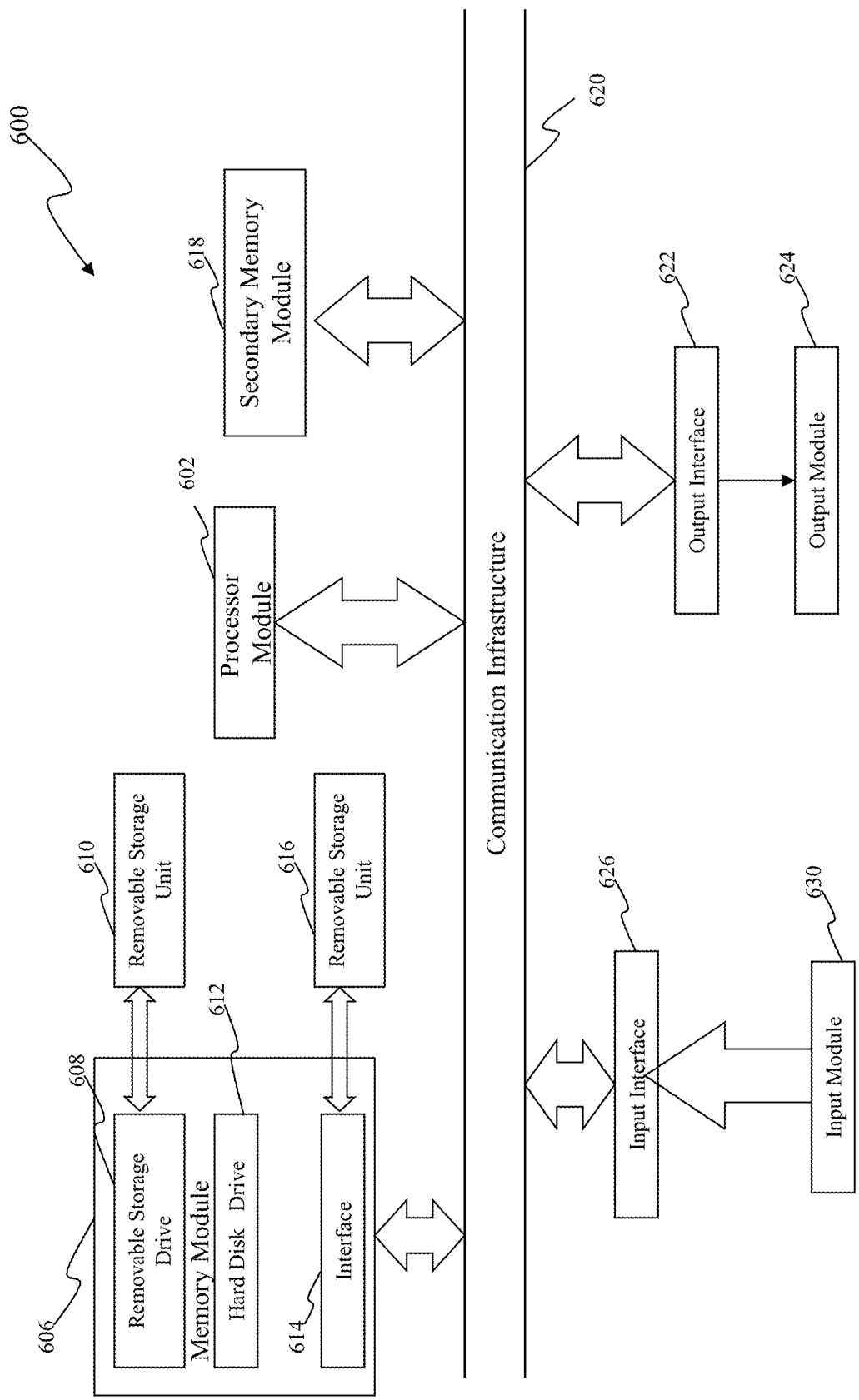
FIG. 6 is an illustration of an example of a system useful in certain aspects and embodiments of the disclosure.

One example of such a computer system is the computer system [600] illustrated in FIG. 6. Computer system [600] may include at least one input module [630] for entering patient data into the computer system [600]. The computer system [600] may include at least one output module [624] for indicating whether a patient has an increased or decreased likelihood of response and/or indicating suggested treatments determined by the computer system [600]. Computer system [600] may include at least one memory module [606] in communication with the at least one input module [630] and the at least one output module [624].

The at least one memory module [606] may include, e.g., a removable storage drive [608], which can be in various forms, including but not limited to, a magnetic tape drive, a floppy disk drive, a VCD drive, a DVD drive, an optical disk drive, etc. The removable storage drive [608] may be compatible with a removable storage unit [610] such that it can read from and/or write to the removable storage unit [610]. Removable storage unit [610] may include a computer usable storage medium having stored therein computer-readable program codes or instructions and/or computer readable data. For example, removable storage unit [610] may store patient data. Example of removable storage unit [610] are well known in the art, including, but not limited to, floppy disks, magnetic tapes, optical disks, and the like. The at least one memory module [606] may also include a hard disk drive [612], which can be used to store computer readable program codes or instructions, and/or computer readable data.

In addition, as shown in FIG. 1, the at least one memory module [606] may further include an interface [614] and a removable storage unit [616] that is compatible with interface [614] such that software, computer readable codes or instructions can be transferred from the removable storage unit [616] into computer system [600]. Examples of interface [614] and removable storage unit [616] pairs include, e.g., removable memory chips (e.g., EPROMs or PROMs) and sockets associated therewith, program cartridges and cartridge interface, and the like. Computer system [600] may also include a secondary memory module [618], such as random access memory (RAM).

Computer system [600] may include at least one processor module [602]. It should be understood that the at least one processor module [602] may consist of any number of devices. The at least one processor module [602] may include a data processing device, such as a microprocessor or microcontroller or a central processing unit. The at least one processor module [602] may include another logic device such as a DMA (Direct Memory Access) processor, an integrated communication processor device, a custom VLSI (Very Large Scale Integration) device or an ASIC (Application Specific Integrated Circuit) device. In addition, the at least one processor module [602] may include any other type of analog or digital circuitry that is designed to perform the processing functions described herein.

As shown in FIG. 6, in computer system [600], the at least one memory module [606], the at least one processor module [602], and secondary memory module [618] are all operably linked together through communication infrastructure [620], which may be a communications bus, system board, cross-bar, etc.). Through the communication infrastructure [620], computer program codes or instructions or computer readable data can be transferred and exchanged. Input interface [626] may operably connect the at least one input module [626] to the communication infrastructure [620]. Likewise, output interface [622] may operably connect the at least one output module [624] to the communication infrastructure [620].

The at least one input module [630] may include, for example, a keyboard, mouse, touch screen, scanner, and other input devices known in the art. The at least one output module [624] may include, for example, a display screen, such as a computer monitor, TV monitor, or the touch screen of the at least one input module [630]; a printer; and audio speakers. Computer system [600] may also include, modems, communication ports, network cards such as Ethernet cards, and newly developed devices for accessing intranets or the internet.

The at least one memory module [606] may be configured for storing patient data entered via the at least one input module [630] and processed via the at least one processor module [602]. Patient data relevant to the present disclosure may include expression level, activity level, copy number and/or sequence information for PTEN and/or a CCG. Patient data relevant to the present disclosure may also include clinical parameters relevant to the patient's disease. Any other patient data a physician might find useful in making treatment decisions/recommendations may also be entered into the system, including but not limited to age, gender, and race/ethnicity and lifestyle data such as diet information. Other possible types of patient data include symptoms currently or previously experienced, patient's history of illnesses, medications, and medical procedures.

The at least one memory module [606] may include a computer-implemented method stored therein. The at least one processor module [602] may be used to execute software or computer-readable instruction codes of the computer-implemented method. The computer-implemented method may be configured to, based upon the patient data, indicate whether the patient has an increased likelihood of recurrence, progression or response to any particular treatment, generate a list of possible treatments, etc.

In certain embodiments, the computer-implemented method may be configured to identify a patient as having or not having an increased likelihood of recurrence or progression. For example, the computer-implemented method may be configured to inform a physician that a particular patient has an increased likelihood of recurrence. Alternatively or additionally, the computer-implemented method may be configured to actually suggest a particular course of treatment based on the answers to/results for various queries.

FIG. 7 illustrates one embodiment of a computer-implemented method [700] of the disclosure that may be implemented with the computer system [600] of the disclosure.

The method [700] begins with one of three queries ([710], [711], [712]), either sequentially or substantially simultaneously. If the answer to/result for any of these queries is "Yes" [720], the method concludes [730] that the patient has an increased likelihood of recurrence. If the answer to/result for all of these queries is "No" [721], the method concludes [731] that the patient does not have an increased likelihood of recurrence. The method [700] may then proceed with more queries, make a particular treatment recommendation ([740], [741]), or simply end.

When the queries are performed sequentially, they may be made in the order suggested by FIG. 7 or in any other order. Whether subsequent queries are made can also be dependent on the results/answers for preceding queries. In some embodiments of the method illustrated in FIG. 7, for example, the method asks about clinical parameters [712] first and, if the patient has one or more clinical parameters identifying the patient as at increased risk for recurrence then the method concludes such [730] or optionally confirms by querying CCG status, while if the patient has no such clinical parameters then the method proceeds to ask about CCG status [711]. Optionally, if CCG status is not elevated, then the method may continue to ask about PTEN status [710]. As mentioned above, the preceding order of queries may be modified. In some embodiments an answer of "yes" to one query (e.g., [712]) prompts one or more of the remaining queries to confirm that the patient has increased risk of recurrence.

In some embodiments, the computer-implemented method of the disclosure [700] is open-ended. In other words, the apparent first step [710, 711, and/or 712] in FIG. 7 may actually form part of a larger process and, within this larger process, need not be the first step/query. Additional steps may also be added onto the core methods discussed above. These additional steps include, but are not limited to, informing a health care professional (or the patient itself) of the conclusion reached; combining the conclusion reached by the illustrated method [700] with other facts or conclusions to reach some additional or refined conclusion regarding the patient's diagnosis, prognosis, treatment, etc.; making a recommendation for treatment (e.g., "patient should/should not undergo radical prostatectomy"); additional queries about additional biomarkers, clinical parameters, or other useful patient information (e.g., age at diagnosis, general patient health, etc.).

Regarding the above computer-implemented method [700], the answers to the queries may be determined by the method instituting a search of patient data for the answer. For example, to answer the respective queries [710, 711, 712], patient data may be searched for PTEN status (e.g., PTEN IHC or mutation screening), CCG status (e.g., CCG expression level data), or clinical parameters (e.g., Gleason score, nomogram score, etc.). If such a comparison has not already been performed, the method may compare these data to some reference in order to determine if the patient has an abnormal (e.g., elevated, low, negative) status. Additionally or alternatively, the method may present one or more of the queries [710, 711, 712] to a user (e.g., a physician) of the computer system [100]. For example, the questions [710, 711, 712] may be presented via an output module [624]. The user may then answer "Yes" or "No" via an input module [630]. The method may then proceed based upon the answer received. Likewise, the conclusions [730, 731] may be presented to a user of the computer-implemented method via an output module [624].

Thus in some embodiments the disclosure provides a method comprising: accessing information on a patient's CCG status, clinical parameters and/or PTEN status stored in a computer-readable medium; querying this information to determine at least one of whether a sample obtained from the patient shows increased expression of at least one CCG, whether the patient has a recurrence-associated clinical parameter, and/or whether the patient has a low/negative PTEN status, outputting [or displaying] the sample's CCG expression status, the patient's recurrence-associated clinical parameter status, and/or the sample's PTEN status. As used herein in the context of computer-implemented embodiments of the disclosure, "displaying" means communicating any information by any sensory manner. Examples include, but are not limited to, visual displays, e.g., on a computer screen or on a sheet of paper printed at the command of the computer, and auditory displays, e.g., computer generated or recorded auditory expression of a patient's genotype.

As discussed at length above, recurrence-associated clinical parameters or PTEN status combined with elevated CCG status indicate a significantly increased likelihood of recurrence. Thus some embodiments provide a computer-implemented method of determining whether a patient has an increased likelihood of recurrence comprising accessing information on a patient's PTEN status (e.g., from a tumor sample obtained from the patient) or clinical parameters and CCG status (e.g., from a tumor sample obtained from the patient) stored in a computer-readable medium; querying this information to determine at least one of whether the patient has a low/negative PTEN status or whether the patient has a recurrence-associated clinical parameter; querying this information to determine whether a sample obtained from the patient shows increased expression of at least one CCG; outputting (or displaying) an indication that the patient has an increased likelihood of recurrence if the patient has a low/negative PTEN status or a recurrence-associated clinical parameter and the sample shows increased expression of at least one CCG. Some embodiments further comprise displaying PTEN, clinical parameters (or their values) and/or the CCGs and their status (including, e.g., expression levels), optionally together with an indication of whether the PTEN or CCG status and/or clinical parameter indicates increased likelihood of risk.

The practice of the present disclosure may also employ conventional biology methods, software and systems. Computer software products of the disclosure typically include computer readable media having computer-executable instructions for performing the logic steps of the method of the disclosure. Suitable computer readable medium include floppy disk, CD-ROM/DVD/DVD-ROM, hard-disk drive, flash memory, ROM/RAM, magnetic tapes and etc. Basic computational biology methods are described in, for example, Setubal et al., INTRODUCTION TO COMPUTATIONAL BIOLOGY METHODS (PWS Publishing Company, Boston, 1997); Salzberg et al. (Ed.), COMPUTATIONAL METHODS IN MOLECULAR BIOLOGY, (Elsevier, Amsterdam, 1998); Rashidi & Buehler, BIOINFORMATICS BASICS: APPLICATION IN BIOLOGICAL SCIENCE AND MEDICINE (CRC Press, London, 2000); and Ouelette & Bzevanis, BIOINFORMATICS: A PRACTICAL GUIDE FOR ANALYSIS OF GENE AND PROTEINS (Wiley & Sons, Inc., $2^{nd}$ ed., 2001); see also, U.S. Pat. No. 6,420,108.

The present disclosure may also make use of various computer program products and software for a variety of purposes, such as probe design, management of data, analysis, and instrument operation. See U.S. Pat. Nos. 5,593,839; 5,795,716; 5,733,729; 5,974,164; 6,066,454; 6,090,555; 6,185,561; 6,188,783; 6,223,127; 6,229,911 and 6,308,170. Additionally, the present disclosure may have embodiments that include methods for providing genetic information over networks such as the Internet as shown in U.S. Ser. Nos. 10/197,621 (U.S. Pub. No. 20030097222); Ser. No. 10/063,559 (U.S. Pub. No. 20020183936), Ser. No. 10/065,856 (U.S. Pub. No. 20030100995); Ser. No. 10/065,868 (U.S. Pub. No. 20030120432); Ser. No. 10/423,403 (U.S. Pub. No. 20040049354).

Techniques for analyzing such expression, activity, and/or sequence data (indeed any data obtained according to the disclosure) will often be implemented using hardware, software or a combination thereof in one or more computer systems or other processing systems capable of effectuating such analysis.

Thus one aspect of the present disclosure provides systems related to the above methods of the disclosure. In one embodiment the disclosure provides a system for determining gene expression in a tumor sample, comprising:

(1) a sample analyzer for determining the expression levels in a sample of a panel of genes including at least 4 CCGs, wherein the sample analyzer contains the sample, RNA from the sample and expressed from the panel of genes, or DNA synthesized from said RNA;

(2) a first computer program for
 (a) receiving gene expression data on at least 4 test genes selected from the panel of genes,
 (b) weighting the determined expression of each of the test genes with a predefined coefficient, and
 (c) combining the weighted expression to provide a test value, wherein the combined weight given to said at least 4 or 5 or 6 CCGs is at least 40% (or 50%, 60%, 70%, 80%, 90%, 95% or 100%) of the total weight given to the expression of all of said plurality of test genes; and optionally (3) a second computer program for comparing the test value to one or more reference values each associated with a predetermined degree of risk of cancer.

In some embodiments at least 20%, 50%, 75%, or 90% of said plurality of test genes are CCGs. In some embodiments the sample analyzer contains reagents for determining the expression levels in the sample of said panel of genes including at least 4 CCGs. In some embodiments the sample analyzer contains CCG-specific reagents as described below.

In another embodiment the disclosure provides a system for determining gene expression in a tumor sample, comprising: (1) a sample analyzer for determining the expression levels of a panel of genes in a tumor sample including at least 4 CCGs, wherein the sample analyzer contains the tumor sample which is from a patient identified as having prostate cancer, breast cancer, brain cancer, bladder cancer, or lung cancer, RNA from the sample and expressed from the panel of genes, or DNA synthesized from said RNA; (2) a first computer program for (a) receiving gene expression data on at least 4 test genes selected from the panel of genes, (b) weighting the determined expression of each of the test genes with a predefined coefficient, and (c) combining the weighted expression to provide a test value, wherein the combined weight given to said at least 4 or 5 or 6 CCGs is at least 40% (or 50%, 60%, 70%, 80%, 90%, 95% or 100%) of the total weight given to the expression of all of said plurality of test genes; and optionally (3) a second computer program for comparing the test value to one or more reference values each associated with a predetermined degree of risk of cancer recurrence or progression of the prostate cancer, breast cancer, brain cancer, bladder cancer, or lung cancer. In some embodiments at least 20%, 50%, 75%, or 90% of said plurality of test genes are CCGs. In some embodiments the system comprises a computer program for determining the patient's prognosis and/or determining (including quantifying) the patient's degree of risk of cancer recurrence or progression based at least in part on the comparison of the test value with said one or more reference values.

In some embodiments, the system further comprises a display module displaying the comparison between the test value and the one or more reference values, or displaying a result of the comparing step, or displaying the patient's prognosis and/or degree of risk of cancer recurrence or progression.

In a preferred embodiment, the amount of RNA transcribed from the panel of genes including test genes (and/or DNA reverse transcribed therefrom) is measured in the sample. In addition, the amount of RNA of one or more housekeeping genes in the sample (and/or DNA reverse transcribed therefrom) is also measured, and used to normalize or calibrate the expression of the test genes, as described above.

In some embodiments, the plurality of test genes includes at least 2, 3 or 4 CCGs, which constitute at least 50%, 75% or 80% of the plurality of test genes, and preferably 100% of the plurality of test genes. In some embodiments, the plurality of test genes includes at least 5, 6 or 7, or at least 8 CCGs, which constitute at least 20%, 25%, 30%, 40%, 50%, 60%, 70%, 75%, 80% or 90% of the plurality of test genes, and preferably 100% of the plurality of test genes. Thus in some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises the top 2, 3, 4, 5, 6, 7, 8, 9, 10, 11, 12, 13, 14, 15, 20, 25, 30, 35, 40 or more CCGs listed in Tables 9-11, & 13-14. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises at least 1, 2, 3, 4, 5, 6, 7, 8, 9, 10, 15, or 20 of the following genes: ASPM, BIRC5, BUB1B, CCNB2, CDC2, CDC20, CDCA8, CDKN3, CENPF, DLGAP5, FOXM1, KIAA0101, KIF11, KIF2C, KIF4A, MCM10, NUSAP1, PRC1, RACGAP1, and TPX2. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, nine, or ten or all of gene numbers 1 & 2, 1 to 3, 1 to 4, 1 to 5, 1 to 6, 1 to 7, 1 to 8, 1 to 9, or 1 to 10 of any of Tables 9-11, & 13-14. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, or nine or all of gene numbers 2 & 3, 2 to 4, 2 to 5, 2 to 6, 2 to 7, 2 to 8, 2 to 9, or 2 to 10 of any of Tables 9-11, & 13-14. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, or eight or all of gene numbers 3 & 4, 3 to 5, 3 to 6, 3 to 7, 3 to 8, 3 to 9, or 3 to 10 of any of Tables 9-11, & 13-14. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, or seven or all of gene numbers 4 & 5, 4 to 6, 4 to 7, 4 to 8, 4 to 9, or 4 to 10 of any of Tables 9-11, & 13-14. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, nine, 10, 11, 12, 13, 14, or 15 or all of gene numbers 1 & 2, 1 to 3, 1 to 4, 1 to 5, 1 to 6, 1 to 7, 1 to 8, 1 to 9, 1 to 10, 1 to 11, 1 to 12, 1 to 13, 1 to 14, or 1 to 15 of any of Tables 9-11, & 13-14.

In some other embodiments, the plurality of test genes includes at least 8, 10, 12, 15, 20, 25 or 30 CCGs, which constitute at least 20%, 25%, 30%, 40%, 50%, 60%, 70%, 75%, 80% or 90% of the plurality of test genes, and preferably 100% of the plurality of test genes.

The sample analyzer can be any instrument useful in determining gene expression, including, e.g., a sequencing machine (e.g., Illumina HiSeq™, Ion Torrent PGM, ABI SOLiD™ sequencer, PacBio RS, Helicos Heliscope™, etc.), a real-time PCR machine (e.g., ABI 7900, Fluidigm BioMark™, etc.), a microarray instrument, etc.

In one aspect, the present disclosure provides methods of treating a cancer patient comprising obtaining CCG status information (e.g., the CCGs in Table 1 or Panels A through G), and recommending, prescribing or administering a treatment for the cancer patient based on the CCG status. In some embodiments, the method further includes obtaining clinical parameter information, and/or obtaining PTEN status information from a sample from the patient and treating the patient with a particular treatment based on the CCG status, clinical parameter and/or PTEN status information. For example, the disclosure provides a method of treating a cancer patient comprising:

(1) determining the status of at least one CCG;
(2) determining the status of at least on clinical parameter;
(3) determining the status of PTEN in a sample obtained from the patient; and
(4) recommending, prescribing or administering either
   (a) an active (including aggressive) treatment if the patient has at least one of increased expression of the CCG, recurrence-associated clinical parameter, or low/negative PTEN status, or
   (b) a passive (or less aggressive) treatment if the patient has none of increased expression of the CCG, recurrence-associated clinical parameter, or low/negative PTEN status.

In some embodiments, the determining steps comprise receiving a report communicating the relevant status (e.g., CCG status). In some embodiments this report communicates such status in a qualitative manner (e.g., "high" or "increased" expression). In some embodiments this report communicates such status indirectly by communicating a score (e.g., prognosis score, recurrence score, combined score as discussed above, etc.) that incorporates such status.

Whether a treatment is aggressive or not will generally depend on the cancer-type, the age of the patient, etc. For example, in breast cancer adjuvant chemotherapy is a common aggressive treatment given to complement the less aggressive standards of surgery and hormonal therapy. Those skilled in the art are familiar with various other aggressive and less aggressive treatments for each type of cancer. "Active treatment" in prostate cancer is well-understood by those skilled in the art and, as used herein, has the conventional meaning in the art. Generally speaking, active treatment in prostate cancer is anything other than "watchful waiting." Active treatment currently applied in the art of prostate cancer treatment includes, e.g., prostatectomy, radiotherapy, hormonal therapy (e.g., GnRH antagonists, GnRH agonists, antiandrogens), chemotherapy, high intensity focused ultrasound ("HIFU"), etc. Each treatment option carries with it certain risks as well as side-effects of varying severity, e.g., impotence, urinary incontinence, etc. Thus it is common for doctors, depending on the age and general health of the man diagnosed with prostate cancer, to recommend a regime of "watchful-waiting."

"Watchful-waiting," also called "active surveillance," also has its conventional meaning in the art. This generally means observation and regular monitoring without invasive treatment. Watchful-waiting is sometimes used, e.g., when an early stage, slow-growing prostate cancer is found in an older man. Watchful-waiting may also be suggested when the risks of surgery, radiation therapy, or hormonal therapy outweigh the possible benefits. Other treatments can be started if symptoms develop, or if there are signs that the cancer growth is accelerating (e.g., rapidly rising PSA, increase in Gleason score on repeat biopsy, etc.).

Although men who choose watchful-waiting avoid the risks of surgery and radiation, watchful-waiting carries its own risks, e.g., increased risk of metastasis. For younger men, a trial of active surveillance may not mean avoiding treatment altogether, but may reasonably allow a delay of a few years or more, during which time the quality of life impact of active treatment can be avoided. Published data to date suggest that carefully selected men will not miss a window for cure with this approach. Additional health problems that develop with advancing age during the observation period can also make it harder to undergo surgery and radiation therapy. Thus it is clinically important to carefully determine which prostate cancer patients are good candidates for watchful-waiting and which patients should receive active treatment.

Thus, the disclosure provides a method of treating a prostate cancer patient or providing guidance to the treatment of a patient. In this method, the status of at least one CCG (e.g., those in Table 1 or Panels A through G), at least one recurrence-associated clinical parameter, and/or the status of PTEN is determined, and (a) active treatment is recommended, initiated or continued if a sample from the patient has an elevated status for at least one CCG, the patient has at least one recurrence-associated clinical parameter, and/or low/negative PTEN status, or (b) watchful-waiting is recommended/initiated/continued if the patient has neither an elevated status for at least one CCG, a recurrence-associated clinical parameter, nor low/negative PTEN status. In certain embodiments, CCG status, the clinical parameter(s) and PTEN status may indicate not just that active treatment is recommended, but that a particular active treatment is preferable for the patient (including relatively aggressive treatments such as, e.g., RP and/or adjuvant therapy).

In general, adjuvant therapy (e.g., chemotherapy, radiotherapy, HIFU, hormonal therapy, etc. after prostatectomy or radiotherapy) is not the standard of care in prostate cancer. According to the present disclosure, however, physicians may be able to determine which prostate cancer patients have particularly aggressive disease and thus should receive adjuvant therapy. Thus in one embodiment, the disclosure provides a method of treating a patient (e.g., a prostate cancer patient) comprising determining the status of at least one CCG (e.g., those in Table 1 or Panels A through G), the status of at least one recurrence-associated clinical parameter, and/or the status of PTEN and initiating adjuvant therapy after prostatectomy or radiotherapy if a sample from the patient has an elevated status for at least one CCG, the patient has at least one recurrence-associated clinical parameter and/or the patient has low/negative PTEN status.

In one aspect, the disclosure provides compositions for use in the above methods. Such compositions include, but are not limited to, nucleic acid probes hybridizing to PTEN or a CCG (or to any nucleic acids encoded thereby or complementary thereto); nucleic acid primers and primer pairs suitable for amplifying all or a portion of PTEN or a CCG or any nucleic acids encoded thereby; antibodies binding immunologically to a polypeptide encoded by PTEN or a CCG; probe sets comprising a plurality of said nucleic acid probes, nucleic acid primers, antibodies, and/or polypeptides; microarrays comprising any of these; kits comprising any of these; etc. In some aspects, the disclosure provides computer methods, systems, software and/or modules for use in the above methods.

In some embodiments the disclosure provides a probe comprising an isolated oligonucleotide capable of selectively hybridizing to PTEN or at least one of the genes in Table 1 or Panels A through G. The terms "probe" and "oligonucleotide" (also "oligo"), when used in the context of nucleic acids, interchangeably refer to a relatively short nucleic acid fragment or sequence. The disclosure also provides primers useful in the methods of the disclosure. "Primers" are probes capable, under the right conditions and with the right companion reagents, of selectively amplifying a target nucleic acid (e.g., a target gene). In the context of nucleic acids, "probe" is used herein to encompass "primer" since primers can generally also serve as probes.

The probe can generally be of any suitable size/length. In some embodiments the probe has a length from about 8 to 200, 15 to 150, 15 to 100, 15 to 75, 15 to 60, or 20 to 55 bases in length. They can be labeled with detectable markers with any suitable detection marker including but not limited to, radioactive isotopes, fluorophores, biotin, enzymes (e.g., alkaline phosphatase), enzyme substrates, ligands and antibodies, etc. See Jablonski et al., NUCLEIC ACIDS RES. (1986) 14:6115-6128; Nguyen et al., BIOTECHNIQUES (1992) 13:116-123; Rigby et al., J. MOL. BIOL. (1977) 113:237-251. Indeed, probes may be modified in any conventional manner for various molecular biological applications. Techniques for producing and using such oligonucleotide probes are conventional in the art.

Probes according to the disclosure can be used in the hybridization/amplification/detection techniques discussed above. Thus, some embodiments of the disclosure comprise probe sets suitable for use in a microarray in detecting, amplifying and/or quantitating PTEN and/or a plurality of CCGs. In some embodiments the probe sets have a certain proportion of their probes directed to CCGs—e.g., a probe set consisting of 10%, 20%, 30%, 40%, 50%, 55%, 60%, 65%, 70%, 75%, 80%, 85%, 90%, 95%, 96%, 97%, 98%, 99%, or 100% probes specific for CCGs. In some embodiments the probe set comprises probes directed to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 60, 70, 80, 90, 100, 125, 150, 175, 200, 250, 300, 350, 400, 450, 500, 600, 700, or 800 or more, or all, of the genes in Table 1 or Panels A through G. Such probe sets can be incorporated into high-density arrays comprising 5,000, 10,000, 20,000, 50,000, 100,000, 200,000, 300,000, 400,000, 500,000, 600,000, 700,000, 800,000, 900,000, or 1,000,000 or more different probes. In other embodiments the probe sets comprise primers (e.g., primer pairs) for amplifying nucleic acids comprising at least a portion of PTEN or of one or more of the CCGs in Table 1 or Panels A through G.

In another aspect of the present disclosure, a kit is provided for practicing the prognosis of the present disclosure. The kit may include a carrier for the various components of the kit. The carrier can be a container or support, in the form of, e.g., bag, box, tube, rack, and is optionally compartmentalized. The carrier may define an enclosed confinement for safety purposes during shipment and storage. The kit includes various components useful in determining the status of one or more CCGs and one or more housekeeping gene markers, using the above-discussed detection techniques. For example, the kit many include oligonucleotides specifically hybridizing under high stringency to mRNA or cDNA of the genes in Table 1 or Panels A through G. Such oligonucleotides can be used as PCR primers in RT-PCR reactions, or hybridization probes. In some embodiments the kit comprises reagents (e.g., probes, primers, and or antibodies) for determining the expression level of a panel of genes, where said panel comprises at least 25%, 30%, 40%, 50%, 60%, 75%, 80%, 90%, 95%, 99%, or 100% CCGs (e.g., CCGs in Table 1 or any of Panels A through G). In some embodiments the kit consists of reagents (e.g., probes, primers, and or antibodies) for determining the expression level of no more than 2500 genes, wherein at least 5, 10, 15, 20, 30, 40, 50, 60, 70, 80, 90, 100, 120, 150, 200, 250, or more of these genes are CCGs (e.g., CCGs in Table 1 or any of Panels A through G).

The oligonucleotides in the detection kit can be labeled with any suitable detection marker including but not limited to, radioactive isotopes, fluorephores, biotin, enzymes (e.g., alkaline phosphatase), enzyme substrates, ligands and antibodies, etc. See Jablonski et al., *Nucleic Acids Res.*, 14:6115-6128 (1986); Nguyen et al., *Biotechniques*, 13:116-123 (1992); Rigby et al., *J. Mol. Biol.*, 113:237-251 (1977). Alternatively, the oligonucleotides included in the kit are not labeled, and instead, one or more markers are provided in the kit so that users may label the oligonucleotides at the time of use.

In another embodiment of the disclosure, the detection kit contains one or more antibodies selectively immunoreactive with one or more proteins encoded by PTEN or one or more CCGs or optionally any additional markers. Examples include antibodies that bind immunologically to PTEN or a protein encoded by a gene in Table 1 or Panels A through G. Methods for producing and using such antibodies have been described above in detail.

Various other components useful in the detection techniques may also be included in the detection kit of this disclosure. Examples of such components include, but are not limited to, Taq polymerase, deoxyribonucleotides, dideoxyribonucleotides, other primers suitable for the amplification of a target DNA sequence, RNase A, and the like. In addition, the detection kit preferably includes instructions on using the kit for practice the prognosis method of the present disclosure using human samples.

Specific Embodiments

Two specific embodiments of the disclosure for use in biopsy and prostatectomy samples are show below. Those skilled in the art will understand that each element of these processes may be altered while retaining the essential features and accomplishing the same goals.

Biopsy

Indications and Use

Formalin-fixed paraffin-embedded (FFPE) tissue from blocks or slides of prostatic adenocarcinoma biopsies may be used. Blocks may include at least 2 mm of tumor on diagnostic H&E slides for sample processing and RNA extraction. In cases where blocks are not available, one 3-5 µm H&E slide followed by ten consecutive 10 µm unstained slides and a final H&E slide may be acceptable. Sample barcodes, which are scanned and tracked, may be applied to each block (or slide). The H&E slides from each case may be evaluated, e.g., by a pathologist, to determine the location and amount of tumor per slide. Using the H&E stained slides as a guide, tumor tissue may be removed from ten unstained slides and total RNA may be extracted from the tissue. The expression of the genes in any of Panels A-F, normalized to that of housekeeping genes, may then be measured in triplicate to generate a test value (e.g., CCP score).

As an optional quality control measure, a no-RNA control and a normal human RNA control with a previously determined CCP score may be analyzed within each sample run. Controls may be analyzed to verify expected results.

Performance Characteristics/Limitations

The CCP score may be used alone or in combination with clinical information to arrive at a clinical prognosis. The CCP score may be combined with the patient's CAPRA nomogram score (see Cooperberg et al., J. Natl. Cancer Inst. (2009) 101(12):878-887 for details on the CAPRA nomogram) according to the following equation: Combined score=(0.58*CCP+0.41*CAPRA).

Clinically Reportable Range

A clinically reportable CCP score range of −1.3 to 4.7 may be applied. A scale of CCP scores may be reported for the American Urological Association (AUA) risk category of the individual patient. The scale may consist of five 1-unit intervals, with the middle interval being centered at the median CCP score for that specific AUA risk category in the U.S. population. There may be approximately a 2-fold change in risk of prostate cancer mortality between intervals, which would be the hazard ratio corresponding to a 1-unit change in the CCP score.

Detection Limit/Linearity

CCP scores between −3.0 and +7.0 may represent the range of scores detectable by the assay. Linearity may be established within in this range as follows: The relevant genes may be pre-amplified, diluted to 7 different concentrations and spiked into a cDNA sample of known concentration. Each spiked sample may then be assayed in triplicate, and the resulting 3 data points may be averaged for each concentration to generate a CCP score.

Interference

In some cases adjuvant hormonal therapy and radiation treatment may affect CCP scores. Thus, in some embodiments the method is applied only to patients who have not received these treatments prior to biopsy.

Limitations

In some embodiments only human FFPE prostate tumor specimens are analyzed.

Interpretive Criteria

CCP Scores within the Technical Range of the Assay and within the Range of Scores for which Clinical Prediction is Validated (e.g., Between −1.3 and 4.7)

The estimated prostate cancer-specific mortality risk may be provided for each CCP score within this range, and in some cases may show how the CCP score differentiates between patients with the same CAPRA score. In addition, the U.S Distribution Percentile for CCP scores may be provided, e.g., for patients in the same CAPRA risk category (low, intermediate, or high). Although the risk percentage may be given across the full range, example risk scores are given below:

| CCP Score | Likelihood of Cancer-Specific Death |
|---|---|
| −1 | 5.9% |
| 0 | 11.6% |
| 1 | 22% |
| 2 | 39.5% |
| 3 | 63.8% |
| 4 | 87.2% |

CCP Scores within the Technical Range of the Assay but Outside the Range of Scores for which Clinical Prediction is Validated (e.g., −1.3 but Greater than −3.0)

If linearity of CCP scores within such a range have been established, then the calculated CCP score may be reported but in some cases the estimated prostate cancer-specific relative mortality risk may not be provided (in some cases the U.S Distribution Percentile for CCP scores, e.g., for patients in the same CAPRA risk category (low, intermediate, or high), may be reported).

CCP Scores Outside the Technical Range of the Assay (e.g., Greater than 4.7 or Less than 7.0)

These scores may lie outside of the verified detection limits of this assay and may represent an artifact or technical error. Thus, in some cases these scores may not be reportable.

Post-Prostatectomy

Indications and Use

Formalin-fixed paraffin-embedded (FFPE) tissue from prostatectomy blocks of prostatic adenocarcinoma may be used. Blocks may include at least 5 mm of tumor on diagnostic H&E slides for sample processing and RNA extraction. In cases where blocks are not available, one 3-5 µm H&E slide followed by five consecutive 10 µm unstained slides and a final H&E slide may be acceptable. Sample barcodes, which are scanned and tracked, may be applied to each block (or slide). The H&E slides from each case may be evaluated, e.g., by a pathologist, to determine the location and amount of tumor per slide. Using the H&E stained slides as a guide, tumor tissue may be removed from five unstained slides and total RNA may be extracted from the tissue.

The expression of the genes in any of Panels A-F, normalized to that of housekeeping genes, may then be measured in triplicate to generate a test value (e.g., CCP score). This CCP score can be used to estimate probability of recurrence (e.g., biochemical recurrence) within a given time period (e.g., within 10 years after surgery). A patient's CCP score can also be compared with the CCP scores of other patients within a U.S. distribution of scores previously observed. For a more accurate estimation of 10-year biochemical recurrence risk, clinical information provided by the healthcare provider may be used to calculate a nomogram score. The CCP score may then be combined with the nomogram score to generate a combined score. This combined score may be used to estimate the 10-year risk of biochemical recurrence, and it can be compared with the combined scores of other patients within a U.S. distribution of scores. In some embodiments, the combined score is only communicated to the healthcare provider if all required clinical information has been provided and, if all required clinical parameters are not provided on the test request form, only the Prolaris Score is reported. In some such embodiments, the combined score may be obtained by inputting the required clinical information subsequent to the reporting of the CCP score by entering clinical parameters required for the nomogram along with the patient's CCP score.

As an optional quality control measure, a no-RNA control and a normal human RNA control with a previously determined CCP score may be analyzed within each sample run. Controls may be analyzed to verify expected results.

Performance Characteristics/Limitations

Clinically Reportable Ranges

A clinically reportable CCP score range of −1.6 to 3.7 may be applied. Individuals with a CCP score of 1.2 or higher may be deemed to have a predicted probability of biochemical recurrence by 10 years of greater than 50%. CCP scores outside the range of −1.6 to 3.7 may be reported but may be qualified with the information that they lie outside the range of the prediction model.

Similarly, a clinically reportable combined score range of −0.9 to 4.5 may be applied for combined scores. Individuals with a combined score of 2.0 or higher may be deemed to have a predicted probability of biochemical recurrence by 10 years of greater than 50%. Combined scores outside of this range may be reported but may be qualified with the information that they lie outside the range of the prediction model.

Detection Limit/Linearity

CCP scores between −8 and 8 are technically detectable by the assay. Linearity may be established within this range as follows: The relevant genes may be pre-amplified, diluted to different concentrations and spiked into a cDNA sample of known concentration. Each spiked sample may be assayed in triplicate, and the resulting 3 data points may be averaged for each concentration to generate a Recurrence score. Linearity may be established for CCP scores ranging from 0 to 8 using this method. Linearity for CCP scores ranging from −8 to 0 may be similarly established.

Interference

In some cases neoadjuvant hormonal therapy and radiation treatment may affect CCP scores. Thus, in some embodiments the method is applied only to patients who have not received these treatments prior to surgery.

Limitations

In some embodiments only human FFPE prostate tumor specimens are analyzed. In some embodiments only samples from patients with PSA levels ≤100 ng/ml are analyzed. In some embodiments only samples yielding at least 125 ng of RNA are analyzed.

Interpretive Criteria

Scores within the Technical Range of the Assay and within the Range of Scores for which Clinical Prediction is Validated (e.g., 1.6 to 3.7 for CCP Scores; −0.9 to 4.5 for Combined Scores)

Both CCP scores and combined scores within this range may be reported together with predicted probability of recurrence. Although the risk percentage may be given continuously across the full range, example risk scores are given below:

| CCP Score | Likelihood of Recurrence |
|---|---|
| −1 | 12.6% |
| 0 | 24.9% |
| 1 | 45.5% |
| 2 | 72.5% |
| 3 | 93.6% |

| Combined Score | Likelihood of Recurrence |
| --- | --- |
| 0 | 11.5% |
| 1 | 25% |
| 2 | 49.3% |
| 3 | 79.8% |
| 4 | 97.7% |

Scores within the Technical Range of the Assay but Outside the Range of Scores for which Clinical Prediction is Validated (e.g., −8 to 1.7 and 3.8 to 8 for CCP; −8 to 1.0 and 4.6 to 8 for Combined scores)

If linearity of CCP scores and combined scores within such a range has been established, then the calculated CCP score or combined score may be reported but in some cases the estimated recurrence risk may not be provided.

Scores Outside the Technical Range of the Assay (e.g., Less than −8 or Greater than 8 for CCP or Combined Scores)

These scores may lie outside of the verified detection limits of this assay and may represent an artifact or technical error. Thus, in some cases these scores may not be reportable.

Additional Specific Embodiments

The following paragraphs describe numerous additional specific embodiments of the present disclosure.

Embodiment 1. A method for determining a test patient's likelihood of cancer recurrence or cancer-specific death, comprising:
(1) measuring, in a sample obtained from said test patient, the expression levels of a panel of genes comprising at least 3 test genes selected from Panel F;
(2) providing a test expression score by (a) weighting the determined expression of each gene in said panel of genes with a predefined coefficient (which may be 0), and (b) combining the weighted expression of each gene in said panel of genes to provide said test expression score, wherein said test genes are weighted to contribute at least 25% to said test expression score; and
(3) diagnosing said test patient as having either (a) an increased likelihood of cancer recurrence or cancer-specific death based at least in part on said test expression score exceeding a first reference expression score or (b) no increased likelihood of cancer recurrence or cancer-specific death based at least in part on said test expression score not exceeding a second reference expression score.

Embodiment 2. The method of Embodiment 1, wherein said test genes are weighted to contribute at least 30%, 40%, 50%, 60%, 70%, 80%, 90%, 95%, 96%, 97%, 98%, 99%, or 100% of the total weight given to the expression of all of said panel of genes in said test expression score.

Embodiment 3. The method of either Embodiment 1 or Embodiment 2, wherein said panel of genes comprises at least 4, 5, 6, 7, 8, 9, 10, 12, 14, 16, 18, 20, 22, 24, 26, 28, 30 or 31 test genes selected from Panel F.

Embodiment 4. The method of any one of Embodiments 1 to 3, wherein said test genes comprise at least the top 3, 4, 5, 6, 7, 8, 9, 10, 12, 14, 16, 18, 20, 22, 24, 26, 28, 30 genes in Panel F.

Embodiment 5. The method of any one of Embodiments 1 to 4, wherein said test genes further comprise KLK3 and KLK3 expression is incorporated into said test expression score such that decreased KLK3 expression increases said score.

Embodiment 6. The method of any one of Embodiments 1 to 5, wherein said test genes further comprise PTEN.

Embodiment 7. The method of any one of Embodiments 1 to 6, wherein said measuring step comprises:
measuring the amount of panel mRNA in said sample transcribed from each of between 3 and 500 panel genes, or measuring the amount of cDNA reverse transcribed from said panel mRNA; and
measuring the amount of housekeeping mRNA in said sample transcribed from one or more housekeeping genes, or measuring the amount of cDNA reverse transcribed from said housekeeping mRNA.

Embodiment 8. The method of any one of Embodiments 1 to 7, wherein said first and second reference expression scores are the same.

Embodiment 9. The method of any one of Embodiments 1 to 8, wherein half of cancer patients in a reference population have an expression score exceeding said first reference expression score and half of cancer patients in said reference population have an expression score not exceeding said first reference expression score.

Embodiment 10. The method of any one of Embodiments 1 to 7, wherein one third of cancer patients in a reference population have an expression score exceeding said first reference expression score and one third of cancer patients in said reference population have an expression score not exceeding said second reference expression score.

Embodiment 11. The method of Embodiment 10, comprising diagnosing said test patient as having (a) an increased likelihood of cancer recurrence or cancer-specific death if said test expression score exceeds said first reference expression score; (b) a decreased likelihood of cancer recurrence or cancer-specific death if said test expression score does not exceed said second reference expression score; or (c) neither increased nor decreased (i.e., consistent) likelihood of cancer recurrence or cancer-specific death if said test expression score exceeds said second reference expression score but does not exceed said first reference expression score.

Embodiment 12. The method of any one of Embodiments 1 to 11, wherein cancer recurrence is chosen from the group consisting of distant metastasis of the primary cancer; local metastasis of the primary cancer; recurrence of the primary cancer; progression of the primary cancer; and development of locally advanced, metastatic disease.

Embodiment 13. A method for determining a cancer patient's likelihood of cancer recurrence or cancer-specific death, comprising:
(1) measuring, in a sample obtained from said patient, the expression levels of a panel of genes comprising at least 3 test genes selected from Panel F;
(2) providing a test expression score by (1) weighting the determined expression of each gene in said panel of genes with a predefined coefficient (which may be 0), and (2) combining the weighted expression to provide said test expression score, wherein said test genes are weighted to contribute at least 25% to said test expression score;
(3) providing a test prognostic score combining said test expression score with at least one test clinical score representing at least one clinical variable; and
(4) diagnosing said patient as having either (a) an increased likelihood of cancer recurrence or cancer-specific death based at least in part on said test prognostic score exceeding a first reference prognostic score or (b) no increased likelihood of cancer recurrence or cancer-specific death based at least in part on said test prognostic score not exceeding a second reference prognostic.

Embodiment 14. The method of Embodiment 13, wherein said at least one clinical score incorporates at least one clinical variable chosen from the group consisting of year of RP, surgical margins, extracapsular extension, seminal vesicle invasion, lymph node involvement, primary Gleason score, secondary Gleason score, or preoperative PSA.

Embodiment 15. The method of either Embodiment 13 or Embodiment 14, wherein said prognostic scores incorporate (a) a first clinical score representing preoperative PSA concentration, optionally incorporated as a numerical concentration of ng/dL transformed by the natural logarithm, adding 1 to avoid zero values; and (b) a second clinical score representing Gleason score, optionally incorporated as a continuous numeric variable or categorized as <7 (reference level), 7, or >7.

Embodiment 16. The method of any one of Embodiments 13 to 15, wherein said prognostic scores are calculated according to a formula comprising the following terms: (A×expression score)+(B×clinical score).

Embodiment 17. The method of Embodiment 16, wherein A=0.58, said clinical score is CAPRA score, and B=0.41.

Embodiment 18. An in vitro method of classifying cancer comprising:
(1) determining the expression of a panel of genes comprising at least 4 CCGs from Table 2 in a sample;
(2) providing a test value by
  (a) weighting the determined expression of each of a plurality of test genes selected from the panel of biomarkers with a predefined coefficient, wherein said plurality of test genes comprises said CCGs; and
  (b) combining the weighted expression to provide the test value, wherein the combined weight given to said CCGs is at least 40% of the total weight given to the expression of said plurality of test genes; and
(3) correlating said test value to
  (a) an unfavorable cancer classification if said test value is representative of high expression of the plurality of test genes; or
  (b) a favorable cancer classification if said test value is representative of low or normal expression of the plurality of test genes.

Embodiment 19. The method of Embodiment 18, wherein at least 75% of said plurality of test genes are CCGs.

Embodiment 20. The method of Embodiment 19, wherein said panel of genes and said plurality of test genes comprise the top 5 genes in any one of Tables 9-11, & 13-14.

Embodiment 21. The method of Embodiment 20, wherein said panel of genes and said plurality of test genes comprise the genes in any one of Tables 1, 2, 7-11, 13-14 and/or Y or Panels A through I.

Embodiment 22. The method of Embodiment 21, wherein said unfavorable cancer classification is chosen from the group consisting of (a) a poor prognosis, (b) an increased likelihood of cancer progression, (c) an increased likelihood of cancer recurrence (e.g., biochemical recurrence), (d) an increased likelihood of cancer-specific death, or (e) a decreased likelihood of response to treatment with a particular regimen.

Embodiment 23. The method of Embodiment 22, wherein said unfavorable cancer classification is an increased likelihood of cancer recurrence.

Embodiment 24. The method of Embodiment 22, wherein said unfavorable cancer classification is an increased likelihood of cancer-specific death.

Embodiment 25. The method of Embodiment 18, wherein said favorable cancer classification is chosen from the group consisting of (a) a good prognosis, (b) no increased likelihood of cancer progression, (c) no increased likelihood of cancer recurrence, (d) no increased likelihood of cancer-specific death, or (e) an increased likelihood of response to treatment with a particular regimen.

Embodiment 26. The method of Embodiment 25, wherein said favorable cancer classification is no increased likelihood of cancer recurrence.

Embodiment 27. The method of Embodiment 25, wherein said favorable cancer classification is no increased likelihood of cancer-specific death.

Embodiment 28. A method of determining gene expression in a tumor sample, comprising:
(1) obtaining a tumor sample from a patient identified as having prostate cancer, lung cancer, bladder cancer or brain cancer;
(2) determining the expression levels of a panel of genes in said tumor sample including at least 4 cell-cycle genes; and
(3) providing a test value by (a) weighting the determined expression of each of a plurality of test genes selected from said panel of genes with a predefined coefficient, and (b) combining the weighted expression to provide said test value, wherein at least 75%, at least 85% or at least 95% of said plurality of test genes are cell-cycle genes.

Embodiment 29. The method of Embodiment 28, wherein at least 90% of said plurality of test genes are cell-cycle genes.

Embodiment 30. The method of Embodiment 28 or 29, wherein said determining step comprises:
measuring the amount of mRNA in said tumor sample transcribed from each of between 6 and 200 cell-cycle genes; and
measuring the amount of mRNA of one or more housekeeping genes in said tumor sample.

Embodiment 31. The method of Embodiment 28 or 29 or 30, wherein the expression of at least 8 cell-cycle genes are determined and weighted.

Embodiment 32. A method of prognosing prostate cancer, lung cancer, bladder cancer or brain cancer, comprising:
(1) determining in a tumor sample from a patient diagnosed of prostate cancer, lung cancer, bladder cancer or brain cancer, the expression of a panel of genes in said tumor sample including at least 4 cell-cycle genes;
(2) providing a test value by (1) weighting the determined expression of each of a plurality of test genes selected from said panel of genes with a predefined coefficient, and (2) combining the weighted expression to provide said test value, wherein at least 75%, at least 85% or at least 95% of said plurality of test genes are cell-cycle genes; and
(3) correlating an increased level of expression of said plurality of test genes to a poor prognosis.

Embodiment 33. The prognosis method of Embodiment 32, further comprising comparing said test value to a reference value, and correlating to an increased likelihood of poor prognosis if said test value is greater than said reference value.

Embodiment 34. The prognosis method of Embodiment 32, wherein the expression levels of from 6 to about 200 cell-cycle genes are measured.

Embodiment 35. The method of any one of Embodiment 32 to 34, wherein said determining step comprises:
measuring the amount of mRNA of from 6 to about 200 cell-cycle genes in said tumor sample; and
measuring the amount of mRNA of one or more housekeeping genes in said tumor sample.

Embodiment 36. A method of treating cancer in a patient identified as having prostate cancer, lung cancer, bladder cancer or brain cancer, comprising:
(1) determining in a tumor sample from a patient diagnosed of prostate cancer, lung cancer, bladder cancer or brain cancer, the expression of a panel of genes in said tumor sample including at least 4 cell-cycle genes;
(2) providing a test value by (1) weighting the determined expression of each of a plurality of test genes selected from said panel of genes with a predefined coefficient, and (2) combining the weighted expression to provide said test value, wherein at least 60% or 75% of said plurality of test genes are cell-cycle genes, wherein an increased level of expression of said plurality of test genes indicates a poor prognosis; and
(3) administering to said patient an anti-cancer drug, or recommending or prescribing or initiating active treatment if a poor prognosis is determined.

Embodiment 37. A diagnostic kit for prognosing cancer in a patient diagnosed of prostate cancer, lung cancer, bladder cancer or brain cancer, comprising, in a compartmentalized container:
(1) a plurality of PCR primer pairs for PCR amplification of at least 5 test genes, wherein less than 10%, 30% or less than 40% of all of said at least 8 test genes are non-cell-cycle genes; and
(2) one or more PCR primer pairs for PCR amplification of at least one housekeeping gene.

Embodiment 38. A diagnostic kit for prognosing cancer in a patient diagnosed of prostate cancer, lung cancer, bladder cancer or brain cancer, comprising, in a compartmentalized container:
(1) a plurality of probes for hybridizing to at least 5 test genes under stringent hybridization conditions, wherein less than 10%, 30% or less than 40% of all of said at least 8 test genes are non-cell-cycle genes; and
(2) one or more probes for hybridizing to at least one housekeeping gene.

Embodiment 39. A kit consisting essentially of, in a compartmentalized container:
(1) a first plurality of PCR reaction mixtures for PCR amplification of between 5 or 10 and 300 test genes, wherein at least 50%, at least 60% or at least 80% of said 5 or 10 to 300 test genes are cell-cycle genes, and wherein each reaction mixture comprises a PCR primer pair for PCR amplifying one of said test genes; and
(2) a second plurality of PCR reaction mixtures for PCR amplification of at least one housekeeping gene.

Embodiment 40. The kit of any one of Embodiments 37 to 39, wherein cell-cycle genes constitute no less than 10% of the total number of said test genes.

Embodiment 41. The kit of any one of Embodiments 37 to 39, wherein cell-cycle genes constitute no less than 20% of the total number of said test genes.

Embodiment 42. Use of
(1) a plurality of PCR primer pairs suitable for PCR amplification of at least 4 cell-cycle genes; and
(2) one or more PCR primer pairs suitable for PCR amplification of at least one housekeeping gene, for the manufacture of a diagnostic product for determining the expression of said test genes in a tumor sample from a patient diagnosed of prostate cancer, lung cancer, bladder cancer or brain cancer, to predict the prognosis of cancer, wherein an increased level of said expression indicates a poor prognosis or an increased likelihood of recurrence of cancer in the patient.

Embodiment 43. The use of Embodiment 42, wherein said plurality of PCR primer pairs are suitable for PCR amplification of at least 8 cell-cycle genes.

Embodiment 44. The use of Embodiment 42 or 43, wherein said plurality of PCR primer pairs are suitable for PCR amplification of from 4 to about 300 test genes, no greater than 10%, 30% or less than 50% of which being non-cell-cycle genes.

Embodiment 45. The use of Embodiment 42 or 43, wherein said plurality of PCR primer pairs are suitable for PCR amplification of from 20 to about 300 test genes, at least 25% of which being cell-cycle genes.

Embodiment 46. Use of
(1) a plurality of probes for hybridizing to at least 4 cell-cycle genes under stringent hybridization conditions; and
(2) one or more probes for hybridizing to at least one housekeeping gene under stringent hybridization conditions, for the manufacture of a diagnostic product for determining the expression of said test genes in a tumor sample from a patient diagnosed of prostate cancer, lung cancer, bladder cancer or brain cancer, to predict the prognosis of cancer, wherein an increased level of said expression indicates a poor prognosis or an increased likelihood of recurrence of cancer in the patient.

Embodiment 47. The use of Embodiment 46, wherein said plurality of probes are suitable for hybridization to at least 8 different cell-cycle genes.

Embodiment 48. The use of Embodiment 46 or 47, wherein said plurality of probes are suitable for hybridization to from 4 to about 300 test genes, no greater than 10%, 30% or less than 50% of which being non-cell-cycle genes.

Embodiment 49. The use of Embodiment 46 or 47, wherein said plurality of probes are suitable for hybridization to from 20 to about 300 test genes, at least 25% of which being cell-cycle genes.

Embodiment 50. A system for prognosing cancer selected from prostate cancer, lung cancer, bladder cancer or brain cancer, comprising:
(1) a sample analyzer for determining the expression levels of a panel of genes in said tumor sample including at least 4 cell-cycle genes, wherein the sample analyzer contains the tumor sample which is from a patient identified as having prostate cancer, lung cancer, bladder cancer or brain cancer, or cDNA molecules from mRNA expressed from the panel of genes; and
(2) a first computer program for (a) receiving gene expression data on at least 4 test genes selected from the panel of genes, (b) weighting the determined expression of each of the test genes, and (c) combining the weighted expression to provide a test value, wherein at least 50%, at least at least 75% of at least 4 test genes are cell-cycle genes; and
(3) a second computer program for comparing the test value to one or more reference values each associated with a predetermined degree of risk of cancer recurrence or progression of the prostate cancer, lung cancer, bladder cancer or brain cancer.

Embodiment 51. The system of Embodiment 50, further comprising a display module displaying the comparison between the test value to the one or more reference values, or displaying a result of the comparing step.

Embodiment 52. The method of any one of Embodiments 1 to 36, wherein said cancer is prostate cancer, wherein said panel of genes or panel of test genes further comprises KLK3.

Embodiment 53. The method of Embodiment 52, wherein KLK3 expression is incorporated into said test expression score such that decreased KLK3 expression increases said test expression score.

Embodiment 54. The method of Embodiment 52, wherein KLK3 expression is incorporated into said test expression score such that decreased KLK3 expression correlates to a test expression score that yields a diagnosis of increased likelihood of cancer recurrence or cancer-specific death.

Embodiment 55. The method of Embodiment 53, wherein said test expression score incorporates the negative of the numerical value of KLK3 expression such that a higher test expression score yields a diagnosis of increased likelihood of cancer recurrence or cancer-specific death.

Embodiment 56. A method of evaluating a patient's AUA prostate cancer risk classification comprising:
(1) obtaining said patient's AUA prostate cancer risk classification (as described in Example 8);
(2) providing a test value by
   (a) weighting the determined expression of each of a plurality of test genes selected from the panel of biomarkers with a predefined coefficient, wherein said plurality of test genes comprises said CCGs; and
   (b) combining the weighted expression to provide the test value, wherein the combined weight given to said CCGs is at least 40% of the total weight given to the expression of said plurality of test genes; and
(3)(a) reclassifying said patient as having a risk higher than that indicated by the AUA classification if said test value is greater than the median test value (e.g., at least 1%, 2%, 3%, 4%, 5%, 6%, 7%, 8%, 9%, 10% 15% 20% or 25% greater than the median test value) for all patients in a reference population having the same AUA classification; or
(3)(b) reclassifying said patient as having a risk lower than that indicated by the AUA classification if said test value is less than the median test value (e.g., at least 1%, 2%, 3%, 4%, 5%, 6%, 7%, 8%, 9%, 10% 15% 20% or 25% less than the median test value) for all patients in a reference population having the same AUA classification; or
(3)(c) confirming said patient's AUA classification if said test value is substantially the same as the median test value (e.g., within 1%, 2%, 3%, 4%, 5%, 6%, 7%, 8%, 9%, 10% 15% 20% or 25% of the median test value) for all patients in a reference population having the same AUA classification.

Example 1

The following cell cycle gene (CCG) signature was tested for predicting time to chemical recurrence after radical prostatectomy.

TABLE A

31-CCG Prostate Recurrence Signature

AURKA
BUB1
CCNB1

TABLE A-continued

31-CCG Prostate Recurrence Signature

CCNB2
CDC2
CDC20
CDC45L
CDCA8
CENPA
CKS2
DLG7
DTL
FOXM1
HMMR
KIF23
KPNA2
MAD2L1
MELK
MYBL2
NUSAP1
PBK
PRC1
PTTG1
RRM2
TIMELESS
TPX2
TRIP13
TTK
UBE2C
UBE2S
ZWINT

Mean mRNA expression for the above 31 CCGs was tested on 440 prostate tumor FFPE samples using a Cox Proportional Hazard model in Splus 7.1 (Insightful, Inc., Seattle Wash.). The p-value for the likelihood ratio test was $3.98 \times 10^{-5}$.

The mean of CCG expression is robust to measurement error and individual variation between genes. In order to determine the optimal number of cell cycle genes for the signature, the predictive power of the mean was tested for randomly selected sets of from 1 to 30 of the CCGs listed above. This simulation showed that there is a threshold number of CCGs in a panel that provides significantly improved predictive power.

Example 2

In a univariate analysis a set of 31 CCGs (Table 7) was found to be a significant predictor of biochemical recurrence (p-value=$1.8 \times 10^{-9}$) after RP in prostate cancer patients. This signature was further evaluated to determine whether it added to an established clinical nomogram for prostate cancer recurrence (the Kattan-Stephenson nomogram). In summary, the nomogram was a highly significant predictor of recurrence (p-value $1.6 \times 10^{-10}$) and, after adjusting for the nomogram, the CCG signature was a significant predictor of biochemical recurrence (p-value $4.8 \times 10^{-5}$, Table C).

Patients and Methods

Eight hundred four consecutive RP patients were followed for a median of 9.5 years. The patient characteristics and the treatment outcomes of the entire cohort have been previously reported (Swanson et al., UROL ONCOL. (2007) 25:110-114). Tissue blocks and/or slides from the final pathological evaluation with enough tissue for analysis were available for 430 patients. The cohort was divided randomly into 212 patients utilized for a training and 199 patient samples as a validation set.

Gene Expression (Statistical methods): Association between biochemical recurrence and CCG expression was evaluated using Cox PH models for time to recurrence. All of the p-values reported in this study were derived from a likelihood ratio test comparing the null model to the model containing the test variable. A set of 31 CCGs (Table 7, supra) was randomly selected. The assays were used to generate expression data from 212 patients in the training set. All of the expression data were generated in triplicate. The expression data were combined into a signature by calculating the mean expression level for 26 CCGs. Association between biochemical recurrence and CCG expression was evaluated using Cox PH models for time to recurrence.

Sample Preparation and Study Design: RNA was isolated from FFPE tumor sections derived from 411 prostate cancer patients treated with RP. Representative 10 μm thick tumor sections were used to isolate RNA. When necessary, a pathologist guided macro- or micro-dissection of the sample was used to enrich for tumor tissue before RNA isolation. None of the samples in the validation cohort were microdissected. Prior to any analysis, the cohort was split into 212 patients for initial characterization of the signature ("training set") and 199 patients for validation. The clinical characteristics of the training and validation cohort are listed on Table B.

TABLE C

|  | N | Co-variates | CCG mean p-value* | Recurrence Hazard Ratio |
|---|---|---|---|---|
| TRAINING (31 CCGs) | 212 | none | 0.00404 | 1.24 |
|  | 204 | post-surgery nomogram | 0.03320 | 1.16 |
| VALIDATION (26-CCG subset) | 199 | none | $1.8 \times 10^{-9}$ | 2.68 |
|  | 197 | post-surgery nomogram | $4.8 \times 10^{-5}$ | 1.94 |

*Mean of cell cycle gene expression with imputation of missing values, likelihood ratio test for Cox proportional hazards model.

To help understand the interaction between the nomogram and the CCG expression signature, a scatter plot comparing these predictors (FIG. 4) was generated (light gray stars represent patients whose cancer recurred while black stars represent patients whose cancer did not). Analysis of the scatter plot by KM means divided the samples into three clusters based on nomogram score only. Subsequently, it was discovered that the clusters were based on well-understood clinical parameters. The patients in the lowest scoring cluster (116/117) had organ-confined disease. Patients in the middle scoring cluster (48/60) had at least one post-surgical parameter known to be associated with poor outcome (i.e., disease through the capsule, disease positive lymph nodes, and/or disease positive seminal vesicles) and low pre-sur-

TABLE B

|  | Training | Validation | p-value | Statistic |
|---|---|---|---|---|
| Age in years at RP, mean (sd) | 67.3 (5.9) | 66.8 (5.8) | 0.355 | t-test |
| Ethnicity (% non-white) | 2.80% | 7.60% | 0.042 | Fisher's exact |
| Dissection method (% lcm) | 24% | 0% | NA | NA |
| Recurrence (%) | 71/212 (33.5%) | 72/199 (36.2%) | 0.605 | Fisher's exact |
| Days to recurrence, median | 910 | 822 | 0.463 | t-test |
| Days to follow-up, median | 3373 | 3387 | 0.173 | t-test |
| Pre-surgery PSA (median) | 7.3 | 6.8 | 0.163 | t-test of log |
| Seminal vesicle | 23/212 (10.8%) | 28/199 (14.1%) | 0.37 | Fisher's exact |
| Bladder | 12/212 (5.7%) | 17/199 (8.5%) | 0.335 | Fisher's exact |
| Lymph node | 8/212 (3.8%) | 10/199 (5.0%) | 0.632 | Fisher's exact |
| Capsular | 100/212 (47.2%) | 101/199 (50.8%) | 0.49 | Fisher's exact |
| Through capsule | 59/212 (27.8%) | 66/199 (33.2%) | 0.283 | Fisher's exact |
| Positive margins | 43/212 (20.3%) | 57/199 (28.6%) | 0.051 | Fisher's exact |
| Post-RP Gleason score > 6 | 80/212 (37.7%) | 66/199 (33.2%) | 0.354 | Fisher's exact |
| Post-RP nomogram, mean (sd) | 137 (19.5) | 138 (23.0) | 0.424 | t-test |

Results

Figure 2:
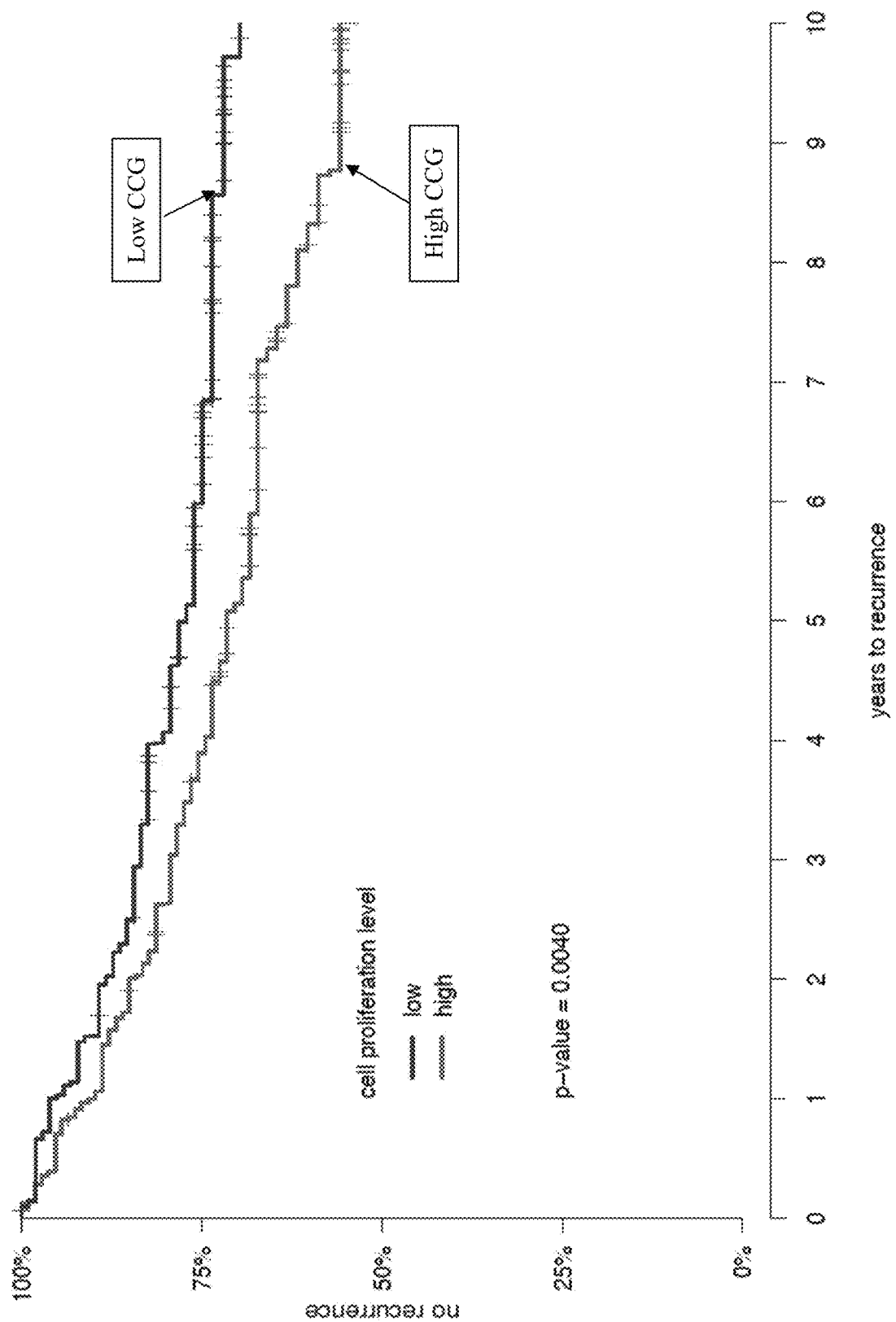
FIG. 2 is an illustration of CCGs predicting time to recurrence.

The CCG expression signature (Table 7, supra) was predictive of disease recurrence in a univariate analysis (p-value=$1.8 \times 10^{-9}$, Table C). The distribution of the signature score was skewed toward higher values (lower expression). The median value of signature score was used to divide the training cohort into two groups containing samples with either high or low CCG expression. The survival versus time for both groups is shown in FIG. 2.

Figure 3:
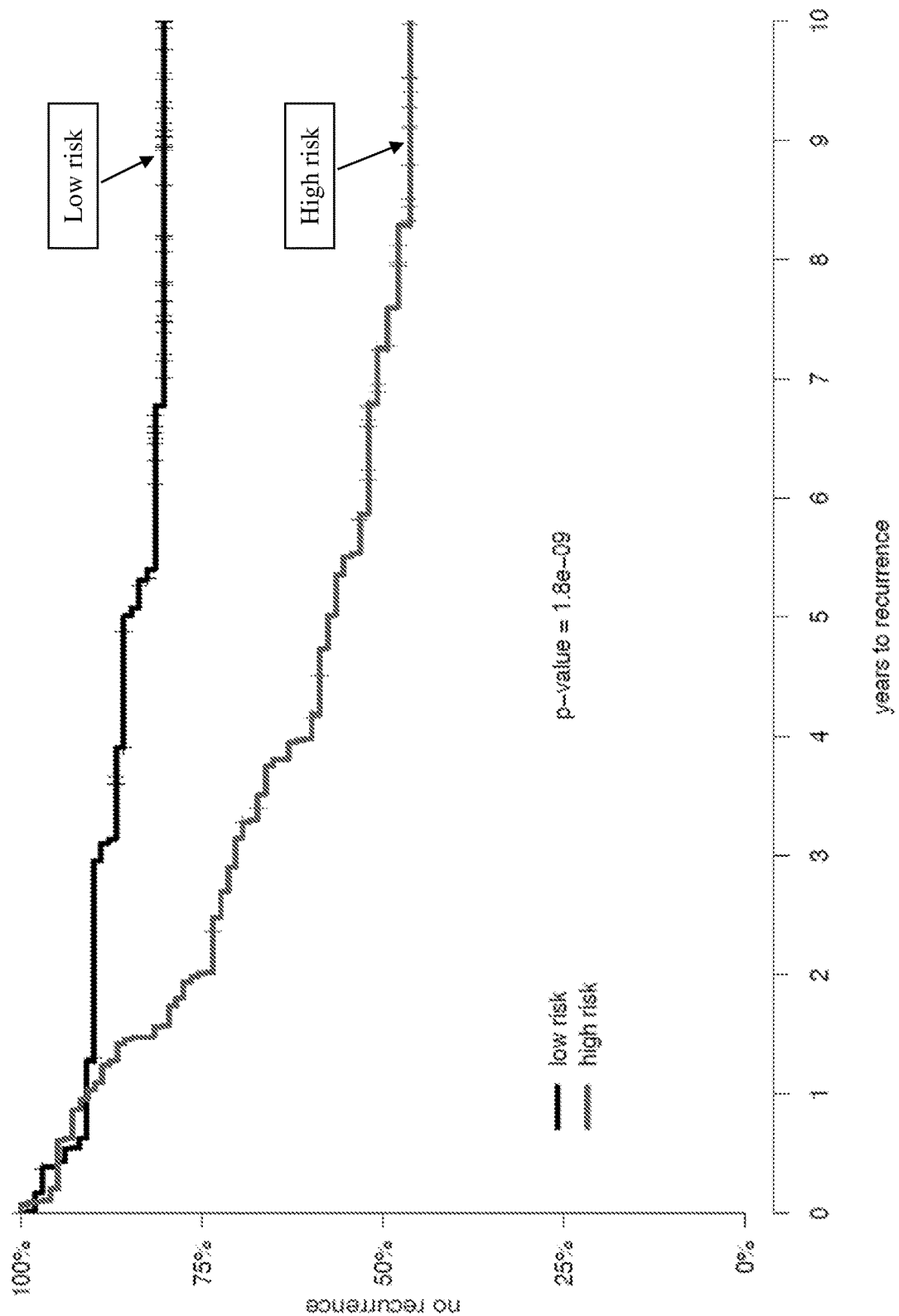
FIG. 3 is an illustration of nomogram predicting time to recurrence.
Figure 5:
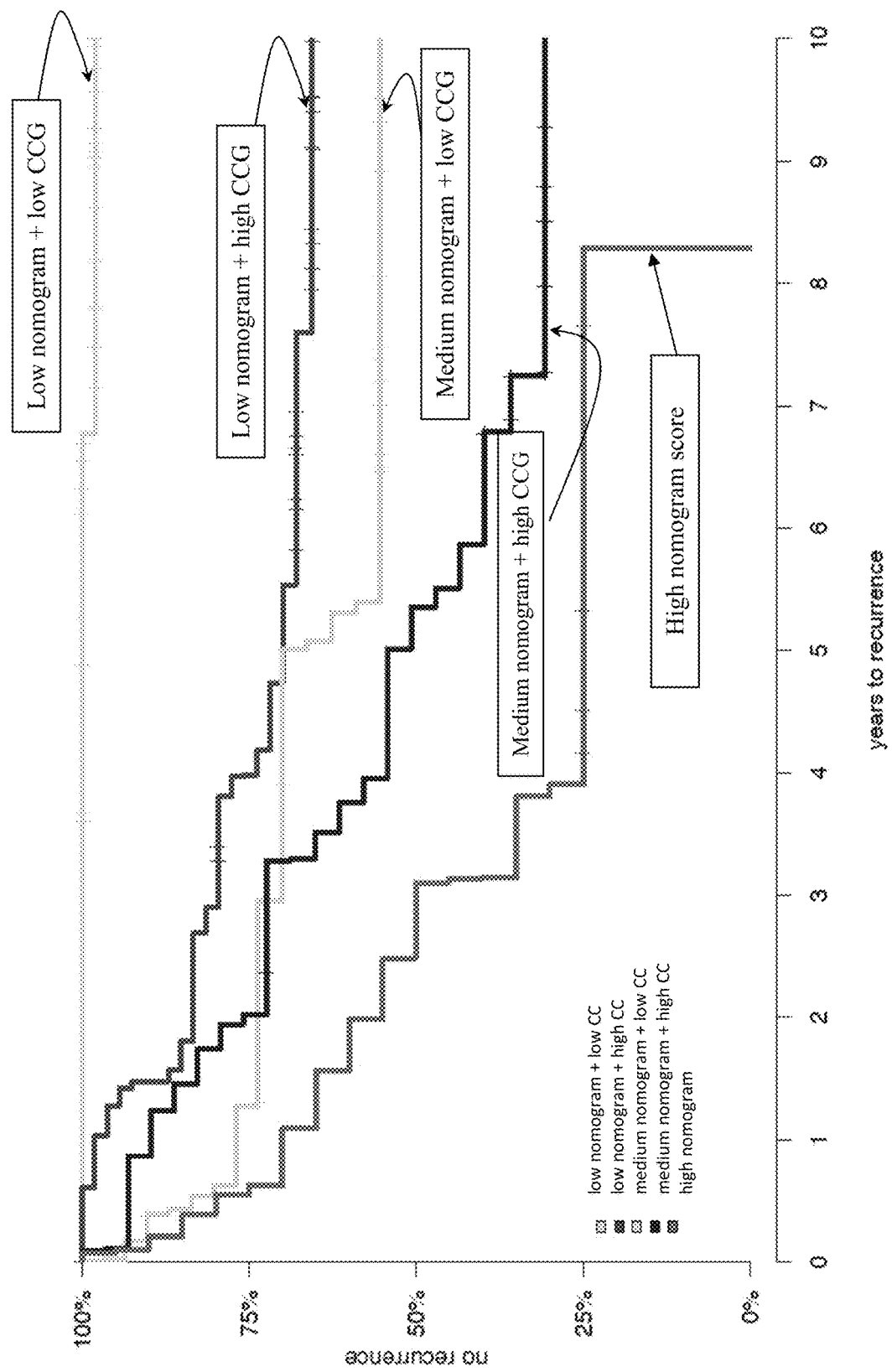
FIG. 5 is an illustration of time to recurrence for several patient populations defined by nomogram and/or CCG status.

Predictive power of the CCG signature after accounting for clinical variables typically included in a post-surgical nomogram (the Kattan-Stephenson nomogram) was also evaluated. The nomogram was a highly significant predictor of recurrence (p-value $1.6 \times 10^{-19}$). After adjusting for the nomogram, the CCG signature was a significant predictor of biochemical recurrence (FIG. 3) in the discovery cohort (p-value 0.03) and in the clinical validation cohort (p-value $4.8 \times 10^{-5}$).

gical PSA (<10 ng/ml). Patients in the highest scoring cluster had at least one unfavorable post-surgical parameter and high pre-surgery PSA. Next, the patients in the low and medium scoring clusters were divided by the mean of the CCG score. Outcomes for patients in the highest scoring cluster are adequately predicted by the nomogram and, therefore, were not divided further. As a result, the scatter plot defines five patient groups with disease recurrence rates of 2%, 40% (for two groups), 65%, and 80% (Table D). The recurrence rate of all five groups versus time is shown in FIG. 5.

TABLE D

|  | Post-RP nomogram | | |
|---|---|---|---|
| CCG score | Low | Medium | High |
| Low | 1/62 (1.6%) | 13/31 (41.9%) | 16/20 (80%) |
| High | 21/55 (38.2%) | 19/29 (65.5%) |  |

Figure 4:
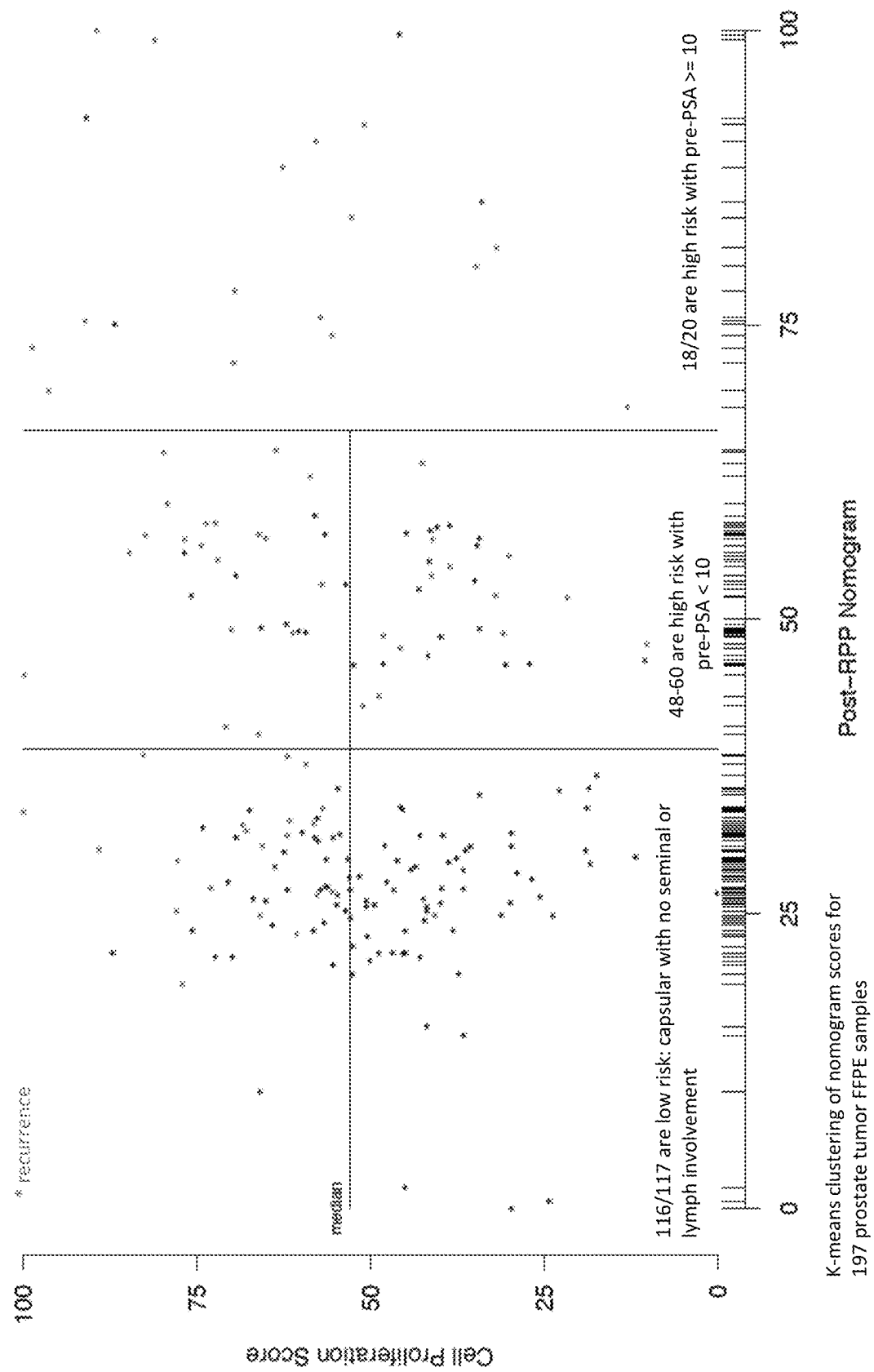
FIG. 4 is an illustration of the non-overlapping recurrence predicted by nomogram and a CCG signature.

The scatter plot shown in FIG. 4 suggests that there is a non-linear interaction between the CCG signature and the post-surgical nomogram. That is, the CCG signature is a better predictor in patients with low nomogram scores. Therefore, the study tested for statistical evidence of an interaction between these variables in a multivariate model for predicting disease recurrence (Table E). There was significant evidence for a favorable interaction in both training and validation studies. Including the interaction term in the model dramatically improved the prognostic significance of the CCG signature after adjusting for the nomogram (p-values of 0.0015 in training and $1.2 \times 10^{-8}$ in validation cohort).

TABLE E

Statistical Summary

| Cohort | N | Independent variables | Co-variates | Interaction p-value | Variable p-value | Recurrence Hazard ratio |
|---|---|---|---|---|---|---|
| Training | 204 | nomogram | none | NA | $1.6 \times 10^{-10}$ | |
| | 212 | CCG signature | none | NA | 0.004 | 1.24 |
| | 204 | CCG signature | nomogram | 0.021 | 0.0015 | |
| Validation | 197 | nomogram | none | NA | $7.7 \times 10^{-13}$ | |
| | 199 | CCG signature | none | NA | $1.8 \times 10^{-9}$ | 2.68 |
| | 197 | CCG signature | nomogram | 0.0001 | $1.28 \times 10^{-8}$ | |

Example 3

The following study aimed at determining the optimal number of CCGs to include in the signature. As mentioned above, CCG expression levels are correlated to each other so it was possible that measuring a small number of genes would be sufficient to predict disease outcome. In fact, single CCGs from the 31-gene set in Table 7 (Panel C) add significantly to the Kattan-Stephenson nomogram, as shown in Table F below (after adjustment for the nomogram and an interaction term between the nomogram and CCG expression):

TABLE F

| Gene # | Gene Symbol | p-value* |
|---|---|---|
| 1 | NUSAP1 | 2.8E−07 |
| 2 | DLG7 | 5.9E−07 |
| 3 | CDC2 | 6.0E−07 |
| 4 | FOXM1 | 1.1E−06 |
| 5 | MYBL2 | 1.1E−06 |
| 6 | CDCA8 | 3.3E−06 |
| 7 | CDC20 | 3.8E−06 |
| 8 | RRM2 | 7.2E−06 |
| 9 | PTTG1 | 1.8E−05 |
| 10 | CCNB2 | 5.2E−05 |
| 11 | HMMR | 5.2E−05 |
| 12 | BUB1 | 8.3E−05 |
| 13 | PBK | 1.2E−04 |
| 14 | TTK | 3.2E−04 |
| 15 | CDC45L | 7.7E−04 |
| 16 | PRC1 | 1.2E−03 |
| 17 | DTL | 1.4E−03 |
| 18 | CCNB1 | 1.5E−03 |
| 19 | TPX2 | 1.9E−03 |
| 20 | ZWINT | 9.3E−03 |
| 21 | KIF23 | 1.1E−02 |
| 22 | TRIP13 | 1.7E−02 |
| 23 | KPNA2 | 2.0E−02 |
| 24 | UBE2C | 2.2E−02 |
| 25 | MELK | 2.5E−02 |
| 26 | CENPA | 2.9E−02 |
| 27 | CKS2 | 5.7E−02 |
| 28 | MAD2L1 | 1.7E−01 |
| 29 | UBE2S | 2.0E−01 |
| 30 | AURKA | 4.8E−01 |
| 31 | TIMELESS | 4.8E−01 |

*p-value for likelihood ratio test of full (post-RP nomogram score + cell cycle expression + nomogram:cell cycle) vs reduced (post-RP nomogram score only) CoxPH model of time-to-recurrence.

To evaluate how smaller subsets of the larger CCG set (i.e., smaller CCG panels) performed, the study also compared how well the signature predicted outcome as a function of the number of CCGs included in the signature (FIG. 1). Time to chemical recurrence after prostate surgery was regressed on the CCG mean adjusted by the post-RP nomogram score. Data consist of TLDA assays expressed as deltaCT for 199 FFPE prostate tumor samples and 26 CCGs and were analyzed by a CoxPH multivariate model. P-values are for the likelihood ratio test of the full model (nomogram+cell cycle mean including interaction) vs the reduced model (nomogram only). As shown in Table G below and FIG. 1, small CCG signatures (e.g., 2, 3, 4, 5, 6 CCGS, etc.) add significantly to the Kattan-Stephenson nomogram:

TABLE G

| # of CCGs | Mean of log10 (p-value)* |
|---|---|
| 1 | −3.579 |
| 2 | −4.279 |
| 3 | −5.049 |
| 4 | −5.473 |
| 5 | −5.877 |
| 6 | −6.228 |

*For 1000 randomly drawn subsets, size 1 through 6, of cell cycle genes.

Example 4

The aim of this experiment was to evaluate the association between PTEN mutations and biochemical recurrence in prostate cancer patients after radical prostatectomy. Somatic mutations in PTEN were found to be significantly associated with recurrence, and importantly, it added prognostic information beyond both the established clinical nomogram for prostate cancer recurrence (the Kattan-Stephenson nomogram) and the CCG signature score (described in Examples 1 & 2, supra).

Patients and Methods

Eight hundred four consecutive RP patients were followed for a median of 9.5 years. The patient characteristics and the treatment outcomes of the entire cohort have been previously reported (Swanson et al., UROL. ONCOL. (2007) 25:110-114). Tissue blocks and/or slides from the final pathological evaluation with enough tissue for analysis were available for 430 patients. Of these, 191 were selected for PTEN mutation screening based on the amount of available tumor.

Genomic DNA was isolated from the FFPE tumor samples for mutation screening of PTEN using the QIAamp DNA FFPE Tissue kit (Qiagen, Valencia, Calif.) according to the kit protocol. The FFPE slides were first stained with hematoxylin and eosin and examined by a pathologist to identify the tumor region. After deparaffinization, tumor tissue was cut out from the slides by a razor blade. For a few samples dissection was aided by laser capture microscopy (LCM), owing to the dispersion of the tumor cells Mutations were detected by designing sequencing primers to interrogate the PTEN genomic sequence. The primers contained M13 forward and reverse tails to facilitate sequencing. After amplification, DNA sequence was determined on a Mega BASE 4500 (GE healthcare) using dye-primer chemistry as described in Frank et al., J. CLINT. ONCOL. (2002) 20:1480-1490. Due to the technical difficulties associated with sequencing DNA derived from FFPE material, each mutation was detected by at least two independent amplification and sequencing reactions.

Statistical methods: Unless otherwise specified, the association between biochemical recurrence and PTEN mutations was evaluated using Cox PH models for time to recurrence. The resultant p-values were derived from a likelihood ratio test comparing the null model to the model containing the test variable. In this example (Example 4), the CCG signature was derived from 26 CCGs (Panel D in Table 2, supra). All of the expression data were generated in triplicate. The expression data were combined into a signature by calculating the mean expression level for 26 CCGs. The clinical data were the variables included in the Kattan-Stephenson nomogram.

Results

PTEN mutations were found in 13 individuals (13/191). In this subset of 191 patients, PTEN was a significant predictor of biochemical recurrence (p-value=0.031). The recurrence rate in mutation carriers was 69% (9/13) compared to 36% (64/178) in non-mutant patients. The difference in recurrence rate is also significant using a Fisher's exact test (p-value=0.034). In the subset of patients with clinical parameter data, CCG signature score, and PTEN mutations, PTEN status was a significant predictor of biochemical recurrence after adjusting for both clinical parameters and CCG signature (p-value 0.024). Finally, the combination of PTEN mutation with CCG signature was a better predictor of outcome after adjusting for clinical parameters than using the CCG signature after adjusting for clinical parameters (p-value=0.0002 for the combination compared to 0.0028 for CCG only). These results show that PTEN mutations provide information about the likelihood of recurrence that is uncorrelated with either clinical parameters or CCG signature, and that using all three parameters to evaluate recurrence risk provides a more accurate estimate of recurrence probability than previously possible.

Example 5

This Example describes further studies to validate and refine some embodiments of the CCG signatures of the disclosure.

Patients and Methods

Eight hundred four consecutive radical prostatectomy patients were followed for a median of 9.5 years. The median age was 67 years. The clinical stage was T1 34%, T2 66% and T3<1%. The median preoperative PSA was 6.6 ng/ml with 72%<10 ng/ml and 28%>10 ng/ml. The specimens were inked and clinical parameters were recorded as to positive bladder neck or urethral margin, invasion into the capsule, extension through the capsule, positive margins and the involvement of the seminal vesicles. Biochemical recurrence was defined as a PSA>0.3 ng/ml. For this study we had access to clinical data on 690 patients. Tissue blocks and/or slides from the final pathological evaluation with enough tissue for analysis were available for 442 patients. The cohort was divided into 195 patients for a training cohort, and 247 patients for validation.

Selection of Genes

Assays of 126 CCGs and 47 HK (housekeeping) genes were run against 96 commercially obtained, anonymous prostate tumor FFPE samples without outcome or other clinical data. The working hypothesis was that the assays would measure with varying degrees of accuracy the same underlying phenomenon (cell cycle proliferation within the tumor for the CCGs, and sample concentration for the HK genes). Assays were ranked by the Pearson's correlation coefficient between the individual gene and the mean of all the candidate genes, that being the best available estimate of biological activity. Results for the correlation of each of the 126 CCGs to the mean are reported in Table 23. Not including CCGs with low average expression, or assays that produced sample failures, approximately half the CCGs had correlations less than 0.58, and a quarter of the HK genes had correlations less than 0.95. These assays were eliminated, leaving a subset of 56 CCGs (Panel G) and 36 HK candidate genes (Tables 11 and 12). Correlation coefficients were recalculated on this subset, and the final selection was made from the ranked list.

Gene Expression

Total RNA was extracted from representative 5 μNI thick FFPE tumor sections. The samples were de-paraffinized using a xylene bath and subsequently hydrated in graded series of ethanol baths. Afterward, the tumor region was dissected from the slide using a razor blade according to the pathologist instructions. Alternatively, the tumor region was dissected directly into an eppendorf tube and the paraffin was removed using xylene and washed with ethanol. After, samples were treated overnight with proteinase K digestion at 55° C. Total RNA was extracted using either RNeasy FFPE or miRNeasy (Qiagen) as described by the manufacturer (with the only exception being the extended proteinase K digestion described above). Isolated total RNA was treated with DNase I (Sigma) prior to cDNA synthesis. Subsequently, we employed the High-capacity cDNA Archive Kit (Applied Biosystems) to convert total RNA into single strand cDNA as described by the manufacturer. A minimum of 200 ng RNA was required for the RT reaction.

Prior to measuring expression levels, the cDNA was pre-amplified with a pooled reaction containing TaqMan™ assays. Pre-amplification reaction conditions were: 14 cycles of 95° C. for 15 sec and 60° C. for 4 minutes. The first cycle was modified to include a 10 minute incubation at 95° C. The amplification reaction was diluted 1:20 using the 1×TE buffer prior to loading on TaqMan™ Low Density Arrays (TLDA, Applied Biosystems) to measure gene expression.

CCG Score

The CCG score is calculated from RNA expression of 31 CCGs (Panel F) normalized by 15 housekeeper genes (HK). The relative numbers of CCGs (31) and HK genes (15) were optimized in order to minimize the variance of the CCG score. The CCG score is the unweighted mean of CT values for CCG expression, normalized by the unweighted mean of the HK genes so that higher values indicate higher expression. One unit is equivalent to a two-fold change in expression. Missing values were imputed using the mean expression for each gene determined in the training set using only good quality samples. The CCG scores were centered by the mean value, again determined in the training set.

A dilution experiment was performed on four of the commercial prostate samples to estimate the measurement error of the CCG score (se=0.10) and the effect of missing values. It was found that the CCG score remained stable as concentration decreased to the point of 5 failures out of the total 31 CCGs. Based on this result, samples with more than 4 missing values were not assigned a CCG score.

The CCG score threshold for determining low-risk was based on the lowest CCG score of recurrences in the training set. The threshold was then adjusted downward by 1 standard deviation in order to optimize the negative predictive value of the test.

Model of Clinical Risk

A Cox proportional hazards model was used to summarize the available clinical parameter data and estimate the prior clinical risk of biochemical recurrence for each patient. The data set consisted of 195 cases from the training set and 248 other cases with clinical parameter information but insufficient sample to measure RNA expression. Univariate tests were performed on clinical parameters known to be associated with outcome (see Table H below). Non-significant parameters were excluded from the model. A composite variable was created for organ-confined disease, with invasion defined as surgical margins, extracapsular extension, or involvement of any of seminal vesicles, bladder neck/urethral margins, or lymph nodes. The composite variable for organ-confined disease proved more significant in the model than any of its five components, some of which were inter-correlated or not prevalent. Model fitting was performed using the AIC criteria for post-operative covariates.

TABLE H

Univariate analysis of clinical parameters and association with biochemical recurrence

| Cinical Variable | p-value* | # occurrences | Total | Frequency |
|---|---|---|---|---|
| BLADDER | 0.0002 | 36 | 443 | 0.081 |
| CAPSULAR | $1.1 \times 10^{-9}$ | 194 | 443 | 0.438 |
| ETHNICITY (WHITE) | 0.6741 | 416 | 439 | 0.948 |
| LYMPHNOD | 0.0009 | 33 | 443 | 0.074 |
| MARG.POS | $6.1 \times 10^{-11}$ | 83 | 443 | 0.187 |
| PATHGLEA | $6.7 \times 10^{-16}$ | NA | 443 | NA |
| PATHGRAD | $2.4 \times 10^{-11}$ | NA | 443 | NA |
| PATHSTAG | $3.1 \times 10^{-15}$ | NA | 443 | NA |
| PRE.PSA.LOG10 | $6.2 \times 10^{-12}$ | NA | 443 | NA |
| SEM.VES | $3.0 \times 10^{-8}$ | 56 | 443 | 0.126 |
| SURGERY.YEAR | 0.0803 | NA | 443 | NA |
| THRU.CAP | $1.3 \times 10^{-10}$ | 114 | 443 | 0.257 |

*Cox PH p-value for likelihood ratio test

Figure 8:
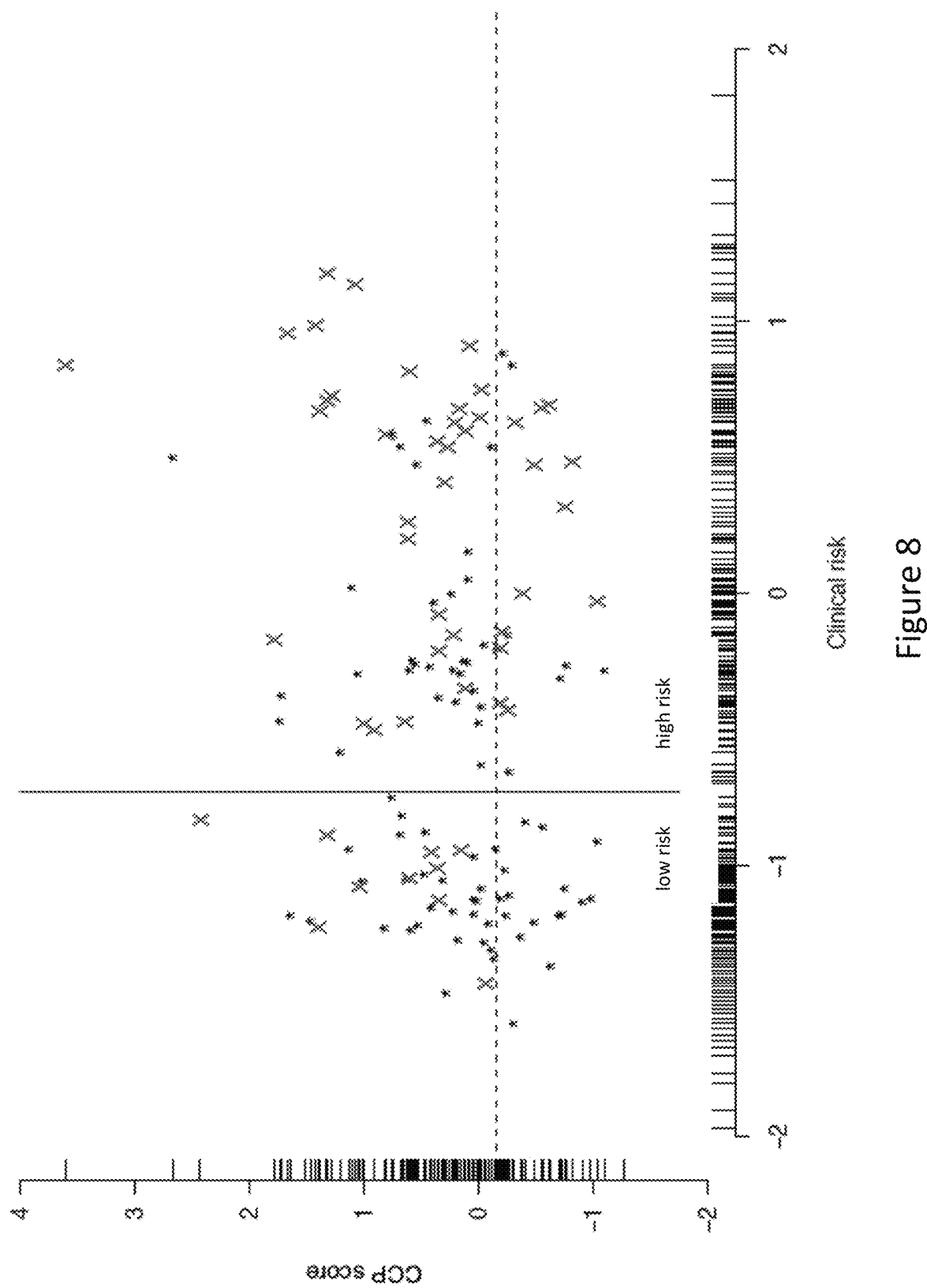
FIG. 8 a scatter plot comparing clinical parameters and CCG score as predictors of recurrence from Example 5.

The final model (i.e., nomogram) has binary variables for organ-confined disease and Gleason score less than or equal to 6, and a continuous variable for logarithmic PSA (Table I). This model includes all of the clinical parameters incorporated in the post-RP nomogram (i.e., Kattan-Stephenson nomogram) except for Year of RP and the two components of the Gleason score. The distribution of prior clinical risk shows three distinct nodes (FIG. 8). K-means clustering with 3 centers was used to set the threshold for the low-risk cluster, which comprises approximately 50% of the sample.

TABLE I

Clinical Model

| Clinical Parameter | Coefficient | HR | p-value* |
|---|---|---|---|
| organ-confined disease | −0.827 | 0.44 | $3.4 \times 10^{-6}$ |
| Gleason score ≤ 6 | −0.8734 | 0.42 | $4.2 \times 10^{-7}$ |
| log PSA | 0.6678 | 1.95 | $2.0 \times 10^{-4}$ |

*Cox PH p-value for likelihood ratio test

Statistical Analysis

Clinical parameters were compared between the training and validation sets using the Student's t-test for continuous parameters and Fisher's exact test for categorical parameters. The prior clinical risk of patients for biochemical recurrence after surgery was estimated by a post-RP nomogram score summarizing 7 covariates. K-means clustering of the nomogram score was used to categorize patients as low or high prior clinical risk. Expression data were expressed as the CT (the PCR cycle at which the fluorescence intensity exceeds a predetermined threshold) of each CCG normalized by the mean of the 15 housekeeper genes (Table 12 above).

Poor quality samples were excluded from analysis to eliminate poor quality samples or dubious readings without compromising the integrity of the signature by inadvertently excluding samples with low CCG expression. Accordingly, the thresholds for cleaning or filtering the data were set conservatively. Mean expression levels of the HK genes for each sample, which were higher than those of the CCGs, were used to identify poor quality samples. Technical metrics for the amplification efficiency and excessively high standard deviations of replicates were used to identify unreliable CT measurements. No failures of HK genes, and no more than 1 failure out of 3 replicates for CCGs, were allowed.

The association between biochemical recurrence and CCG expression after adjusting for clinical risk predicted by clinical parameters was evaluated using a Cox proportional hazards model for time-to-recurrence. The proportional hazards assumption of no time-dependence was tested for the full model of the CCG signature plus the binary clinical parameter score with an interaction term, and for the CCG signature only in the clinical risk subsets. It was not significant in either training or validation, indicating that there is no evidence for time-dependence. All of the p-values reported are from a likelihood ratio test comparing the reduced or null model to the model containing the test variable. Kaplan-Meier plots are used to show estimated survival probabilities for subsets of patients; however, p-values are from the Cox likelihood ratio test for the continuous values of the variable. All statistical analyses were performed in S+Version 8.1.1 for Linux (TIBCO Spotfire) or R 2.9.0 (http://www.r-project.org).

Results

We isolated RNA from FFPE tumor sections derived from 442 prostate cancer patients treated with RP. The cohort was split into 195 patients for initial characterization of the signature ("training set") and 247 patients for validation. The clinical parameters of the training and validation cohort are listed in Table J. There were no significant differences after adjusting for multiple comparisons.

TABLE J

Clinical parameters of training and validation patient cohorts

| Clinical Parameter | Training | Validation | p-value | Statistical Analysis |
|---|---|---|---|---|
| Age in years at RP, mean (sd) | 67.5 (6.2) | 66.8 (5.6) | 0.204 | t-test |
| Ethnicity (% non-white) | 3.10% (2 Black, 3 Hispanic, 1 other) | 7.30% (10 Black, 7 Hispanic, 1 other) | 0.058 | Fisher's exact |
| Recurrence | 73/195 (37.4%) | 90/247 (36.4%) | 0.843 | Fisher's exact |
| Days to recurrence, median | 839 | 736 | 0.308 | t-test |
| Days to follow-up, median | 3300 | 3332 | 0.556 | t-test |
| Pre-RP surgery PSA, median | 7.4 | 6.4 | 0.022 | t-test of log |
| Seminal vesicles | 23/195 (11.8%) | 33/247 (13.4%) | 0.668 | Fisher's exact |
| Bladder neck/urethral margin | 12/195 (6.2%) | 16/247 (6.5%) | 1 | Fisher's exact |
| Lymph nodes | 8/195 (4.1%) | 12/247 (4.9%) | 0.819 | Fisher's exact |
| Capsular penetration | 104/195 (53.3%) | 115/247 (46.6%) | 0.18 | Fisher's exact |
| Through the capsule | 66/195 (33.8%) | 73/247 (29.6%) | 0.354 | Fisher's exact |
| Positive margins | 51/195 (26.2%) | 61/247 (24.7%) | 0.742 | Fisher's exact |
| Post-RP Gleason score <7 | 114/195 (58.5%) | 166/247 (67.2%) | 0.06 | Fisher's exact |
| Organ-confined disease | 108/195 (55.4%) | 156/247 (63.2%) | 0.118 | Fisher's exact |
| 10-year PFP (95% CI) | 61% (52%, 69%) | 67% (60%, 73%) | 0.905 | Log-rank test |

To analyze the CCG signature for this study, we tested 126 CCGs on RNA derived from 96 prostate tumors (Table 11). The tumor samples were anonymous and not associated with clinical data. From this set of genes, we selected 31 genes (Panel F) for inclusion in our signature (Table K). The genes were selected based on their technical performance, and by how well each gene correlated with the mean expression level of the entire CCG set, in the 96 anonymous samples.

TABLE K

CCG Signature from Training Set (Panel F)

| Symbol | GeneID |
|---|---|
| ASF1B | 55723 |
| ASPM | 259266 |
| BIRC5 | 332 |
| BUB1B | 701 |
| C18orf24 | 220134 |
| CDC2 | 983 |
| CDC20 | 991 |
| CDCA3 | 83461 |
| CDCA8 | 55143 |
| CDKN3 | 1033 |
| CENPF | 1063 |
| CENPM | 79019 |
| CEP55 | 55165 |
| DLGAP5 | 9787 |
| DTL | 51514 |
| FOXM1 | 2305 |

TABLE K-continued

CCG Signature from Training Set (Panel F)

| Symbol | GeneID |
|---|---|
| KIAA0101 | 9768 |
| KIF11 | 3832 |
| KIF20A | 10112 |
| MCM10 | 55388 |
| NUSAP1 | 51203 |
| ORC6L | 23594 |
| PBK | 55872 |
| PLK1 | 5347 |
| PRC1 | 9055 |
| PTTG1 | 9232 |
| RAD51 | 5888 |
| RAD54L | 8438 |
| RRM2 | 6241 |
| TK1 | 7083 |
| TOP2A | 7153 |

To evaluate the prognostic utility of the CCG signature, we generated expression data on 195 patients in the training set. Since the individual gene expression levels were correlated, we combined them into a signature score by calculating the mean expression for the entire set of 31 genes (Panel F), normalized by 15 housekeepers (Table 12). The CCG score distribution was centered at zero, and each score unit corresponds to a 2-fold change in expression level. Poor quality samples were identified by observing either low expression of housekeeping genes or an unacceptable number of CCG failures, and excluded from the analysis. After applying our exclusion rules, there were 140 samples available for analysis. Association between biochemical recurrence and CCG expression was evaluated using Cox PH models for time to recurrence. A high CCG expression value was predictive of disease recurrence in a univariate analysis (p-value=0.01, Table 17).

Next, we evaluated the prognostic utility of the CCG signature after accounting for clinical parameters known to be associated with recurrence after RP. To account for clinical measures in our analysis, we created a model/nomogram that included preoperative PSA, Gleason score, and evidence of disease outside the prostate (i.e., any of either extracapsular extension, or positive post-surgical pathology on lymph nodes, margins, bladder neck, urethral margin or seminal vesicles). The model was optimized in 443 patients (Tables 13 & 14), including all patients for whom we had clinical data but were not in the validation set, and was a highly significant predictor of recurrence in the training cohort (p-value=$2.5 \times 10^{-11}$). The distribution of the scores from the clinical model contained several modes (FIG. 8), separating high- and low-risk patient groups. Therefore, the score was used subsequently as a binary variable (high or low risk). The low-risk cluster correlated with a consistent set of clinical parameters. Specifically, the vast majority (215/218) had organ-confined disease and Gleason score <7. In addition, 80% had low pre-surgical PSA (<10 ng/ml). Patients in the high-risk cluster (N=225) were more heterogeneous, but tended to have clinical characteristics known to be associated with poor outcome (e.g., Gleason>6 and/or disease through the capsule).

Multivariate analysis of the training set incorporating our binary clinical model, showed evidence for a non-linear interaction between the expression signature and clinical parameters (Table L). To help us understand the nature of this interaction, we generated a scatter plot comparing these predictors (FIG. 8). As evident from the figure, the CCG score proved useful for evaluating recurrence risk in patients defined as low risk by clinical parameters. In fact, even after adjusting for the clinical model within the low risk patients, the CCG signature was a strong predictor of biochemical recurrence (p-value=0.0071).

TABLE L

Statistical Summary

| Subset based on clin. model | 31-gene training N = 195 | | | 31-gene validation N = 247 | | |
|---|---|---|---|---|---|---|
| | Main effect p-value | Interaction p-value | n | Main effect p-value | Interaction p-value | n |
| CCG score | | 0.01 | | 140 | $5.8 \times 10^{-8}$ | | 218 |
| Binary clin. risk (low vs high) | | $5.1 \times 10^{-6}$ | | 133 | $1.1 \times 10^{-10}$ | | 215 |
| CCG score adjusted for binary clin. risk + interaction | | 0.018 | 0.032 | 133 | $8.3 \times 10^{-7}$ | 0.026 | 215 |
| CCG score only | low-risk | 0.0038 | | 54 | $7.5 \times 10^{-5}$ | | 112 |
| Clin. risk score | low-risk | 0.22 | | 54 | 0.044 | | 112 |
| CCG score adjusted for clin. risk (clin. risk vs clin. risk + CCG) | low-risk | 0.0071 | | 54 | 0.00019 | | 112 |
| CCG score | high-risk | 0.48 | | 79 | $5.8 \times 10^{-4}$ | | 103 |
| Clin. risk score | high-risk | $2.8 \times 10^{-6}$ | | 79 | 0.0076 | | 103 |
| CCG score adjusted for clin. risk (clin. risk vs clin. risk + CCG) | high-risk | 0.51 | | 79 | 0.0026 | | 103 |

Figure 12:
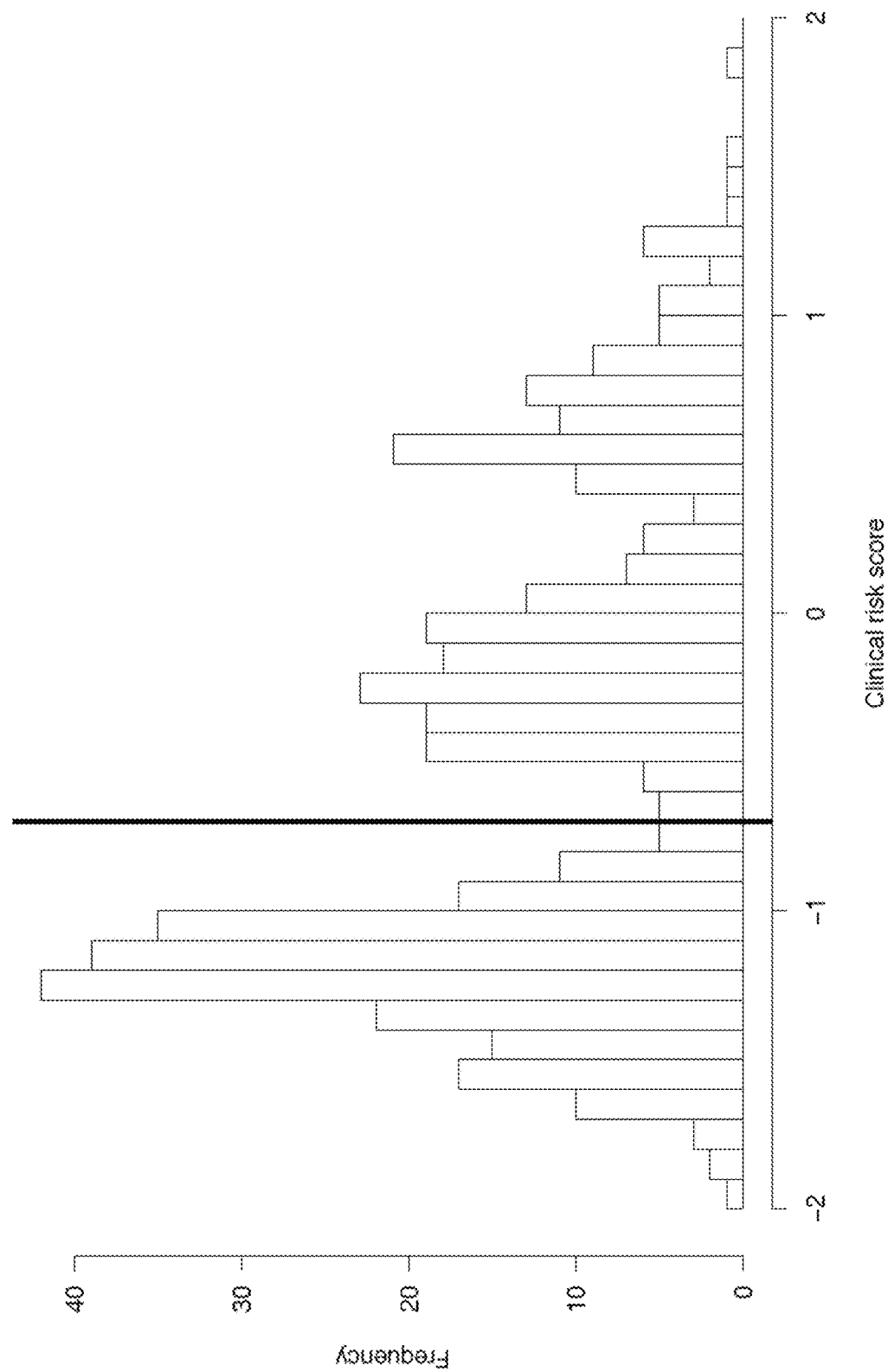
FIG. 12 illustrates the distribution of clinical risk score in 443 patients studied in Example 5. The dark vertical line represents the threshold chosen by KM means to divide low- and high-risk patients and used throughout this study.
Figure 13:
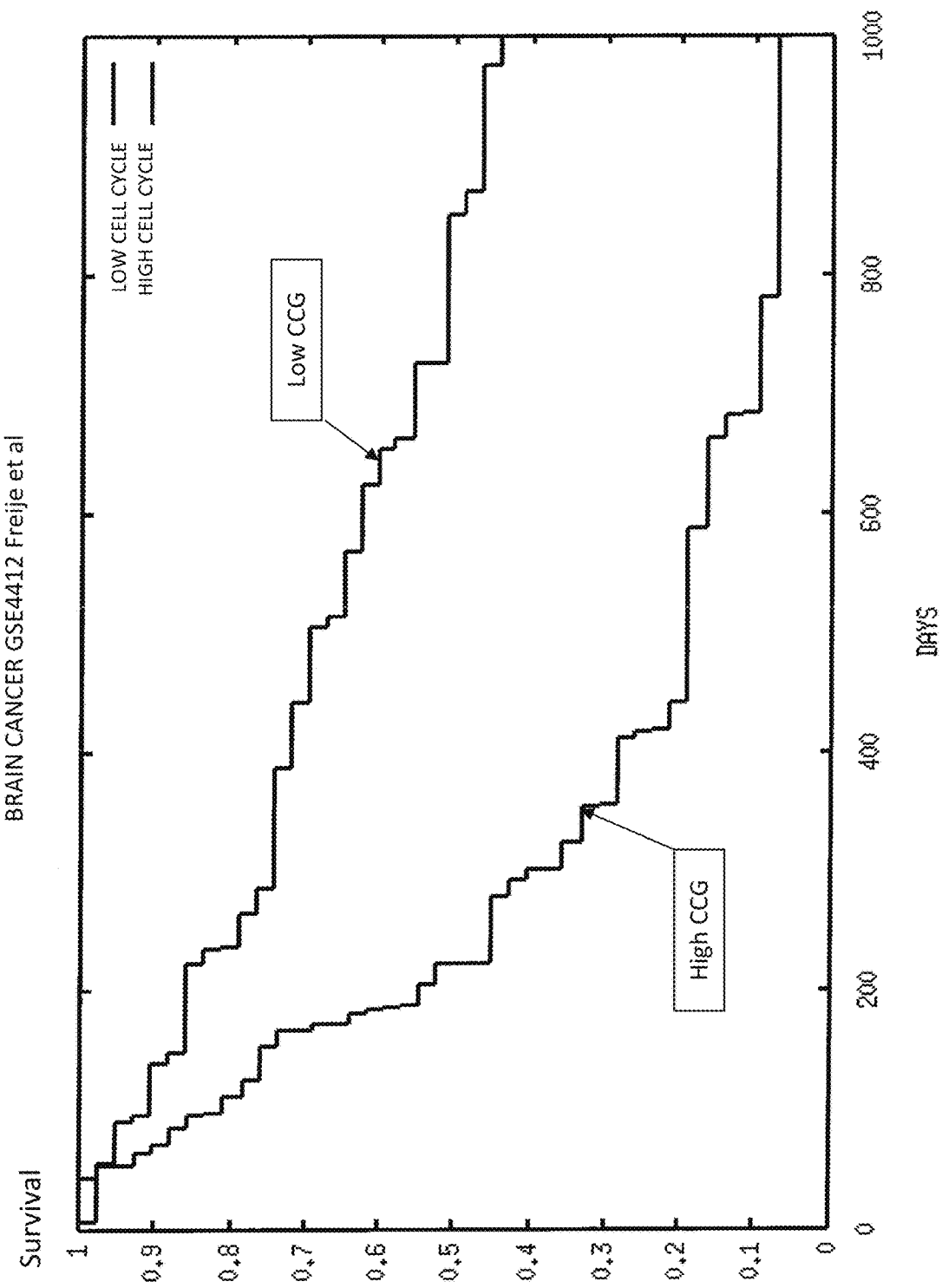
FIG. 13 illustrates the correlation between CCP score and survival in brain cancer.
Figure 14:
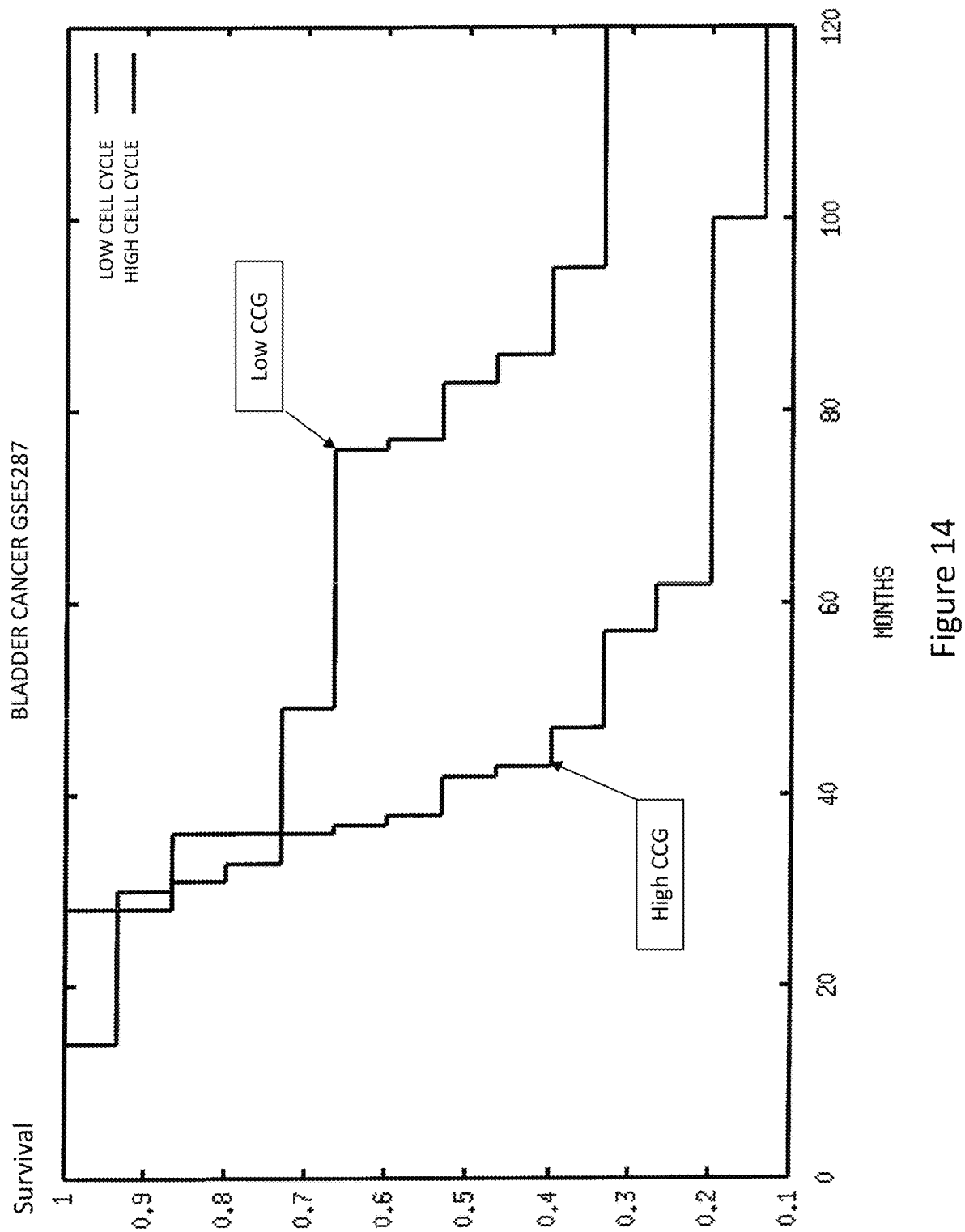
FIG. 14 illustrates the correlation between CCP score and survival in bladder cancer.
Figure 15:
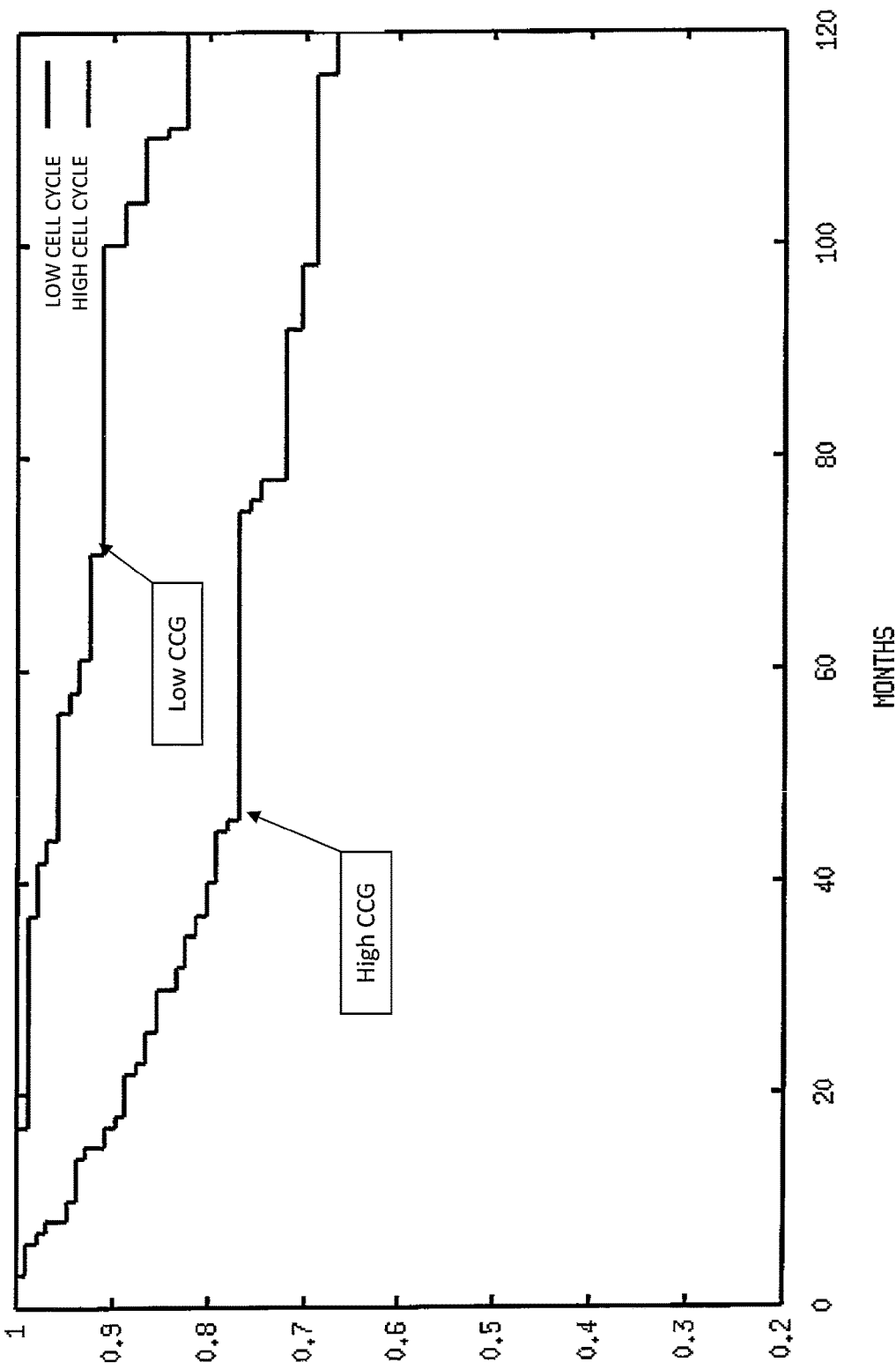
FIG. 15 illustrates the correlation between CCP score and survival in breast cancer.
Figure 16:
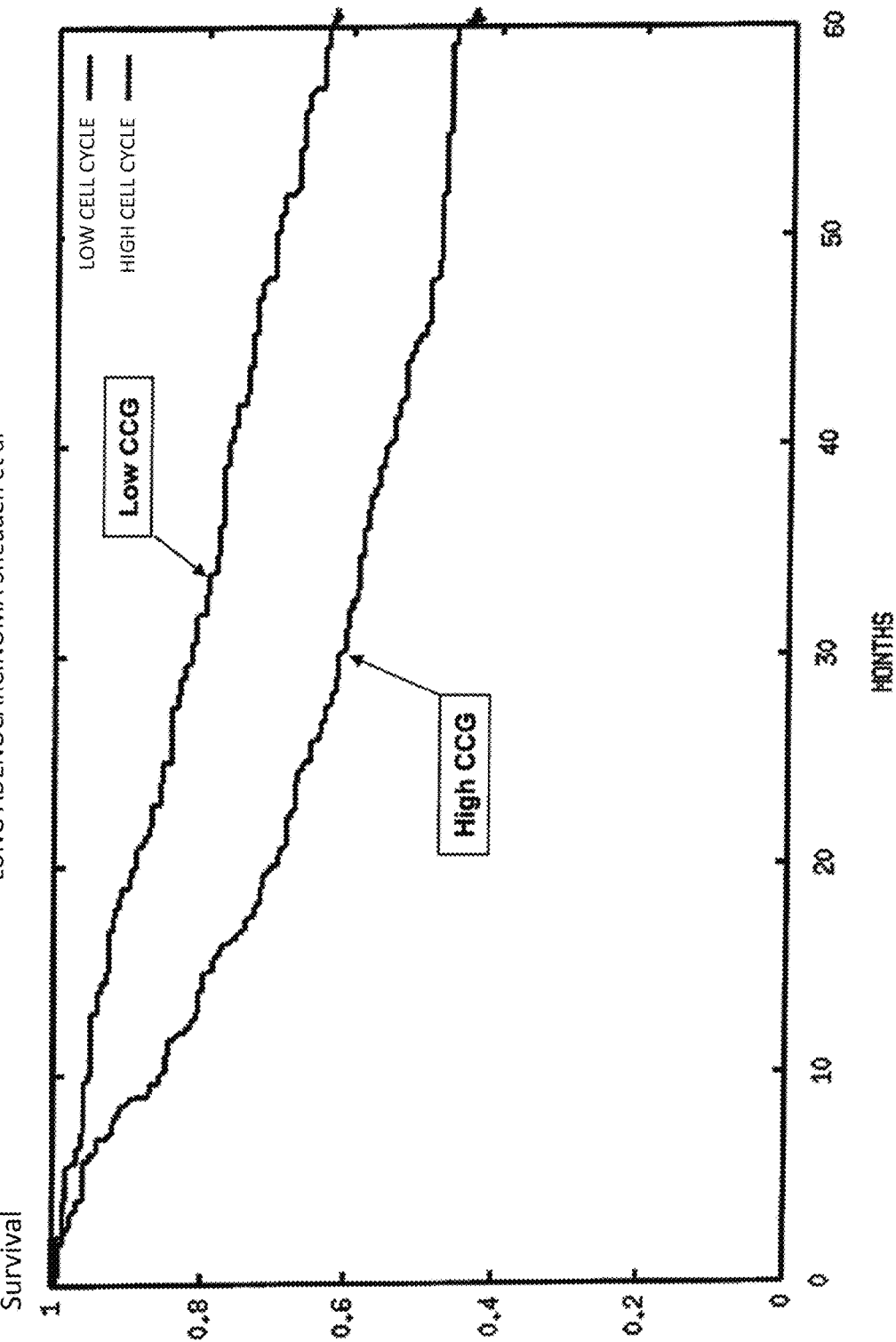
FIG. 16 illustrates the correlation between CCP score and survival in lung cancer.

We used our training data in the scatter plot to establish an optimized threshold score of −0.16 for the CCG signature (the mean CCG score is zero). FIG. 12 shows this threshold applied to the 443 patients studied in this example. Forty percent of low-risk patients fall below this threshold, and it was selected so that there were no recurrences 10-years after RP (i.e., negative predictive value (NPV) of 100%). As a result of establishing threshold values for both the clinical model and CCG score, the scatter plot was divided into four sections with recurrence rates of 0% (low CCG) and 26% (high CCG) for low-risk patients; and 60% (low CCG) and 50% for high-risk patients.

Next, we generated CCG expression data on 247 patients in our validation cohort. Thirty-two samples were eliminated from further analysis according to the exclusion rules developed on the training cohort. Panel F was a significant predictor of biochemical recurrence in a univariate analysis (p-value=$5.8 \times 10^{-8}$, Table L). After adjusting for the binary clinical model, the CCG signature was highly predictive of recurrence in the validation cohort (p-value $8.3 \times 10^{-7}$), and as in the training set, there was significant evidence for a non-linear interaction between variables. The CCG signature was informative across the entire spectrum of clinically defined risk (Table 17). In terms of validating the training results, the p-value for association between recurrence and CCG signature in low-risk patients was $1.9 \times 10^{-4}$.

Figure 9:
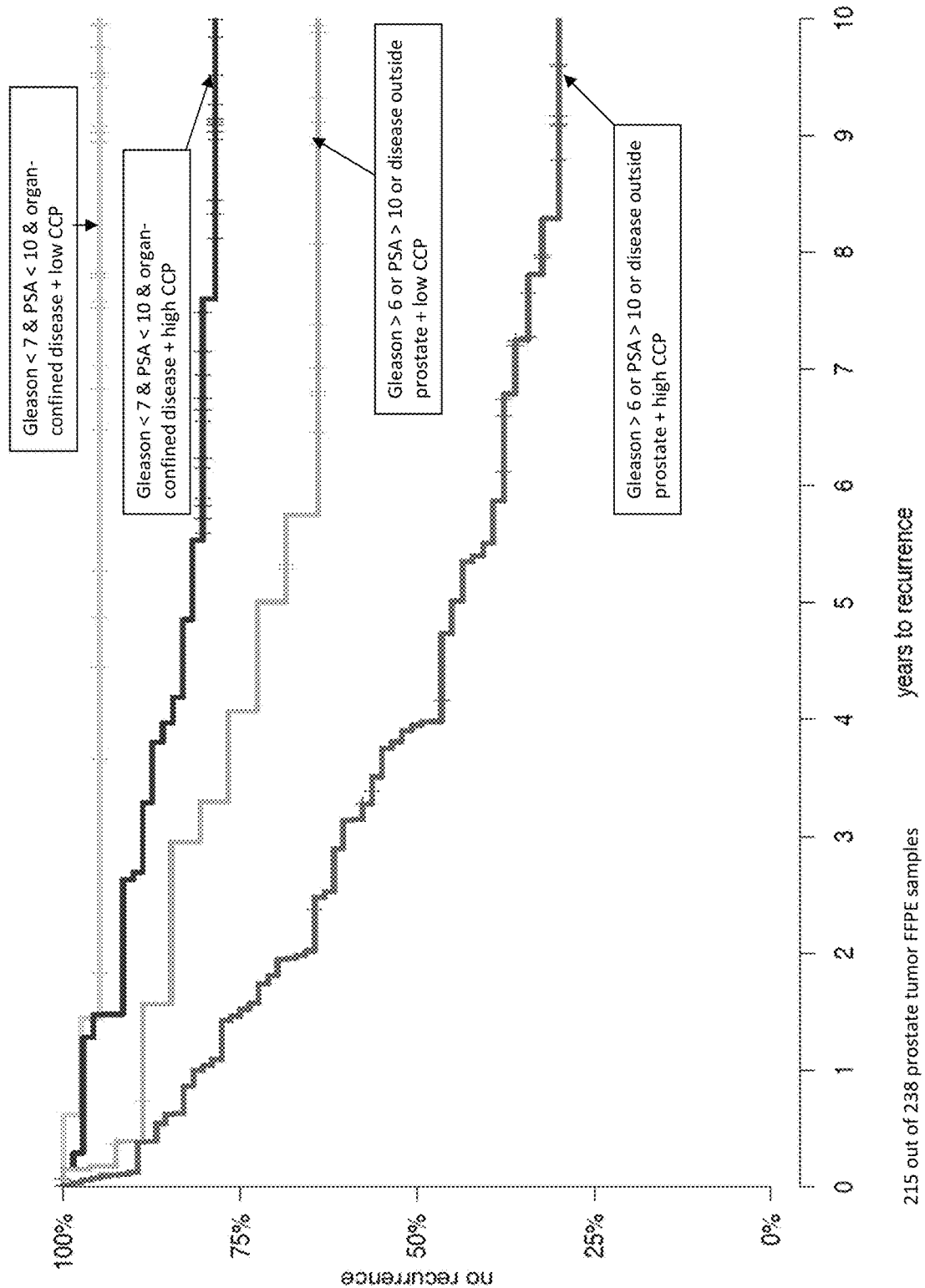
FIG. 9 illustrates, from Example 5, the CCG threshold derived from analysis of the training cohort to the validation data set, with the CCG signature score effectively subdividing patients identified as low-risk using clinical parameters into patients with very low recurrence rates and a higher risk of recurrence.
Figure 10:
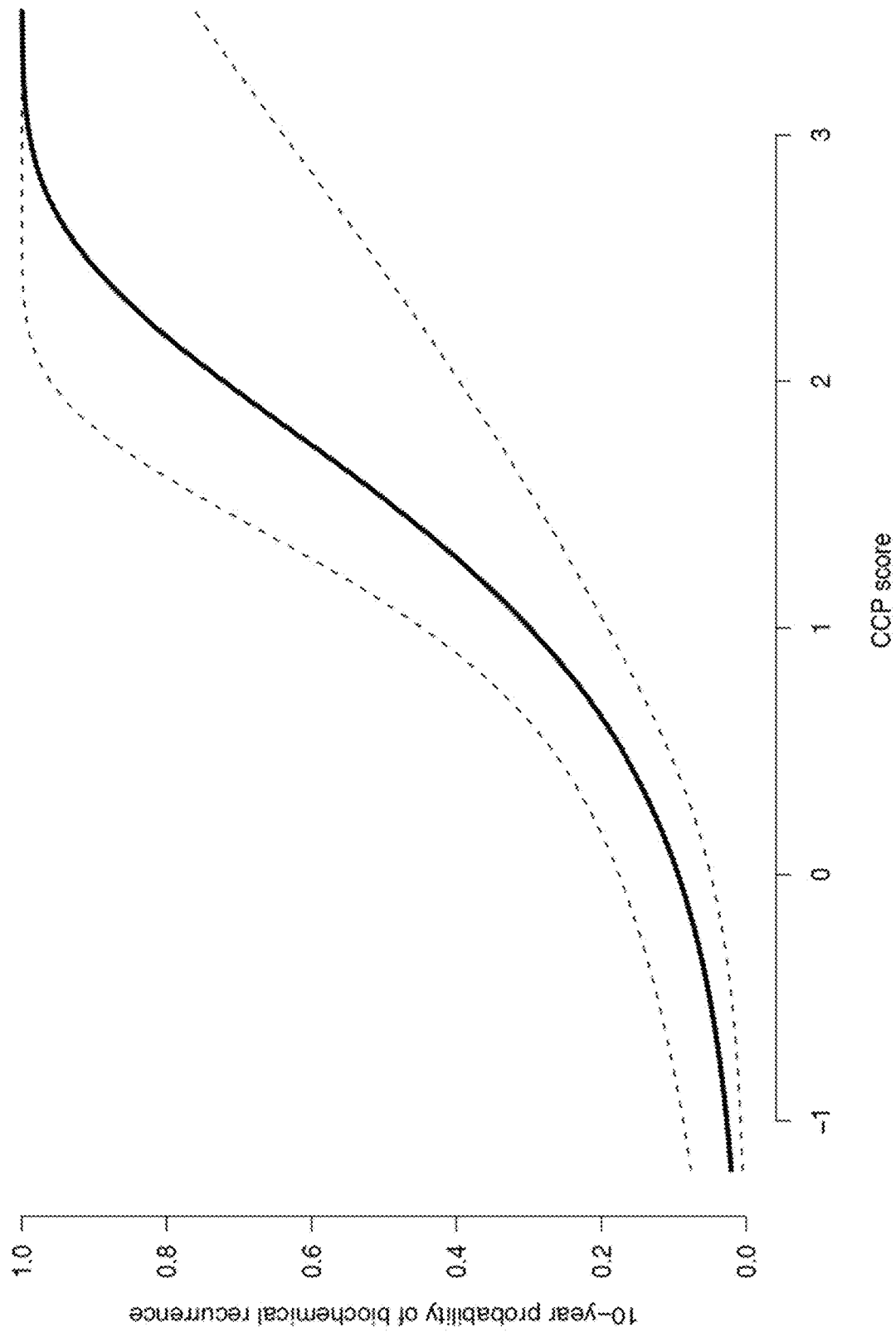
FIG. 10 illustrates the predicted recurrence rate versus CCG score for patients in the validation cohort of Example 5.
Figure 11:
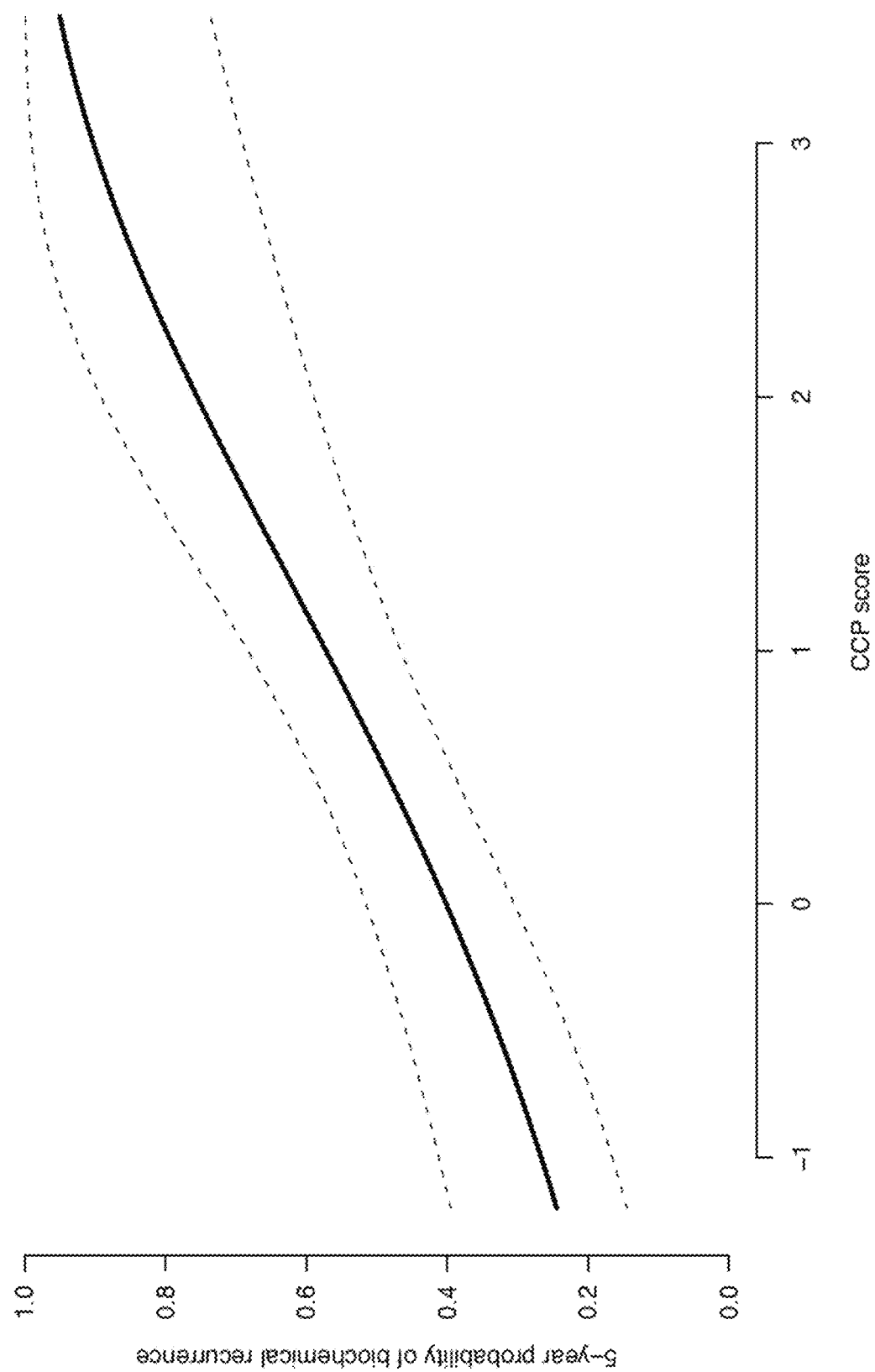
FIG. 11 illustrates the predicted recurrence rate versus CCG score for patients in the validation cohort of Example 5.

We applied the CCG threshold derived from our analysis of the training cohort to our validation data set (FIG. 9). Low risk patients with CCG scores below the threshold had a 10-year predicted recurrence rate of 5% (equivalent to validated NPV of 0.95). Overall, the combination of CCG score and clinical parameters divided the cohort into four groups with 10 year predicted recurrence rates of 5%, 22%, 36% and 70% (Table M). The predicted recurrence rate versus CCG score for patients in the validation cohort is shown in FIGS. 10 & 11.

TABLE M

Summary of recurrence rates in validation cohort defined by clinical risk and CCG score

| | | 10-year recurrence rate | |
|---|---|---|---|
| Clinical risk | CCG score | Kaplan-Meier estimate | n |
| low | low | 0.05 | 39 |
| low | high | 0.22 | 73 |
| high | low | 0.36 | 27 |
| high | high | 0.7 | 76 |

We tested our validated threshold versus various definitions of low-risk patients (Table N). The signature score was a significant prognostic indicator in a variety of low-risk clinical definitions, and depending on definition, generated a 10-year predicted recurrence rate of 0.05 to 0.10.

TABLE N

NPV of CCG signature in other definitions of low-risk patients

| | low CCP* | | |
|---|---|---|---|
| Clinical definition of low risk | 10-yr predicted recurrence** | n | p-value*** |
| Organ-confined disease and Gleason score < 7 & PSA < 10 | 0.05 | 39 | $9.4 \times 10^{-4}$ |
| Organ-confined disease and Gleason score < 7 | 0.08 | 40 | $5.8 \times 10^{-3}$ |
| Organ-confined disease and Gleason score < 8 & PSA < 10 | 0.07 | 42 | $8.7 \times 10^{-4}$ |

TABLE N-continued

NPV of CCG signature in other definitions of low-risk patients

| | low CCP* | | |
|---|---|---|---|
| Clinical definition of low risk | 10-yr predicted recurrence** | n | p-value*** |
| Organ-confined disease and Gleason score < 8 | 0.1 | 43 | $4.1 \times 10^{-3}$ |
| Organ-confined disease only | 0.1 | 44 | $2.4 \times 10^{-3}$ |

*defined by validated threshold
**Kaplan-Meier estimates
***for difference between KM estimates for low and high risk adjusted by Greenwood variance.

Comment

We have developed and validated a prognostic molecular signature for prostate cancer. The signature is based on measuring mRNA expression levels of cell cycle genes (CCGs). By definition, expression of CCGs is regulated as a function of cell cycle stage. That is, they are turned on at specific cell cycle stages, so that actively growing cells have higher expression levels of CCG than quiescent cells. Presumably this fact underlies the signature's ability to predict cancer progression. Without wishing to be bound by theory, it is thought that by measuring the expression levels of CCG we are indirectly measuring the growth rate and inherent aggressiveness of the tumor, which ultimately impacts on the likelihood of prostate cancer recurrence after prostatectomy.

There is an important distinction between this study and many others that have attempted to generate prognostic molecular signatures. Often, similar studies begin with a very large number of candidate biomarkers (sometimes exceeding 1000's of genes) that are then evaluated for association with a clinical phenotype of interest. This approach may at times suffer from inherent multiple testing which can make the significance of the derived signature uncertain. Here we have tested a single hypothesis: CCG would be prognostic in prostate cancer (in fact we selected genes based on their correlation with CCG expression, not based on association with recurrence). And since CCG expression is correlated, we combined the expression data into a predictive signature by determining the mean expression value of all the genes in the signature. The simplicity of this approach, biologically and computationally, supports the view that the central claim of this study is likely to be highly robust, and replicated in subsequent studies.

The CCG signature (Panel F) is independently predictive and adds significantly to the predictive power of the clinical parameters typically employed to predict disease recurrence after surgery. This is true in both our training and validation cohorts.

The signature is immediately useful for defining the risk of patients who present with low-risk clinical parameters. Here, we essentially defined low-risk as Gleason<7, PSA<10 and organ-confined disease. The CCG signature score effectively subdivides the low-risk group into patients with very low recurrence rates (5%), and a higher risk of recurrence (22%) (FIG. 9 & Table M). This is the most dramatic effect of the molecular signature—accurately redefining the risk of patients previously defined as low-risk based on clinical parameters. It is noteworthy that within this patient subpopulation (i.e., patients defined as low-risk based on clinical parameters) clinical parameters are not particularly prognostic (see Table L). Therefore as a diagnostic test, the signature could be useful for a large number of patients. In this study, nearly 60% of the cohort was characterized as low-risk and 40% of those are expected to have low CCG scores. Therefore, the CCG signature can predict indolent disease in a quarter of the patients who have previously been identified as high-risk (and therefore identified as candidates for radical prostatectomy). Finally, the validation data in particular suggests that the CCG signature may be useful for defining risk in all patients. Specifically, it helped to divide patients defined as high-risk according to clinical parameters into those with 30% and 70% recurrence rates (Table M).

The combination of clinical parameters and CCG signature enables physicians to more accurately predict risk of surgical failure, and therefore, identify the appropriate course of therapeutic intervention. As we have shown, the signature dramatically improves the recurrence prediction for patients who present with general clinical parameters of non-aggressive disease (Table N). Within this clinical subgroup, patients with low CCG scores would benefit from the absolute reassurance that no further treatment is indicated. Conversely, the high CCG group may warrant immediate intervention. Patients with unfavorable post-surgical clinical parameters benefit from adjuvant radiation therapy. Therefore the CCG signature should predict the efficacy of adjuvant radiation for patients with low-risk clinical characteristics and high CCG scores. In the validation cohort, patients with high CCG scores and disease beyond the prostate have a recurrence rate of 70%, which should clearly identify patients who are good candidates for adjuvant radiation. Thus the combination of clinical parameters and CCG signature clearly leads to more accurately defined patient risk, which should enable a more intelligent assessment of the need for further treatment.

Example 6

Some of the CCGs panels described herein were further evaluated for their ability to prognose additional cancers. Panels C, D, and F were found to be prognostic to varying degrees in bladder, brain, breast, and lung cancer.

Methods

Gene expression and patient data was obtained from the following publicly available datasets: GSE7390 (Desmedt et al., CLIN. CANCER RES. (2007) 13:3207-14; PMID 17545524); GSE11121 (Schmidt et al., CANCER RES. (2008) 68:5405-13; PMID 18593943); GSE8894 (Son et al.; no publication); Shedden (Shedden et al., NATURE MED. (2008) 14:822; PMID 18641660); GSE4412 (Freije et al., CANCER RES. (2004) 64:6503-10; PMID 15374961); GSE4271 (Phillips et al., CANCER CELL (2006) 9:157-73; PMID 16530701); GSE5287 (Als et al., CLIN. CANCER RES. (2007) 13:4407-14; PMID 17671123). Each of these datasets has an associated detailed description of the experimental procedures used in gathering expression and patient data. The expression microarrays used to generate each dataset are summarized below in Table O.

TABLE O

| Dataset | Array |
|---|---|
| GSE7390 | Affymetrix U133 A |
| GSE11121 | Affymetrix U133 A |
| GSE8894 | Affymetrix U133 plus 2.0 |
| Shedden | Affymetrix U133 A |

TABLE O-continued

| Dataset | Array |
|---|---|
| GSE4412 | Affymetrix U133 A and B |
| GSE4271 | Affymetrix U133 A and B |
| GSE5287 | Affymetrix U133 A |

Expression data for each of the genes in Panels C, D and F was gathered from these datasets and the mean expression level for each Panel was determined for each patient, whose clinical outcome was known (e.g., recurrence, progression, progression-free survival, overall survival, etc.). CCG score is an average expression of the genes in a panel. If a gene is represented by more than one probe set on the array, the gene expression is an average expression of all the probe sets representing the gene. The association between CCG score and survival or disease recurrence was tested using univariate and multivariate Cox proportional hazard model. Multivariate analysis was performed when relevant clinical parameters (grade in brain cancer, stage in lung cancer, NPI in breast cancer) were available.

Results

As shown in Table P below, each Panel, in univariate analysis, was a prognostic factor in each of the cancers analyzed.

TABLE P

| | | p-value | | |
|---|---|---|---|---|
| Cancer Type | Dataset | Panel C | Panel F | Panel B |
| ER positive breast cancer | GSE7390 | $2.4 \times 10^{-3}$ | $2.3 \times 10^{-3}$ | $4.3 \times 10^{-3}$ |
| ER positive breast cancer | GSE11121 | $1.2 \times 10^{-5}$ | $8.7 \times 10^{-6}$ | $1.5 \times 10^{-5}$ |
| Lung adenocarcinoma | GSE8894 | $2.0 \times 10^{-3}$ | $2.5 \times 10^{-3}$ | $5.6 \times 10^{-3}$ |
| Lung adenocarcinoma | Shedden | $1.3 \times 10^{-7}$ | $2.6 \times 10^{-7}$ | $2.2 \times 10^{-7}$ |
| Brain cancer | GSE4412 | $3.2 \times 10^{-5}$ | $2.2 \times 10^{-5}$ | $9.0 \times 10^{-5}$ |
| Brain cancer | GSE4271 | $1.3 \times 10^{-3}$ | $1.0 \times 10^{-3}$ | $2.8 \times 10^{-4}$ |
| Bladder cancer | GSE5287 | $6.4 \times 10^{-2}$ | $5.0 \times 10^{-2}$ | $8.6 \times 10^{-2}$ |

As shown in Table Q below, each Panel was also prognostic in multivariate analysis when combined with at least one clinical parameter (or nomogram).

TABLE Q

| | | p-value | | | Additional Clinical |
|---|---|---|---|---|---|
| Cancer Type | Dataset | Panel C | Panel F | Panel B | Variable/Nomogram |
| Brain cancer | GSE4271 | 0.022 | 0.017 | 0.0065 | grade |
| Lung adenocarcinoma | Shedden | $1 \times 10^{-6}$ | $2.1 \times 10^{-6}$ | $1.4 \times 10^{-6}$ | stage |
| ER positive breast cancer | GSE7390 | 0.0077 | 0.0064 | 0.011 | Nottingham Prognostic Index (NPI) |
| ER positive breast cancer | GSE11121 | 0.0041 | 0.0027 | 0.0045 | NPI |

Example 7

Figure 18:
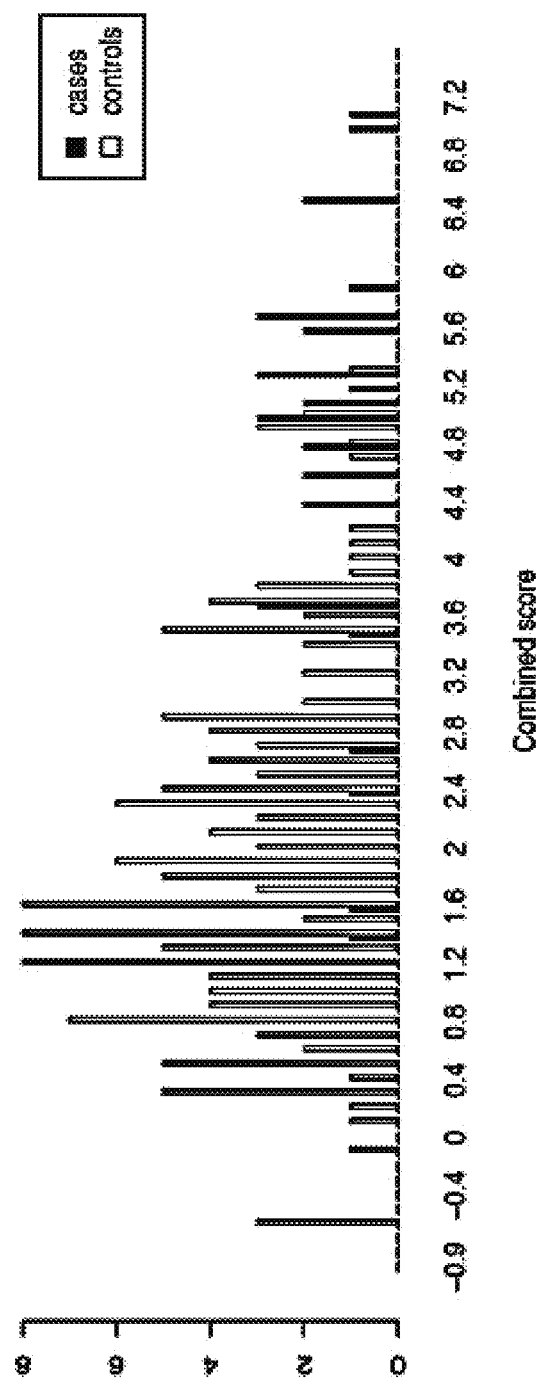
FIG. 18 shows the distribution of cases and controls by combined score in Example 7.

For the present experiment, cases were defined as men who died from prostate cancer within 5 years. Controls were defined as men who lived for at least 10 years. Next, cases and controls were rank ordered by combined score. The distribution of cases and controls by combined score is given in FIG. 18.

We selected 25 cases with the lowest combined scores and 31 controls with the highest combined scores for expression analysis of the transcriptome using Illumina™ Hi-Seq 2000™. RNA isolation and library construction were done according to the manufacture's protocol.

Statistical Analysis

RNA expression is measured for all transcript products (TP). Raw counts were normalized by the $75^{111}$ percentile of all TP's for each sample and run, then converted to the base 2 logarithm. Multiple TP's for the same gene locus are combined into a unified gene (UG).

RNA expression data for each sample were compiled from the TP's for the set of loci with single TP's, and UG's from the set of loci with multiple TP's. In order to be able to include transcripts with zero counts, we used the base 2 logarithm of the normalized counts+1 for the analysis.

The primary analysis was designed to find associations between RNA expression and case-control status. Kolmogorov-Smirnov tests were performed at each locus, and the results were ranked by p-value. In addition, each of the candidate genes was tested in a logistic regression model including CCP score, serum PSA, and Gleason.

Results

Figure 19:
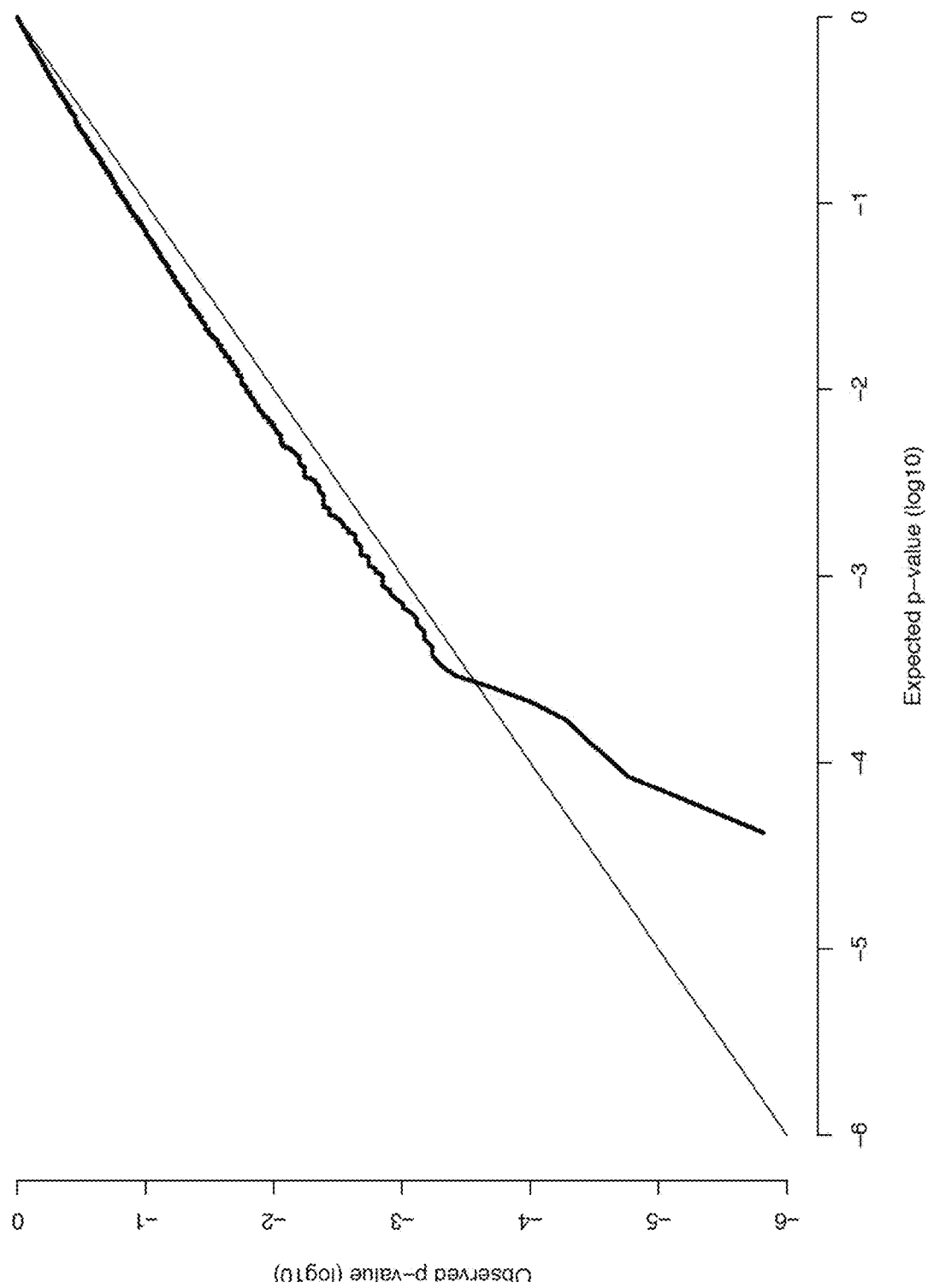
FIG. 19 shows the distribution of observed p-values compared to the expected (given no association) in Example 7.

Based on the analysis of the whole transcriptome, we identified six candidate genes (Table R) as being associated with prostate cancer death after adjustment for CCP score and clinical parameters. All of these genes had a p-value of less than 0.001 in the multivariate model. The distribution of observed p-values compared to the expected (given no association) is given in FIG. 19. Some p-values were more significantly associated with prostate cancer death than expected by chance.

TABLE R

| Panel H | | | |
|---|---|---|---|
| Gene # | Gene Symbol | Gene ID | p-value |
| 1 | KLK3 | 354 | $2 \times 10^{-6}$ |
| 2 | STX4 | 6810 | $1.7 \times 10^{-5}$ |
| 3 | TAF5L | 27097 | $3.3 \times 10^{-5}$ |
| 4 | GTPB5 | 26164 | $5.2 \times 10^{-5}$ |

TABLE R-continued

| Panel H | | | |
|---|---|---|---|
| Gene # | Gene Symbol | Gene ID | p-value |
| 5 | SIRT3 | 23410 | $9.7 \times 10^{-5}$ |
| 6 | EIF3D | 8664 | $1.97 \times 10^{-4}$ |

With slightly different parameters, the following genes were identified as the best predictors (Figure S):

TABLE S

Panel H

| Gene # | Gene Symbol | Gene ID | p-value |
|---|---|---|---|
| 1 | KLK3 | 354 | $1.7 \times 10^{-5}$ |
| 2 | GTPBP5 | 26164 | $1.4 \times 10^{-4}$ |
| 3 | LOC100126784 | 100126784 | $2.2 \times 10^{-4}$ |
| 4 | ABCG1 | 9619 | $3.93 \times 10^{-4}$ |
| 5 | CYP1B1-AS1 | 1545 | $3.96 \times 10^{-4}$ |
| 6 | CECR6 | 27439 | $4.8 \times 10^{-4}$ |

Figure 20:
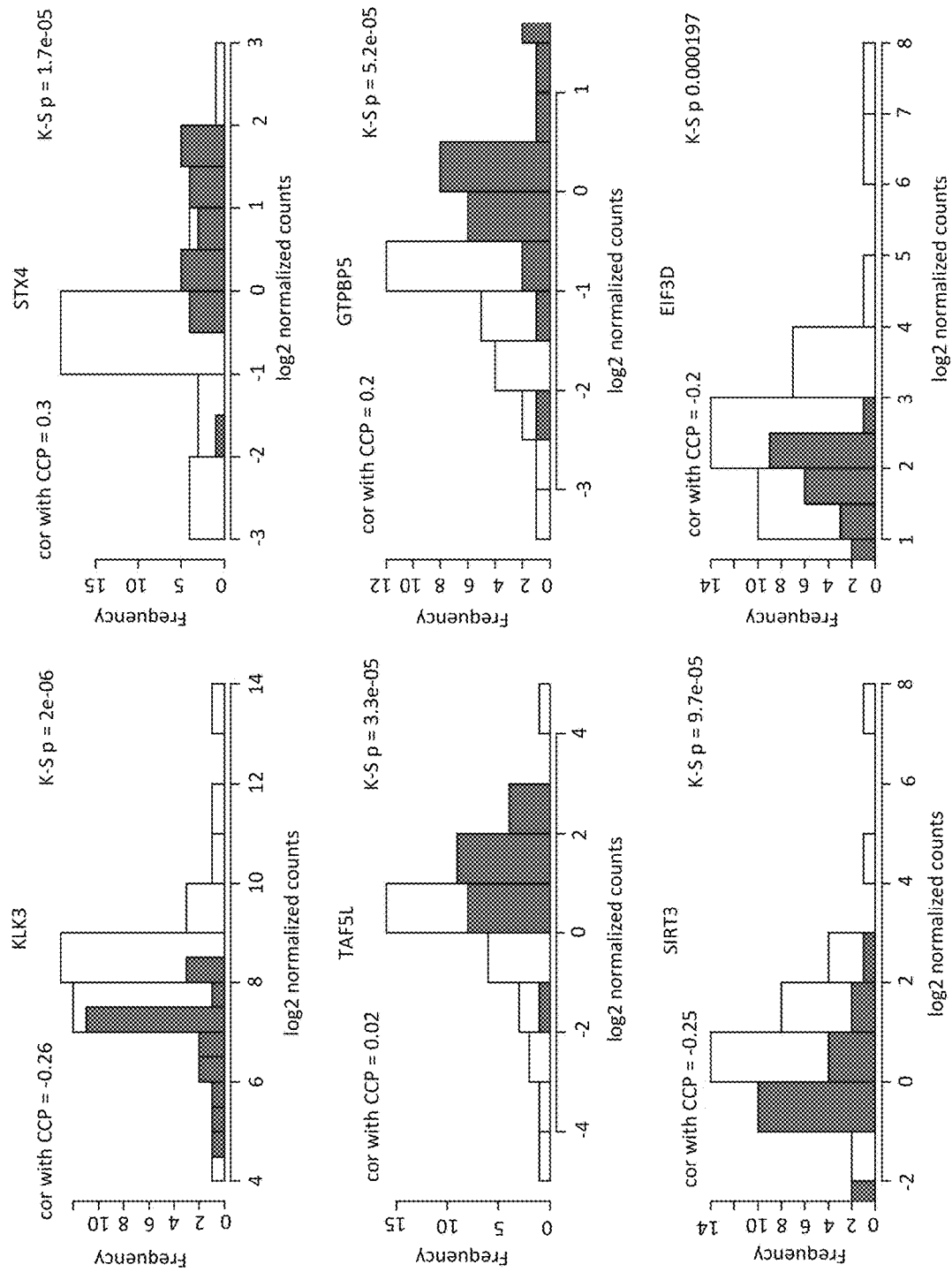
FIG. 20 shows the RNA expression profiles underlying the significant p-values of six of the genes highlighted in Example 7.
Figure 21:
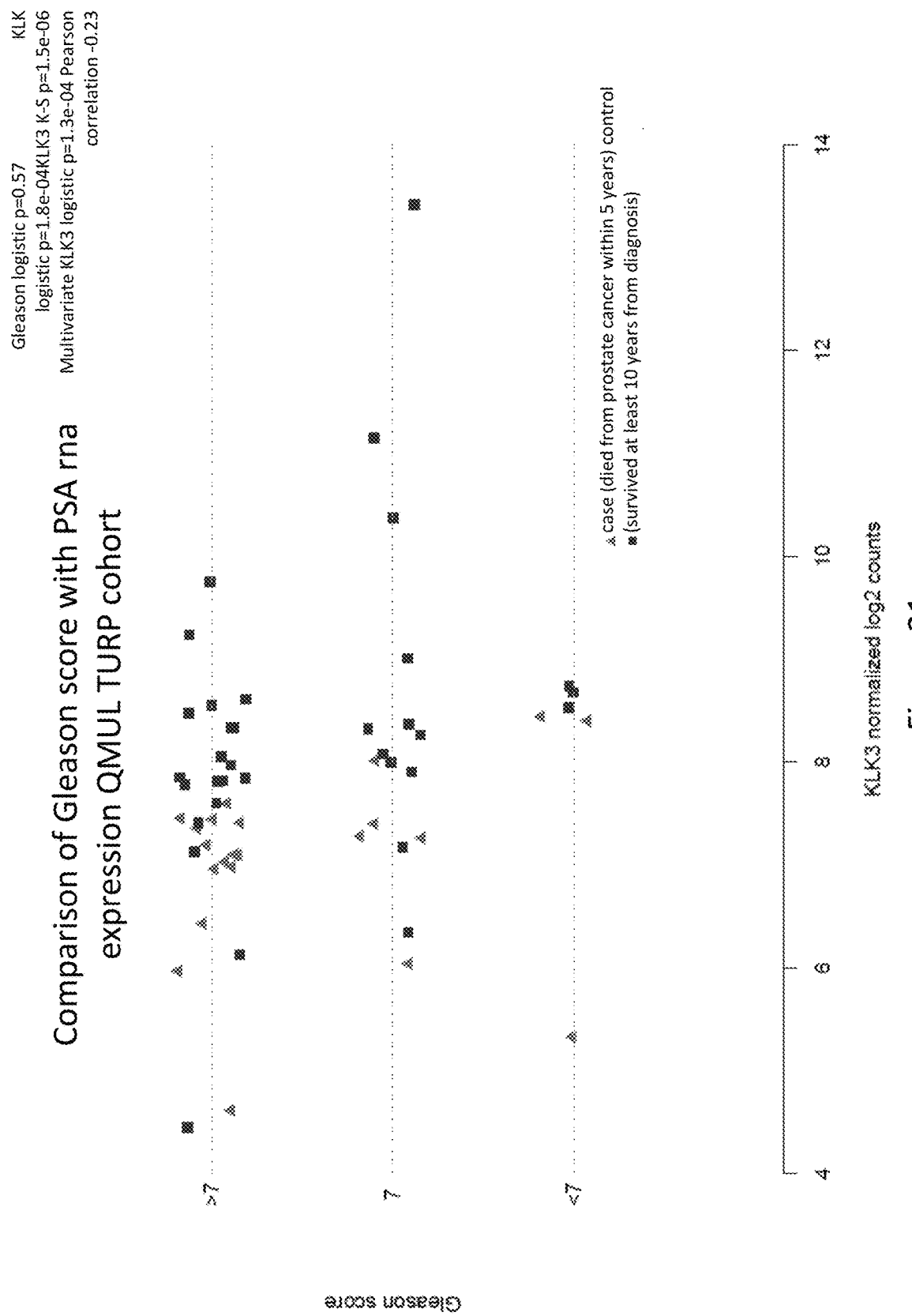
FIG. 21 shows how KLK3 RNA expression levels predict case-control status independently of Gleason in Example 7.
Figure 22:
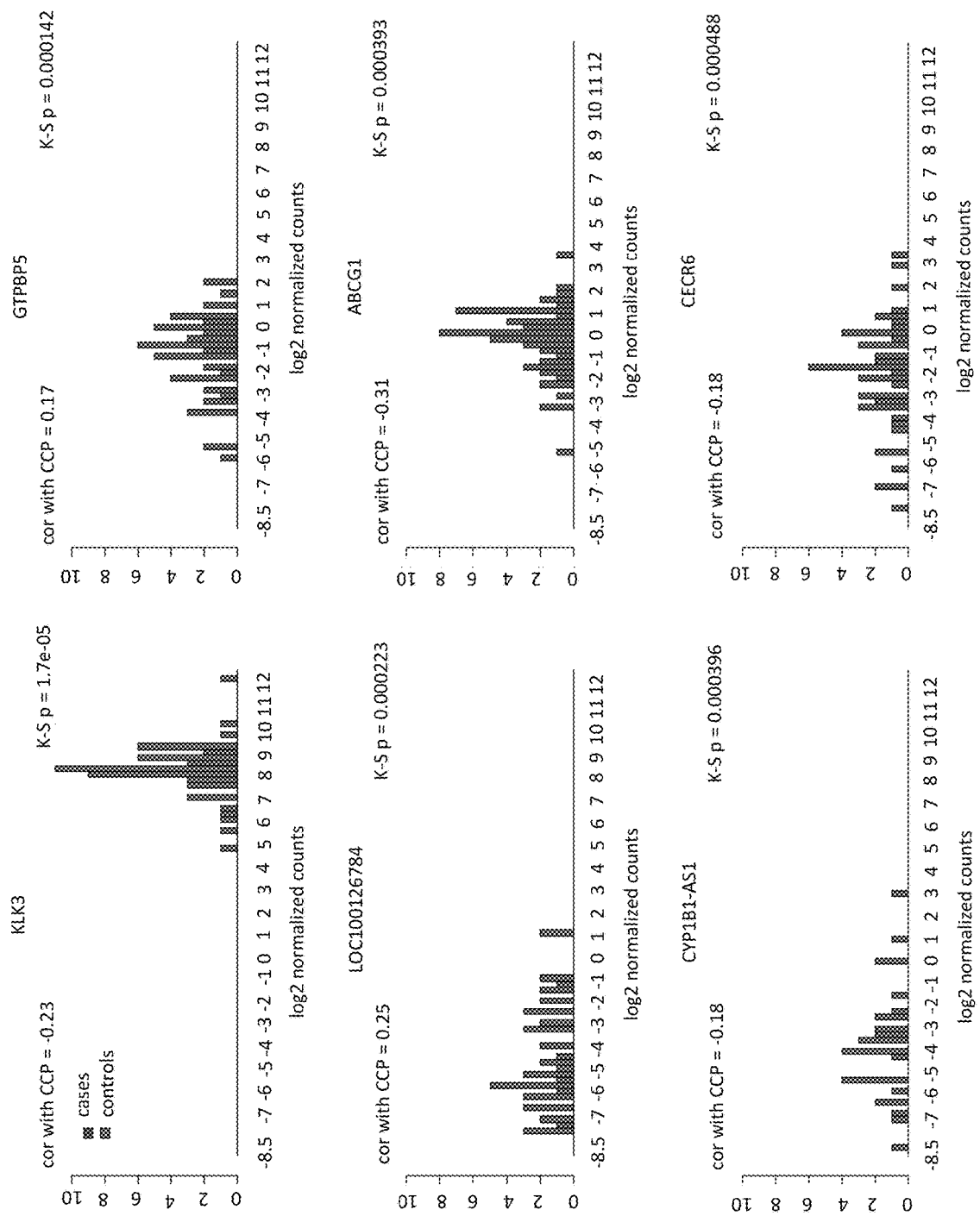
FIG. 22 shows the RNA expression profiles underlying the significant p-values of six of the genes highlighted in Example 7.

The RNA expression profiles underlying the significant p-values are given in FIGS. 20 & 22. The highest ranked gene was KLK3. Low levels of KLK3 RNA were associated with poor prognosis. KLK3 RNA expression levels were uncorrelated with serum PSA (Pearson correlation coefficient with log of serum PSA=0.13, p-value=0.33). KLK3 RNA expression predicts case control status independently of Gleason (FIG. 21).

Example 8

Panel F was combined with certain clinical features and/or clinical risk stratifiers and the combination(s) was shown to predict risk of prostate cancer-specific death in biopsy samples.

Patients and Samples

Samples were analyzed using the process described in the preceding Examples (in some cases data was used from the actual sample analysis described in the preceding Examples). Data from prostate cancer patient samples were combined from six different cohorts, designated P1, P2, P3, P4, P5A, P5B, and P7 (P5A and P5B were distinguishable subsets (radical prostatectomy v. radiation) of a larger P5 cohort). Characteristics of these cohorts are given in Table T.

TABLE T

| Cohort # | Patients Clinical | Patients Total | Sample Type | Treatment | Outcome Measure |
|---|---|---|---|---|---|
| P1 | 200 | 337 | TURP | conservative (active surveillance) | death from prostate cancer |
| P2 | 180 | 349 | needle biopsy | conservative (active surveillance) | death from prostate cancer |
| P3 | 353 | 353 | surgical tumor | radical prostatectomy | biochemical recurrence |
| P4 | 388 | 413 | surgical tumor | radical prostatectomy | biochemical recurrence |
| P5A | 131 | 179 | needle biopsy | radical prostatectomy | biochemical recurrence |
| P5B | 118 | 142 | needle biopsy | radiation | biochemical recurrence |
| P7 | 272 | 281 | needle biopsy | unknown | unknown |

Patients were only included if they had all the clinical information required to calculate the CAPRA score. Patients who could be assigned to an AUA risk category but who did not have a CAPRA score were also excluded from any analysis. Time-to-event data were censored at 10 years in all cohorts. Inception was date of diagnosis for patients with TURP and needle biopsy samples, and date of surgery for patients with surgical tumor samples. Times were recorded as days for all studies except P1, P5A & P5B, which were in months, and converted to days by a factor of 365.25/12. For patients whose clinical stage did not include the substage, the following conversions were made: T1 to T1A, T2 to T2A, and T3 to T3A.

Three different subsets were defined to train the Combined score (Training), validate the Combined score and estimate risk of prostate cancer death (Validation), and characterize the distribution of the CCP score in the US clinical population (US clinical). These are presented in Table U.

TABLE U

| Training | Validation | US clinical |
|---|---|---|
| P1 | | |
| | P2 | |
| P3 | | P3 |
| P4 | | P4 |
| | | P5A |
| P5B | | P5B |
| | | P7 |
| N = 1059 | N = 180 | N = 1219 |

AUA Risk Stratification

The AUA nomogram/guideline stratifies the risk of PSA failure and prostate cancer-specific mortality following radical prostatectomy, external beam radiotherapy, or interstitial prostate brachytherapy. See American Urological Association, *Guideline for the Management of Clinically Localized Prostate Cancer:* 2007 *Update* (available at AUA website). Each patient's risk category was determined according to guidelines interpreted below (AUA Guidelines 2007, page 10). Individuals with clinical stage T1A or TIB, or clinical stage T3, were assigned to risk categories even though the AUA guidelines are technically not applicable at these stages.

Low: PSA≤10 ng/mL AND Gleason score≤6 AND clinical stage≤T2A

Intermediate: (PSA>10 and ≤20 ng/mL OR Gleason score=7 OR clinical stage=T2B) AND not qualifying for High Risk High: PSA>20 ng/mL OR Gleason score>7 OR clinical stage≥T2C CAPRA Nomogram CAPRA is a preoperative predictor of disease recurrence after radical prostatectomy. See Cooperberg et al., J. UROL. (2005) 173:1938-1942. The scores (0 to 10) were calculated according to a point system, interpreted below (see Cooperberg et al. at Table 1). Patients with clinical stage T3B or higher were assigned a score although technically the scoring system did not apply. Patients with PSA≤2 ng/mL were included in the lowest interval, which is (2, 6] in Cooperberg et al. Clinical stage and Gleason grades were used instead of pathological data in the post-prostatectomy cohorts, although the CCP score was from a sample of the surgical tumor instead of a biopsy.

PSA (ng/mL)

0 [0, 6]
1 (6, 10]
2 (10, 20]
3 (20, 30]
4 (30, 100]
Excluded patients with PSA >100
as per study inclusion criteria.
Clinical stage 0 T1/T2
1 ≥ T3A
Percent positive cores 0 < 34%
1 ≥ 34%
Gleason score 0 Primary 1-3; Secondary 1-3
1 Primary 1-3; Secondary 4-5
3 Primary 4-5; Secondary 1-5
Gleason score for patients with
component grades 0 Gleason < 7
1 Gleason 7
3 Gleason > 7
Age at diagnosis 0 <50 years
1 ≥50 years Developing the Combined Score The Combined score was fit in the training set by a Cox Proportional Hazards model stratified by cohort. Cohort stratification adjusted for the differences in survival profiles that might be produced by various treatment regimens and endpoints in each cohort. CAPRA was treated as an integer-valued variable (0-10), and CCP score as a continuous numeric variable. To assure that CAPRA was an approximately linear predictor, we tested the quadratic term. It was significant ($X^2=8$; p-value=0.0041), but minor in comparison to the linear term ($X^2=53$, p-value<$10^{12}$).

Interactions with cohort were tested in a preliminary model to confirm that the prognostication of CAPRA and CCP score was not dependent on cohort. The interaction had a p-value of 0.059 with CAPRA; and a p-value of 0.050 with CCP score, and was not included in the final model (Table V).

TABLE V

| Variable | Coefficient | HR (95% CI) | $X^2$ (1df) | p-value |
|---|---|---|---|---|
| CAPRA | 0.394 | 1.48 (1.38, 1.59) | 116 | <$10^{-26}$ |
| CCP score | 0.567 | 1.76 (1.51, 2.05) | 48 | <$10^{-11}$ |

Based on this model, the Combined score was defined as

Combined Score=0.39*CAPRA+0.57*CCP score

Validating the Combined Score

The Combined score was validated in P2, a needle biopsy cohort of conservatively managed (active surveillance/watchful waiting) patients with death from prostate cancer as the outcome (Table W). There were 33 (18%) deaths among the 180 patients. In a multivariate model where CAPRA was added to the Combined score, the p-value for the Combined score was 0.0028, and the p-value for CAPRA was 0.58, confirming that the Combined score adequately accounted for both CAPRA and CCP score in the validation cohort.

TABLE W

| Variable | Coefficient | HR (95% CI) | $X^2$ (1df) | p-value |
|---|---|---|---|---|
| Combined score | 0.82 | 2.27 (1.63, 3.16) | 28 | <$10^{-6}$ |
| CAPRA | 0.35 | 1.42 (1.20, 1.68) | 19 | <$10^{-4}$ |
| CCP score | 0.75 | 2.12 (1.49, 3.03) | 18 | <$10^{-4}$ |

Predicting Mortality Risk

The predicted risk of prostate cancer death within 10 years of diagnosis was estimated in the P2 validation cohort. Times were censored at 10 years (120 months) and the predicted risk was estimated at the time of the last event (118.1109 months). The range of CCP scores in the validation set (n=180) was −0.8 to 4.1.

Restratifying AUA Risk Based on CCP Score or Combined Score

The percentile corresponding to each 0.1 increment of the CCP score was determined for the US clinical samples from each cohort within each AUA risk category. Individuals with clinical stages of T3 were excluded, leaving 1219 (97%) of the available 1262. The percentile for each patient was the fraction of patients within that AUA risk category who had a lower CCP score. Where multiple patients shared the same CCP score, rounded to a tenth, the percentile would be the same; namely, the fraction of patients with CCP scores lower than the rounded score.

The median CCP score of the US clinical samples from each cohort within each AUA risk category was used to assess cancer aggressiveness, as described in the following section. We compared the CCP score of each individual to the average CCP score of patients in the same AUA risk category in order to offer a relative assessment of cancer aggressiveness and in order to modify or confirm the risk prediction given using AUA guidelines.

The scale of CCP scores for each AUA risk category consisted of five 1-unit intervals, with the middle interval being centered at the median CCP score for that category in our sample cohort. There was approximately a 2-fold change in risk between intervals, which was the hazard ratio corresponding to a 1-unit change in the CCP score. We have given each section a qualitative label (Table X).

TABLE X

| | | CCP Range and CCP Classification Relative to AUA Category | | | | |
|---|---|---|---|---|---|---|
| | | Considerably Less Aggressive | Less Aggressive | Consistent | More Aggressive | Considerably More Aggressive |
| AUA Risk Category | Low | [−2.7, −1.7] | (−1.7, −0.7] | (−0.7, 0.3) | [0.3, 1.3) | [1.3, 2.3] |
| | Intermediate | [−2.6, −1.6] | (−1.6, −0.6] | (−0.6, 0.4) | [0.4, 1.4) | [1.4, 2.4] |
| | High | [−2.5, −1.5] | (−1.5, −0.5] | (−0.5, 0.5) | [0.5, 1.5) | [1.5, 2.5] |

Example 9

The prognostic utility of CCP genes (in this case, Panel F) and various candidate genes including KLK3, all using assay techniques as discussed above, was evaluated.

Patients

The patients whose samples were used in this experiment were incidentally diagnosed with prostate cancer after undergoing TURP and managed conservatively. The cohort has been described previously (in the Examples above and in Cuzick et al., Long-term outcome among men with conservatively treated localised prostate cancer, BR. J. CANCER (2006) 95:1186-1194). A portion of this cohort (but not including any of the men this experiment) was previously used for evaluating the clinical utility of the CCP score as discussed in the Examples above. Patients unique to this experiment, and not part of any previous evaluation of CCP score or KLK3) are referred to herein as TURP1B. Patients were excluded from the present analysis if their clinical records were missing information about PSA levels, Gleason score, or extent of disease. Clinical and molecular data were obtained for 303 individuals with 66 prostate cancer specific deaths for analyses with the CCP score, and 291 individuals for with 61 prostate cancer specific deaths for our analyses with KLK3. Patient data was censored at 10 years.

Statistics

Association between expression levels and prostate cancer-specific mortality were tested using univariate and multivariate Cox proportional hazard models. Multivariate analysis was performed using relevant clinical parameters indicated below. Hazard ratios are reported per unit increase in gene expression score (equivalent to a doubling in gene expression).

Results

The CCP score significantly predicted prostate cancer-specific mortality in the TURP1B samples. The univariate and multivariate summary statistics are below:

Univariate: CCP p-value<$10^{-15}$; HR=3.3 (2.5, 4.3)
Multivariate:
  CCP p-value<$10^{-5}$; HR=2.1 (1.5, 2.8)
  Gleason p-value=0.00035
  log PSA p-value=0.013

The prognostic utility of adding KLK3 to CCP score was also validated. In these analyses we used the negative of KLK3 expression, so that higher values would correspond to increased risk, as they do for CCP. This is because, for KLK3, lower expression predicts higher risk of recurrence or prostate cancer-specific mortality. The univariate and multivariate summary statistics are below:

Univariate: KLK3 p-value<$10^{-6}$; HR=1.8 (95% CI 1.5, 2.2)
Multivariate:
  CCP p-value<$10^{-5}$; HR=2.2 (95% CI 1.6, 3.0)
  KLK3 p-value 0.00019; HR=1.6 (93% CI 1.3, 2.1)
  Gleason p-value=0.0055
  log PSA p-value=0.055

In addition to KLK3, several other candidate genes were assessed for their ability to add independent prognostic information to the CCP score. The results a summarized in FIG. 25, which shows univariate p-values for association with prostate cancer specific mortality (x-axis) and p-values after adjusting for CCP score (y-axis). The additional genes are listed in Table Y below (a subset of which form Panel I of the disclosure), ranked according to p-value after adjusting for CCP score.

TABLE Y

| Gene # | Gene Symbol | Independent pvalue | hr | hr.lcl | hr.ucl | Adjusted for CCP score pvalue | hr | hr.lcl | hr.ucl | Example ABI Assay ID |
|---|---|---|---|---|---|---|---|---|---|---|
| 1 | SLC45A3^ | 3.01E-06 | 1.72 | 1.39 | 2.13 | 6.47E-07 | 1.82 | 1.45 | 2.28 | Hs00263832_m1 |
| 2 | ACPP^ | 1.14E-09 | 1.71 | 1.46 | 1.99 | 3.09E-06 | 1.59 | 1.32 | 1.91 | Hs00173475_m1 |
| 3 | TRPM8^ | 5.54E-08 | 1.47 | 1.29 | 1.67 | 4.02E-06 | 1.39 | 1.22 | 1.59 | Hs00375481_m1 |
| 4 | MSMB^ | 1.65E-07 | 1.41 | 1.25 | 1.61 | 1.28E-05 | 1.33 | 1.17 | 1.51 | Hs00159303_m1 |
| 5 | KLK3^ | 8.48E-07 | 1.77 | 1.44 | 2.17 | 2.21E-05 | 1.67 | 1.34 | 2.08 | Hs03063374_m1 |
| 6 | GTPBP5 | 9.79E-01 | 1.00 | 0.75 | 1.34 | 5.42E-05 | 2.04 | 1.44 | 2.88 | Hs00534998_m1 |
| 7 | IRF1 | 1.04E-02 | 1.50 | 1.10 | 2.04 | 1.43E-04 | 1.64 | 1.28 | 2.10 | Hs00971965_m1 |
| 8 | FOXA1 | 5.03E-01 | 1.13 | 0.80 | 1.58 | 2.50E-04 | 2.12 | 1.44 | 3.11 | Hs00270129_m1 |
| 9 | SLC30A4 | 2.24E-03 | 1.56 | 1.19 | 2.04 | 2.91E-04 | 1.78 | 1.31 | 2.41 | Hs00203308_m1 |
| 10 | AZGP1 | 1.18E-07 | 1.45 | 1.28 | 1.63 | 2.97E-04 | 1.32 | 1.15 | 1.52 | Hs00426651_m1 |
| 11 | MARC1 | 4.20E-01 | 1.15 | 0.82 | 1.60 | 3.10E-04 | 1.82 | 1.32 | 2.50 | Hs00224227_m1 |
| 12 | PTPRC | 2.25E-02 | 1.35 | 1.04 | 1.74 | 3.51E-04 | 1.57 | 1.23 | 2.00 | Hs00894732_m1 |
| 13 | PCA3 | 2.53E-03 | 1.12 | 1.05 | 1.20 | 3.68E-04 | 1.14 | 1.07 | 1.22 | Hs01371939_g1 |
| 14 | PMEPA1 | 5.43E-04 | 1.84 | 1.30 | 2.61 | 4.38E-04 | 1.77 | 1.29 | 2.43 | Hs00375306_m1 |
| 15 | TMPRSS2 | 3.41E-04 | 1.39 | 1.20 | 1.61 | 6.13E-04 | 1.37 | 1.18 | 1.59 | Hs01120965_m1 |
| 16 | CDH1 | 5.57E-01 | 1.10 | 0.80 | 1.51 | 1.13E-03 | 1.67 | 1.25 | 2.24 | Hs01023894_m1 |
| 17 | NKX3 | 4.24E-02 | 1.46 | 1.03 | 2.08 | 1.75E-03 | 1.89 | 1.29 | 2.77 | Hs00171834_m1 |
| 18 | KLK2 | 1.57E-04 | 1.68 | 1.31 | 2.15 | 3.07E-03 | 1.58 | 1.19 | 2.10 | Hs00428383_m1 |
| 19 | SORD | 8.49E-05 | 1.79 | 1.36 | 2.37 | 4.73E-03 | 1.51 | 1.14 | 2.01 | Hs00973148_m1 |
| 20 | IRF4 | 2.07E-01 | 1.14 | 0.93 | 1.41 | 8.35E-03 | 1.33 | 1.07 | 1.65 | Hs00180031_m1 |
| 21 | TARP; TRGC2 | 1.18E-03 | 1.50 | 1.19 | 1.88 | 1.66E-02 | 1.32 | 1.06 | 1.65 | Hs00827007_m1 |
| 22 | STX4 | 2.61E-01 | 1.40 | 0.78 | 2.54 | 1.93E-02 | 2.09 | 1.14 | 3.84 | Hs00190266_m1 |
| 23 | KLK4 | 8.50E-06 | 1.70 | 1.36 | 2.13 | 5.23E-02 | 1.30 | 1.00 | 1.69 | Hs00191772_m1 |
| 24 | KLK3 (alt. assay) | 3.56E-03 | 1.43 | 1.13 | 1.81 | 7.27E-02 | 1.28 | 0.98 | 1.66 | Hs02576345_m1 |
| 25 | HLA-DRA | 2.13E-02 | 1.42 | 1.06 | 1.89 | 1.11E-01 | 1.24 | 0.96 | 1.61 | Hs00219575_m1 |
| 26 | SIRT3 | 2.32E-01 | 1.21 | 0.89 | 1.65 | 1.55E-01 | 1.27 | 0.92 | 1.77 | Hs00202030_m1 |
| 27 | EIF3D | 1.44E-02 | 1.55 | 1.11 | 2.17 | 1.94E-01 | 1.24 | 0.90 | 1.71 | Hs00388727_m1 |
| 28 | IGJ | 4.28E-01 | 1.05 | 0.92 | 1.20 | 2.69E-01 | 1.08 | 0.94 | 1.24 | Hs00950678_g1 |
| 29 | HLA-DPA1 | 1.47E-01 | 1.40 | 0.89 | 2.22 | 3.18E-01 | 1.24 | 0.81 | 1.91 | Hs01072899_m1 |
| 30 | IGLL5; CKAP2 | 1.58E-01 | 0.85 | 0.67 | 1.06 | 3.49E-01 | 1.15 | 0.86 | 1.53 | Hs00382306_m1 |

TABLE Y-continued

| Gene | | Independent | | | | Adjusted for CCP score | | | | Example ABI |
|---|---|---|---|---|---|---|---|---|---|---|
| Gene # | Symbol | pvalue | hr | hr.lcl | hr.ucl | pvalue | hr | hr.lcl | hr.ucl | Assay ID |
| 31 | HOXB13 | 4.16E-01 | 0.86 | 0.60 | 1.24 | 5.42E-01 | 0.88 | 0.58 | 1.33 | Hs00197189_m1 |
| 32 | STEAP2 | 5.33E-02 | 1.66 | 0.99 | 2.78 | 7.87E-01 | 1.08 | 0.60 | 1.96 | Hs00537786_m1 |
| 33 | AR | 5.77E-01 | 0.91 | 0.64 | 1.29 | 8.47E-01 | 1.04 | 0.73 | 1.47 | Hs00171172_m1 |
| 34 | CREB3L4 | 4.80E-01 | 1.10 | 0.85 | 1.43 | 9.24E-01 | 1.01 | 0.77 | 1.34 | Hs00370116_m1 |
| 35 | MKI67 | 2.97E-12 | 0.40 | 0.32 | 0.52 | 9.83E-01 | 0.99 | 0.60 | 1.65 | Hs01032443_m1 |
| 36 | HLA-E | 8.24E-02 | 1.34 | 0.96 | 1.87 | 9.85E-01 | 1.00 | 0.74 | 1.36 | Hs03045171_m1 |

^These genes form Panel I of the disclosure
* "hr" = hazard ratio; "hr.lcl" = hazard ratio lower 95% confidence limit; "hr.ucl" = hazard ratio upper 95% confidence limit Table 1 below provides a large, but not exhaustive, list of CCGs.

TABLE 1

Gene (Name and/or Symbol) or Number (EST, cDNA clone, or Accession)

1. STK15: serine/threonine kinase 15 Hs.48915 R11407
2. PLK: polo (*Drosophia*)-like kinase Hs.77597 AA629262
3. UBCH10: ubiquitin carrier protein E2-C Hs.93002 AA430504
4. MAPK13: mitogen-activated protein kinase 13 Hs.178695 AA157499 p38delta mRNA = stress-activated protein kinase 4
5. CDC2: cell division cycle 2, G1 to S and G2 to M Hs.184572 AA598974
6. TOP2A: topoisomerase (DNA) II alpha (170 kD) Hs.156346 AA504348
7. CENPE: centromere protein E (312 kD) Hs.75573 AA402431 CENP-E = putative kinetochore motor that accumulates just befo
8. TOP2A: topoisomerase (DNA) II alpha (170 kD) Hs.156346 AA026682
9. KPNA2: karyopherin alpha 2 (RAG cohort 1, importin alpha 1) Hs.159557 AA676460
10. FLJ10468: hypothetical protein FLJ10468 Hs.48855 N63744
11. CCNF: cyclin F Hs.1973 AA676797
12. DKFZp762E1312: hypothetical protein DKFZp762E1312 Hs.104859 T66935
13. CKS2: CDC2-Associated Protein CKS2 Hs.83758 AA292964
14. C20ORF1: chromosome 20 open reading frame 1 Hs.9329 H73329
15. BUB1: budding uninhibited by benzimidazoles 1 (yeast homolog) Hs.98658 AA430092 BUB1 = putative mitotic checkpoint protein ser/thr kinase
16. TOP2A: **topoisomerase (DNA) II alpha (170 kD) Hs.156346 AI734240
17. CKS2: CDC2-Associated Protein CKS1 Hs.83758 AA010065 ckshs2 = homolog of Cks1 = p34Cdc28/Cdc2-associated protein
18. ARL6IP: ADP-ribosylation factor-like 6 interacting protein Hs.75249 H20558
19. L2DTL: L2DTL protein Hs.126774 R06900
20. STK15: **serine/threonine kinase 15 Hs.48915 H63492 aurora/IPL1-related kinase
21. E2-EPF: ubiquitin carrier protein Hs.174070 AA464019
22. UBCH10: ubiquitin carrier protein E2-C Hs.93002 R80790
23. KNSL5: kinesin-like 5 (mitotic kinesin-like protein 1) Hs.270845 AA452513 Mitotic kinesin-like protein-1
24. CENPF: centromere protein F (350/400 kD, mitosin) Hs.77204 AA701455
25. CCNA2: cyclin A2 Hs.85137 AA608568 Cyclin A
26. CDC2: cell division cycle 2, G1 to S and G2 to M Hs.184572 AA278152 CDC2 = Cell division control protein 2 homolog = P34 protein kin
27. HMMR: **hyaluronan-mediated motility receptor (RHAMM) Hs.72550 AA171715
28. KIAA0008: KIAA0008 gene product Hs.77695 AA262211
29. HSPC145: HSPC145 protein Hs.18349 R22949
30. FLJ20510: hypothetical protein FLJ20510 Hs.6844 N53214
31. *Homo sapiens* NUF2R mRNA, complete cds Hs.234545 AA421171:
32. HSPC216: hypothetical protein Hs.13525 T87341
33. P37NB: 37 kDa leucine-rich repeat (LRR) protein Hs.155545 AA423870
34. CDC20:
35. CCNE1: cyclin E1 Hs.9700 T54121
36. ESTs: Hs.221754 R84407
37. FLJ11252: hypothetical protein FLJ11252 Hs.23495 N30185
38. LOC51203: clone HQ0310 PRO0310p1 Hs.279905 AA620485
39. FLJ10491: hypothetical protein FLJ10491 Hs.274283 AA425404
40. KNSL1: kinesin-like 1 Hs.8878 AA504625
41. CENPA: centromere protein A (17 kD) Hs.1594 AI369629
42. *Homo sapiens*, clone IMAGE: 2823731, mRNA, partial cds Hs.70704 R96941:
43. CDC6: CDC6 (cell division cycle 6, *S. cerevisiae*) homolog Hs.69563 H59203
44. *Homo sapiens* DNA helicase homolog (PIF1) mRNA, partial cds Hs.112160 AA464521:
45. ESTs: Hs.48480 AA135809
46. TSN: translin Hs.75066 AA460927
47. KPNA2: karyopherin alpha 2 (RAG cohort 1, importin alpha 1) Hs.159557 AA489087
48. RRM2: ribonucleotide reductase M2 polypeptide Hs.75319 AA187351
49. ESTs: Hs.14119 AA204830
50. CCNB1: cyclin B1 Hs.23960 R25788

TABLE 1-continued

| | Gene (Name and/or Symbol) or Number (EST, cDNA clone, or Accession) |
|---|---|
| 51 | GTSE1: G-2 and S-phase expressed 1 Hs.122552 AI369284 |
| 52 | C20ORF1: chromosome 20 open reading frame 1 Hs.9329 AA936183 |
| 53 | TACC3: transforming, acidic coiled-coil containing protein 3 Hs.104019 AA279990 JkR1 mRNA downregulated upon T-cell activation |
| 54 | E2F1: E2F transcription factor 1 Hs.96055 H61303 |
| 55 | BUB1B: budding uninhibited by benzimidazoles 1 (yeast homolog), beta Hs.36708 AA488324 |
| 56 | ESTs,: Weakly similar to CGHU7L collagen alpha 1(III) chain precursor [*H. sapiens*] Hs.19322 AA088457 |
| 57 | KIAA0074: KIAA0074 protein Hs.1192 N54344 |
| 58 | MPHOSPH1: M-phase phosphoprotein 1 Hs.240 AA282935 |
| 59 | ANLN: anillin (*Drosophila* Scraps homolog), actin binding protein Hs.62180 R12261 |
| 60 | BIRC5: baculoviral IAP repeat-containing 5 (survivin) Hs.1578 AA460685 Survivin = apoptosis inhibitor = effector cell protease EPR-1 |
| 61 | PTTG1: pituitary tumor-transforming 1 Hs.252587 AA430032 |
| 62 | KIAA0159: chromosome condensation-related SMC-associated protein 1 Hs.5719 AA668256 |
| 63 | ESTs,: Weakly similar to OS-4 protein [*H. sapiens*] Hs.18714 W93120 |
| 64 | HMMR: hyaluronan-mediated motility receptor (RHAMM) Hs.72550 R10284 |
| 65 | DKFZp762E1312: hypothetical protein DKFZp762E1312 Hs.104859 AA936181 |
| 66 | CKAP2: cytoskeleton associated protein 2 Hs.24641 T52152 |
| 67 | RAMP: RA-regulated nuclear matrix-associated protein |
| 68 | SMAP: thyroid hormone receptor coactivating protein Hs.5464 AA481555 |
| 69 | FLJ22624: hypothetical protein FLJ22624 Hs.166425 AA488791 |
| 70 | CKS1: CDC2-Associated Protein CKS1 Hs.77550 N48162 |
| 71 | NEK2: NIMA (never in mitosis gene a)-related kinase 2 Hs.153704 W93379 |
| 72 | MKI67: antigen identified by monoclonal antibody Ki-67 |
| 73 | TTK: TTK protein kinase Hs.169840 AI337292 |
| 74 | VEGFC: vascular endothelial growth factor C Hs.79141 H07899 vascular endothelial growth factor related protein VRP |
| 75 | CDKN3: cyclin-dependent kinase inhibitor 3 (CDK2-associated dual specificity phosphatase) Hs.84113 AA284072 CIP2 = Cdi1 = KAP1 phosphatase = G1/S cell cycle gene |
| 76 | *Homo sapiens* NUF2R mRNA, complete cds Hs.234545 R92435: |
| 77 | *Homo sapiens* cDNA FLJ10325 fis, clone NT2RM2000569 Hs.245342 AA235662: |
| 78 | HSPC145: HSPC145 protein Hs.18349 AA628867 |
| 79 | HSU54999: LGN protein Hs.278338 W92010 |
| 80 | FLJ20333: hypothetical protein FLJ20333 Hs.79828 R27552 |
| 81 | KNSL2: kinesin-like 2 Hs.20830 N69491 |
| 82 | ESTs: Hs.133294 AI053446 |
| 83 | **ESTs: Hs.41294 H95819 |
| 84 | SMTN: smoothelin Hs.149098 AA449234 |
| 85 | FLJ23311: hypothetical protein FLJ23311 Hs.94292 N73916 |
| 86 | USF1: upstream transcription factor 1 Hs.247842 AA719022 |
| 87 | LOC51203: clone HQ0310 PRO0310p1 Hs.279905 AA779949 |
| 88 | ADH4: alcohol dehydrogenase 4 (class II), pi polypeptide Hs.1219 AA007395 |
| 89 | ESTs: Hs.186579 AA960844 |
| 90 | CCNB2: cyclin B2 Hs.194698 AA774665 |
| 91 | *Homo sapiens*, Similar to gene rich cluster, C8 gene, clone MGC: 2577, mRNA, complete cds Hs.30114 AA634371: |
| 92 | ESTs: Hs.99480 AA485454 |
| 93 | *Homo sapiens* IRE1b mRNA for protein kinase/ribonuclease IRE1 beta, complete cds Hs.114905 AA088442: |
| 94 | PCNA: proliferating cell nuclear antigen Hs.78996 AA450264 PCNA = proliferating cell nuclear antigen |
| 95 | AA075920: |
| 96 | GTSE1: G-2 and S-phase expressed 1 Hs.122552 AA449474 |
| 97 | CKS1: CDC2-Associated Protein CKS1 Hs.77550 AA278629 |
| 98 | CDC25B: cell division cycle 25B Hs.153752 AA448659 cdc25B = M-phase inducer phosphatase 2 |
| 99 | ESTs,: Weakly similar to unnamed protein product [*H. sapiens*] Hs.99807 AA489023 Unknown UG Hs.99807 ESTs sc_id384 |
| 100 | PCNA: proliferating cell nuclear antigen Hs.78996 H05891 |
| 101 | LTBP3: **latent transforming growth factor beta binding protein 3 Hs.289019 R60197 |
| 102 | *Homo sapiens* mRNA; cDNA DKFZp434D0818 (from clone DKFZp434D0818) Hs.5855 N95578: |
| 103 | ESTs: Hs.126714 AA919126 |
| 104 | CIT: citron (rho-interacting, serine/threonine kinase 21) Hs.15767 H10788 |
| 105 | LBR: lamin B receptor Hs.152931 AA099136 |
| 106 | E2F1: E2F transcription factor 1 Hs.96055 AA424949 |
| 107 | AA699928: |
| 108 | CDKN2C: cyclin-dependent kinase inhibitor 2C (p18, inhibits CDK4) Hs.4854 N72115 p18-INK6 = Cyclin-dependent kinase 6 inhibitor |
| 109 | STK12: serine/threonine kinase 12 Hs.180655 H81023 ARK2 = aurora-related kinase 2 |
| 110 | ESTs: Hs.111471 AA682533 |
| 111 | ESTs: Hs.44269 AA465090 |
| 112 | MCM4: minichromosome maintenance deficient (*S. cerevisiae*) 4 Hs.154443 AA485983 |

TABLE 1-continued

| | Gene (Name and/or Symbol) or Number (EST, cDNA clone, or Accession) |
|---|---|
| 113 | PMSCL1: **polymyositis/scleroderma autoantigen 1 (75 kD) Hs.91728 AA458994 Cyclin A |
| 114 | MKI67: antigen identified by monoclonal antibody Ki-67 Hs.80976 AA425973 Ki67 (long type) |
| 115 | ESTs: Hs.133294 AI144063 |
| 116 | CDC25B: cell division cycle 25B Hs.153752 H14343 cdc25B = M-phase inducer phosphatase 2 |
| 117 | FOXM1: forkhead box M1 Hs.239 AA129552 MPP2 = putative M phase phosphoprotein 2 |
| 118 | FLJ11029: hypothetical protein FLJ11029 Hs.274448 AI124082 |
| 119 | H2AFX: H2A histone family, member X Hs.147097 H95392 |
| 120 | FLJ20333: hypothetical protein FLJ20333 Hs.79828 AA147792 |
| 121 | SLC17A2: solute carrier family 17 (sodium phosphate), member 2 Hs.19710 H60423 |
| 122 | *Homo sapiens* IRE1b mRNA for protein kinase/ribonuclease IRE1 beta, complete cds Hs.114905 AA102368: |
| 123 | ESTs: Hs.163921 AA573689 |
| 124 | MCM5: minichromosome maintenance deficient (*S. cerevisiae*) 5 (cell division cycle 46) Hs.77171 AA283961 |
| 125 | CDKN1B: cyclin-dependent kinase inhibitor 1B (p27, Kip1) Hs.238990 AA630082 |
| 126 | AA779865: |
| 127 | PTTG1: pituitary tumor-transforming 1 Hs.252587 AI362866 |
| 128 | RAD21: RAD21 (*S. pombe*) homolog Hs.81848 AA683102 |
| 129 | *Homo sapiens* cDNA FLJ10325 fis, clone NT2RM2000569 Hs.245342 AA430511: |
| 130 | NEK2: NIMA (never in mitosis gene a)-related kinase 2 Hs.153704 AA682321 |
| 131 | FLJ20101: LIS1-interacting protein NUDE1, rat homolog Hs.263925 N79612 |
| 132 | FZR1: Fzr1 protein Hs.268384 AA621026 |
| 133 | ESTs: Hs.120605 AI220472 |
| 134 | KIAA0855: golgin-67 Hs.182982 AA098902 |
| 135 | SRD5A1: steroid-5-alpha-reductase, alpha polypeptide 1 (3-oxo-5 alpha-steroid delta 4-dehydrogenase alpha 1) Hs.552 H16833 |
| 136 | RAD51: RAD51 (*S. cerevisiae*) homolog (*E coli* RecA homolog) Hs.23044 N70010 |
| 137 | KNSL2: kinesin-like 2 Hs.20830 R11542 |
| 138 | KIAA0097: KIAA0097 gene product Hs.76989 AA598942 |
| 139 | TUBB: tubulin, beta polypeptide Hs.179661 AA427899 |
| 140 | HEC: highly expressed in cancer, rich in leucine heptad repeats Hs.58169 W72679 |
| 141 | TROAP: trophinin associated protein (tastin) Hs.171955 H94949 |
| 142 | ESTs: Hs.49047 N64737 |
| 143 | ESTs: Hs.15091 AA678348 |
| 144 | ESTs: Hs.133431 AI061169 |
| 145 | KIAA0042: KIAA0042 gene product Hs.3104 AA477501 |
| 146 | FZR1: Fzr1 protein Hs.268384 AA862886 |
| 147 | FEN1: flap structure-specific endonuclease 1 Hs.4756 AA620553 |
| 148 | CKS1: CDC2-Associated Protein CKS1 Hs.77550 AA459292 ckshs1 = homolog of Cks1 = p34Cdc28/Cdc2-associated protein |
| 149 | ESTs: Hs.193379 N57936 |
| 150 | CASP8AP2: CASP8 associated protein 2 Hs.122843 H50582 |
| 151 | BIRC2: baculoviral IAP repeat-containing 2 Hs.289107 R19628 c-IAP1 = MIHB = IAP homolog B |
| 152 | CKAP2: cytoskeleton associated protein 2 Hs.24641 AA504130 |
| 153 | HLA-DRA: major histocompatibility complex, class II, DR alpha Hs.76807 R47979 |
| 154 | HBP: Hairpin binding protein, histone Hs.75257 AA629558 |
| 155 | FLJ10483: hypothetical protein FLJ10483 Hs.6877 H12254 |
| 156 | CASP3: caspase 3, apoptosis-related cysteine protease Hs.74552 R14760 CASPASE-3 = CPP32 isoform alpha = yama = cysteine protease |
| 157 | **ESTs,: Weakly similar to protein that is immuno-reactive with anti-PTH polyclonal antibodies [*H. sapiens*] Hs.301486 AA088258 |
| 158 | HMG2: high-mobility group (nonhistone chromosomal) protein 2 Hs.80684 AA019203 |
| 159 | PRO2000: PRO2000 protein Hs.46677 H58234 |
| 160 | FLJ20333: hypothetical protein FLJ20333 Hs.79828 T48760 |
| 161 | T56726: |
| 162 | TIMP1: tissue inhibitor of metalloproteinase 1 (erythroid potentiating activity, collagenase inhibitor) Hs.5831 H80214 |
| 163 | ESTs: Hs.102004 R94281 |
| 164 | FLJ10858: hypothetical protein FLJ10858 Hs.134403 AA677552 |
| 165 | *Homo sapiens* cDNA FLJ11883 fis, clone HEMBA1007178 Hs.157148 N62451: |
| 166 | RFC4: replication factor C (activator 1) 4 (37 kD) Hs.35120 N93924 replication factor C |
| 167 | PRO2000: PRO2000 protein Hs.46677 N47113 |
| 168 | ECT2: epithelial cell transforming sequence 2 oncogene Hs.132808 AI031571 |
| 169 | ESTs: Hs.165909 AA629538 |
| 170 | PCF11: PCF11p homolog Hs.123654 AA053411 |
| 171 | BIRC3: baculoviral IAP repeat-containing 3 Hs.127799 H48533 c-IAP2 = MIHC = IAP homolog C = TNFR2-TRAF signalling complex prot |
| 172 | EST,: Weakly similar to dJ45P21.2 [*H. sapiens*] Hs.326451 AA931528 |
| 173 | KIAA0952: KIAA0952 protein Hs.7935 AA454989 |
| 174 | KIF5B: kinesin family member 5B Hs.149436 AA608707 |
| 175 | DKFZP566C134: DKFZP566C134 protein Hs.20237 N39306 |
| 176 | ANLN: anillin (*Drosophila* Scraps homolog), actin binding protein Hs.62180 R17092 |

TABLE 1-continued

| | Gene (Name and/or Symbol) or Number (EST, cDNA clone, or Accession) |
|---|---|
| 177 | ORC1L: origin recognition complex, subunit 1 (yeast homolog)-like Hs.17908 H51719 |
| 178 | ESTs: Hs.14139 T77757 |
| 179 | IFIT1: interferon-induced protein with tetratricopeptide repeats 1 Hs.20315 AA074989 |
| 180 | MGC5338: hypothetical protein MGC5338 Hs.99598 AA463627 |
| 181 | COPEB: core promoter element binding protein Hs.285313 AA013481 |
| 182 | UK114: translational inhibitor protein p14.5 Hs.18426 N72715 |
| 183 | ESTs: Hs.265592 H67282 |
| 184 | HMG4: high-mobility group (nonhistone chromosomal) protein 4 Hs.19114 AA670197 |
| 185 | MDS025: hypothetical protein MDS025 Hs.154938 AI225067 |
| 186 | DKFZP564A122: DKFZP564A122 protein Hs.187991 N53236 |
| 187 | TSC22: transforming growth factor beta-stimulated protein TSC-22 Hs.114360 AA664389 |
| 188 | AAAS: aladin Hs.125262 AA916726 |
| 189 | PLAG1: **pleiomorphic adenoma gene 1 Hs.14968 AA418251 |
| 190 | FLJ23293: **hypothetical protein FLJ23293 similar to ARL-6 interacting protein-2 Hs.31236 R91583 |
| 191 | H11: protein kinase H11; small stress protein-like protein HSP22 Hs.111676 AA010110 |
| 192 | POLD3: polymerase (DNA directed), delta 3 Hs.82502 AA504204 |
| 193 | SERPINB3: serine (or cysteine) proteinase inhibitor, clade B (ovalbumin), member 3 Hs.227948 AA292860 |
| 194 | DNAJB1: DnaJ (Hsp40) homolog, subfamily B, member 1 Hs.82646 AA435948 |
| 195 | ESTs: Hs.99480 AA458886 |
| 196 | BUB3: BUB3 (budding uninhibited by benzimidazoles 3, yeast) homolog Hs.40323 AA405690 |
| 197 | TUBB2: tubulin, beta, 2 Hs.251653 AI000256 |
| 198 | Homo sapiens SNC73 protein (SNC73) mRNA, complete cds Hs.293441 H28469: |
| 199 | BUB3: BUB3 (budding uninhibited by benzimidazoles 3, yeast) homolog Hs.40323 H38804 |
| 200 | FLJ20699: hypothetical protein FLJ20699 Hs.15125 AA459420 |
| 201 | KIAA0013: KIAA0013 gene product Hs.172652 N63575 |
| 202 | ESTs: Hs.20575 N20305 |
| 203 | CDC25C: cell division cycle 25C Hs.656 W95000 cdc25C = M-phase inducer phosphatase 3 |
| 204 | FLJ11186: hypothetical protein FLJ11186 Hs.89278 AA394225 |
| 205 | TOPK: PDZ-binding kinase; T-cell originated protein kinase Hs.104741 AA448898 |
| 206 | KIAA0165: extra spindle poles, S. cerevisiae, homolog of Hs.153479 AA948058 |
| 207 | LOC51659: HSPC037 protein Hs.108196 AA961752 |
| 208 | ESTs: Hs.10338 AA436456 |
| 209 | SUCLG2: succinate-CoA ligase, GDP-forming, beta subunit Hs.247309 AA465233 |
| 210 | ZNF265: zinc finger protein 265 Hs.194718 AA452256 |
| 211 | SKP2: S-phase kinase-associated protein 2 (p45) Hs.23348 R22188 |
| 212 | NS1-BP: NS1-binding protein Hs.197298 AA486796 |
| 213 | C21ORF50: chromosome 21 open reading frame 50 Hs.4055 AA416628 |
| 214 | BIRC2: baculoviral IAP repeat-containing 2 Hs.289107 AA702174 |
| 215 | BIRC3: baculoviral IAP repeat-containing 3 Hs.127799 AA002125 c-IAP2 = MIHC = IAP homolog C = TNFR2-TRAF signalling complex prot |
| 216 | INDO: indoleamine-pyrrole 2,3 dioxygenase Hs.840 AA478279 |
| 217 | DEEPEST: mitotic spindle coiled-coil related protein Hs.16244 T97349 |
| 218 | ESTs: Hs.105826 AA534321 |
| 219 | C20ORF1: chromosome 20 open reading frame 1 Hs.9329 AI654707 |
| 220 | Homo sapiens cDNA: FLJ21869 fis, clone HEP02442 Hs.28465 R63929: |
| 221 | RGS3: regulator of G-protein signalling 3 Hs.82294 AI369623 |
| 222 | Homo sapiens DC29 mRNA, complete cds Hs.85573 AA186460: |
| 223 | MCM6: minichromosome maintenance deficient (mis5, S. pombe) 6 Hs.155462 AA663995 |
| 224 | NPAT: nuclear protein, ataxia-telangiectasia locus Hs.89385 AA284172 NPAT = E14 = gene in ATM locus |
| 225 | KNSL6: kinesin-like 6 (mitotic centromere-associated kinesin) Hs.69360 AA400450 |
| 226 | HN1: hematological and neurological expressed 1 Hs.109706 AA459865 |
| 227 | TUBA3: Tubulin, alpha, brain-specific Hs.272897 AA865469 |
| 228 | ESTs: Hs.221197 N55457 |
| 229 | KIAA0175: KIAA0175 gene product Hs.184339 AA903137 |
| 230 | CLASPIN: homolog of Xenopus Claspin Hs.175613 AA857804 |
| 231 | CTNNA1: **catenin (cadherin-associated protein), alpha 1 (102 kD) Hs.178452 AA026631 |
| 232 | ESTs: Hs.221962 AA229644 |
| 233 | SMC4L1: SMC4 (structural maintenance of chromosomes 4, yeast)-like 1 Hs.50758 AA452095 |
| 234 | ICBP90: transcription factor Hs.108106 AA026356 |
| 235 | EXO1: exonuclease 1 Hs.47504 AA703000 |
| 236 | Homo sapiens TRAF4 associated factor 1 mRNA, partial cds Hs.181466 T84975: |
| 237 | ESTs: Hs.186814 AA700879 |
| 238 | FLJ11269: hypothetical protein FLJ11269 Hs.25245 R37817 |
| 239 | SFPQ: splicing factor proline/glutamine rich (polypyrimidine tract-binding protein-associated) Hs.180610 AA425258 |
| 240 | ZF: HCF-binding transcription factor Zhangfei Hs.29417 AA164474 |

TABLE 1-continued

| | Gene (Name and/or Symbol) or Number (EST, cDNA clone, or Accession) |
|---|---|
| 241 | TUBA2: tubulin, alpha 2 Hs.98102 AA626698 |
| 242 | Homo sapiens mRNA; cDNA DKFZp434M0435 (from clone DKFZp434M0435) Hs.25700 N94435: |
| 243 | FLJ20530: **hypothetical protein FLJ20530 Hs.279521 AA425442 |
| 244 | BTEB1: basic transcription element binding protein 1 Hs.150557 N80235 |
| 245 | LOC51053: geminin Hs.234896 H51100 |
| 246 | D21S2056E: DNA segment on chromosome 21 (unique) 2056 expressed sequence Hs.110757 AI362799 |
| 247 | HDAC3: histone deacetylase 3 Hs.279789 H88540 |
| 248 | USP1: ubiquitin specific protease 1 Hs.35086 AA099033 |
| 249 | C21ORF50: chromosome 21 open reading frame 50 Hs.4055 AA135912 |
| 250 | FLJ13046: **hypothetical protein FLJ13046 similar to exportin 4 Hs.117102 T95333 |
| 251 | ESTs: Hs.181059 AA912032 |
| 252 | FLJ22009: hypothetical protein FLJ22009 Hs.123253 AA401234 |
| 253 | ESTs: Hs.62711 AA056377 |
| 254 | RAD51C: RAD51 (S. cerevisiae) homolog C Hs.11393 R37145 RAD51C = Recombination/repair Rad51-related protein |
| 255 | ESTs: Hs.268919 H53508 |
| 256 | Homo sapiens cDNA FLJ11381 fis, clone HEMBA1000501 Hs.127797 AA885096: |
| 257 | SAP30: sin3-associated polypeptide, 30 kD Hs.20985 AA126982 |
| 258 | H4FG: H4 histone family, member G Hs.46423 AA868008 |
| 259 | TUBA1: tubulin, alpha 1 (testis specific) Hs.75318 AA180742 tubulin-alpha-4 |
| 260 | DHFR: dihydrofolate reductase Hs.83765 R00884 DHFR = Dihydrofolate reductase |
| 261 | DHFR: dihydrofolate reductase Hs.83765 N52980 |
| 262 | MGC5528: hypothetical protein MGC5528 Hs.315167 AA934904 |
| 263 | NNMT: nicotinamide N-methyltransferase Hs.76669 T72089 |
| 264 | TUBB: tubulin, beta polypeptide Hs.179661 AI672565 |
| 265 | HSPA1L: heat shock 70 kD protein-like 1 Hs.80288 H17513 HSP70-HOM = Heat shock 70 KD protein 1 |
| 266 | TUBA1: **tubulin, alpha 1 (testis specific) Hs.75318 R36063 |
| 267 | PRO1073: **PRO1073 protein Hs.6975 AA176999 CIP4 = Cdc42-interacting protein 4 |
| 268 | POLD3: polymerase (DNA directed), delta 3 Hs.82502 AI017254 |
| 269 | ESTs,: Moderately similar to T50635 hypothetical protein DKFZp762L0311.1 [H. sapiens] Hs.47378 N38809 |
| 270 | DKFZP564A122: DKFZP564A122 protein Hs.187991 N57723 |
| 271 | LRRFIP1: **leucine rich repeat (in FLII) interacting protein 1 Hs.326159 T84633 |
| 272 | ESTs: Hs.55468 AA165312 |
| 273 | ESTs: Hs.31444 H16772 |
| 274 | AFAP: actin filament associated protein Hs.80306 R69355 |
| 275 | CXCR4: chemokine (C—X—C motif), receptor 4 (fusin) Hs.89414 T62491 CXC chemokine receptor 4 = fusin = neuropeptide Y receptor = L3 |
| 276 | MSH2: **mutS (E. coli) homolog 2 (colon cancer, nonpolyposis type 1) Hs.78934 AA679697 |
| 277 | ESTs: Hs.48474 N62074 |
| 278 | AA677337: |
| 279 | ESTs,: Moderately similar to TBB2_HUMAN TUBULIN BETA-2 CHAIN [H. sapiens] Hs.23189 AA629908 |
| 280 | HP1-BP74: HP1-BP74 Hs.142442 H79795 |
| 281 | FLJ20101: LIS1-interacting protein NUDE1, rat homolog Hs.263925 AA459394 |
| 282 | Homo sapiens mRNA; cDNA DKFZp434D1428 (from clone DKFZp434D1428); complete cds Hs.321775 AA431268: |
| 283 | ESTs: Hs.265592 AA992658 |
| 284 | ESTs: |
| 285 | DDX11: DEAD/H (Asp-Glu-Ala-Asp/His) box polypeptide 11 (S. cerevisiae CHL1-like helicase) Hs.27424 AA402879 |
| 286 | CDC27: cell division cycle 27 Hs.172405 T81764 |
| 287 | ARGBP2: Arg/Abl-interacting protein ArgBP2 Hs.278626 N89738 |
| 288 | DKFZP564A122: DKFZP564A122 protein Hs.187991 AA025807 |
| 289 | OPN3: opsin 3 (encephalopsin) Hs.279926 AA150060 |
| 290 | DKFZP566C134: DKFZP566C134 protein Hs.20237 AA456319 |
| 291 | KIAA0855: golgin-67 Hs.182982 H15101 |
| 292 | PIN: dynein, cytoplasmic, light polypeptide Hs.5120 AA644679 |
| 293 | ESTs,: Weakly similar to LIP1_HUMAN PANCREATIC LIPASE RELATED PROTEIN 1 PRECURSO [H. sapiens] Hs.68864 AA088857 |
| 294 | HDAC3: histone deacetylase 3 Hs.279789 AA973283 |
| 295 | DONSON: downstream neighbor of SON Hs.17834 AA417895 |
| 296 | LOC51053: geminin Hs.234896 AA447662 |
| 297 | FLJ10545: hypothetical protein FLJ10545 Hs.88663 AA460110 |
| 298 | MAD2L1: MAD2 (mitotic arrest deficient, yeast, homolog)-like 1 Hs.79078 AA481076 mitotic feedback control protein Madp2 homolog |
| 299 | TASR2: TLS-associated serine-arginine protein 2 Hs.3530 H11042 |
| 300 | MCM6: minichromosome maintenance deficient (mis5, S. pombe) 6 Hs.155462 N57722 |
| 301 | CIT: citron (rho-interacting, serine/threonine kinase 21) Hs.15767 W69425 |
| 302 | **ESTs: Hs.205066 AA284803 |
| 303 | ICAM1: intercellular adhesion molecule 1 (CD54), human rhinovirus receptor Hs.168383 R77293 CD54 = ICAM-1 |
| 304 | KIAA0855: golgin-67 Hs.182982 AA456818 |

TABLE 1-continued

| | Gene (Name and/or Symbol) or Number (EST, cDNA clone, or Accession) |
|---|---|
| 305 | ESTs,: Weakly similar to putative p150 [*H. sapiens*] Hs.300070 R10422 |
| 306 | DEEPEST: mitotic spindle coiled-coil related protein Hs.16244 AI652290 |
| 307 | MCM2: minichromosome maintenance deficient (*S. cerevisiae*) 2 (mitotin) Hs.57101 AA454572 |
| 308 | *Homo sapiens* cDNA: FLJ22272 fis, clone HRC03192 Hs.50740 AA495943: |
| 309 | WISP1: **WNT1 inducible signaling pathway protein 1 Hs.194680 T54850 |
| 310 | KIAA0855: golgin-67 Hs.182982 AA280248 |
| 311 | TEM8: tumor endothelial marker 8 Hs.8966 H58644 |
| 312 | BITE: p10-binding protein Hs.42315 H96392 |
| 313 | RAN: RAN, member RAS oncogene family Hs.10842 AA456636 |
| 314 | EZH2: enhancer of zeste (*Drosophila*) homolog 2 Hs.77256 AA428252 |
| 315 | MCM4: minichromosome maintenance deficient (*S. cerevisiae*) 4 Hs.154443 W74071 |
| 316 | DKFZp434J0310: hypothetical protein Hs.278408 AA279657 Unknown UG Hs.23595 ESTs sc_id6950 |
| 317 | PPP1R10: protein phosphatase 1, regulatory subunit 10 Hs.106019 AA071526 |
| 318 | H11: protein kinase H11; small stress protein-like protein HSP22 Hs.111676 H57493 |
| 319 | ESTs,: Weakly similar to KIAA1074 protein [*H. sapiens*] Hs.200483 AA463220 |
| 320 | ESTs,: Weakly similar to ALU8_HUMAN ALU SUBFAMILY SX SEQUENCE CONTAMINATION WARNING ENTRY [*H. sapiens*] Hs.226414 N72576 |
| 321 | AA775033: |
| 322 | LOC51004: CGI-10 protein Hs.12239 AA677920 |
| 323 | ESTs: Hs.150028 AI292036 |
| 324 | MCM6: minichromosome maintenance deficient (mis5, *S. pombe*) 6 Hs.155462 AA976533 |
| 325 | ESTs,: Moderately similar to T50635 hypothetical protein DKFZp762L0311.1 [*H. sapiens*] Hs.47378 AA406348 |
| 326 | UCP4: uncoupling protein 4 Hs.40510 H60279 |
| 327 | MSH5: mutS (*E. coli*) homolog 5 Hs.112193 AA621155 |
| 328 | ROCK1: Rho-associated, coiled-coil containing protein kinase 1 Hs.17820 AA872143 |
| 329 | KIAA0855: golgin-67 Hs.182982 AA694481 |
| 330 | AA705332: |
| 331 | CDC27: cell division cycle 27 Hs.172405 N47994 |
| 332 | DONSON: downstream neighbor of SON Hs.17834 AI732249 |
| 333 | SH3GL2: SH3-domain GRB2-like 2 Hs.75149 R12817 |
| 334 | PRC1: protein regulator of cytokinesis 1 Hs.5101 AA449336 |
| 335 | ESTs,: Weakly similar to unnamed protein product [*H. sapiens*] Hs.99807 AA417744 Unknown UG Hs.119424 ESTs sc_id2235 |
| 336 | Human: clone 23719 mRNA sequence Hs.80305 AA425722 |
| 337 | *Homo sapiens* mRNA; cDNA DKFZp564O2364 (from clone DKFZp564O2364) Hs.28893 W90240: |
| 338 | ESTs,: Weakly similar to LIP1_HUMAN PANCREATIC LIPASE RELATED PROTEIN 1 PRECURSO [*H. sapiens*] Hs.68864 AA132858 |
| 339 | TUBA3: Tubulin, alpha, brain-specific Hs.272897 AA864642 |
| 340 | AI283530: |
| 341 | ESTs: Hs.302878 R92512 |
| 342 | PPP1R10: protein phosphatase 1, regulatory subunit 10 Hs.106019 T75485 |
| 343 | SFRS5: splicing factor, arginine/serine-rich 5 Hs.166975 R73672 |
| 344 | SFRS3: splicing factor, arginine/serine-rich 3 Hs.167460 AA598400 |
| 345 | PRIM1: primase, polypeptide 1 (49 kD) Hs.82741 AA025937 DNA primase (subunit p48) |
| 346 | FLJ20333: hypothetical protein FLJ20333 Hs.79828 H66982 |
| 347 | HSPA8: heat shock 70 kD protein 8 Hs.180414 AA620511 |
| 348 | C4A: complement component 4A Hs.170250 AA664406 |
| 349 | DKC1: dyskeratosis congenita 1, dyskerin Hs.4747 AA052960 |
| 350 | HP1-BP74: HP1-BP74 Hs.142442 T84669 |
| 351 | ETV4: ets variant gene 4 (E1A enhancer-binding protein, E1AF) Hs.77711 AA010400 E1A-F = E1A enhancer binding protein = ETS translocation variant |
| 352 | *Homo sapiens* cDNA: FLJ23037 fis, clone LNG02036, highly similar to HSU68019 *Homo sapiens* mad protein homolog (hMAD-3) mRNA Hs.288261 W42414 Smad3 = hMAD-3 = Homologue of Mothers Against Decapentaplegic (M: |
| 353 | KIAA0952: KIAA0952 protein Hs.7935 AA679150 |
| 354 | STK9: serine/threonine kinase 9 Hs.50905 N80713 |
| 355 | NXF1: **nuclear RNA export factor 1 Hs.323502 R01238 |
| 356 | FLJ12892: hypothetical protein FLJ12892 Hs.17731 AA449357 |
| 357 | UNG: uracil-DNA glycosylase Hs.78853 H15111 |
| 358 | STK17B: **serine/threonine kinase 17b (apoptosis-inducing) Hs.120996 AA419485 |
| 359 | YWHAH: tyrosine 3-monooxygenase/tryptophan 5-monooxygenase activation protein, eta polypeptide Hs.75544 N69107 |
| 360 | FLJ13154: hypothetical protein FLJ13154 Hs.25303 AA923560 |
| 361 | LOC51116: CGI-91 protein Hs.20776 AA459419 |
| 362 | SSXT: synovial sarcoma, translocated to X chromosome Hs.153221 N59206 |
| 363 | KIAA0978: KIAA0978 protein Hs.3686 AA485878 |
| 364 | EST: Hs.147907 AI223432 |
| 365 | FLJ23468: hypothetical protein FLJ23468 Hs.38178 AA431741 |
| 366 | FLJ10339: **hypothetical protein FLJ10339 Hs.203963 N95450 |
| 367 | BMP2: bone morphogenetic protein 2 Hs.73853 AA011061 |
| 368 | PIR51: RAD51-interacting protein Hs.24596 AI214426 |
| 369 | FLJ20364: hypothetical protein FLJ20364 Hs.32471 AA676296 |

TABLE 1-continued

| | Gene (Name and/or Symbol) or Number (EST, cDNA clone, or Accession) |
|---|---|
| 370 | EIF4A2: **eukaryotic translation initiation factor 4A, isoform 2 Hs.173912 H54751 |
| 371 | ESTs,: Weakly similar to MCAT_HUMAN MITOCHONDRIAL CARNITINE/ACYLCARNITINE CARRIER PROTEIN [*H. sapiens*] Hs.27769 AA469975 |
| 372 | FLJ11323: hypothetical protein FLJ11323 Hs.25625 AA775600 |
| 373 | DKFZP564D0764: DKFZP564D0764 protein Hs.26799 AA460732 |
| 374 | CTL2: CTL2 gene Hs.105509 AA454710 |
| 375 | ESTs: Hs.293419 AA775845 |
| 376 | IFIT1: interferon-induced protein with tetratricopeptide repeats 1 Hs.20315 AA489640 Interferon-induced 56-KDa protein |
| 377 | RBBP8: retinoblastoma-binding protein 8 Hs.29287 H23021 |
| 378 | **Homo sapiens* clone 25061 mRNA sequence Hs.183475 R38944: |
| 379 | Human: DNA sequence from clone RP3-383J4 on chromosome 1q24.1-24.3 Contains part of a gene encoding a kelch motif containing protein, part of a novel gene encoding a protein similar to Aspartyl-TRNA sy Hs.117305 N29457 |
| 380 | FLJ12888: hypothetical protein FLJ12888 Hs.284137 N68390 |
| 381 | ESTs,: Weakly similar to IF38_HUMAN EUKARYOTIC TRANSLATION INITIATION FACTOR 3 SUBUNIT 8 [*H. sapiens*] Hs.222088 AI139629 |
| 382 | ESTs: Hs.241101 AA133590 |
| 383 | H4FI: H4 histone family, member I Hs.143080 AI218900 |
| 384 | SP38: zona pellucida binding protein Hs.99875 AA400474 |
| 385 | GABPB1: GA-binding protein transcription factor, beta subunit 1 (53 kD) Hs.78915 H91651 |
| 386 | LCHN: LCHN protein Hs.12461 AA029330 |
| 387 | DKFZP564D0462: hypothetical protein DKFZp564D0462 Hs.44197 N32904 |
| 388 | LENG8: leukocyte receptor cluster (LRC) encoded novel gene 8 Hs.306121 AA464698 |
| 389 | HIF1A: hypoxia-inducible factor 1, alpha subunit (basic helix-loop-helix transcription factor) Hs.197540 AA598526 |
| 390 | ESTs: Hs.93714 R09201 |
| 391 | FLJ23468: hypothetical protein FLJ23468 Hs.38178 AA454949 |
| 392 | DKFZP566C134: DKFZP566C134 protein Hs.20237 AA448164 |
| 393 | PPP3CA: protein phosphatase 3 (formerly 2B), catalytic subunit, alpha isoform (calcineurin A alpha) Hs.272458 W60310 |
| 394 | HMGE: GrpE-like protein cochaperone Hs.151903 H55907 |
| 395 | CDK7: cyclin-dependent kinase 7 (homolog of *Xenopus* MO15 cdk-activating kinase) Hs.184298 R22624 CAK = cdk7 = NRTALRE = sdk = CDK activating kinase |
| 396 | ABCC5: **ATP-binding cassette, sub-family C (CFTR/MRP), member 5 Hs.108660 AA186613 |
| 397 | AA477707: |
| 398 | **ESTs: Hs.15607 R92899 |
| 399 | LOC57209: Kruppel-type zinc finger protein Hs.25275 N50827 |
| 400 | FLJ20101: LIS1-interacting protein NUDE1, rat homolog Hs.263925 R87716 |
| 401 | KNSL4: kinesin-like 4 Hs.119324 AA430503 |
| 402 | E2F5: E2F transcription factor 5, p130-binding Hs.2331 AA455521 E2F-5 = pRB-binding transcription factor |
| 403 | TMPO: thymopoietin Hs.11355 T63980 |
| 404 | POLQ: polymerase (DNA directed), theta Hs.241517 AI057325 |
| 405 | TGIF: TG-interacting factor (TALE family homeobox) Hs.90077 H51705 |
| 406 | TRIP13: thyroid hormone receptor interactor 13 Hs.6566 AA630784 |
| 407 | GAS6: growth arrest-specific 6 Hs.78501 AA461110 |
| 408 | HN1: hematological and neurological expressed 1 Hs.109706 AA035429 |
| 409 | BARD1: BRCA1 associated RING domain 1 Hs.54089 AA558464 |
| 410 | DHFR: dihydrofolate reductase Hs.83765 AA424790 |
| 411 | AA490946: |
| 412 | ESTs: Hs.130435 AA167114 |
| 413 | HSPA8: heat shock 70 kD protein 8 Hs.180414 AA629567 |
| 414 | RRM2: ribonucleotide reductase M2 polypeptide Hs.75319 AA826373 |
| 415 | FLJ20036: hypothetical protein FLJ20036 Hs.32922 H59114 |
| 416 | COPEB: core promoter element binding protein Hs.285313 AA055584 CPBP = CBA1 = DNA-binding protein |
| 417 | FLJ10604: hypothetical protein FLJ10604 Hs.26516 N72697 |
| 418 | ESTs,: Weakly similar to cDNA EST yk415c12.5 comes from this gene [*C. elegans*] Hs.108824 H97880 |
| 419 | UBE2D3: **ubiquitin-conjugating enzyme E2D 3 (homologous to yeast UBC4/5) Hs.118797 AA017199 |
| 420 | FLJ10890: **hypothetical protein FLJ10890 Hs.17283 AA004210 |
| 421 | ESTs: Hs.214410 AA579336 |
| 422 | OLR1: oxidised low density lipoprotein (lectin-like) receptor 1 Hs.77729 AA682386 |
| 423 | FLJ13231: hypothetical protein FLJ13231 Hs.156148 W92787 |
| 424 | EST: Hs.323101 W40398 |
| 425 | ESTs,: Weakly similar to R06F6.5b [*C. elegans*] Hs.180591 N59330 |
| 426 | *Homo sapiens* cDNA: FLJ23285 fis, clone HEP09071 Hs.90424 N26163: |
| 427 | *Homo sapiens* mRNA full length insert cDNA clone EUROIMAGE 42408 Hs.284123 AA211446: |
| 428 | NFKB1: nuclear factor of kappa light polypeptide gene enhancer in B-cells 1 (p105) Hs.83428 AA451716 NFkB1 = NF-kappaB p105 = p50 |
| 429 | LOC58486: transposon-derived Buster1 transposase-like protein Hs.25726 AA630256 |

TABLE 1-continued

| | Gene (Name and/or Symbol) or Number (EST, cDNA clone, or Accession) |
|---|---|
| 430 | Homo sapiens cDNA FLJ10976 fis, clone PLACE1001399 Hs.296323 AA424756: |
| 431 | KIAA0182: KIAA0182 protein Hs.75909 AI023801 |
| 432 | RANGAP1: Ran GTPase activating protein 1 Hs.183800 AA991855 |
| 433 | PKMYT1: membrane-associated tyrosine- and threonine-specific cdc2-inhibitory kinase Hs.77783 AA478066 Myt1 kinase |
| 434 | HSPA8: heat shock 70 kD protein 8 Hs.180414 H64096 |
| 435 | LUC7A: cisplatin resistance-associated overexpressed protein Hs.3688 AA411969 |
| 436 | RRM1: ribonucleotide reductase M1 polypeptide Hs.2934 AA633549 |
| 437 | SET07: PR/SET domain containing protein 7 Hs.111988 AA421470 |
| 438 | **ESTs,: Weakly similar to ALU1_HUMAN ALU SUBFAMILY J SEQUENCE CONTAMINATION WARNING ENTRY [H. sapiens] Hs.193452 W96179 |
| 439 | Homo sapiens clone 25058 mRNA sequence Hs.179397 R38894: |
| 440 | ESTs,: Weakly similar to KIAA0973 protein [H. sapiens] Hs.14014 AA780791 |
| 441 | EST: Hs.105298 AA489813 |
| 442 | CTCF: CCCTC-binding factor (zinc finger protein) Hs.57419 H89996 |
| 443 | HRB: HIV-1 Rev binding protein Hs.171545 AA485958 |
| 444 | **ESTs: Hs.294083 AA447679 |
| 445 | KIAA0878: KIAA0878 protein Hs.188006 AA599094 |
| 446 | ESTs,: Weakly similar to ALUB_HUMAN !!!! ALU CLASS B WARNING ENTRY !!! [H. sapiens] Hs.180552 AA481283 |
| 447 | OGT: O-linked N-acetylglucosamine (GlcNAc) transferase (UDP-N-acetylglucosamine:polypeptide-N-acetylglucosaminyl transferase) Hs.100293 AA425229 |
| 448 | Homo sapiens mRNA for KIAA1700 protein, partial cds Hs.20281 N40952: |
| 449 | Human: DNA sequence from clone RP1-187J11 on chromosome 6q11.1-22.33. Contains the gene for a novel protein similar to S. pombe and S. cerevisiae predicted proteins, the gene for a novel protein simila Hs.72325 AA159962 |
| 450 | KIAA1265: KIAA1265 protein Hs.24936 AA479302 |
| 451 | H1F0: H1 histone family, member 0 Hs.226117 H57830 |
| 452 | ARGBP2: Arg/Abl-interacting protein ArgBP2 Hs.278626 H02525 |
| 453 | ODF2: outer dense fibre of sperm tails 2 Hs.129055 AA149882 |
| 454 | CD97: CD97 antigen Hs.3107 AI651871 |
| 455 | BMI1: **murine leukemia viral (bmi-1) oncogene homolog Hs.431 AA193573 |
| 456 | POLG: polymerase (DNA directed), gamma Hs.80961 AA188629 |
| 457 | XPR1: xenotropic and polytropic retrovirus receptor Hs.227656 AA453474 |
| 458 | ESTs: Hs.128096 AA971179 |
| 459 | DNAJB1: DnaJ (Hsp40) homolog, subfamily B, member 1 Hs.82646 AA481022 |
| 460 | ARL4: ADP-ribosylation factor-like 4 Hs.201672 AI142552 |
| 461 | SFRS5: splicing factor, arginine/serine-rich 5 Hs.166975 AA598965 |
| 462 | ESTs: Hs.25933 R11605 |
| 463 | RIG-I: RNA helicase Hs.145612 AA126958 |
| 464 | FLJ10339: hypothetical protein FLJ10339 Hs.203963 AA628231 |
| 465 | DR1: down-regulator of transcription 1, TBP-binding (negative cofactor 2) Hs.16697 AA043503 |
| 466 | Homo sapiens, Similar to hypothetical protein FLJ20093, clone MGC: 1076, mRNA, complete cds Hs.298998 AA703249: |
| 467 | HSPC163: HSPC163 protein Hs.108854 H98963 |
| 468 | DKFZP564A122: DKFZP564A122 protein Hs.187991 R27345 |
| 469 | FLJ10128: uveal autoantigen with coiled coil domains and ankyrin repeats Hs.49753 T47624 |
| 470 | DSCR1: Down syndrome critical region gene 1 Hs.184222 AA629707 |
| 471 | FLJ10342: hypothetical protein FLJ10342 Hs.101514 AA490935 |
| 472 | Homo sapiens mRNA; cDNA DKFZp586N1323 (from clone DKFZp586N1323) Hs.24064 R26176: |
| 473 | ESTs: Hs.4983 H59921 |
| 474 | ESTs,: Weakly similar to ALUB_HUMAN !!!! ALU CLASS B WARNING ENTRY !!! [H. sapiens] Hs.117949 H91167 |
| 475 | CDC45L: CDC45 (cell division cycle 45, S. cerevisiae, homolog)-like Hs.114311 AA700904 |
| 476 | STAT5B: signal transducer and activator of transcription 5B Hs.244613 AA280647 STAT5A/5B |
| 477 | Homo sapiens cDNA FLJ14028 fis, clone HEMBA1003838 Hs.281434 AA454682: |
| 478 | KIAA1524: KIAA1524 protein Hs.151343 AI248987 |
| 479 | CTSD: cathepsin D (lysosomal aspartyl protease) Hs.79572 AA485373 |
| 480 | Homo sapiens, Similar to hypothetical protein FLJ20093, clone MGC: 1076, mRNA, complete cds Hs.298998 AA682274: |
| 481 | GTPBP2: GTP binding protein 2 Hs.13011 T67069 |
| 482 | LOC51003: CGI-125 protein Hs.27289 AA485945 |
| 483 | VCL: vinculin Hs.75350 AA486727 |
| 484 | KIF5B: kinesin family member 5B Hs.149436 AA046613 |
| 485 | CDC25A: cell division cycle 25A Hs.1634 AA071514 |
| 486 | LOC51141: insulin induced protein 2 Hs.7089 AA045308 |
| 487 | **ESTs,: Moderately similar to CALD_HUMAN CALDESMON [H. sapiens] Hs.117774 H48508 |
| 488 | TBX3-iso: TBX3-iso protein Hs.267182 T48941 |
| 489 | KIAA0176: KIAA0176 protein Hs.4935 R44371 |
| 490 | PRKAR1A: protein kinase, cAMP-dependent, regulatory, type I, alpha (tissue specific extinguisher 1) Hs.183037 N25969 PKA-R1 alpha = cAMP-dependent protein kinase |

TABLE 1-continued

| | Gene (Name and/or Symbol) or Number (EST, cDNA clone, or Accession) |
|---|---|
| | type I-alpha-cata |
| 491 | ESTs: Hs.268991 H77818 |
| 492 | ESTs,: Weakly similar to A53028 isopentenyl-diphosphate Delta-isomerase [*H. sapiens*] Hs.9270 R17362 |
| 493 | ESTs,: Weakly similar to B34087 hypothetical protein [*H. sapiens*] Hs.120946 H50656 |
| 494 | TRN2: karyopherin beta 2b, transportin Hs.278378 R08897 |
| 495 | LMNA: lamin A/C Hs.77886 AA489582 |
| 496 | NFE2L2: nuclear factor (erythroid-derived 2)-like 2 Hs.155396 AA629687 |
| 497 | DKFZp762L0311: hypothetical protein DKFZp762L0311 Hs.16520 AA486418 |
| 498 | ESTs,: Weakly similar to S71752 giant protein p619 [*H. sapiens*] Hs.14870 T96829 |
| 499 | *Homo sapiens* mRNA; cDNA DKFZp434A1315 (from clone DKFZp434A1315); complete cds Hs.298312 AA991355: |
| 500 | E2IG4: hypothetical protein, estradiol-induced Hs.8361 R13844 |
| 501 | RANGAP1: Ran GTPase activating protein 1 Hs.183800 AA485734 |
| 502 | H1F0: H1 histone family, member 0 Hs.226117 W69399 |
| 503 | KIAA0239: KIAA0239 protein Hs.9729 AA454740 |
| 504 | ESTs,: Weakly similar to ALU7_HUMAN ALU SUBFAMILY SQ SEQUENCE CONTAMINATION WARNING ENTRY [*H. sapiens*] Hs.68647 R96804 |
| 505 | PRO0650: PRO0650 protein Hs.177258 N54333 |
| 506 | DNAJB9: DnaJ (Hsp40) homolog, subfamily B, member 9 Hs.6790 AA045792 |
| 507 | *Homo sapiens* cDNA: FLJ21971 fis, clone HEP05790 Hs.71331 AA774678: |
| 508 | LOC56996: **cation-chloride cotransporter-interacting protein Hs.119178 AA037466 |
| 509 | AP3D1: adaptor-related protein complex 3, delta 1 subunit Hs.75056 AA630776 |
| 510 | SGK: serum/glucocorticoid regulated kinase Hs.159640 AA486082 sgk = putative serine/threonine protein kinase transcriptional |
| 511 | HSPC148: hypothetical protein Hs.42743 R23666 |
| 512 | MRPL19: mitochondrial ribosomal protein L19 Hs.75574 AA521243 KIAA0104 |
| 513 | AA455102: |
| 514 | ESTs: Hs.150325 AI278813 |
| 515 | **ESTs: Hs.40527 AA029844 |
| 516 | HSPC145: HSPC145 protein Hs.18349 AI271431 |
| 517 | KIAA0170: KIAA0170 gene product Hs.277585 H68789 |
| 518 | FLJ11127: hypothetical protein Hs.91165 T98200 |
| 519 | KIAA0182: KIAA0182 protein Hs.75909 H05099 |
| 520 | FLJ23151: hypothetical protein FLJ23151 Hs.137260 AA284259 |
| 521 | AMD1: S-adenosylmethionine decarboxylase 1 Hs.262476 AA425692 |
| 522 | FLJ10342: **hypothetical protein FLJ10342 Hs.101514 AA934516 |
| 523 | SPS: SELENOPHOSPHATE SYNTHETASE; Human selenium donor protein Hs.124027 AA486372 |
| 524 | KIAA1586: KIAA1586 protein Hs.180663 AA779733 |
| 525 | ICBP90: transcription factor Hs.108106 AA908902 |
| 526 | *Homo sapiens* cDNA: FLJ21971 fis, clone HEP05790 Hs.71331 AI002036: |
| 527 | ABCC2: ATP-binding cassette, sub-family C (CFTR/MRP), member 2 Hs.193852 R91502 |
| 528 | ARHGDIB: Rho GDP dissociation inhibitor (GDI) beta Hs.83656 AA487426 LyGDI = Rho GDP-dissociation inhibitor 2 = RHO GDI 2 |
| 529 | RAD53: protein kinase Chk2 Hs.146329 AI653182 |
| 530 | R96880: |
| 531 | TNFAIP3: tumor necrosis factor, alpha-induced protein 3 Hs.211600 AA433807 |
| 532 | ESTs: Hs.26979 H23469 |
| 533 | AOC2: amine oxidase, copper containing 2 (retina-specific) Hs.143102 N50959 |
| 534 | *Homo sapiens* mRNA; cDNA DKFZp586N1323 (from clone DKFZp586N1323) Hs.24064 R30941: |
| 535 | AA452872: |
| 536 | ESTs: Hs.124169 R58970 |
| 537 | ACYP1: acylphosphatase 1, erythrocyte (common) type Hs.18573 W78754 |
| 538 | SIL: TAL1 (SCL) interrupting locus Hs.323032 AA704809 |
| 539 | AA016234: |
| 540 | *Homo sapiens* mRNA; cDNA DKFZp566P1124 (from clone DKFZp566P1124) Hs.321022 N50895: |
| 541 | KIAA1067: KIAA1067 protein Hs.325530 AA099138 |
| 542 | SMC4L1: SMC4 (structural maintenance of chromosomes 4, yeast)-like 1 Hs.50758 AA283006 |
| 543 | ESTs: Hs.29074 R70174 |
| 544 | SNK: serum-inducible kinase Hs.3838 AA460152 |
| 545 | FANCG: Fanconi anemia, complementation group G Hs.8047 AA427484 |
| 546 | *Homo sapiens* cDNA: FLJ21531 fis, clone COL06036 Hs.102941 N95440: |
| 547 | *Homo sapiens* mRNA; cDNA DKFZp547B086 (from clone DKFZp547B086) Hs.36606 N48700: |
| 548 | C1ORF2: chromosome 1 open reading frame 2 Hs.19554 H11464 cote1 = ORF in glucocerebrosidase locus |
| 549 | HTF9C: HpaII tiny fragments locus 9C Hs.63609 H17888 |
| 550 | ATF4: activating transcription factor 4 (tax-responsive enhancer element B67) Hs.181243 AA600217 |
| 551 | ESTs: Hs.101014 AA194941 |

TABLE 1-continued

| | Gene (Name and/or Symbol) or Number (EST, cDNA clone, or Accession) |
|---|---|
| 552 | CDC25A: cell division cycle 25A Hs.1634 AA913262 |
| 553 | TOPK: PDZ-binding kinase; T-cell originated protein kinase Hs.104741 AI002631 |
| 554 | ASIP: agouti (mouse)-signaling protein Hs.37006 AI220203 |
| 555 | DKFZP564F013: **hypothetical protein DKFZp564F013 Hs.128653 R14908 |
| 556 | ZNF265: zinc finger protein 265 Hs.194718 N66014 |
| 557 | SLC30A1: solute carrier family 30 (zinc transporter), member 1 Hs.55610 AA195463 |
| 558 | ESTs: Hs.28462 R63922 |
| 559 | ESTs: Hs.114055 R27431 |
| 560 | IL6: interleukin 6 (interferon, beta 2) Hs.93913 N98591 IL-6 |
| 561 | H3F3B: H3 histone, family 3B (H3.3B) Hs.180877 AA608514 |
| 562 | ESTs: Hs.81263 W81524 |
| 563 | *Homo sapiens* cDNA: FLJ23538 fis, clone LNG08010, highly similar to BETA2 Human MEN1 region clone epsilon/beta mRNA Hs.240443 AA400234: |
| 564 | AMD1: S-adenosylmethionine decarboxylase 1 Hs.262476 R82299 |
| 565 | MAP3K2: mitogen-activated protein kinase kinase kinase 2 Hs.28827 AA447971 |
| 566 | NET1: neuroepithelial cell transforming gene 1 Hs.25155 R24543 |
| 567 | CHAF1A: chromatin assembly factor 1, subunit A (p150) Hs.79018 AA704459 |
| 568 | MGC5585: hypothetical protein MGC5585 Hs.5152 H50655 |
| 569 | KIAA1598: KIAA1598 protein Hs.23740 H17868 |
| 570 | PNN: pinin, desmosome associated protein Hs.44499 W86139 |
| 571 | ESTs: Hs.238797 N70848 |
| 572 | ESTs,: Weakly similar to ALUB_HUMAN !!!! ALU CLASS B WARNING ENTRY !!! [*H. sapiens*] Hs.180552 AA600192 |
| 573 | PDGFA: platelet-derived growth factor alpha polypeptide Hs.37040 AA701502 |
| 574 | *Homo sapiens* clone FLC0675 PRO2870 mRNA, complete cds Hs.306117 AA443127: |
| 575 | ESTs: Hs.143375 AA001841 |
| 576 | TUBB: tubulin, beta polypeptide Hs.179661 H37989 |
| 577 | MSH2: mutS (*E. coli*) homolog 2 (colon cancer, nonpolyposis type 1) Hs.78934 AA219060 MSH2 = DNA mismatch repair mutS homologue |
| 578 | TOPBP1: topoisomerase (DNA) II binding protein Hs.91417 R97785 |
| 579 | KIAA0869: KIAA0869 protein Hs.21543 R43798 |
| 580 | H4FH: H4 histone family, member H Hs.93758 AA702781 |
| 581 | FLJ23293: hypothetical protein FLJ23293 similar to ARL-6 interacting protein-2 Hs.31236 AA629027 |
| 582 | ***Homo sapiens* cDNA: FLJ23538 fis, clone LNG08010, highly similar to BETA2 Human MEN1 region clone epsilon/beta mRNA Hs.240443 AA053165: |
| 583 | KIAA0978: KIAA0978 protein Hs.3686 N64780 |
| 584 | KIAA1547: KIAA1547 protein Hs.31305 AA057737 |
| 585 | DKFZP761C169: hypothetical protein DKFZp761C169 Hs.71252 AA608709 |
| 586 | WS-3: novel RGD-containing protein Hs.39913 AA449975 |
| 587 | FRZB: frizzled-related protein Hs.153684 H87275 |
| 588 | BRCA1: breast cancer 1, early onset Hs.194143 H90415 BRCA1 = Mutated in breast and ovarian cancer |
| 589 | ESTs: Hs.4983 H22936 |
| 590 | HSPC150: HSPC150 protein similar to ubiquitin-conjugating enzyme Hs.5199 AA460431 |
| 591 | *Homo sapiens* mRNA for KIAA1712 protein, partial cds Hs.29798 H54592: |
| 592 | FLJ11186: hypothetical protein FLJ11186 Hs.89278 AA504111 Unknown UG Hs.89278 ESTs |
| 593 | ESTs,: Weakly similar to unnamed protein product [*H. sapiens*] Hs.118338 R25481 |
| 594 | APEXL2: apurinic/apyrimidinic endonuclease(APEX nuclease)-like 2 protein Hs.154149 AI674393 |
| 595 | CDR2: cerebellar degeneration-related protein (62 kD) Hs.75124 AA074613 |
| 596 | ESTs: Hs.69662 AA459724 |
| 597 | PSCD2L: pleckstrin homology, Sec7 and coiled/coil domains 2-like Hs.8517 AA464957 |
| 598 | CRK: v-crk avian sarcoma virus CT10 oncogene homolog Hs.306088 H75530 |
| 599 | CCNE2: cyclin E2 Hs.30464 AA520999 Unknown UG Hs.30464 cyclin E2 |
| 600 | LOC51240: hypothetical protein Hs.7870 AA988037 |
| 601 | FLJ11259: hypothetical protein FLJ11259 Hs.184465 AA485877 |
| 602 | PTP4A1: protein tyrosine phosphatase type IVA, member 1 Hs.227777 AA482193 |
| 603 | *Homo sapiens* cDNA: FLJ22355 fis, clone HRC06344 Hs.288283 AA026375: |
| 604 | Human: clone 23719 mRNA sequence Hs.80305 H43437 |
| 605 | *Homo sapiens* clone FLC0675 PRO2870 mRNA, complete cds Hs.306117 AA485453: |
| 606 | MSE55: serum constituent protein Hs.148101 H73234 |
| 607 | CFLAR: CASP8 and FADD-like apoptosis regulator Hs.195175 AA453766 |
| 608 | *Homo sapiens* cDNA: FLJ22844 fis, clone KAIA5181 Hs.296322 AA975103: |
| 609 | Human: DNA sequence from clone RP11-371L19 on chromosome 20 Contains two novel genes, the gene for a novel protein similar to 40S ribosomal protein S10 (RPS10), ESTs, STSs, GSSs and five CpG islands Hs.19002 R00846 |
| 610 | ESTs: Hs.60054 R26390 |
| 611 | ESTs,: Weakly similar to ALU7_HUMAN ALU SUBFAMILY SQ SEQUENCE CONTAMINATION WARNING ENTRY [*H. sapiens*] Hs.325158 AA032084 |
| 612 | FLJ10980: hypothetical protein FLJ10980 Hs.29716 N45467 |
| 613 | IFIT1: **interferon-induced protein with tetratricopeptide repeats 1 Hs.20315 AA157787 |
| 614 | ESTs: Hs.21734 AA429809 |
| 615 | DKFZP434C245: DKFZP434C245 protein Hs.59461 AA705518 |

TABLE 1-continued

| | Gene (Name and/or Symbol) or Number (EST, cDNA clone, or Accession) |
|---|---|
| 616 | RNPS1: RNA-binding protein S1, serine-rich domain Hs.75104 AA496837 |
| 617 | FLJ13639: hypothetical protein FLJ13639 Hs.101821 AA131681 |
| 618 | PCF11: PCF11p homolog Hs.123654 W73749 |
| 619 | EIF4G3: eukaryotic translation initiation factor 4 gamma, 3 Hs.25732 N92469 |
| 620 | Homo sapiens cDNA: FLJ21971 fis, clone HEP05790 Hs.71331 AA130595: |
| 621 | STAT1: signal transducer and activator of transcription 1, 91 kD Hs.21486 AA079495 |
| 622 | BIRC3: baculoviral IAP repeat-containing 3 Hs.127799 R07870 |
| 623 | HP1-BP74: HP1-BP74 Hs.142442 N20589 |
| 624 | HSPC228: hypothetical protein Hs.267288 AI734268 |
| 625 | KIAA0675: KIAA0675 gene product Hs.165662 AA454867 |
| 626 | AMD1: S-adenosylmethionine decarboxylase 1 Hs.262476 AA504772 |
| 627 | EST: Hs.149338 AI249089 |
| 628 | PWP1: nuclear phosphoprotein similar to *S. cerevisiae* PWP1 Hs.172589 AA485992 |
| 629 | AI336973: |
| 630 | DUSP4: dual specificity phosphatase 4 Hs.2359 AA444049 |
| 631 | FLJ12788: hypothetical protein FLJ12788 Hs.20242 AA497041 |
| 632 | HSPC150: HSPC150 protein similar to ubiquitin-conjugating enzyme Hs.5199 AA985450 |
| 633 | FLJ11729: hypothetical protein FLJ11729 Hs.286212 W15533 |
| 634 | KLF4: Kruppel-like factor 4 (gut) Hs.7934 H45668 |
| 635 | FLJ11058: hypothetical protein FLJ11058 Hs.180817 N63911 |
| 636 | FLJ23468: hypothetical protein FLJ23468 Hs.38178 AA460299 |
| 637 | ESTs: Hs.115315 AI278336 |
| 638 | EBI3: Epstein-Barr virus induced gene 3 Hs.185705 AA425028 EBI3 = cytokine receptor |
| 639 | ESTs: Hs.293797 N63988 |
| 640 | MGAT2: mannosyl (alpha-1,6-)-glycoprotein beta-1,2-N-acetylglucosaminyltransferase Hs.172195 AA485653 |
| 641 | H2BFQ: H2B histone family, member Q Hs.2178 AA456298 |
| 642 | NMB: neuromedin B Hs.83321 AI650675 |
| 643 | SSR3: signal sequence receptor, gamma (translocon-associated protein gamma) Hs.28707 AA453486 |
| 644 | HSPC196: hypothetical protein Hs.239938 R78498 |
| 645 | EST: Hs.44522 N33610 |
| 646 | BRF1: butyrate response factor 1 (EGF-response factor 1) Hs.85155 AA723035 |
| 647 | MAN1A2: mannosidase, alpha, class 1A, member 2 Hs.239114 H97940 |
| 648 | KIAA1201: KIAA1201 protein Hs.251278 AA427719 |
| 649 | NUCKS: similar to rat nuclear ubiquitous casein kinase 2 Hs.118064 AA158345 |
| 650 | MAGEF1: MAGEF1 protein Hs.306123 AA425302 |
| 651 | Human: Chromosome 16 BAC clone CIT987SK-A-362G6 Hs.6349 N75498 |
| 652 | R40377: |
| 653 | AP3M2: adaptor-related protein complex 3, mu 2 subunit Hs.77770 R14443 |
| 654 | ESTs,: Weakly similar to 1207289A reverse transcriptase related protein [*H. sapiens*] Hs.272135 AA705010 |
| 655 | Homo sapiens mRNA for FLJ00116 protein, partial cds Hs.72363 AA159893: |
| 656 | EIF4E: eukaryotic translation initiation factor 4E Hs.79306 AA193254 |
| 657 | Homo sapiens mRNA for hypothetical protein (TR2/D15 gene) Hs.180545 N47285: |
| 658 | ESTs: Hs.99542 AA461474 |
| 659 | CTNND1: catenin (cadherin-associated protein), delta 1 Hs.166011 AA024656 |
| 660 | ESTs: Hs.188554 R75884 |
| 661 | ZNF217: zinc finger protein 217 Hs.155040 R81830 |
| 662 | FLJ12892: hypothetical protein FLJ12892 Hs.17731 AI243595 |
| 663 | ETV5: ets variant gene 5 (ets-related molecule) Hs.43697 AA460265 |
| 664 | EST: Hs.251574 T54821 |
| 665 | RPS25: ribosomal protein S25 Hs.113029 T98662 |
| 666 | CNN2: calponin 2 Hs.169718 AA284568 |
| 667 | ESTs,: Weakly similar to plakophilin 2b [*H. sapiens*] Hs.12705 AA485365 |
| 668 | PAPPA: pregnancy-associated plasma protein A Hs.75874 AA609463 |
| 669 | TFF3: trefoil factor 3 (intestinal) Hs.82961 N74131 |
| 670 | AI204264: |
| 671 | DJ328E19.C1.1: hypothetical protein Hs.218329 AA486041 |
| 672 | ME3: malic enzyme 3, NADP(+)-dependent, mitochondrial Hs.2838 AA779401 |
| 673 | ESTs,: Weakly similar to IEFS_HUMAN TRANSFORMATION-SENSITIVE PROTEIN IEF SSP 3521 [*H. sapiens*] Hs.43213 AA490554 |
| 674 | FLJ13181: hypothetical protein FLJ13181 Hs.301526 AA057266 |
| 675 | KIAA1547: KIAA1547 protein Hs.31305 AA136692 |
| 676 | ZNF281: zinc finger protein 281 Hs.59757 N47468 |
| 677 | Homo sapiens cDNA: FLJ23260 fis, clone COL05804, highly similar to HSU90911 Human clone 23652 mRNA sequence Hs.13996 AA463961: |
| 678 | ESTs: Hs.25933 AA411392 |
| 679 | NCBP1: nuclear cap binding protein subunit 1, 80 kD Hs.89563 AA278749 nuclear cap binding protein |
| 680 | H2BFL: H2B histone family, member L Hs.239884 H70774 |
| 681 | DKFZP564A122: DKFZP564A122 protein Hs.187991 H66150 |
| 682 | NASP: nuclear autoantigenic sperm protein (histone-binding) Hs.243886 AA644128 |
| 683 | **ESTs,: Weakly similar to KIAA0822 protein [*H. sapiens*] Hs.98368 AA422008 |
| 684 | MAP2K6: mitogen-activated protein kinase kinase 6 Hs.118825 H07920 |
| 685 | ESTs: Hs.158357 AA865842 |

TABLE 1-continued

| | Gene (Name and/or Symbol) or Number (EST, cDNA clone, or Accession) |
|---|---|
| 686 | GADD45A: growth arrest and DNA-damage-inducible, alpha Hs.80409 AA147214 GADD45 alpha = growth arrest and DNA-damage-inducible protein |
| 687 | DHFR: dihydrofolate reductase Hs.83765 AA488803 |
| 688 | AA151930: |
| 689 | Homo sapiens mRNA; cDNA DKFZp434P116 (from clone DKFZp434P116); complete cds Hs.103378 AA431133: |
| 690 | Homo sapiens mRNA; cDNA DKFZp564D156 (from clone DKFZp564D156) Hs.9927 T55704: |
| 691 | ESTs: Hs.32204 R93719 |
| 692 | PRPSAP1: phosphoribosyl pyrophosphate synthetase-associated protein 1 Hs.77498 R20005 |
| 693 | ZNF42: zinc finger protein 42 (myeloid-specific retinoic acid-responsive) Hs.169832 AA987906 |
| 694 | **ESTs: Hs.43712 N25936 |
| 695 | RUNX1: runt-related transcription factor 1 (acute myeloid leukemia 1; aml1 oncogene) Hs.129914 AA146826 |
| 696 | Homo sapiens mRNA; cDNA DKFZp547C244 (from clone DKFZp547C244) Hs.9460 T64452: |
| 697 | TYMS: thymidylate synthetase Hs.82962 AA663310 |
| 698 | MGC5528: hypothetical protein MGC5528 Hs.315167 AA843451 |
| 699 | ESTs: Hs.268685 R22952 |
| 700 | SFPQ: splicing factor proline/glutamine rich (polypyrimidine tract-binding protein-associated) Hs.180610 AA418910 |
| 701 | ESTs: Hs.155105 AI221390 |
| 702 | FLJ10624: hypothetical protein FLJ10624 Hs.306000 AA489592 |
| 703 | TRIP8: thyroid hormone receptor interactor 8 Hs.6685 AA425205 |
| 704 | DNAJB6: DnaJ (Hsp40) homolog, subfamily B, member 6 Hs.181195 AA496105 |
| 705 | ESTs: Hs.18331 T98244 |
| 706 | RBM14: RNA binding motif protein 14 Hs.11170 AA421233 |
| 707 | SCYA2: small inducible cytokine A2 (monocyte chemotactic protein 1, homologous to mouse Sig-je) Hs.303649 AA425102 MCP-1 = MCAF = small inducible cytokine A2 = JE = chemokine |
| 708 | MGC4161: hypothetical protein MGC4161 Hs.177688 AI224867 |
| 709 | TUBB2: tubulin, beta, 2 Hs.251653 AA888148 |
| 710 | FLJ20280: hypothetical protein FLJ20280 Hs.270134 N74086 |
| 711 | TERA: TERA protein Hs.180780 AA465096 |
| 712 | CPS1: **carbamoyl-phosphate synthetase 1, mitochondrial Hs.50966 N68399 |
| 713 | KIAA0802: KIAA0802 protein Hs.27657 W55875 |
| 714 | FYN: FYN oncogene related to SRC, FGR, YES Hs.169370 N22980 |
| 715 | Homo sapiens PRO2751 mRNA, complete cds Hs.283978 H12784: |
| 716 | CLTH: Clathrin assembly lymphoid-myeloid leukemia gene Hs.7885 AA441930 |
| 717 | CHMP1.5: CHMP1.5 protein Hs.42733 W85875 |
| 718 | SMARCB1: SWI/SNF related, matrix associated, actin dependent regulator of chromatin, subfamily b, member 1 Hs.159971 AA446018 |
| 719 | AA487823: SRF = c-fos serum response element-binding transcription facto |
| 720 | **ESTs: Hs.130741 AA608725 |
| 721 | Homo sapiens cDNA FLJ10976 fis, clone PLACE1001399 Hs.296323 R36085: |
| 722 | FLJ20036: hypothetical protein FLJ20036 Hs.32922 N91145 |
| 723 | C11ORF5: chromosome 11 open reading frame 5 Hs.121025 AA776702 |
| 724 | AF3P21: SH3 protein Hs.102929 N94372 |
| 725 | LOC54104: hypothetical protein Hs.12871 H05934 |
| 726 | DF: D component of complement (adipsin) Hs.155597 AA233549 |
| 727 | CEP4: Cdc42 effector protein 4; binder of Rho GTPases 4 Hs.3903 AA449061 |
| 728 | KIF5B: kinesin family member 5B Hs.149436 AA644218 |
| 729 | MGC5627: hypothetical protein MGC5627 Hs.237971 H02336 |
| 730 | G3BP: Ras-GTPase-activating protein SH3-domain-binding protein Hs.220689 AA449834 |
| 731 | ESTs: Hs.293987 AA229758 |
| 732 | ESTs: Hs.36828 AA194796 |
| 733 | Homo sapiens mRNA for FLJ00101 protein, partial cds Hs.221600 W92262: |
| 734 | Homo sapiens cDNA: FLJ21288 fis, clone COL01927 Hs.6019 R07184: |
| 735 | ESTs,: Weakly similar to 1207289A reverse transcriptase related protein [H. sapiens] Hs.250594 H86813 |
| 736 | Homo sapiens cDNA FLJ11941 fis, clone HEMBB1000649 Hs.124106 AI301573: |
| 737 | ESTs: Hs.24908 H77726 |
| 738 | TOB2: transducer of ERBB2, 2 Hs.4994 AA486088 |
| 739 | ESTs: Hs.143900 AI193212 |
| 740 | Homo sapiens clone FLC0675 PRO2870 mRNA, complete cds Hs.306117 H16589: |
| 741 | ESTs,: Weakly similar to KIAA0638 protein [H. sapiens] Hs.296288 T83657 |
| 742 | FLJ20039: hypothetical protein FLJ20039 Hs.267448 AA448268 |
| 743 | RPA2: replication protein A2 (32 kD) Hs.79411 R13557 |
| 744 | GAS1: growth arrest-specific 1 Hs.65029 AA025819 |
| 745 | Human: DNA sequence from clone 967N21 on chromosome 20p12.3-13. Contains the CHGB gene for chromogranin B (secretogranin 1, SCG1), a pseudogene similar to part of KIAA0172, the gene for a novel protein Hs.88959 R56678 |
| 746 | ESTs: Hs.21175 AI341642 |
| 747 | LBC: lymphoid blast crisis oncogene Hs.301946 AA135716 |
| 748 | ESTs: Hs.194595 R06761 |

TABLE 1-continued

| | Gene (Name and/or Symbol) or Number (EST, cDNA clone, or Accession) |
|---|---|
| 749 | MGC4707: hypothetical protein MGC4707 Hs.291003 R14653 |
| 750 | ZNF183: zinc finger protein 183 (RING finger, C3HC4 type) Hs.64794 AA132766 |
| 751 | RAD18: postreplication repair protein hRAD18p Hs.21320 R59197 |
| 752 | EIF4EBP2: **eukaryotic translation initiation factor 4E binding protein 2 Hs.278712 H15159 |
| 753 | **_Homo sapiens_ mRNA; cDNA DKFZp586M0723 (from clone DKFZp586M0723) Hs.27860 AA446650: |
| 754 | ORC3L: origin recognition complex, subunit 3 (yeast homolog)-like Hs.74420 H99257 |
| 755 | CDK7: cyclin-dependent kinase 7 (homolog of _Xenopus_ MO15 cdk-activating kinase) Hs.184298 AI311067 |
| 756 | USP10: ubiquitin specific protease 10 Hs.78829 AA455233 |
| 757 | KIAA0733: TAK1-binding protein 2; KIAA0733 protein Hs.109727 AA931658 |
| 758 | R89286: |
| 759 | ALDH4: aldehyde dehydrogenase 4 (glutamate gamma-semialdehyde dehydrogenase; pyrroline-5-carboxylate dehydrogenase) Hs.77448 AA181378 |
| 760 | IDN3: IDN3 protein Hs.225767 N62911 |
| 761 | ESTs: Hs.50180 H48143 |
| 762 | MIG2: mitogen inducible 2 Hs.75260 H29252 |
| 763 | KIAA0856: KIAA0856 protein Hs.13264 R12847 |
| 764 | EST: Hs.47763 N54162 |
| 765 | _Homo sapiens_ mRNA; cDNA DKFZp547C244 (from clone DKFZp547C244) Hs.9460 AA447553: |
| 766 | KIAA0855: golgin-67 Hs.182982 AA775625 |
| 767 | ESTs,: Weakly similar to JH0148 nucleolin - rat [_R. norvegicus_] Hs.30120 R54659 |
| 768 | FLJ22313: hypothetical protein FLJ22313 Hs.30211 H52061 |
| 769 | ESTs: Hs.71818 AI028074 |
| 770 | KIAA0618: KIAA0618 gene product Hs.295112 AA455506 |
| 771 | ESTs: Hs.59413 W93056 |
| 772 | ESTs: Hs.165607 AA992090 |
| 773 | UBAP: ubiquitin associated protein Hs.75425 AA446016 |
| 774 | HAN11: WD-repeat protein Hs.176600 AA725641 |
| 775 | USP16: ubiquitin specific protease 16 Hs.99819 AA489619 |
| 776 | ESTs: Hs.67776 AA464963 |
| 777 | SM-20: similar to rat smooth muscle protein SM-20 Hs.6523 H56028 |
| 778 | CCNG2: cyclin G2 Hs.79069 AA489647 |
| 779 | _Homo sapiens_ mRNA; cDNA DKFZp566P1124 (from clone DKFZp566P1124) Hs.321022 N62953: |
| 780 | FLJ20094: hypothetical protein FLJ20094 Hs.29700 N95490 |
| 781 | LOC51174: delta-tubulin Hs.270847 W33133 |
| 782 | _Homo sapiens_ mRNA; cDNA DKFZp434I1820 (from clone DKFZp434I1820); partial cds Hs.14235 N52394: |
| 783 | FANCA: Fanconi anemia, complementation group A Hs.284153 AA644129 |
| 784 | P5-1: MHC class I region ORF Hs.1845 T58146 |
| 785 | DNA2L: DNA2 (DNA replication helicase, yeast, homolog)-like Hs.194665 AA974495 KIAA0083 |
| 786 | LOC51578: **adrenal gland protein AD-004 Hs.279586 AA150301 |
| 787 | ESTs: Hs.326417 AA913304 |
| 788 | CDKN2D: cyclin-dependent kinase inhibitor 2D (p19, inhibits CDK4) Hs.29656 R77517 p19-INK4D = Cyclin-dependent kinase 4 inhibitor D |
| 789 | FABP1: fatty acid binding protein 1, liver Hs.5241 AA682392 |
| 790 | TERA: TERA protein Hs.180780 AA906997 |
| 791 | ESTs: Hs.145383 AI253072 |
| 792 | SLC7A5: solute carrier family 7 (cationic amino acid transporter, y+ system), member 5 Hs.184601 AA419176 |
| 793 | AXL: AXL receptor tyrosine kinase Hs.83341 H15336 axl = ufo = tyrosine kinase receptor |
| 794 | LOC57190: selenoprotein N Hs.8518 AA284276 |
| 795 | ESTs: Hs.99037 AA443948 |
| 796 | STCH: stress 70 protein chaperone, microsome-associated, 60 kD Hs.288799 H85311 |
| 797 | ESTs: Hs.88523 AA278591 Unknown UG Hs.88523 ESTs |
| 798 | ESD: **esterase D/formylglutathione hydrolase Hs.82193 AA250931 |
| 799 | ESTs: Hs.122444 R31021 |
| 800 | ESTs: Hs.283127 AI291262 |
| 801 | KIAA0480: **KIAA0480 gene product Hs.92200 H91332 |
| 802 | HP1-BP74: HP1-BP74 Hs.142442 AA598791 |
| 803 | **ESTs,: Moderately similar to ALU1_HUMAN ALU SUBFAMILY J SEQUENCE CONTAMINATION WARNING ENTRY [_H. sapiens_] Hs.144662 AA987667 |
| 804 | TTF2: transcription termination factor, RNA polymerase II Hs.142157 AI023603 |
| 805 | ESTs: Hs.13740 T70541 |
| 806 | DJ37E16.5: hypothetical protein dJ37E16.5 Hs.5790 AA400021 |
| 807 | CDH24: cadherin-like 24 Hs.155912 AI732266 |
| 808 | DJ465N24.2.1: **hypothetical protein dJ465N24.2.1 Hs.8084 AA932375 |
| 809 | ESTs,: Weakly similar to S57447 HPBRII-7 protein [_H. sapiens_] Hs.16346 AA410490 |
| 810 | _Homo sapiens_ cDNA: FLJ23285 fis, clone HEP09071 Hs.90424 AI005038: |
| 811 | KRAS2: v-Ki-ras2 Kirsten rat sarcoma 2 viral oncogene homolog Hs.184050 N95249 |
| 812 | FLJ20038: hypothetical protein FLJ20038 Hs.72071 H96090 |
| 813 | ESTs,: Weakly similar to ALU4_HUMAN ALU SUBFAMILY SB2 SEQUENCE CONTAMINATION WARNING ENTRY [_H. sapiens_] Hs.28848 AA486607 |

TABLE 1-continued

| | Gene (Name and/or Symbol) or Number (EST, cDNA clone, or Accession) |
|---|---|
| 814 | H2AFN: H2A histone family, member N Hs.134999 AI095013 |
| 815 | RERE: arginine-glutamic acid dipeptide (RE) repeats Hs.194369 AA490249 |
| 816 | USP1: ubiquitin specific protease 1 Hs.35086 T55607 |
| 817 | TIP47: cargo selection protein (mannose 6 phosphate receptor binding protein) Hs.140452 AA416787 |
| 818 | KIAA0135: KIAA0135 protein Hs.79337 AA427740 KIAA0135 = related to pim-1 kinase. |
| 819 | ESTs: Hs.214410 T95273 |
| 820 | PPP1R2: protein phosphatase 1, regulatory (inhibitor) subunit 2 Hs.267819 N52605 |
| 821 | Homo sapiens cDNA: FLJ21210 fis, clone COL00479 Hs.325093 AA978323: |
| 822 | CSNK2A2: casein kinase 2, alpha prime polypeptide Hs.82201 AA054996 |
| 823 | HSRTSBETA: rTS beta protein Hs.180433 N66132 |
| 824 | FLJ13110: hypothetical protein FLJ13110 Hs.7358 AA431233 |
| 825 | ESTs: Hs.238797 N30704 |
| 826 | FYN: FYN oncogene related to SRC, FGR, YES Hs.169370 N35086 |
| 827 | RBM8A: RNA binding motif protein 8A Hs.65648 AA448402 |
| 828 | ESTs: Hs.21906 AA608546 |
| 829 | ESTs: Hs.128081 AA971042 |
| 830 | PP591: hypothetical protein PP591 Hs.118666 AA626336 |
| 831 | N63866: |
| 832 | HM74: putative chemokine receptor; GTP-binding protein Hs.137555 R02739 |
| 833 | MID1: midline 1 (Opitz/BBB syndrome) Hs.27695 AA598640 |
| 834 | KIAA1586: KIAA1586 protein Hs.180663 AA938639 |
| 835 | Homo sapiens clone CDABP0014 mRNA sequence Hs.92679 AA443139: |
| 836 | HSU79274: protein predicted by clone 23733 Hs.150555 AA451900 |
| 837 | AOC3: amine oxidase, copper containing 3 (vascular adhesion protein 1) Hs.198241 AA036974 |
| 838 | AA548037: |
| 839 | FLJ10154: hypothetical protein FLJ10154 Hs.179972 AA457133 |
| 840 | THBS1: thrombospondin 1 Hs.87409 AA464532 |
| 841 | DNAJB6: DnaJ (Hsp40) homolog, subfamily B, member 6 Hs.181195 AA431203 |
| 842 | KIAA1547: KIAA1547 protein Hs.31305 AI216623 |
| 843 | GATA2: GATA-binding protein 2 Hs.760 R32405 |
| 844 | ESTs: Hs.176950 R82522 |
| 845 | KIAA1018: KIAA1018 protein Hs.5400 AA156859 |
| 846 | B4GALT1: **UDP-Gal:betaGlcNAc beta 1,4-galactosyltransferase, polypeptide 1 Hs.198248 AA043795 |
| 847 | HMGCR: 3-hydroxy-3-methylglutaryl-Coenzyme A reductase Hs.11899 AA779417 |
| 848 | ESTs,: Weakly similar to 1819485A CENP-E protein [H. sapiens] Hs.167652 H94466 |
| 849 | ESTs: Hs.294088 AA971073 |
| 850 | KIAA1637: coactivator independent of AF-2 (CIA); KIAA1637 protein Hs.288140 AA918007 |
| 851 | HSPC196: hypothetical protein Hs.239938 H66023 |
| 852 | DR1: down-regulator of transcription 1, TBP-binding (negative cofactor 2) Hs.16697 AA132007 |
| 853 | CG1I: putative cyclin G1 interacting protein Hs.10028 AA486444 |
| 854 | IGSF4: immunoglobulin superfamily, member 4 Hs.70337 AA487505 |
| 855 | ESTs: Hs.179309 AA664350 |
| 856 | HSPC163: HSPC163 protein Hs.108854 AA053139 |
| 857 | FLJ12788: hypothetical protein FLJ12788 Hs.20242 AI061317 |
| 858 | FEM1B: FEM-1 (C. elegans) homolog b Hs.6048 H82273 |
| 859 | FXR1: fragile X mental retardation, autosomal homolog 1 Hs.82712 N62761 |
| 860 | NCOA3: nuclear receptor coactivator 3 Hs.225977 AA156793 |
| 861 | H2BFB: H2B histone family, member B Hs.180779 N33927 |
| 862 | ESTs: Hs.23830 AA460601 |
| 863 | CDK7: cyclin-dependent kinase 7 (homolog of Xenopus MO15 cdk-activating kinase) Hs.184298 AA031961 CAK = cdk7 = NRTALRE = sdk = CDK activating kinase |
| 864 | FLJ20259: hypothetical protein FLJ20259 Hs.9956 T55949 |
| 865 | Homo sapiens cDNA FLJ20678 fis, clone KAIA4163 Hs.143601 T95823: |
| 866 | RPS19: ribosomal protein S19 Hs.298262 T72208 |
| 867 | Homo sapiens mRNA; cDNA DKFZp434M0420 (from clone DKFZp434M0420) Hs.326048 AA443976: |
| 868 | TP53: tumor protein p53 (Li-Fraumeni syndrome) Hs.1846 R39356 p53 |
| 869 | FBI1: HIV-1 inducer of short transcripts binding protein Hs.104640 R06252 |
| 870 | GOT1: glutamic-oxaloacetic transaminase 1, soluble (aspartate aminotransferase 1) Hs.597 H22855 |
| 871 | FLJ21434: hypothetical protein FLJ21434 Hs.298503 AA680129 |
| 872 | DNMT2: DNA (cytosine-5-)-methyltransferase 2 Hs.97681 R95731 |
| 873 | ESTs: Hs.55272 W02785 |
| 874 | H2BFQ: H2B histone family, member Q Hs.2178 AA010223 |
| 875 | NFIC: nuclear factor I/C (CCAAT-binding transcription factor) Hs.184771 N20996 |
| 876 | NPTX1: neuronal pentraxin I Hs.84154 H22445 |
| 877 | TLOC1: translocation protein 1 Hs.8146 AA450205 |
| 878 | MGC5302: endoplasmic reticulum resident protein 58; hypothetical protein MGC5302 Hs.44970 N39195 |

TABLE 1-continued

| | Gene (Name and/or Symbol) or Number (EST, cDNA clone, or Accession) |
|---|---|
| 879 | ACTR2: ARP2 (actin-related protein 2, yeast) homolog Hs.42915 AA032090 |
| 880 | AI287555: |
| 881 | ABCA7: ATP-binding cassette, sub-family A (ABC1), member 7 Hs.134514 AI668632 |
| 882 | COL7A1: collagen, type VII, alpha 1 (epidermolysis bullosa, dystrophic, dominant and recessive) Hs.1640 AA598507 |
| 883 | RFC2: replication factor C (activator 1) 2 (40 kD) Hs.139226 AA663472 |
| 884 | FLJ22583: hypothetical protein FLJ22583 Hs.287700 AA135836 |
| 885 | **ESTs,: Weakly similar to ORF2 [*M. musculus*] Hs.172208 AI820570 |
| 886 | ESTs: Hs.21667 R15709 |
| 887 | RBBP4: retinoblastoma-binding protein 4 Hs.16003 AA705035 |
| 888 | *Homo sapiens* mRNA; cDNA DKFZp434J1027 (from clone DKFZp434J1027); partial cds Hs.22908 820166: |
| 889 | ESTs: Hs.166539 AI080987 |
| 890 | NKTR: natural killer-tumor recognition sequence Hs.241493 AA279666 NK-tumor recognition protein = cyclophilin-related protein |
| 891 | MUC1: mucin 1, transmembrane Hs.89603 AA486365 |
| 892 | AP4B1: adaptor-related protein complex 4, beta 1 subunit Hs.28298 AA481045 |
| 893 | ESTs: Hs.94943 AA452165 |
| 894 | MITF: microphthalmia-associated transcription factor Hs.166017 N66177 |
| 895 | ESTs: Hs.183299 AA286914 Unknown UG Hs.183299 ESTs sc_id2032 |
| 896 | BAG3: BCL2-associated athanogene 3 Hs.15259 AI269958 |
| 897 | INSR: insulin receptor Hs.89695 AA001106 |
| 898 | TRIP: TRAF interacting protein Hs.21254 AA186426 |
| 899 | EST: Hs.307975 R22182 |
| 900 | **Homo sapiens* cDNA: FLJ23037 fis, clone LNG02036, highly similar to HSU68019 *Homo sapiens* mad protein homolog (hMAD-3) mRNA Hs.288261 W72201: |
| 901 | HLA-DNA: major histocompatibility complex, class II, DN alpha Hs.11135 AA702254 Major histocompatibility complex, class II, DN alpha |
| 902 | FLJ10392: **hypothetical protein FLJ10392 Hs.20887 AI261305 |
| 903 | MPHOSPH1: **M-phase phosphoprotein 1 Hs.240 N63752 |
| 904 | STAG1: stromal antigen 1 Hs.286148 R36160 |
| 905 | USP1: ubiquitin specific protease 1 Hs.35086 AA970066 |
| 906 | ESTs,: Moderately similar to ALU4_HUMAN ALU SUBFAMILY SB2 SEQUENCE CONTAMINATION WARNING ENTRY [*H. sapiens*] Hs.181315 AA448251 |
| 907 | PA26: p53 regulated PA26 nuclear protein Hs.14125 AA447661 |
| 908 | ESTs,: Weakly similar to zinc finger protein [*H. sapiens*] Hs.71243 N92478 |
| 909 | SH3PX1: SH3 and PX domain-containing protein SH3PX1 Hs.7905 R69163 |
| 910 | **Homo sapiens* cDNA: FLJ22554 fis, clone HSI01092 Hs.93842 H58317: |
| 911 | RPS25: ribosomal protein S25 Hs.113029 AA779404 |
| 912 | ESTs,: Weakly similar to A49134 Ig kappa chain V-I region [*H. sapiens*] Hs.5890 N34799 fra-2 = fos-related antigen 2 |
| 913 | TXNRD1: thioredoxin reductase 1 Hs.13046 AA453335 Thioredoxin reductase |
| 914 | **ESTs: Hs.184378 N77828 |
| 915 | GCSH: glycine cleavage system protein H (aminomethyl carrier) Hs.77631 R71327 |
| 916 | *Homo sapiens* cDNA FLJ11904 fis, clone HEMBB1000048 Hs.285519 AA447098: |
| 917 | NCOA3: nuclear receptor coactivator 3 Hs.225977 H51992 AIB1 = Amplified in Breast Cancer = TRAM-1 = RAC3 = ACTR = CAGH16 = nucl |
| 918 | FLJ20159: hypothetical protein FLJ20159 Hs.288809 R33122 |
| 919 | IL7R: interleukin 7 receptor Hs.237868 AA487121 |
| 920 | RAB23: RAB23, member RAS oncogene family Hs.94769 AA134569 |
| 921 | ESTs: Hs.132493 AA923168 |
| 922 | ESTs: Hs.87507 AA236015 |
| 923 | SHC1: SHC (Src homology 2 domain-containing) transforming protein 1 Hs.81972 R52960 |
| 924 | KIAA1321: KIAA1321 protein Hs.24336 W37999 |
| 925 | GLI: glioma-associated oncogene homolog (zinc finger protein) Hs.2693 AI373071 |
| 926 | ESTs: Hs.183299 AA291137 Unknown UG Hs.183299 ESTs sc_id2032 |
| 927 | GPRK6: G protein-coupled receptor kinase 6 Hs.76297 AA291284 |
| 928 | ESTs: Hs.93704 AA702684 |
| 929 | CAPS: calcyphosine Hs.26685 AA858390 |
| 930 | *Homo sapiens* cDNA FLJ10976 fis, clone PLACE1001399 Hs.296323 R27711: |
| 931 | C6: complement component 6 Hs.1282 N59396 |
| 932 | UBE2D3: ubiquitin-conjugating enzyme E2D 3 (homologous to yeast UBC4/5) Hs.118797 AA465196 |
| 933 | DDX8: DEAD/H (Asp-Glu-Ala-Asp/His) box polypeptide 8 (RNA helicase) Hs.171872 AA465387 RNA helicase (HRH1) |
| 934 | DKFZP434B168: DKFZP434B168 protein Hs.48604 N62684 |
| 935 | FLJ10512: hypothetical protein FLJ10512 Hs.93581 T39933 |
| 936 | *Homo sapiens* mRNA; cDNA DKFZp564F093 (from clone DKFZp564F093) Hs.18724 W87709: |
| 937 | F8A: coagulation factor VIII-associated (intronic transcript) Hs.83363 AA463924 |
| 938 | HSU53209: transformer-2 alpha (htra-2 alpha) Hs.24937 AA465172 |
| 939 | UBQLN2: ubiquilin 2 Hs.4552 R43580 |
| 940 | EIF2C2: eukaryotic translation initiation factor 2C, 2 Hs.193053 N93082 |
| 941 | *Homo sapiens* mRNA for FLJ00012 protein, partial cds Hs.21051 H17645: |
| 942 | KIAA0841: KIAA0841 protein Hs.7426 R20299 |

TABLE 1-continued

| Gene (Name and/or Symbol) or Number (EST, cDNA clone, or Accession) |
|---|
| 943 KCNAB2: potassium voltage-gated channel, shaker-related subfamily, beta member 2 Hs.298184 H14383 |
| 944 KIAA1637: coactivator independent of AF-2 (CIA); KIAA1637 protein Hs.288140 AA521358 |
| 945 ESTs: Hs.27379 H17455 |
| 946 FLJ11323: hypothetical protein FLJ11323 Hs.25625 R49707 |
| 947 SSP29: acidic protein rich in leucines Hs.84264 AA489201 |
| 948 ESTs: Hs.69280 AA486011 |
| 949 ADAMTS1: a disintegrin-like and metalloprotease (reprolysin type) with thrombospondin type 1 motif, 1 Hs.8230 AA057170 |
| 950 ESTs: Hs.43466 N23889 |
| 951 MLLT4: myeloid/lymphoid or mixed-lineage leukemia (trithorax (*Drosophila*) homolog); translocated to, 4 Hs.100469 AA010818 |
| 952 ESTs: Hs.271034 AA406581 |
| 953 LMNB1: lamin B1 Hs.89497 AA983462 |
| 954 *Homo sapiens* cDNA FLJ13547 fis, clone PLACE1007053 Hs.7984 AA629264: |
| 955 PTMS: parathymosin Hs.171814 R10451 |
| 956 H2AFL: H2A histone family, member L Hs.28777 AI268551 |
| 957 FLJ21603: hypothetical protein FLJ21603 Hs.129691 R72794 |
| 958 FLJ13287: hypothetical protein FLJ13287 Hs.53263 AA621725 |
| 959 CXCR4: chemokine (C—X—C motif), receptor 4 (fusin) Hs.89414 AA479357 |
| 960 INSM1: insulinoma-associated 1 Hs.89584 R38640 |
| 961 FREQ: frequenin (*Drosophila*) homolog Hs.301760 H16821 |
| 962 LOC58486: transposon-derived Buster1 transposase-like protein Hs.25726 AA868020 |
| 963 SMARCD1: SWI/SNF related, matrix associated, actin dependent regulator of chromatin, subfamily d, member 1 Hs.79335 H91691 |
| 964 ESTs: Hs.242998 T96522 |
| 965 INADL: PDZ domain protein (*Drosophila* inaD-like) Hs.321197 AA005153 |
| 966 ESTs,: Weakly similar to putative p150 [*H. sapiens*] Hs.37751 AA436174 |
| 967 MGC5338: hypothetical protein MGC5338 Hs.99598 H50550 |
| 968 W85890: |
| 969 NUCKS: similar to rat nuclear ubiquitous casein kinase 2 Hs.118064 AI053436 |
| 970 *Homo sapiens* clone 25110 mRNA sequence Hs.27262 H18031: |
| 971 AI333214: |
| 972 GAS41: glioma-amplified sequence-41 Hs.4029 T62072 |
| 973 LOC51170: retinal short-chain dehydrogenase/reductase retSDR2 Hs.12150 N79745 |
| 974 H2BFG: **H2B histone family, member G Hs.182137 R98472 |
| 975 ABCC1: **ATP-binding cassette, sub-family C (CFTR/MRP), member 1 Hs.89433 AA424804 |
| 976 EFNA1: ephrin-A1 Hs.1624 AA857015 |
| 977 *Homo sapiens* mRNA; cDNA DKFZp434A1014 (from clone DKFZp434A1014); partial cds Hs.278531 H00596: |
| 978 PPP2CA: protein phosphatase 2 (formerly 2A), catalytic subunit, alpha isoform Hs.91773 AA599092 |
| 979 ESTs,: Weakly similar to unnamed protein product [*H. sapiens*] Hs.118338 W85843 |
| 980 *Homo sapiens* cDNA FLJ11643 fis, clone HEMBA1004366 Hs.111496 AA598803: |
| 981 ESTs,: Moderately similar to ALUE_HUMAN !!!! ALU CLASS E WARNING ENTRY !!! [*H. sapiens*] Hs.125407 AA878944 |
| 982 ESTs,: Moderately similar to ALU1_HUMAN ALU SUBFAMILY J SEQUENCE CONTAMINATION WARNING ENTRY [*H. sapiens*] Hs.144662 AI191290 |
| 983 KIAA0916: KIAA0916 protein Hs.151411 R91388 |
| 984 CDC25A: cell division cycle 25A Hs.1634 R09062 |
| 985 PRIM2A: primase, polypeptide 2A (58 kD) Hs.74519 R61073 |
| 986 DSP: desmoplakin (DPI, DPII) Hs.74316 H90899 |
| 987 KIAA0101: KIAA0101 gene product Hs.81892 W68219 |
| 988 ESTs,: Weakly similar to putative p150 [*H. sapiens*] Hs.268026 AA411454 |
| 989 ESTs: Hs.18140 T97707 |
| 990 H2AFL: H2A histone family, member L Hs.28777 AA457566 |
| 991 *Homo sapiens* mRNA for KIAA1700 protein, partial cds Hs.20281 H00287: |
| 992 STAG3: stromal antigen 3 Hs.20132 AA453028 |
| 993 ZNF207: zinc finger protein 207 Hs.62112 N59119 |
| 994 BMP6: bone morphogenetic protein 6 Hs.285671 AA424833 |
| 995 ESTs,: Moderately similar to sertolin [*R. norvegicus*] Hs.91192 H60690 |
| 996 LOC51064: **glutathione S-transferase subunit 13 homolog Hs.279952 W88497 |
| 997 NUCKS: similar to rat nuclear ubiquitous casein kinase 2 Hs.118064 AA927182 |
| 998 ESTs,: Weakly similar to T00370 hypothetical protein KIAA0659 [*H. sapiens*] Hs.131899 W93155 |
| 999 FLJ13057: hypothetical protein FLJ13057 similar to germ cell-less Hs.243122 R23254 |
| 1000 ESTs: Hs.144796 AI219737 |
| 1001 FLJ10511: hypothetical protein FLJ10511 Hs.106768 R25877 |
| 1002 DKFZP564A122: DKFZP564A122 protein Hs.187991 N31577 |
| 1003 ODF2: outer dense fibre of sperm tails 2 Hs.129055 AA400407 |
| 1004 AMY2A: amylase, alpha 2A; pancreatic Hs.278399 R64129 |
| 1005 **ESTs,: Weakly similar to plakophilin 2b [*H. sapiens*] Hs.12705 N91589 |
| 1006 CYP1B1: cytochrome P450, subfamily I (dioxin-inducible), polypeptide 1 (glaucoma 3, primary infantile) Hs.154654 AA029776 |
| 1007 CAPN7: calpain 7 Hs.7145 N46420 |
| 1008 FLJ20069: hypothetical protein FLJ20069 Hs.273294 AA229966 |

TABLE 1-continued

| Gene (Name and/or Symbol) or Number (EST, cDNA clone, or Accession) |
| --- |

1009 FLJ10618: hypothetical protein FLJ10618 Hs.42484 AA478847
1010 KIAA1637: **coactivator independent of AF-2 (CIA); KIAA1637 protein Hs.288140 AA452531
1011 FLJ20004: **hypothetical protein FLJ20004 Hs.17311 AA487895
1012 FLJ12892: hypothetical protein FLJ12892 Hs.17731 AA670363
1013 PLU-1: putative DNA/chromatin binding motif Hs.143323 AA464869
1014 **ESTs: Hs.36828 AA418448
1015 KIAA0586: KIAA0586 gene product Hs.77724 AA905278
1016 MTHFD2: methylene tetrahydrofolate dehydrogenase (NAD+ dependent), methenyltetrahydrofolate cyclohydrolase Hs.154672 AA480994
1017 BRF1: **butyrate response factor 1 (EGF-response factor 1) Hs.85155 AA424743
1018 TFAP2A: transcription factor AP-2 alpha (activating enhancer-binding protein 2 alpha) Hs.18387 R38044
1019 VIL2: villin 2 (ezrin) Hs.155191 AA411440
1020 SDC1: syndecan 1 Hs.82109 AA074511
1021 RNTRE: related to the N terminus of tre Hs.278526 AA281057
1022 HSPC207: hypothetical protein Hs.75798 H99997
1023 FLJ22376: hypothetical protein FLJ22376 Hs.29341 AI199155
1024 RNF10: ring finger protein 10 Hs.5094 H73586
1025 PNN: pinin, desmosome associated protein Hs.44499 AA707321
1026 FLJ20516: hypothetical protein FLJ20516 Hs.70811 AA122393
1027 RPL13A: ribosomal protein L13a Hs.119122 AI254200
1028 H2BFB: H2B histone family, member B Hs.180779 AA885642
1029 OGT: O-linked N-acetylglucosamine (GlcNAc) transferase (UDP-N-acetylglucosamine:polypeptide-N-acetylglucosaminyl transferase) Hs.100293 R13317
1030 KIAA0155: KIAA0155 gene product Hs.173288 AA133684
1031 ILF2: interleukin enhancer binding factor 2, 45 kD Hs.75117 H95638
1032 Homo sapiens mRNA; cDNA DKFZp586I1518 (from clone DKFZp586I1518) Hs.21739 AA287917:
1033 PKNOX1: PBX/knotted 1 homeobox 1 Hs.158225 AI350546
1034 KMO: **kynurenine 3-monooxygenase (kynurenine 3-hydroxylase) Hs.107318 AA044326
1035 VCAM1: vascular cell adhesion molecule 1 Hs.109225 H16591 CD106 = VCAM-1
1036 N54811:
1037 KIAA0618: KIAA0618 gene product Hs.295112 H81940
1038 MAFG: v-maf musculoaponeurotic fibrosarcoma (avian) oncogene family, protein G Hs.252229 N21609 MafG = basic-leucine zipper transcription factor
1039 MATN2: matrilin 2 Hs.19368 AA071473
1040 HOXB4: homeo box B4 Hs.126666 AA918749
1041 FLJ10466: hypothetical protein FLJ10466 Hs.121073 AA453607
1042 FLJ22557: hypothetical protein FLJ22557 Hs.106101 AA127879
1043 EST: Hs.149260 AI247680
1044 KIAA0677: KIAA0677 gene product Hs.155983 AA026751
1045 EST: Hs.104123 AA197344
1046 UCP4: uncoupling protein 4 Hs.40510 H94680
1047 EST: Hs.144224 N93807
1048 GATA2: GATA-binding protein 2 Hs.760 H00625 GATA-binding protein 2
1049 ESTs: Hs.14743 H61082
1050 EST: Hs.116174 AA626786
1051 ITGB3: integrin, beta 3 (platelet glycoprotein IIIa, antigen CD61) Hs.87149 AA666269
1052 FLJ23399: hypothetical protein FLJ23399 Hs.299883 R19895
1053 ESTs: Hs.21734 N72976
1054 FLJ20425: hypothetical protein FLJ20425 Hs.71040 AA424566
1055 CUL4A: cullin 4A Hs.183874 AA598836
1056 PTP4A1: protein tyrosine phosphatase type IVA, member 1 Hs.227777 R61007 protein tyrosine phosphatase PTPCAAX1 (hPTPCAAX1)
1057 ESTs: Hs.7913 N35592
1058 GRO1: GRO1 oncogene (melanoma growth stimulating activity, alpha) Hs.789 W46900
1059 ESTs,: Moderately similar to NRD2 convertase [H. sapiens] Hs.309734 H78796
1060 FLJ10826: hypothetical protein FLJ10826 Hs.24809 AA486738
1061 TOM34: translocase of outer mitochondrial membrane 34 Hs.76927 AA457118
1062 H2AFL: H2A histone family, member L Hs.28777 AA452933
1063 D10S170: **DNA segment, single copy, probe pH4 (transforming sequence, thyroid-1, Hs.315591 N35493
1064 SCYA2: small inducible cytokine A2 (monocyte chemotactic protein 1, homologous to mouse Sig-je) Hs.303649 T77816 MCP-1 = MCAF = small inducible cytokine A2 = JE = chemokine
1065 FLJ10688: hypothetical protein FLJ10688 Hs.118793 AA465358
1066 PTD017: PTD017 protein Hs.274417 AA160498
1067 KIAA0026: MORF-related gene X Hs.173714 AA676604
1068 BMP2: bone morphogenetic protein 2 Hs.73853 AA489383
1069 MNT: MAX binding protein Hs.25497 AA455508
1070 KIAA1170: KIAA1170 protein Hs.268044 H80507
1071 CRYBA1: crystallin, beta A1 Hs.46275 AA487614
1072 KATNA1: katanin p60 (ATPase-containing) subunit A 1 Hs.289099 AA609740
1073 Homo sapiens cDNA FLJ20796 fis, clone COL00301 Hs.113994 N53458:

TABLE 1-continued

| Gene (Name and/or Symbol) or Number (EST, cDNA clone, or Accession) |
|---|

1074 CEP4: Cdc42 effector protein 4; binder of Rho GTPases 4 Hs.3903 W32509
1075 ESTs: Hs.117261 AA682521
1076 CYP1B1: cytochrome P450, subfamily I (dioxin-inducible), polypeptide 1 (glaucoma 3, primary infantile) Hs.154654 AA040872
1077 ALTE: Ac-like transposable element Hs.9933 AA630498
1078 RAD51: RAD51 (*S. cerevisiae*) homolog (E coli RecA homolog) Hs.23044 AA873056
1079 MAN1A2: mannosidase, alpha, class 1A, member 2 Hs.239114 R78501
1080 H53763:
1081 MET: met proto-oncogene (hepatocyte growth factor receptor) Hs.285754 AA410591
1082 DYRK1A: dual-specificity tyrosine-(Y)-phosphorylation regulated kinase 1A Hs.75842 AA676749
1083 ARHGAP8: **Rho GTPase activating protein 8 Hs.102336 AA037410
1084 LMO4: LIM domain only 4 Hs.3844 H27986
1085 ADCY6: adenylate cyclase 6 Hs.12373 AA148044
1086 EST: Hs.135448 AI078552
1087 NCOA3: nuclear receptor coactivator 3 Hs.225977 W46433
1088 DNAJB4: DnaJ (Hsp40) homolog, subfamily B, member 4 Hs.41693 AA081471
1089 NAB1: NGFI-A binding protein 1 (ERG1 binding protein 1) Hs.107474 AA486027
1090 ESTs,: Weakly similar to T08663 hypothetical protein DKFZp547G0910.1 [*H. sapiens*] Hs.172084 N63646
1091 KIAA0735: KIAA0735 gene product; synaptic vesicle protein 2B homolog Hs.8071 R56082
1092 GNB1: guanine nucleotide binding protein (G protein), beta polypeptide 1 Hs.215595 AA487912
1093 *Homo sapiens* mRNA for KIAA1716 protein, partial cds Hs.21446 R49763:
1094 KINESIN: HEAVY CHAIN
1095 CCND1: cyclin D1 (PRAD1: parathyroid adenomatosis 1) Hs.82932 AA487486 Cyclin D1 = BCL1 = PRAD1 = Translocated in mantle cell leukemia
1096 ESTs: Hs.106129 R56716
1097 AA431931:
1098 PSEN1: presenilin 1 (Alzheimer disease 3) Hs.3260 AA403083
1099 ESTs: Hs.193804 AA010918
1100 DKFZp762P2111: hypothetical protein DKFZp762P2111 Hs.14217 AA429586
1101 KIAA1350: KIAA1350 protein Hs.101799 W37627
1102 FLJ20847: hypothetical protein FLJ20847 Hs.13479 H16996
1103 HDCMA18P: HDCMA18P protein Hs.278635 N64387
1104 FLJ12890: hypothetical protein FLJ12890 Hs.43299 N62475
1105 ESTs: Hs.127453 AA973625
1106 BAIAP2: BAI1-associated protein 2 Hs.7936 R60328
1107 ESTs: Hs.317584 AA191424
1108 DKFZP434J046: DKFZP434J046 protein Hs.116244 AI024401
1109 ESTs: Hs.114055 AA701352
1110 ESTs: Hs.44380 N93122
1111 ESTs: Hs.20142 AA625570
1112 UBL3: ubiquitin-like 3 Hs.173091 T82438
1113 H2AFL: H2A histone family, member L Hs.28777 N50797
1114 SUCLG2: **succinate-CoA ligase, GDP-forming, beta subunit Hs.247309 N68557
1115 ZWINT: ZW10 interactor Hs.42650 AA706968
1116 FLJ10583: hypothetical protein FLJ10583 Hs.105633 R00425
1117 FLJ20552: hypothetical protein FLJ20552 Hs.69554 AA463982
1118 FADD: Fas (TNFRSF6)-associated via death domain Hs.86131 AA430751 FADD = MORT
1119 SFRS7: splicing factor, arginine/serine-rich 7 (35 kD) Hs.184167 AA418813
1120 RAD54L: RAD54 (*S. cerevisiae*)-like Hs.66718 AI372035
1121 MYLE: MYLE protein Hs.11902 T68845
1122 LOC51334: mesenchymal stem cell protein DSC54 Hs.157461 R63841
1123 PRIM2A: primase, polypeptide 2A (58 kD) Hs.74519 AA434404
1124 KIAA0056: KIAA0056 protein Hs.13421 AA430545
1125 ESTs,: Moderately similar to ALU7_HUMAN ALU SUBFAMILY SQ SEQUENCE CONTAMINATION WARNING ENTRY [*H. sapiens*] Hs.82590 N53024
1126 ESTs: Hs.117269 AA705050
1127 NSAP1: NS1-associated protein 1 Hs.155489 AA186327
1128 CEACAM5: carcinoembryonic antigen-related cell adhesion molecule 5 Hs.220529 AA130547
1129 FLJ11021: hypothetical protein FLJ11021 similar to splicing factor, arginine/serine-rich 4 Hs.81648 AA291183 Unknown UG Hs.202583 ESTs, Weakly similar to arginine-rich
1130 FOSL1: FOS-like antigen-1 Hs.283565 T82817 fra-1 = fos-related antigen 1
1131 U3-55K: U3 snoRNP-associated 55-kDa protein Hs.153768 AA465355
1132 DNAJC6: DnaJ (Hsp40) homolog, subfamily B, member 6 Hs.44896 AA455940
1133 KIAA1382: amino acid transporter 2 Hs.298275 R27255 Similar to transporter protein
1134 PCAF: p300/CBP-associated factor Hs.199061 N74637 P/CAF = p300/CBP-associated factor
1135 ESTs: Hs.130460 AA927252
1136 ESTs: Hs.112570 AI014667
1137 FLJ10209: hypothetical protein FLJ10209 Hs.260150 AA454626
1138 ESTs: Hs.99014 AA485679
1139 ESTs: Hs.99621 AA464707

TABLE 1-continued

Gene (Name and/or Symbol) or Number (EST, cDNA clone, or Accession)

1140 *Homo sapiens* cDNA FLJ11904 fis, clone HEMBB1000048 Hs.285519 N74617:
1141 AA928536:
1142 SQSTM1: **sequestosome 1 Hs.182248 AA931964
1143 **Homo sapiens* cDNA FLJ13700 fis, clone PLACE2000216, highly similar to SPECTRIN BETA CHAIN, BRAIN Hs.324648 AA018591:
1144 SLC22A3: solute carrier family 22 (extraneuronal monoamine transporter), member 3 Hs.81086 AA460012
1145 FLJ22557: hypothetical protein FLJ22557 Hs.106101 H00595
1146 FLJ20539: hypothetical protein FLJ20539 Hs.118552 R36152
1147 AA991624:
1148 TRAP150: thyroid hormone receptor-associated protein, 150 kDa subunit Hs.108319 W85832
1149 ESTs: Hs.221847 R91557
1150 TCFL1: transcription factor-like 1 Hs.2430 AA443950
1151 ESTs,: Highly similar to oxytocinase splice variant 1 [*H. sapiens*] Hs.203271 AA487918
1152 PLAB: prostate differentiation factor Hs.296638 AA450062
1153 RBM14: RNA binding motif protein 14 Hs.11170 AA417283
1154 EGFL5: EGF-like-domain, multiple 5 Hs.5599 W67981
1155 H2AFO: H2A histone family, member O Hs.795 AA047260
1156 ESTs,: Weakly similar to A46661 leukotriene B4 omega-hydroxylase [*H. sapiens*] Hs.169001 N45556
1157 W78784:
1158 TOP3A: topoisomerase (DNA) III alpha Hs.91175 N21546
1159 W73732: Host cell factor-1 = VP16 transactivator interacting protein
1160 CYP1B1: cytochrome P450, subfamily I (dioxin-inducible), polypeptide 1 (glaucoma 3, primary infantile) Hs.154654 AA448157 Cytochrome P450 IB1 (dioxin-inducible)
1161 ESTs: Hs.135276 AI092102
1162 RHEB2: Ras homolog enriched in brain 2 Hs.279903 AA482117
1163 ESTs,: Highly similar to EF-9 [*M. musculus*] Hs.8366 H94467
1164 POLA: polymerase (DNA directed), alpha Hs.267289 AA707650
1165 KIAA1008: KIAA1008 protein Hs.323346 AA863115
1166 PIK3CD: phosphoinositide-3-kinase, catalytic, delta polypeptide Hs.162808 AA281652
1167 T53625:
1168 **Homo sapiens* mRNA; cDNA DKFZp434A1114 (from clone DKFZp434A1114) Hs.326292 AA417274:
1169 ESTs: Hs.26744 H16988
1170 FLJ13912: hypothetical protein FLJ13912 Hs.47125 W74133
1171 *Homo sapiens* mRNA; cDNA DKFZp762B195 (from clone DKFZp762B195) Hs.284158 AA625574:
1172 SSA2: Sjogren syndrome antigen A2 (60 kD, ribonucleoprotein autoantigen SS-A/Ro) Hs.554 AA010351
1173 BK1048E9.5: hypothetical protein bK1048E9.5 Hs.6657 N68512
1174 TOP1: topoisomerase (DNA) I Hs.317 AA232856 Topoisomerase I
1175 ESTs: Hs.15386 H18472
1176 KPNB1: karyopherin (importin) beta 1 Hs.180446 AA121732
1177 MGC861: hypothetical protein MGC861 Hs.208912 N69694
1178 PMS2L8: **postmeiotic segregation increased 2-like 8 Hs.323954 T62577
1179 TSC22: **transforming growth factor beta-stimulated protein TSC-22 Hs.114360 R16390
1180 C8ORF1: chromosome 8 open reading frame 1 Hs.40539 AA278836
1181 ESTs: Hs.129165 AA989211
1182 DMTF: cyclin D binding Myb-like transcription factor 1 Hs.5671 AA129860
1183 CDC7L1: CDC7 (cell division cycle 7, *S. cerevisiae*, homolog)-like 1 Hs.28853 N62245 Cdc7-related kinase
1184 LOC51700: cytochrome b5 reductase b5R.2 Hs.22142 AA425316
1185 FLNA: filamin A, alpha (actin-binding protein-280) Hs.195464 AA598978
1186 FLJ20257: hypothetical protein FLJ20257 Hs.178011 H78675
1187 *Homo sapiens* cDNA FLJ13604 fis, clone PLACE1010401 Hs.23193 AA406599:
1188 ESTs: Hs.205227 R73480
1189 SCYB14: small inducible cytokine subfamily B (Cys-X-Cys), member 14 (BRAK) Hs.24395 AA953842
1190 MAPK8IP2: **mitogen-activated protein kinase 8 interacting protein 2 Hs.80545 AA418293
1191 ZNF42: zinc finger protein 42 (myeloid-specific retinoic acid-responsive) Hs.169832 AA932642
1192 ESTs: Hs.127054 AA862450
1193 NUDT4: nudix (nucleoside diphosphate linked moiety X)-type motif 4 Hs.92381 AA425630
1194 *Homo sapiens* cDNA FLJ10632 fis, clone NT2RP2005637 Hs.202596 H82421:
1195 LOC51042: zinc finger protein Hs.102419 AA033532
1196 NUMA1: nuclear mitotic apparatus protein 1 Hs.301512 AA679293
1197 ESTs,: Highly similar to A56429 I-kappa-B-related protein [*H. sapiens*] Hs.144614 AA293771
1198 ESTs: Hs.127703 AA947258
1199 *Homo sapiens* cDNA FLJ14214 fis, clone NT2RP3003576 Hs.321236 AA903913:
1200 NFKBIA: nuclear factor of kappa light polypeptide gene enhancer in B-cells inhibitor, TABLE 1-continued

| Gene (Name and/or Symbol) or Number (EST, cDNA clone, or Accession) |
|---| alpha Hs.81328 W55872 IkB alpha
1201 ESTs: Hs.120029 AA707598
1202 ESTs,: Moderately similar to A Chain A, Human Glucosamine-6-Phosphate Deaminase Isomerase At 1.75 A [*H. sapiens*] Hs.21398 AA172012
1203 NFIA: nuclear factor I/A Hs.173933 AI912047
1204 RECQL4: RecQ protein-like 4 Hs.31442 AA620446
1205 **ESTs,: Weakly similar to ALU1_HUMAN ALU SUBFAMILY J SEQUENCE CONTAMINATION WARNING ENTRY [*H. sapiens*] Hs.318894 R96212
1206 *Homo sapiens* cDNA: FLJ21686 fis, clone COL09379 Hs.20787 R11371:
1207 LOC57168: similar to aspartate beta hydroxylase (ASPH) Hs.184390 H17272
1208 ESTs: Hs.26096 R54109
1209 *Homo sapiens* OSBP-related protein 6 mRNA, complete cds Hs.318775 AA680281:
1210 APACD: ATP binding protein associated with cell differentiation Hs.153884 N80741
1211 VIM: **vimentin Hs.297753 AI668662
1212 *Homo sapiens* cDNA FLJ13618 fis, clone PLACE1010925 Hs.17448 AA427980:
1213 NR3C1: nuclear receptor subfamily 3, group C, member 1 Hs.75772 N30428 Glucocorticoid receptor
1214 *Homo sapiens* cDNA: FLJ21814 fis, clone HEP01068 Hs.289008 R12808:
1215 BRD7: bromodomain-containing 7 Hs.279762 AA488428
1216 MAP3K8: **mitogen-activated protein kinase kinase kinase 8 Hs.248 W42450
1217 ESTs: Hs.23213 H29336
1218 ESTs: Hs.122444 AA939019
1219 TUSP: tubby super-family protein Hs.102237 H78234
1220 KIAA1117: KIAA1117 protein Hs.278398 H01516
1221 Human: clone 137308 mRNA, partial cds Hs.322149 H91303
1222 ESTs: Hs.130214 AA456631
1223 RAB3A: RAB3A, member RAS oncogene family Hs.27744 H14230
1224 AA598795: Protein phosphatase 2 (formerly 2A), regulatory subunit B (P
1225 H2BFC: H2B histone family, member C Hs.137594 AI340654
1226 CFLAR: CASP8 and FADD-like apoptosis regulator Hs.195175 N94588
1227 CD24: CD24 antigen (small cell lung carcinoma cluster 4 antigen) Hs.286124 H59915
1228 EST: Hs.48532 N62402
1229 CCRK: cell cycle related kinase Hs.26322 H17616
1230 HECH: heterochromatin-like protein 1 Hs.278554 AI139106
1231 DKFZp547O146: hypothetical protein DKFZp547O146 Hs.91246 T80848
1232 ESTs: Hs.71574 AA135328
1233 HLXB9: homeo box HB9 Hs.37035 AI459915
1234 AA600222:
1235 SPINK5: serine protease inhibitor, Kazal type, 5 Hs.5476 W92134
1236 RNUT1: RNA, U transporter 1 Hs.21577 AA447799
1237 *Homo sapiens* cDNA: FLJ23013 fis, clone LNG00740 Hs.13075 AA464543:
1238 KIAA0063: KIAA0063 gene product Hs.3094 T82263
1239 DYRK2: dual-specificity tyrosine-(Y)-phosphorylation regulated kinase 2 Hs.173135 R63622
1240 R94947:
1241 *Homo sapiens* cDNA FLJ14337 fis, clone PLACE4000494 Hs.180187 AA004903:
1242 FLJ20624: hypothetical protein FLJ20624 Hs.52256 AA431909
1243 ESTs: Hs.43838 R38261
1244 FLJ23053: hypothetical protein FLJ23053 Hs.94037 R25654
1245 MGC11266: hypothetical protein MGC11266 Hs.293943 AA400456
1246 ESTs,: Moderately similar to ALU8_HUMAN ALU SUBFAMILY SX SEQUENCE CONTAMINATION WARNING ENTRY [*H. sapiens*] Hs.34174 AA126603
1247 PLAUR: plasminogen activator, urokinase receptor Hs.179657 AA147962
1248 TSG101: tumor susceptibility gene 101 Hs.118910 AA670215
1249 HCNGP: transcriptional regulator protein Hs.27299 AA457232
1250 KIAA0978: KIAA0978 protein Hs.3686 AA857017
1251 ESTs: Hs.61708 AA033867
1252 ESTs: Hs.120734 AA827482
1253 ESTs: Hs.5909 AA972654
1254 CDH24: cadherin-like 24 Hs.155912 AI668564
1255 CCND1: cyclin D1 (PRAD1: parathyroid adenomatosis 1) Hs.82932 T77237
1256 ESTs: Hs.43148 AA284775
1257 ESTs: Hs.222566 T50982
1258 ESTs: Hs.194125 N52822
1259 EST: Hs.154621 AI138644
1260 MAN1A2: mannosidase, alpha, class 1A, member 2 Hs.239114 R22905
1261 MAN2A2: mannosidase, alpha, class 2A, member 2 Hs.295605 AA454175
1262 Human DNA sequence from clone 967N21 on chromosome 20p12.3-13. Contains the CHGB gene for chromogranin B (secretogranin 1, SCG1), a pseudogene similar to part of KIAA0172, the gene for a novel protein Hs.88959 W94690
1263 ESTs,: Highly similar to CIKG_HUMAN VOLTAGE-GATED POTASSIUM CHANNEL PROTEIN KV3.4 [*H. sapiens*] Hs.106486 H11376
1264 *Homo sapiens* HT023 mRNA, complete cds Hs.237225 AA169496:
1265 FLJ10339: **hypothetical protein FLJ10339 Hs.203963 H72354
1266 N66278:
1267 ESTs: Hs.6195 AA454745

TABLE 1-continued

Gene (Name and/or Symbol) or Number (EST, cDNA clone, or Accession)

1268 KIAA1404: KIAA1404 protein Hs.200317 W72798
1269 PMAIP1: phorbol-12-myristate-13-acetate-induced protein 1 Hs.96 AA458838 APR = immediate-early-response gene = ATL-derived PMA-responsive
1270 G3BP: Ras-GTPase-activating protein SH3-domain-binding protein Hs.220689 AA598628
1271 *Homo sapiens* cDNA: FLJ22807 fis, clone KAIA2887 Hs.261734 R26854:
1272 *Homo sapiens*, clone IMAGE: 3535294, mRNA, partial cds Hs.80449 T57359:
1273 CDC16: CDC16 (cell division cycle 16, *S. cerevisiae*, homolog) Hs.1592 AA410559
1274 FGA: **fibrinogen, A alpha polypeptide Hs.90765 AA026626
1275 ESTs: Hs.33446 N53560
1276 *Homo sapiens* cDNA FLJ14175 fis, clone NT2RP2002979 Hs.288613 AA054704:
1277 ESTs: Hs.44243 AA011390
1278 *Homo sapiens* mRNA full length insert cDNA clone EUROIMAGE 42408 Hs.284123 R61732:
1279 ESTs: Hs.53455 AA454165
1280 FLJ11264: hypothetical protein FLJ11264 Hs.11260 AI219094
1281 MBD4: methyl-CpG binding domain protein 4 Hs.35947 AA010492
1282 FLJ11305: hypothetical protein FLJ11305 Hs.7049 N94612
1283 *Homo sapiens*, Similar to CG5057 gene product, clone MGC: 5309, mRNA, complete cds Hs.13885 AA460004:
1284 ARHB: ras homolog gene family, member B Hs.204354 H88963
1285 ITPR3: inositol 1,4,5-triphosphate receptor, type 3 Hs.77515 AA865667
1286 HMG20B: high-mobility group 20B Hs.32317 AA775743
1287 ESTs: Hs.146276 AI214204
1288 PTPN9: protein tyrosine phosphatase, non-receptor type 9 Hs.147663 AA434420
1289 *Homo sapiens* clone FLB9213 PRO2474 mRNA, complete cds Hs.21321 AA486770:
1290 H21107:
1291 HSPC157: HSPC157 protein Hs.279842 N20480
1292 *Homo sapiens* mRNA; cDNA DKFZp564O2363 (from clone DKFZp564O2363) Hs.321403 AA406332:
1293 ESTs: Hs.150623 AA693532
1294 EST: Hs.188697 AA199733
1295 CLECSF2: C-type (calcium dependent, carbohydrate-recognition domain) lectin, superfamily member 2 (activation-induced) Hs.85201 H11732 AICL = activation-induced C-type lectin
1296 ITPR1: inositol 1,4,5-triphosphate receptor, type 1 Hs.198443 AA035450
1297 CHML: choroideremia-like (Rab escort protein 2) Hs.170129 R91881
1298 CDC42: cell division cycle 42 (GTP-binding protein, 25 kD) Hs.146409 AA668681
1299 FKBP5: **FK506-binding protein 5 Hs.7557 AA872767

All publications and patent applications mentioned in the specification are indicative of the level of those skilled in the art to which this disclosure pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing disclosure has been described in some detail by way of illustration and example for purposes of clarity of understanding, it will be obvious that certain changes and modifications may be practiced within the scope of the appended claims.

What is claimed is:

1. A method for treating a prostate cancer patient having an increased likelihood of cancer recurrence or cancer-specific death, the method comprising:
   (1) measuring, in a prostate cancer sample obtained from said prostate cancer patient, the mRNA expression levels of a panel of genes comprising at least 3 test genes selected from Panel F, wherein one of the at least 3 test genes is MCM10, and wherein the test genes of Panel F are ASF1B, ASPM, BIRC5, BUB1B, C18orf24, CDC2, CDC20, CDCA3, CDCA8, CDKN3, CENPF, CENPM, CEP55, DLGAP5, DTL, FOXM1, KIAA0101, KIF11, KIF20A, MCM10, NUSAP1, ORC6L, PBK, PLK1, PRC1, PTTG1, RAD51, RAD54L, RRM2, TK1, and TOP2A;
   (2) providing a test expression score by determining expression of each gene in said panel of genes and incorporating the expression of each gene in said panel of genes into said test expression score;
   (3) providing a test prognostic score combining said test expression score with at least one test clinical score representing at least one clinical variable, wherein the test prognostic score is calculated according to a formula comprising the following terms: (A×test expression score)+(B×clinical score), wherein A=0.58, said clinical score is CAPRA score, and B=0.41;
   (4) prognosing said prostate cancer patient as having an increased likelihood of cancer recurrence or cancer-specific death based at least in part on said test prognostic score exceeding a reference prognostic score; and
   (5) administering one or more of hormonal therapy, chemotherapy, radiation therapy or surgery to said prostate cancer patient prognosed as having an increased likelihood of cancer recurrence or cancer-specific death.

2. The method of claim 1, wherein said prognostic scores incorporate (a) a first clinical score representing preoperative PSA concentration, incorporated as a numerical concentration of ng/dL transformed by the natural logarithm, adding 1 to avoid zero values; and (b) a second clinical score representing a Gleason score, incorporated as a continuous numeric variable or categorized as <7 (reference level), 7, or >7.

3. The method of claim 1, wherein one of the at least 3 test genes is DLGAP5.

4. A method for treating a prostate cancer patient having an increased likelihood of cancer recurrence or cancer-specific death, the method comprising:
  (1) measuring, in a prostate cancer sample obtained from said prostate cancer patient, the mRNA expression levels of a panel of genes comprising at least 3 test genes selected from Panel F, wherein one of the at least 3 test genes is MCM10, and wherein the test genes of Panel F are ASF1B, ASPM, BIRC5, BUB1B, C18orf24, CDC2, CDC20, CDCA3, CDCA8, CDKN3, CENPF, CENPM, CEP55, DLGAP5, DTL, FOXM1, KIAA0101, KIF11, KIF20A, MCM10, NUSAP1, ORC6L, PBK, PLK1, PRC1, PTTG1, RAD51, RAD54L, RRM2, TK1, and TOP2A;
  (2) providing a test expression score by determining expression of each gene in said panel of genes and incorporating the expression of each gene in said panel of genes into said test expression score;
  (3) providing a test prognostic score combining said test expression score with at least one test clinical score representing at least one clinical variable, wherein the test prognostic score is calculated according to a formula comprising the following terms: (A×test expression score)+(B×clinical score), wherein A=0.58, said clinical score is CAPRA score, and B=0.41;
  (4) prognosing said prostate cancer patient as having no increased likelihood of cancer recurrence or cancer-specific death based at least in part on said test prognostic score not exceeding a reference prognostic score;
  (5) administering active surveillance to said prostate cancer patient prognosed as having no increased likelihood of cancer recurrence or cancer-specific death; and
  (6) further administering one or more of hormonal therapy, chemotherapy, radiation therapy or surgery to said prostate cancer patient based on the presence of prostate cancer symptoms and/or signs of accelerated prostate cancer growth to said prostate cancer patient administered active surveillance.

\* \* \* \* \*